United States Patent [19]
Wright et al.

[11] Patent Number: 6,004,276
[45] Date of Patent: Dec. 21, 1999

US006004276A

[54] OPEN ARCHITECTURE CARDIOLOGY INFORMATION SYSTEM

[75] Inventors: Gregory John Wright, Seattle; Philip Scott Hochberg, Kirkland; Darcy B. Bellusci, Redmond; Eric Gregory Brinster, Everett; Mark Willard Brinton, Bellevue; Sue R. Folkerts, Snohomish; Brian Timothy Foster, Suquamish; Anthony Edward King; Kevin Patrick Maloney, both of Seattle; Todd Edwin Newell, Kent; Eric David Peterson, Redmond; Thomas Dean Pierce, Edmonds; David L. Rabbers, Newcastle; Linda Jean Shoemaker, Edmonds; John Joseph Tolan, Snohomish; James M. Wootten, Kirkland; Gregory Allin Bolles, Snohomish; Kathie Goddard, Bellevue; John Anthony Malley, Seattle; Kurt Schmidt, Redmond; Chou Ying Ly, Kirkland, all of Wash.

[73] Assignee: Quinton Instrument Company, Bothell, Wash.

[21] Appl. No.: 08/805,841

[22] Filed: Mar. 3, 1997

[51] Int. Cl.$^6$ .................................................. A61N 5/04
[52] U.S. Cl. ........................................ 600/508; 128/923
[58] Field of Search ................................ 600/508, 509, 600/523; 128/906, 920, 923

[56] References Cited

U.S. PATENT DOCUMENTS

| | | | |
|---|---|---|---|
| 3,058,458 | 10/1962 | Daneman | 128/2.06 |
| 3,566,370 | 2/1971 | Worthington, Jr. et al. | 340/172.5 |
| 4,483,346 | 11/1984 | Slavin | 128/710 |
| 4,739,772 | 4/1988 | Hokanson et al. | 128/731 |
| 4,804,950 | 2/1989 | Moon et al. | 600/523 |
| 5,002,062 | 3/1991 | Suzuki | 128/696 |
| 5,086,778 | 2/1992 | Mueller et al. | 128/696 |
| 5,189,609 | 2/1993 | Tivig et al. | 364/413.01 |
| 5,193,541 | 3/1993 | Hatsuwi | 128/630 |
| 5,206,807 | 4/1993 | Hatke et al. | 364/413.03 |
| 5,277,184 | 1/1994 | Sacker | 600/508 |
| 5,331,549 | 6/1994 | Crawford, Jr. | 600/523 |
| 5,355,892 | 10/1994 | Saltzstein et al. | 128/710 |
| 5,701,894 | 12/1997 | Charry et al. | 600/509 |

*Primary Examiner*—William E. Kamm
*Attorney, Agent, or Firm*—Graybeal Jackson Haley LLP

[57] ABSTRACT

A clinical information reporting system for use with an electronic database for a health care facility, the electronic database being a rotational and modular database for the provision of a scalable and extensible configuration preferably consisting of a workstation as the base configuration and being configurable for use in small and medium network situations and being particularly adapted for the receipt, manipulation, modification and generation of cardiology reports such as resting ECG records and stress ECG records.

14 Claims, 100 Drawing Sheets

Microfiche Appendix Included
(13 Microfiche, 2693 Pages)

FIG. 14A

| PATIENT NAME | ID | STATUS | PROCEDURE | DATE | STATUS |
|---|---|---|---|---|---|
| SMITH, JOLENE R. | 000-11-2222 | IN-PATIENT | NEWEST CARDIOLOGY THING | 07/17/94 | SCHEDULED |
| SMITH, JOLENE R. | 000-11-2222 | IN-PATIENT | EXERCISE STRESS TEST | 07/11/94 | UNCONFIRMED |
| SMITH, JOLENE R. | 000-11-2222 | IN-PATIENT | EXERCISE STRESS TEST | 07/09/93 | CONFIRMED |
| SMITH, JON K. | 999-88-7777 | EXPIRED | CATH-ANGIOPLASTY | 07/16/94 | CONFIRMED |
| SMITH, JON K. | 999-88-7777 | EXPIRED | RESTING ECG | 07/14/94 | UNCONFIRMED |
| SMITH, JUNE M. | 123-45-6789 | OFF-SITE | RESTING ECG | 07/16/94 | TRANSFERRED |

FIG. 14B

| PATIENT NAME | ID | STATUS | PROCEDURE | DATE | STATUS |
|---|---|---|---|---|---|
| SMITH, JON K. | 999-88-7777 | EXPIRED | RESTING ECG | 07/14/94 | UNCONFIRMED |
| SMITH, JUNE M. | 123-45-6789 | OFF-SITE | RESTING ECG | 07/16/94 | TRANSFERRED |

FIG. 14C

| PATIENT NAME | ID | STATUS |
|---|---|---|
| SMITH, JOLENE R. | 000-11-2222 | IN-PATIENT |
| SMITH, JON K. | 999-88-7777 | EXPIRED |
| SMITH, JUNE M. | 123-45-6789 | OFF-SITE |

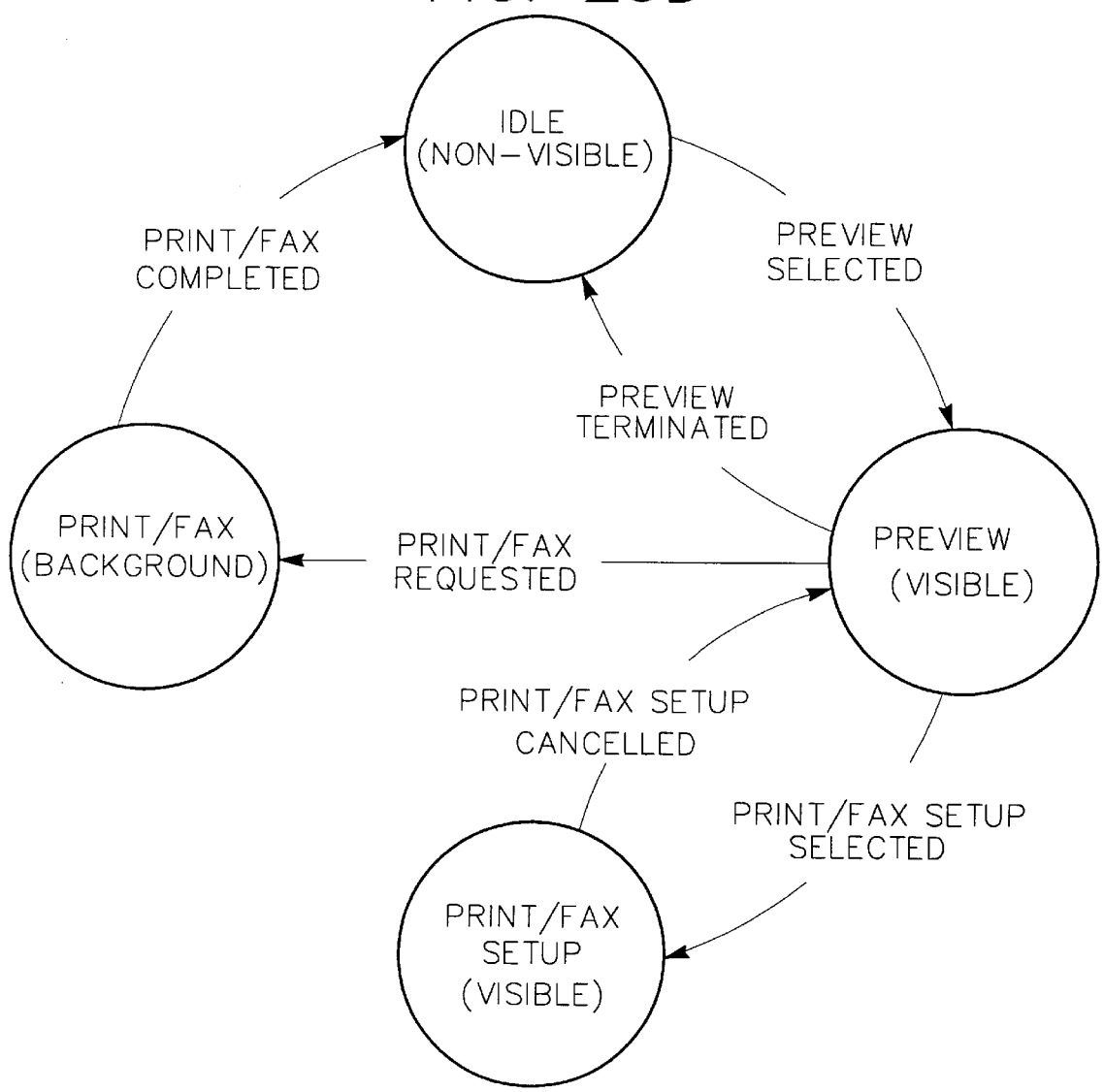

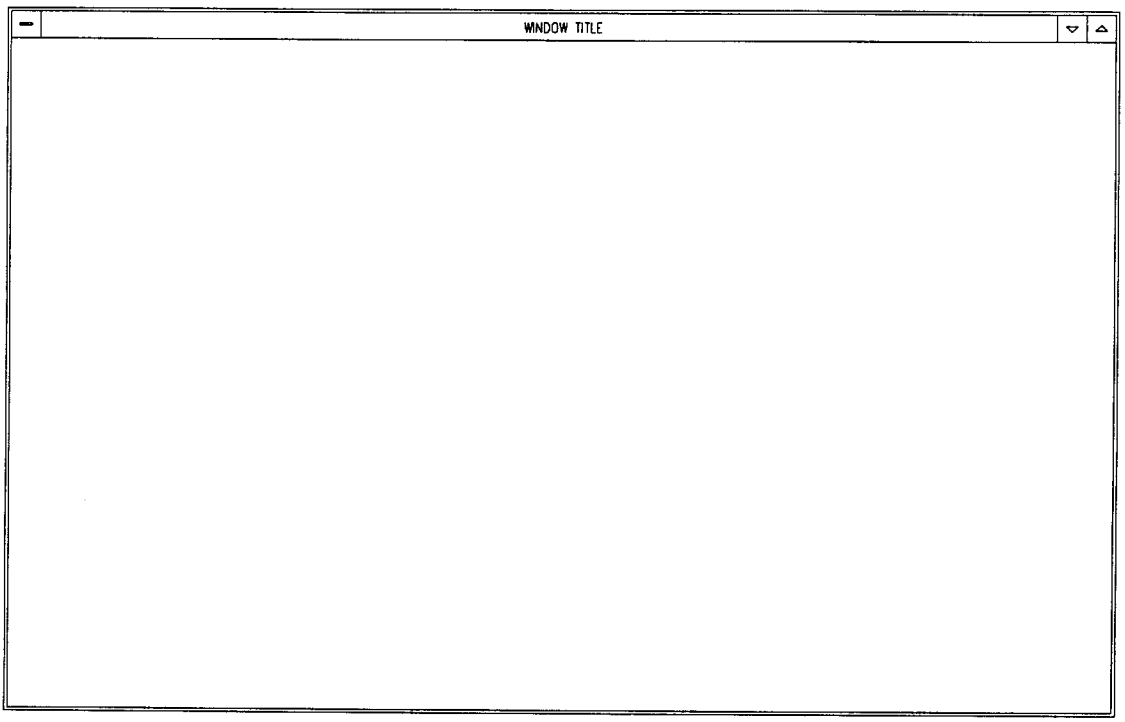

FIG. 68

| DEMOGRAPHICS | TEST INFO | MEASUREMENTS | WAVEFORM | 12 LEAD REPORT |
|---|---|---|---|---|
| COMMON | REST | STRESS | | |

FIG. 69

| STATUS: | UNCONFIRMED | NAME: | AGUILERRA, VIRGINIA. | MRN | 102-22-1233 | 12 LEAD SIMULTANEOUS |
|---|---|---|---|---|---|---|
| DEMOGRAPHICS | | TEST INFO | MEASUREMENTS | WAVEFORM | 12 LEAD REPORT | |

FIG. 70A

| | | | WINDOW TITLE | | | |
|---|---|---|---|---|---|---|
| STATUS: UNCONFIRMED | NAME: AGUILERRA, VIRGINIA L/ | | MRN 102-22-1233 | | DATE/TIME 3/29/95 19:09 | |
| DEMOGRAPHICS | TEST INFO | MEASUREMENTS | WAVEFORM | 12 LEAD REPORT | | |
| COMMON | REST | STRESS | | | | |

PRINT... | FORMAT... | DISTRIBUTE... | << PREVIOUS | NEXT >> | SEND | CONFIRM... | CLOSE

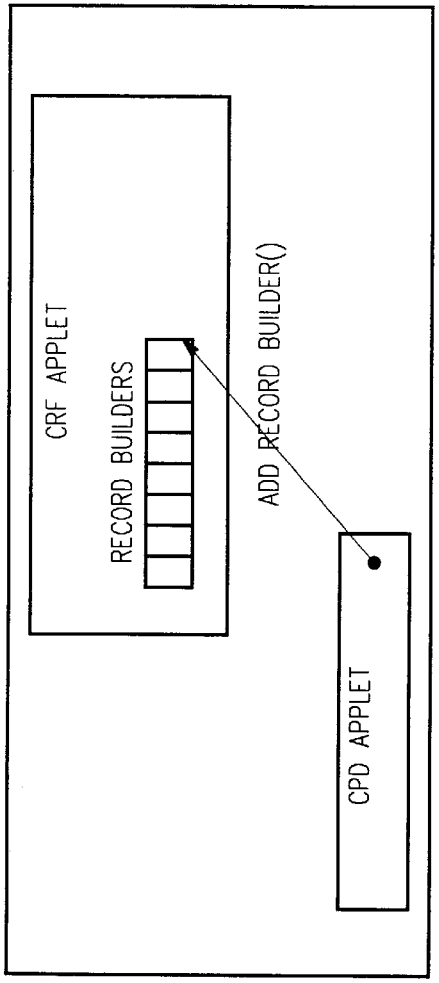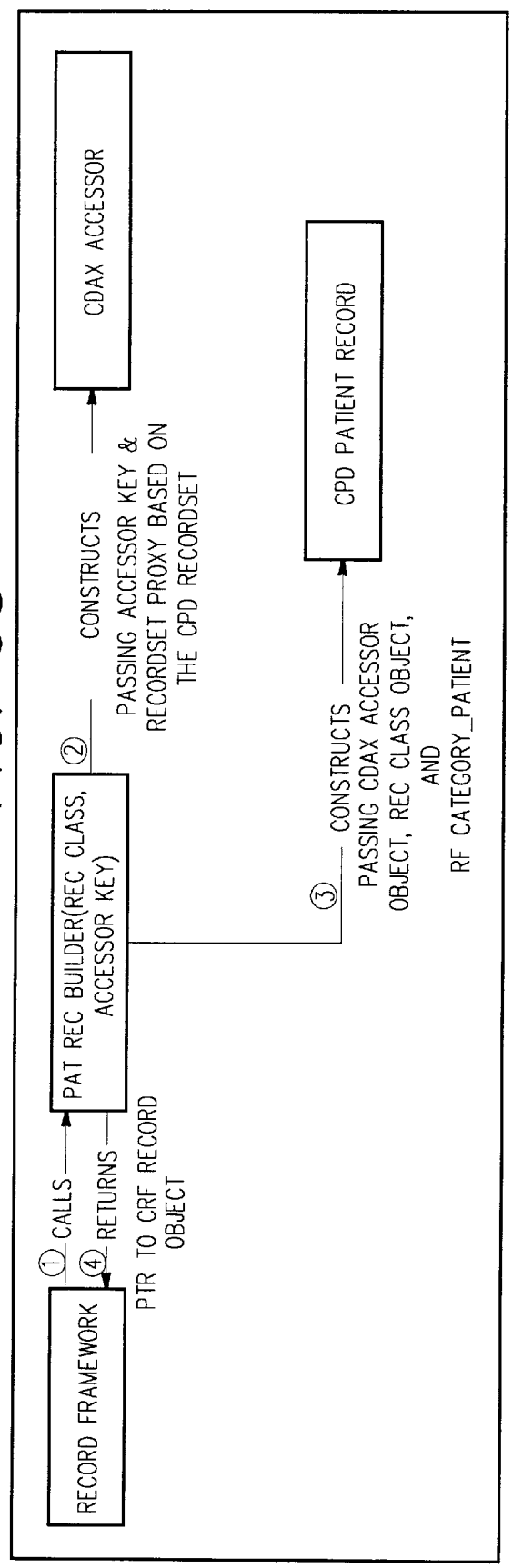

OPEN ARCHITECTURE CARDIOLOGY INFORMATION SYSTEM

Microfiche appendix: 13 microfiche, 2693 frames

FIELD OF THE INVENTION

The present invention is directed to an improved object oriented information system for use in a hospital and more particularly for use by the cardiology and administrative departments of a hospital.

BACKGROUND OF THE INVENTION

Many hospitals today have a hospital information system (HIS), although the quality and sophistication of the HIS systems vary dramatically. The HIS typically is the backbone of the hospital computer network and contains the basic information for all of the hospital's patient records, billing, ordering and other business information.

The medical records of a patient in a hospital typically contain laboratory and test data, physicians orders and other information which is important to the treatment of the patient and which is also typically not available on the HIS. Additionally, with the increase in insurance and other third party payment plans, it is important for a hospital to accurately bill for the services and treatment provided as well as to monitor their costs of providing the treatment and services. In many hospitals which provide the full range of cardiac services, the hospital may receive between 25 and 35 percent of their revenues from cardiology patients. This category of patients also has one of the highest needs for rapid and complete access to their medical records.

In about 1976, the Marquette Electronics Company introduced a computerized electrocardiography management system. This system provided data storage, viewing, retrieval and report generation capabilities for diagnostic 12 lead electrocardiographs acquired from Marquette equipment. This type of system is known as a closed system because it communicates only with electrocardiography equipment purchased from the manufacturer of the management system. Therefore, once a hospital purchases a closed management system, all future pieces of medical equipment must be purchased from the same manufacturer in order to communicate with the management system. With the increased concerns about the increasing costs of healthcare, it is increasingly important that each piece of equipment purchased by a hospital or clinic communicate with existing equipment and perform as many functions as possible.

ECG management systems are a vital component of the computerized ECG equipment market. These systems expedite the flow of ECG reports in a hospital by improving the access to records for copies and serial comparison analysis. The computer also assists with the information routing tasks such as editing, sorting, tracking and printing of the ECG records. Many of the functions of a cardiology department are significantly improved by the increased access to the ECG information. The staffing required to process ECGs may be reduced with the addition of an ECG management system.

The cardiology diagnostic department of a hospital uses an ECG management system extensively. One part of an ECG management system is typically a computer based ECG interpretation program. Although this program is not as skilled as a cardiologist, the program often provides a useful initial review from which the cardiologist may make further revisions and provide the final diagnosis.

Additionally, the computer program adds the ECG measurements and interpretation in a text format that may be edited by the clerical staff. This improves the accuracy, throughput and efficiency of the entire department in maintaining the medical records of a patient. Additionally, both adult and pediatric ECG records are typically managed and stored by the ECG management system for use in follow-up or subsequent visits of the patient.

Some of the basic functions of the current ECG management systems are data storage, data retrieval, data viewing and the streamlining of the overread process. In the prior practice which used paper copies of the ECG of a patient's records or with an ECG management system, an unconfirmed report of the ECG test is provided to the central station for later overreading or review by a cardiologist. A second copy of the unconfirmed report is typically left in the patient's record at the nurse's station. At some point, the physician on duty will pick up the ECG tracings from the central station and overread or edit them as time permits. The annotated reports are then returned to the central station for editing and data entry. Once the edited record is entered, the confirmed report is then printed and dispatched to the nurse's station to replace the unconfirmed report in the patient's record. It is extremely important that the patient's records not be lost or delayed. The major advantage of the ECG management system is that the transfer to the patient's primary record is instantaneous once it has been entered and there is no likelihood that the confirmed report will be lost or delayed in the hospital delivery system. Additionally, there is less opportunity for data entry errors because it is no longer necessary to clerically enter the physician's comments or diagnosis.

A further advantage of the ECG management system is that a hospital administrator may request a status report from an ECG management system to determine how many ECGs are at the various stages of being overread. In larger hospitals, this allows the administrator to monitor the need for data entry personnel or to monitor the efficiency of various other medical personnel.

Additionally, smaller hospitals, clinics or cardiology offices may contract with outside services for data storage and/or overread services. The ECG management system provides the smaller facility with the benefit of an ECG management system without the additional investment or additional staff. The administrator of the facility may also obtain traffic and management information to help their facility to be more cost effective and efficient.

The currently available ECG management systems have only touched the surface of potential applications for a cardiology information system (CIS). This inability to reach their full potential has resulted primarily from the use of closed systems which limit their own usefulness to the breadth of the product line offered by their manufacturer. As a result of the existence of "closed" systems, a number of software development companies have begun selling "translation boxes" to hospitals to enable the various acquisition devices to communicate with the pre-existing hospital systems.

It is an axiom of a hospital that the most vital record is the hardest to access and the most likely to be lost. Whether the record is an ECG or an x-ray film, the more handling it receives, the more likely it is to be lost or damaged. The ECG management system can easily produce high quality duplicate master records which may be printed or transmitted to other sites for review, editing, printing or storage. With remote transmission capabilities, hospitals may efficiently offer ECG management services or support to satellite facilities.

In addition to the record management benefits described above, a cardiology patient typically has other procedures and records which must be managed and archived. For example, the cardiology patient may have HOLTER records, stress test records, catheterization laboratory records, echocardiographic records, electrophysiology, telemetry, metabolic testing records or pacemaker follow-up test records. At present, only a few of these records are accessible to a hospital through the current ECG management system.

Therefore, there is a need for a cardiology information system which provides individual and integrated procedure reports that incorporate key clinical data from all available procedures to reliably and accurately provide proper clinical decision making and accurate reimbursement.

Additionally, there is a need for a cardiology system that provides a simple graphic user interface and standard PC hardware which also uses other standard PC software for word processing, spreadsheet and desktop publishing applications.

There is yet another need is for a cardiology information system which provides a standardized hospital information system connection so that common patient census data, billing capture, results reporting and order driven systems may be used throughout the hospital.

There is a further need for a cardiology information system which provides a standardized communication protocol so that common patient data, billing information, procedure results and medical records information may be acquired by nearly any currently available data acquisition device which may then be reviewed throughout the hospital.

SUMMARY OF THE INVENTION

The present invention is directed to an open architecture cardiology information system which preferably has modular object oriented software to allow for easy expansion, relational database management, custom reporting, local and wide area networks and communication with equipment from a variety of manufacturers and which is readily expandable for use in cardiology group clinics as well as in small, medium and large hospitals.

The cardiology information system of the present invention preferably includes resting and exercise ECG modules; procedural management modules; administrative reporting modules; interfaces with other manufacturers equipment and is preferably a MICROSOFT SOLUTION PROVIDER product. Additionally, the present invention provides modules which allow for the communication with various cardiac catheterization laboratory systems and electrophysiology systems and includes a HIS connection. Furthermore, it is anticipated that the present system may be expanded to include modules which allow for the communication with systems that perform cardiac imaging, Holter monitoring, telemetry, echocardiography, stress echo cardiography and pacer detection as well as administrative functions such as procedure coding, scheduling, inventory management, outcomes management and custom reporting. This is accomplished by the modular nature of the present invention and the provision of a versatile shell operating module which also allows for the use by multiple users to perform multiple tasks including word processing, integrated spread sheets and the storage of other data. The framework provides the basic building blocks or classes that may be used by workstation products to implement the desired records, fields or data repositories. The framework does not implement any records but does provide abstract classes which are used by the workstation products to implement the records. In the present invention, the workstation functions as the basic fundamental operating unit of the system. The workstation enables the user to review, edit and store various physiological signals acquired from physiological signal acquisition devices in combination with other patient related data and patient information.

An important feature of the shell framework is the concept of dynamic extensibility. The shell provides the dynamic and automatic recognition of the presence of modules provided by the workstation products and to recognize the presence of framework based modules and includes the ability to automatically reconfigure itself to satisfy the requirements of these modules. Additionally, the shell framework provides the ability for various workstation products to provide record building services from various record builder possibilities. Another framework feature is the ability to implement Applets. One or more Applets may form a dynamic load library that implements an additional interface as defined by the framework of the workstation product. Therefore, the framework provides class definitions that serve as building blocks for the work station product specific Applets.

In the present invention, the cardiology information system design generally includes software modules for framework shell modules; framework applet modules;

dynamically-loadable framework applet modules; and dynamically-loadable CIS applet modules. The framework shell modules generally consist of a client shell or service shell and an applet interface layer which includes an applet interface and an applet loader. The framework applet modules include modules for a services layer; a rendering layer; a manipulation layer; and an access layer.

The services layer includes modules for an event logger applet and an access services applet. The rendering layer includes modules for a record presentation applet and an applet widgets applet. The manipulation layer includes modules for a field framework applet and a record framework applet. The access layer includes a module for a database access applet. The dynamically-loadable framework layer includes modules for administrative reports applets;

patient demographics applets; record list applets and transfer standard communications protocol applets. The dynamically-loadable CIS applet of the present embodiment includes modules for resting ECG interpretation and stress testing ECG interpretation.

The modules of the workstation products framework preferably run together as a single process under a defined software operating system such as WINDOWS NT. The shell module is the sole executable module of the software operating system process. The remaining modules are operating system dynamic load libraries. Within this single process, all modules run as a single operating system thread, although it is anticipated that additional threads may be used such as for requests made to persistent storage by a database access module.

The framework shell and applet modules together provide the base functionality of the workstation products. The dynamically-loadable applet modules provide each product's unique functionality. This approach allows additional dynamically-loadable applets to be installed on top of a running workstation product in a customer environment. The existing product automatically recognizes the newly installed applets and makes the additional functionality available to the user. In this way an existing customer may have one or more existing applets installed on their system and may add further applets or delete existing applets without affecting the operation of their CIS system.

BRIEF DESCRIPTION OF THE DRAWINGS

FIGS. 14A–C are diagrammatic views illustrating some of the various list views available with the present invention;

FIGS. 29A–D diagrammatically illustrate the state transition diagrams for the various scenarios of the print, fax and/or preview functions of the present invention;

FIG. 64 is a diagrammatic view illustrating a normal child window displayed by a frame widget of the present invention;

FIGS. 65A and 65B are diagrammatic views illustrating information block widgets as formed by the present invention;

FIG. 68 is a diagrammatic view illustrating nested tab control widgets as formed by the present invention;

FIG. 69 is a diagrammatic view illustrating a tab combo box widget as formed by the present invention;

FIGS. 70A and 70B are diagrammatic views illustrating multiple widgets on a single screen as formed by the present invention;

FIG. 97 is a diagrammatic view illustrating the Applet initialization of the Patient Demographics module of the present invention;

FIG. 98 is a diagrammatic view of the Record Builder of the Patient Demographics module of the present invention;

DETAILED DESCRIPTION OF THE PREFERRED EMBODIMENT

The cardiology information system (CIS) is a member of the family of workstation systems. It is a computer-based cardiology data management system with controlled security access. An important purpose of the CIS is to provide a means to establish, maintain and access organized electronic storage of complete cardiology patient records. The CIS will provide for several configurations, ranging from a single computer to a dedicated server for a large computer network supporting a large number of hard-wired and modem-access PCs.

Once the user has logged into the system and gained access to Shell, the user will have access to a variety of data management functions. Functions uniquely available in the preferred form of the CIS product configuration will include Stress ECG Final Reports generation, review and editing, Stress ECG Reports setup, Resting ECG Reports generation, review and editing and Resting ECG Reports setup.

The CIS procedure reports functions allow the user access to elements of the procedure records stored by the CIS. This data may be used to generate, preview, edit, save and print reports for specific medical procedures. Initially, the preferred form of the present invention will support Resting ECG and Stress ECG reports, and it is anticipated that data, reports and records acquired from other physiological signal acquisition devices such as cardiac catheterization laboratory systems and electrophysiology systems may also be readily incorporated.

Figure 1:
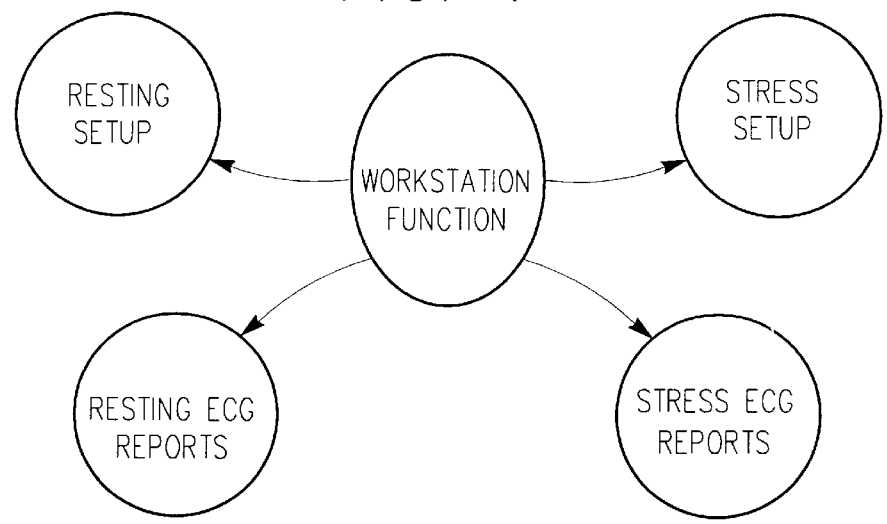
FIG. 1 is a diagrammatic view illustrating a functional overview of the CIS system of the present invention.

FIG. 1 shows the general interface between standard workstation functionality and functions specific to preferred form of the CIS. There are no unique physical characteristics to distinguish CIS from the standard Workstation family of products.

As discussed above, the CIS system preferably serves as a data repository for medical records, allowing multiple users access to the information with the ability to view or edit the data. The CIS can transfer records to or from a variety of instruments as desired. The operator interacts with the CIS system using a client or server workstation which are preferably standard PCs running commercially available software such as Microsoft Windows NT. Connection to another workstation system is also supported if the other system is accessible on the network.

In the preferred form of the present invention, the system architecture of the CIS uses client-server technology; CIS clients will run standard PC applications and the CIS uses standard, "off-the-shelf" hardware and components where feasible. The three basic system configurations of the present invention include single-client, which consists of 1 workstation acting as both client and server; small-network which consists of 1 server (which may also function as a client), 1 to 11 clients (local or remote) and at least 4 Mbit/sec network topology and medium-network which consists of 1 to 50 clients (local or remote), 1 dedicated server (cannot function as a client), and at least 16 Mbit/sec network topology.

A CIS "System" as used herein generally refers to the combination of a single server and the CIS server software, one or more clients and the CIS client software, the connecting network (if any) and any resources available on the connecting network (if any). Although more than one CIS Server can be installed on a physical network, a user must indicate the primary CIS system server.

The preferred form of the present invention also include certain basic architectural features such as providing for upgradability to allow the user the ability to scale (single to small to medium system) without loss of data; remote access to provide the user with the ability to log on to system from a remote client workstation;serial ports which are capable of standard rates up to 9600 baud, for record transfer; modems which are capable of standard rates up to 28.8 Kbits/sec, for record transfer, fax and fax polling; floppy disk to provide support for 3½" (1.44 MB) and 5½" (1.2 MB) diskettes; a bar code reader to provide the user with support for identifying patient reports via bar code/OCR; CD-ROM capabilities to provide in-service and configuration support via CD-ROM; a scanner to provide support for scanning reports to create records; a pager to allow for notification of personnel via pagers; inter-network capabilities to enable support for connection to other CIS systems; system backup capabilities to perform backup or restore of server & clients and system archive capabilities to provide the user with the ability to archive or retrieve records from the server.

A major architectural goal of the preferred form of the present invention is to isolate the software that is developed for the CIS product from the hardware configurations. That is, the hardware and network configuration are transparent to the application software.

Figure 2:
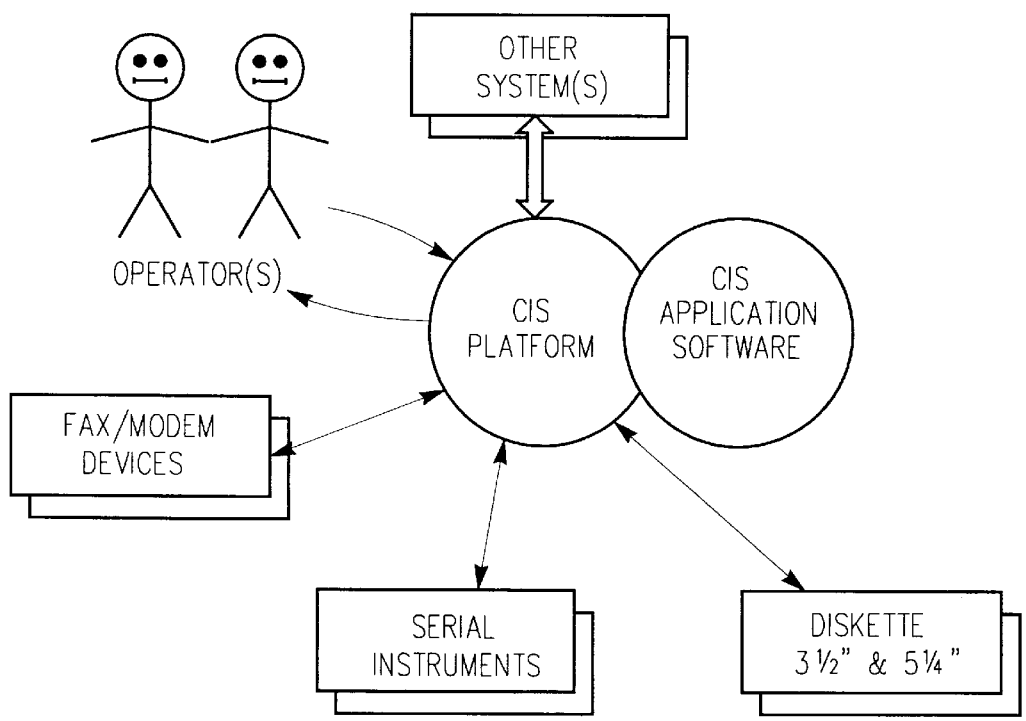
FIG. 2 is a diagrammatic view illustrating the functional system partitions of the CIS portion of the present invention.
Figure 3:
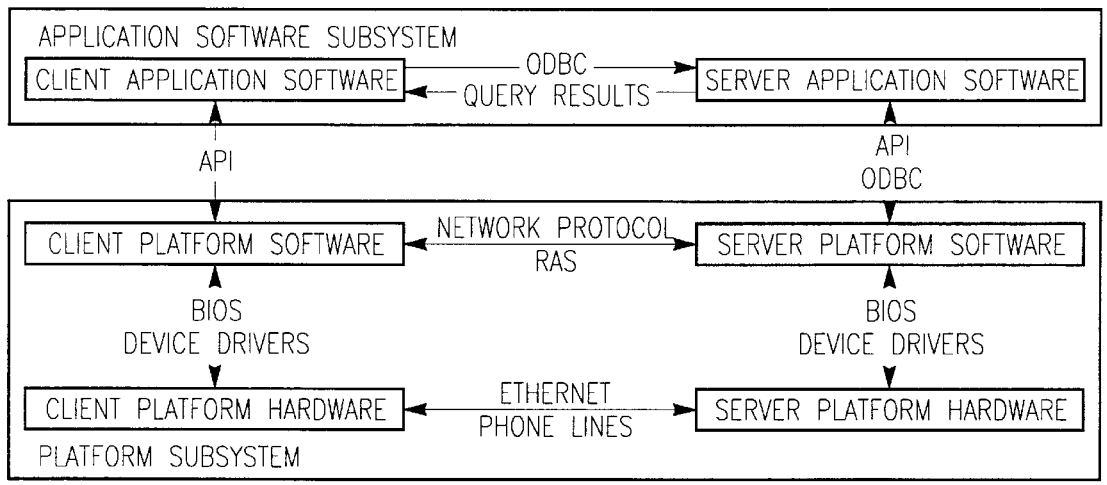
FIG. 3 is a diagrammatic view illustrating the functional CIS platform and application subsystem partitioning of the present invention.

As shown in FIGS. 2 and 3, the CIS system is preferably partitioned into two major subsystems, the CIS platform and the CIS application software. The CIS platform represents the hardware and the support software which is used to run the CIS application software. It includes the client hardware and client operating system, server hardware and server operating system, network hardware and network operating system and peripheral devices and device drivers. The CIS application software is the software which has been developed to implement the product-specific CIS requirements. The CIS application software includes the client and server application software and third-party software (other than Platform software) used to satisfy system requirements. The interface between the two CIS subsystems, Platform and Application Software, is preferably defined by a WIN32 API which is the Windows NT Application Interface and an ODBC which is a generic Database query language.

Figure 4:
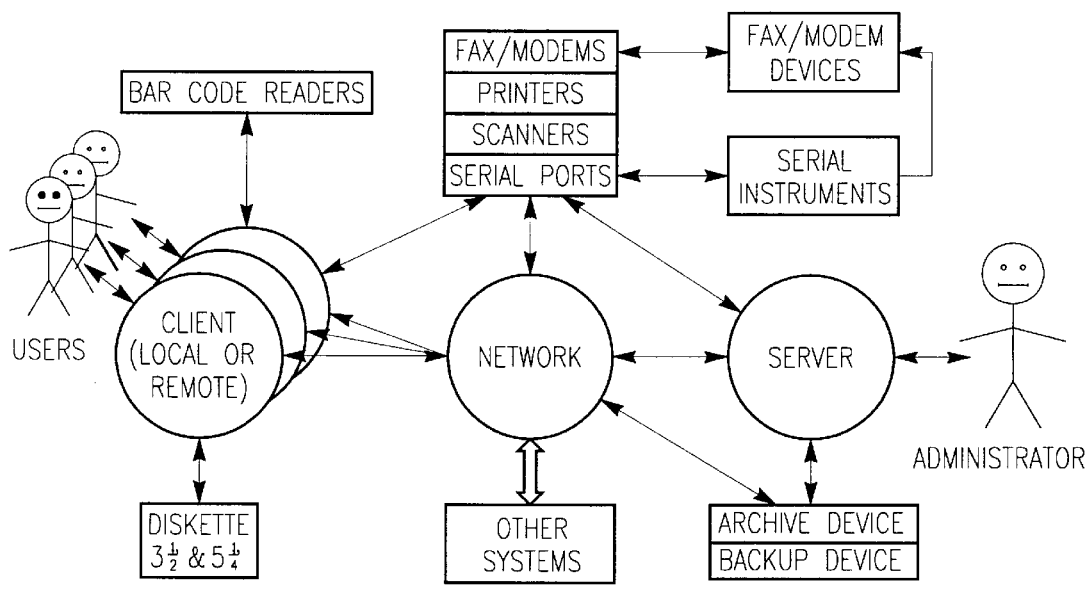
FIG. 4 is a diagrammatic view illustrating the functional CIS platform subsystem partitioning of the present invention.

The client/server model as used in the preferred form of the present invention, decrees three basic subsystems, the client, the server and the client/server interface. In addition to the Client/Server/Network subsystems, there are peripheral devices which are supported in the CIS system to help satisfy product requirements. These peripheral devices include, printers, scanners, serial ports, fax/modems, bar code readers, archive device(s) and backup device(s). FIG. 4 is a CIS platform subsystem partitioning diagram which indicates the connections (or possible connections) of these components.

Figure 5A:
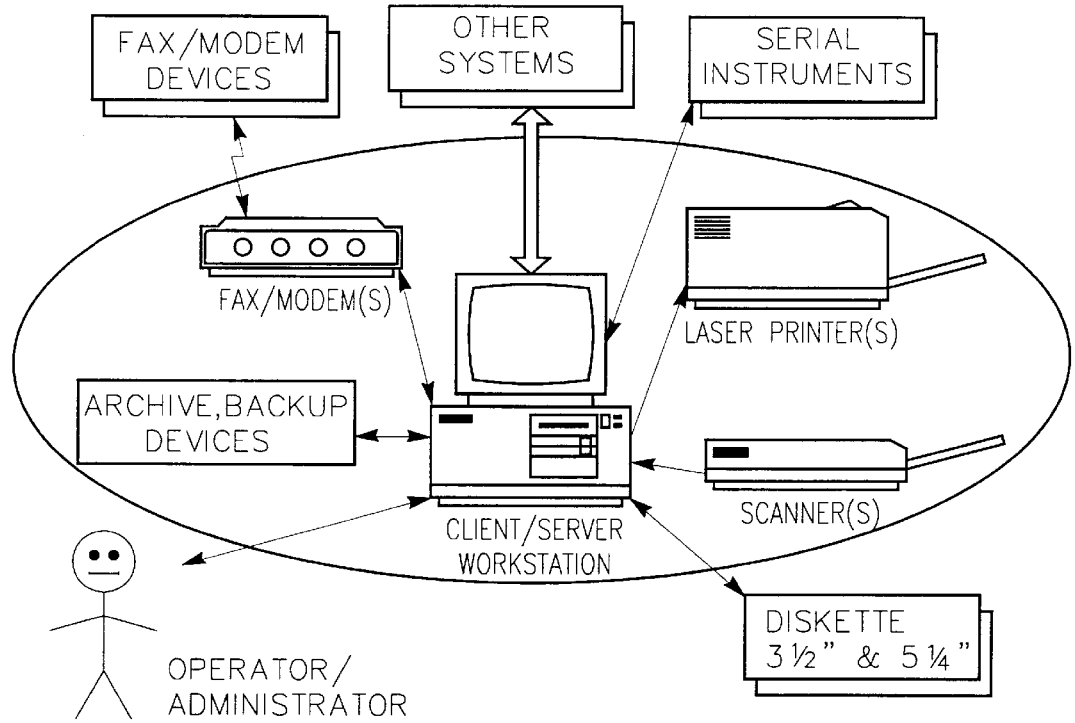
FIGS. 5A–C are diagrammatic views illustrating the platform configurations of the CIS of the present invention.

This section identifies and defines the components which comprise the preferred form of CIS platform subsystem. The components specified herein reflect a "standard" CIS configuration. These three configurations include the "single-client" configuration which is based on a single "client/server" workstation that functions as both the server and a client so that even if this configuration is connected to a network, the client/server workstation will not function as a server for other clients on the network. This type of development approach allows the client/server technology developed for the other models to be leveraged in the present model and also allows for an easy upgrade path between the various models of the present invention. In this embodiment, the client/server workstation may serve as a client on a different system. As shown in FIG. 5A, the single-client model preferably includes the client/server workstation, an archive device and a backup device. The single-client model also preferably supports up to about 8 fax/modems, one printer and one scanner. The CIS application software preferably does not distinguish the single-client configuration from true networked configurations.

Figure 5B:
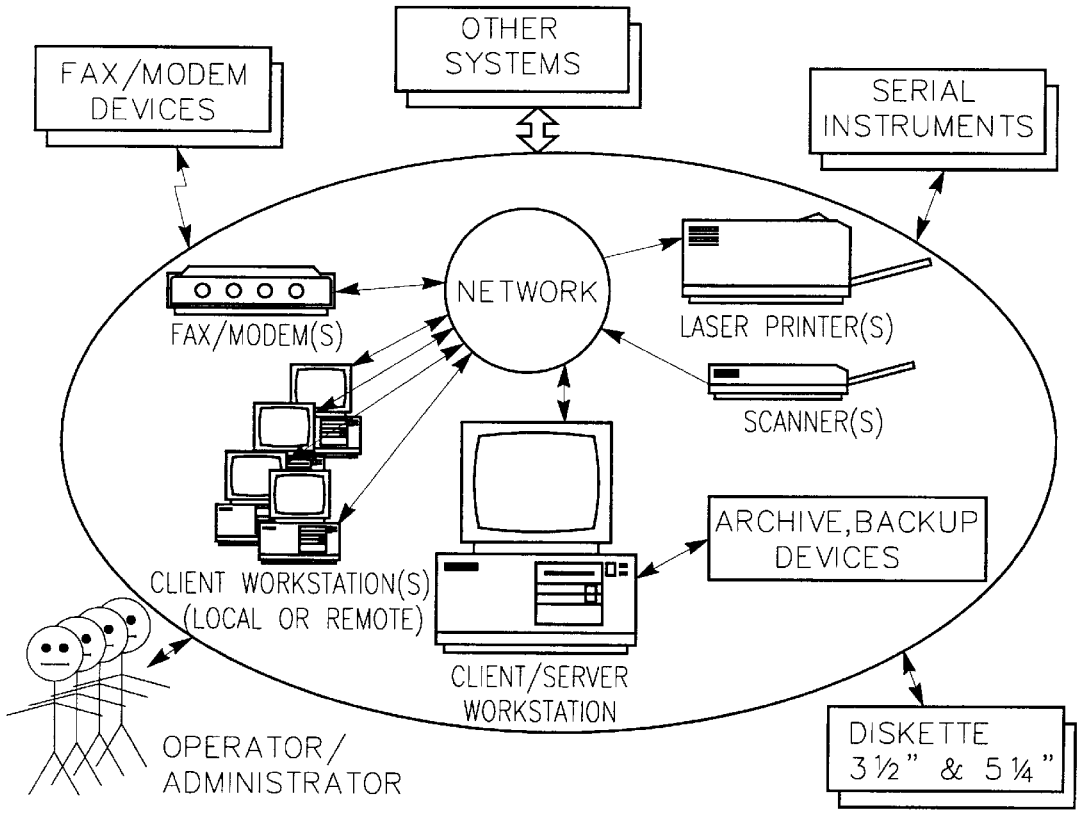

The small-network configuration of the preferred form of the present invention uses the same client/server workstation defined for the single-client model, but adds a network, external clients (local or remote), and optional network resources as shown in FIG. 5B. The small-network model preferably includes a client/server workstation, up to about 11 client workstations, a network system, an archive device and a backup device. The small-network model also preferably supports up to about 12 printers on the system, up to about 3 scanners on the system and up to about 12 fax/modem devices. The network depicted in FIG. 5B is not necessarily a Local-Area Network (LAN). If the only clients are remote, then the "network" may be a Wide-Area Network (WAN) of telephone lines.

Figure 5C:
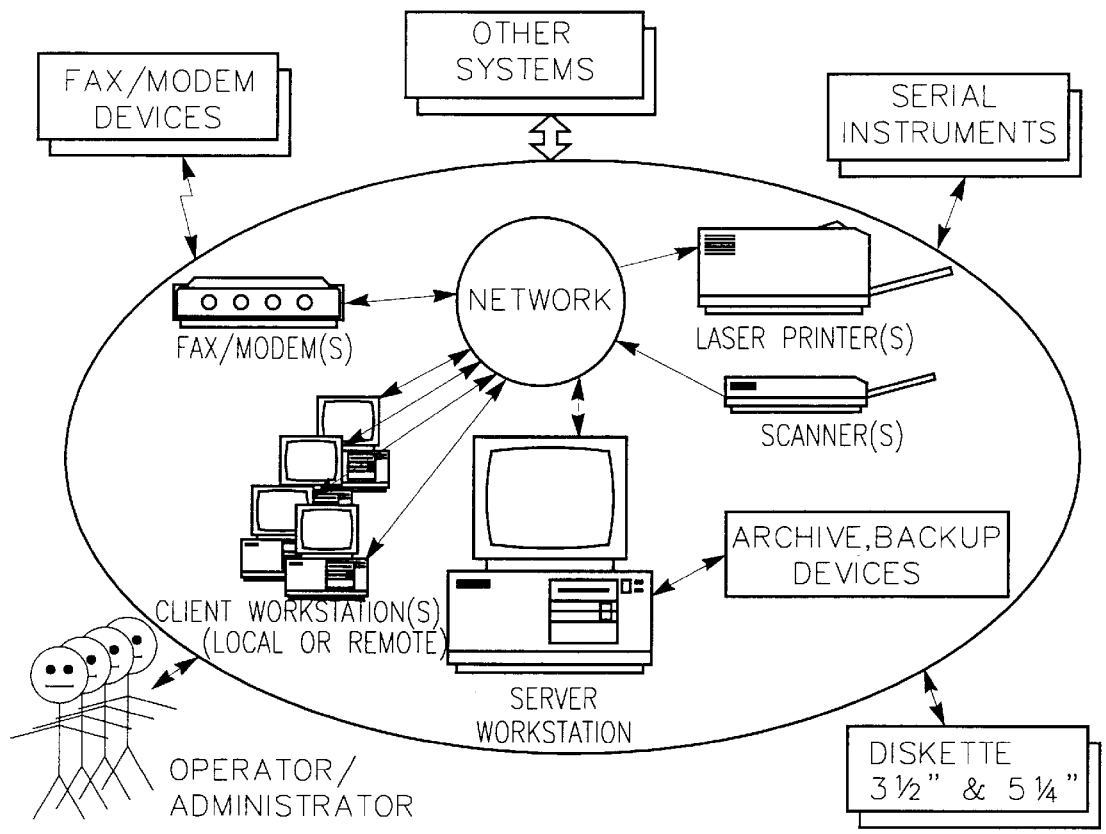

The medium-network model of the present invention preferably uses a dedicated server and supports up to about 50 client workstations. As shown in FIG. 5C, the medium-network model preferably includes a server workstation, up to about 50 client workstations, a network, an archive device and a backup device. The medium network also preferably supports up to about 25 network printers, up to about 5 network scanners and up to about 50 fax/modem devices The small network and medium network models define a preferred maximum number of clients. These numbers represent the preferred maximum number of clients which may be logged into the CIS application at one time. There may be other workstations on the network, but the network performance requirements presume that there is no network traffic other than that generated by CIS clients of the CIS system being monitored.

In the preferred form of the present invention, there are two Local Area Network (LAN) configurations supported by CIS, one for the small network configuration and one for the medium network configuration. Both physical networks preferably employ standard network hardware to physically connect the workstations. Several manufacturers have commercially available products which offer extremely flexible scalability and simple installation and maintenance requirements. Modular bridges and routers may also be included in particular CIS applications should high network traffic make those options necessary. A multi-client system may be implemented without a LAN, if all of the clients are remote.

The preferred operating system used for the network of the present invention is Windows NT. The network preferably conforms to Ethernet standards IEEE 802.3 and two network speeds are supported. The first network speed is 10Base-T which supports 10 Mbps transfer rates. This is preferably the standard network used for the small network model. A bus or star topology may be supported and the cabling may be unshielded twisted pair which is UTP category 3, 4, or 5 and RJ-45 connectors, thin-net, with BNC connector or co-ax, with AUI connectors. The second network speed may be 100Base-T which supports 100 Mbps transfer rates. This is preferably the standard network used for the medium network model. Only a star topology may be supported in this embodiment. Using a switched hub, a single network may run with some workstations using 10Base-T and others using 100Base-T. The cable is preferably unshielded twisted pair, UTP category 5 using RJ-45 connectors.

The default transport protocol used on the network is preferably IPX/SPX. Other protocols (TCP/IP, NetBEUI, etc.) may co-exist on the network if required to communicate with a particular peripheral device. This is preferred in the present embodiment because TCP/IP requires a greater installation effort because each network node must be manually assigned an IP address. The IPX/SPX protocol requires less network overhead than NetBEUI. The IPX/SPX protocol may also allow the use of NetWare server devices.

The ability to allow a user to log in to the system from a remote site may also be supported in the preferred form of the present invention using the Windows NT "Remote Access Service" (RAS). The RAS allows a user to connect to the network from a remote site and work with the CIS application as though they were physically in the office, directly connected to the network or local database (although network access to a remote workstation will be slower). The system preferably allows three types of remote connection. A modem on the remote Client may be connected across standard telephone lines to a modem on the system network. Standard modem data rates up to about 28.8 kbits/sec are supported. The ISDN mode is also supported because this mode uses dedicated phone lines to support high speed data links (up to 128 kbits/sec). Because ISDN requires support from a local telephone carrier; it is not universally available, but most major metropolitan areas have it. This solution would serve well for a physicians' office connecting to a local hospital CIS system. The third type of remote connection is X.25. This is desirable because it is an international standard used for exchanging data across public telephone networks and it may use leased lines, if available, for fast local connections.

Figure 6:
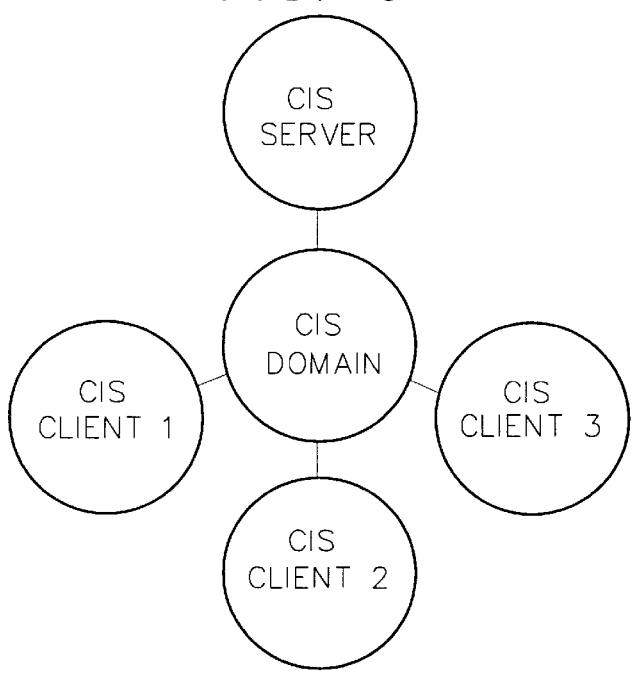
FIG. 6 is a diagrammatic view illustrating the single domain/single server domain configuration of the present invention.
Figure 7:
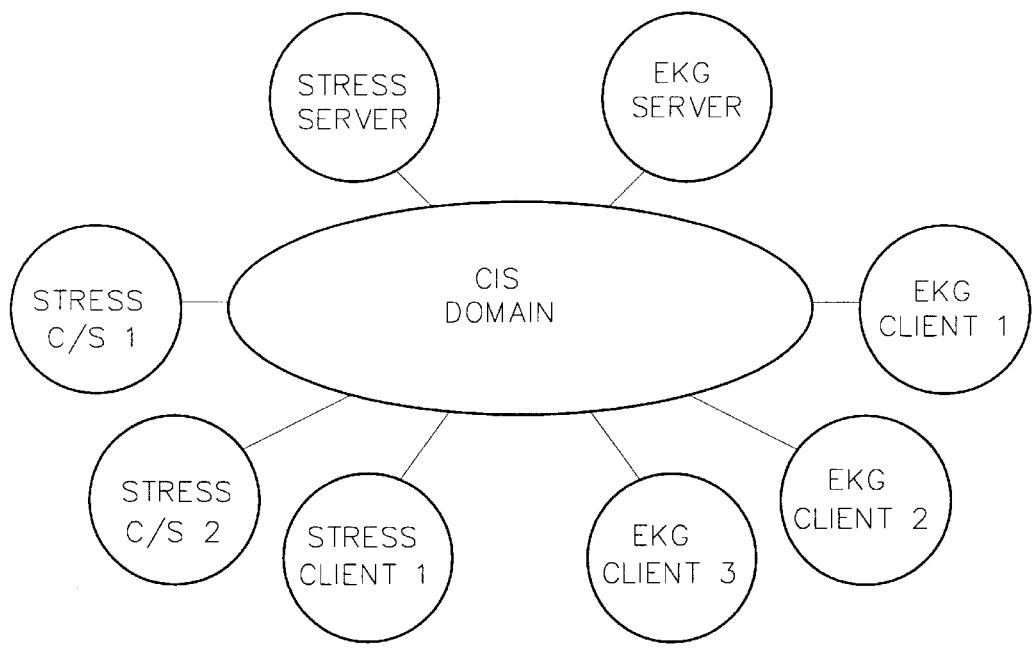
FIG. 7 is a diagrammatic view illustrating the single domain/multiple server domain configuration of the present invention.
Figure 8:
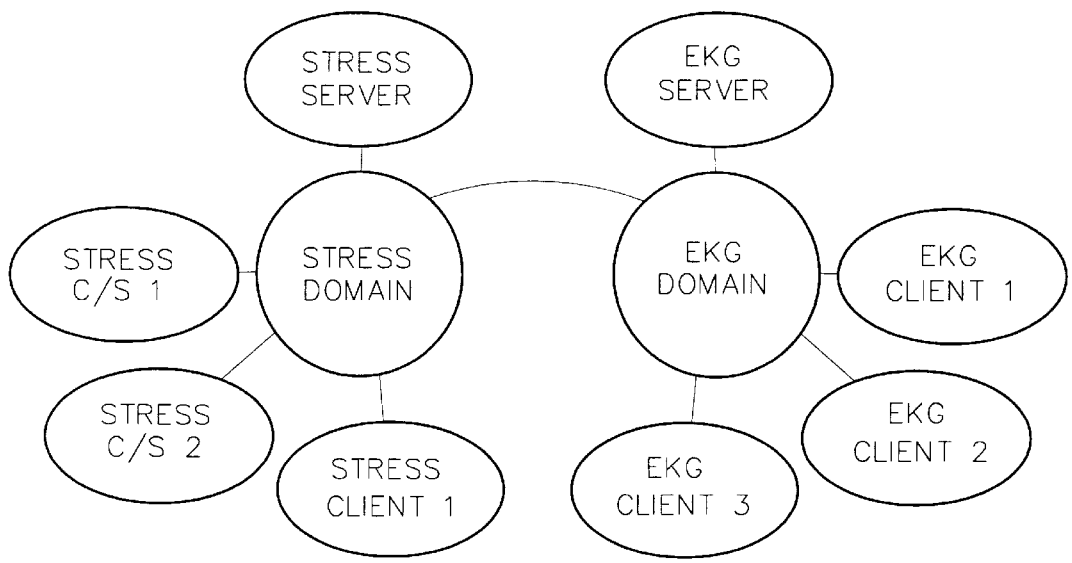
FIG. 8 is a diagrammatic view illustrating the multiple domain configuration of the present invention.

The use of the Windows NT Server in the preferred form of the present invention provides a domain-based naming and logon system. A domain is an aggregation of workstations for administrative purposes. Multiple servers within a single domain can share a user database and can be administered from a single workstation. Multiple domains may be established, each with its own user database; "trust relationships" may be created between domains which allow selected users from one domain to have access to a different domain. Both single domain and multiple domain configurations are supported by CIS. In the present invention, in a single domain/single server system, all CIS users are preferably maintained by the single server and all patient and procedure records are stored by the single server as shown in FIG. 6. In a single domain/multiple server scenario as shown in FIG. 7, all CIS users also preferably share a common user database (which is replicated on all servers). Conceptually, a user logs on to the domain, rather than to a particular server and a user selects one of the servers as the primary CIS server; this primary server is then the default for running queries on the CIS database. A user can access data on any other server to which the user has rights. In the scenario shown in FIG. 7, all EKG procedure records reside on one server and all the Stress procedure records reside on the other; patient information records would reside on both, with duplication for patients with both procedures. As shown in FIG. 8, with multiple domains, separate user databases are maintained for each domain. With multiple domains, each procedure record type may reside on its respective server and patient information records may be stored on both servers. A "trust relationship" is preferably established to give users in one domain access to data in the other domain. For example, the group 'Stress Tech' in the Stress domain might be given rights to read EKG records from the EKG domain.

In accordance with the present invention, it is also desirable to allow the PC-based acquisition instruments to have the ability to function as a local server while running real-time, but still have access to network resources. This may be accomplished by creating a local workstation user. This allows a user the ability to log on to the workstation even if no network is available. If a network is available, this user can be given whatever network access is deemed appropriate.

Because of the various system configurations supported in the present invention, the client and server subsystems are not independent. Therefore, these two subsystems are combined and referred to herein as "workstations". A workstation serves as the user's interface to the CIS application software. There are three CIS workstation types used in various combinations to address the three CIS system configurations in the preferred form of the present invention. Each of these workstation types are preferably a PC capable of running a Windows NT software program. The client workstation preferably runs the CIS client software and is used in both the small network and medium network models. The software is preferably Microsoft Windows NT workstation software. The server workstation is preferably used to run the network operating system and CIS database server software. Depending on the individual system configuration, the server workstation may also provide one or more network services including printer and modem sharing, digital scanner services, client data backup service, etc. This workstation is preferably used only in the medium network model and the software is preferably Microsoft Windows NT Server with a Microsoft SQL-Server.

The client/server workstation combines the functions of both a client and a server workstation on a single platform. Depending on the preferred system configuration, the client/server workstation may also provide one or more network services as described above for the server workstation. The client/server workstation is preferably used in the single client model and in the small network model. The software for the client/server workstation is preferably Microsoft Windows NT Server with a Microsoft SQL-Server. All CIS workstations (client and server) include commonly available components such as a keyboard port, a keyboard, a mouse port, mouse, serial ports, a parallel port and diskette drives.

The client workstation configuration is preferably the same for both the small and medium network configurations, except for the throughput of the network card. The client workstation preferably includes a Pentium 100 (or faster) processor with a 250 Watt minimum power supply and a cache RAM of about 256 Kbytes minimum and RAM which is at least 16 MB minimum and expandable to at least 64 MB, a Hard drive with 1 GB minimum, expandable to 4 GB and MTBF of at least 500,000 hours, a video controller with a PCI bus, 64-bit, 2 MB VRAM, capable of at least 256 colors at a resolution of 1280×1024 at 72 Hz refresh rate, a 17" color monitor capable of supporting 1280×1024 resolution at 72 Hz with a minimum of 256 colors; dot-pitch of 0.26 mm or less and Network I/F for Local clients with a 10Base-T Ethernet on the small network, or 100Base-T Ethernet on the medium network and Remote clients with 28.8 Kbits/sec, V.34 modem, or an ISDN I/F card at 128 kbps, or an X.25 I/F card.

The client/server workstation is preferably used in the single client and small network configurations. It is preferably a standard PC with a Pentium 100 (or faster) processor, a 250 Watt minimum power supply, a 512 Kbytes minimum of L2 cache RAM, a 32 MB RAM minimum, expandable to at least 128 MB, a FAST SCSI-2 hard drive, 4 GB minimum, expandable to at least 16 GB; MTBF of at least 500,000 hours, a video controller with a PCI bus, 64-bit, 2 MB VRAM, capable of at least 256 colors at a resolution of 1280×1024 at 72 Hz refresh rate, a 17" color monitor capable of supporting 1280×1024 resolution at 72 Hz with a minimum of 256 colors; dot-pitch of 0.26 mm or less, a Network I/F for the single-client model which is a 10Base-T Ethernet card or an optional 10/100Base-T, a CD-ROM which is at least double speed and a UPS which is capable of sustaining the client/server workstation for a minimum of 30 minutes.

The Server workstation is preferably a dedicated server (not also used as a client) for the medium network configuration. It is a high performance PC with a Dual Pentium 90 (or better) processor, a 300 Watts minimum power supply, 512 Kbytes per processor minimum L2 cache RAM, 64 MB ECC RAM, expandable to at least 256 Mb, a 5 GB FAST SCSI-2 hard drive, expandable to at least 20 GB; MTBF of at least 500,000 hours, standard SVGA video controller, capable of at least 256 colors at a resolution of 800×600 at 72 Hz refresh rate, a 15" color monitor capable of supporting 800×600 resolution at 72 Hz., a 100Base-T Ethernet card and RJ-45 connector, a CD-ROM which is at least double speed and an UPS capable of sustaining the server for a minimum of 30 minutes. Both the server and client/server workstations include a CD-ROM. This device preferably can be used to install third-party software (Windows NT, SQL-Server, Office, etc.), as well as the CIS application software. It may also be used as a system resource for on-line help for the third-party or CIS software.

Any system resource attached to a Server workstation, is preferably also available to all CIS Clients on the system. A resource attached to a client workstation may be local or global, but if it is global the client performance requirements shall not apply. One preferred peripheral device system is a laser printer with two paper cassette trays and at least 300×300 dpi. The printer may be attached as a node on the network or to a workstation. Additionally, a digital scanner and PC interface card are desired to provide the user with a means of integrating existing paper-based reports into the CIS system. The scanner preferably has a resolution of at least 300×300 dpi, and supports multiple sheet operation. The scanner may be attached as a node on the network or to a workstation. The Serial ports are preferably a standard feature on each workstation, but the serial interface may be expanded with the inclusion of intelligent I/O boards for a workstation or a network. An external, intelligent serial port box may also be attached as a node on the network or to a workstation and a V.34 fax/modem may be installed as part of a workstation (either internal or external) or attached as a node on the network. In the preferred form of the present invention only one modem is supported on a client workstation and multiple modems, if needed, may be installed on a server or on the network. A wand-type bar code reader with serial RS-232 interface and even more preferably, a bar code reader with OCR capabilities, is also a preferred peripheral device and it may be installed as part of a client workstation. An archive device is also preferably employed to allow long term storage of data which may be accessed by the system within the time-frame allowed by the system performance specifications. A backup device is also preferably employed to ensure the day to day integrity of CIS data.

As discussed briefly above and as discussed in more detail below, the software design of the present invention is preferably based on an object oriented software design to provide the present invention with the flexibility necessary to accommodate upgrades and scalability. The design philosophy is generally based on a three-tiered Donovan model which enables the CIS application to "plug and play" with different components for each of the three tiers while the system requirements change. This approach confines the modification impacts to a specific tier and therefore; increases the reusability of the other tiers. With this approach, the top tier provides a mechanism for the user to interact with the application. This top tier provides the invocation and navigation functionality of the system. Various interfaces communicate between the top tier and the second tier. The second tier preferably provides the business logic and decision making infrastructure for the system. This middle tier also provides the translations and controls between the top tier and bottom tier. Various other interfaces communicate between the second tier and the third tier. The third tier is somewhat protected from the user interactions with the top tier and provides the basic control, management and integrity services for the data supported by the application. The software of the CIS also preferably employs various industry standards for portability such as OLE and ODBC programming languages. The philosophy of the software design places a great deal of emphasis on identifying and designing the system based on the stable elements of the system, such as patient information, test procedures and users. The volatile design elements, such as operating system specific or DBMS related functions are isolated with a wrapper or interface so that the application may be readily moved to different operating systems or to accommodate software operational related changes. Additionally, common mechanisms or common protocols have also been designed for functions that have a common way of operating or communicating. For example, as discussed more fully below, the adoption of SCP+ as a communication standard for communication. This allows the CIS application software to use one protocol to communicate with all external acquisition devices or instruments and any necessary data translation is performed external to the core of the CIS. The benefit of this approach is that the CIS framework does not need to know the data format details of each acquisition instrument, and both the CIS and instrument specific software become self contained modules.

The design interfaces of the present invention are also designed to accommodate future add-ons without modifying the existing interfaces and the actual implementation of the service routines may be redesigned to reflect the changes. The software is also designed as a self contained, single minded and passive service provider so that the service provider stays idle until invoked by a caller, and then provides services without requiring specific knowledge about the caller. The only interaction between the caller and the service provider is through the pre-defined interfaces and this interaction is kept to a minimum.

A further advantage of this design approach is that the commonly shared data and functions are centralized so that duplicative functionality is minimized. The centralization is not related to the physical location of the data and functions, but relates more to the operational functionality of the data and functions. In the preferred form of this invention, only one implementation of a function exists within the application. This approach reduces the number of routines and files which need to be modified and updated and therefore, the software is more maintainable. Similarly, this approach uses and controls constrained resources wisely by eliminating unnecessary network data exchanges by keeping the data and processes lose to where the action occurs. This is particularly important for the database and network resources which are typically overburdened.

The CIS supports various system configurations, including a stand-alone configuration in which, the client and server run on the same hardware platform (workstation) and may or may not be a node on a larger network. In this stand alone configuration, the scope of the system is limited to the physical resources of the dedicated workstation, and any peripheral devices configured for use by the client or server as described more fully below. The CIS will also support a Networked, Isolated Database referred to herein as a small network. In this configuration, the server platform is a node on a network. Each properly configured virtual network node, including the server, may be allowed access to the server as a system client. In the small network configuration, the scope of the system is limited to the physical resources of all properly configured network nodes, and any peripheral devices configured for use by client or server applications on the nodes as described more fully below. Small networks preferably employ at least a 4 MB/sec. topology (or the equivalent) and allows no more than about twelve local and remote clients concurrently (use of the server as a client counts as one of the twelve clients).

The CIS also supports a system configuration referred to herein as a medium network. In this system configuration, as in the small network, the server platform is a node on a network. Each properly configured virtual network node, excluding the server, may be allowed access to the server as a system client. In this configuration, the scope of the system is limited to the physical resources of all properly configured network nodes, and any peripheral devices configured for use by client or server applications on the nodes as described more fully below. The medium networks preferably employ at least a 16 MB/sec. topology (or the equivalent) and allow no more than about fifty local and remote clients concurrently.

The CIS system software of the present invention preferably supports upgrades of stand-alone systems to small or medium network systems, and also support the upgrade of small network systems to medium network systems. Specifically, in the present CIS, all system requirements still apply following system upgrades, all data which is accessible to the server prior to system upgrade remains accessible to the server and the system configuration data for nodes configured prior to system upgrade are retained after the upgrade.

The CIS system functionally operates as one or more client applications attached to one database server at a time. In the preferred form of the present invention, the CIS system is a workstation based product. Requirements to support additional functionality provided by the CIS product are described more fully below. For example, the CIS product allows the user to select a record in the list using a bar-code scanner and if a bar-code scanner is used to select the record, the record is automatically opened for review. The CIS product also allows the user to enter patient data using the bar-code scanner so that fields represented by the bar code such as MRN and patient name would be automatically filled in. The CIS product also allows various communication paths, interface protocols, and operational scenarios to be supported by the workstation.

The preferred requirements for the CIS are described below. For example, the CIS system provides for transfer of records via serial ports (1200 baud and above), modem links (1200 baud and above), inter-network connections and floppy disk (such as via Nike-net). The CIS system also supports the communication protocols necessary for records transmitted in the Standard Communications Protocol (SCP) protocol, Records from commercially available instruments complying to various interface standards, records via CLM link protocol, records from devices supporting the Computer Link protocol and faxed and scanned data records.

As discussed more fully below, If the user has installed the optional Resting ECG Reports Application, the user is also able to perform a number of functions, including those described below, for all Resting ECG records in the CIS database. The optional Resting ECG Reports Application provides the user with report review, serial presentation report review, record editing, record abridgment, report distribution and notification, report printing and resting ECG report setup features. Also as discussed more fully below, if the user has installed the optional Stress ECG Reports Application, the user will be able to perform a number of functions, including those listed below, for all Stress ECG records in the CIS database. For example, the user will be able to perform report review, serial presentation report review, record editing, record abridgment, report distribution and notification, report printing and stress ECG report setup.

The CIS system also supports various faxing and printing capabilities as described below. To accommodate the needs of the three basic system configurations described briefly above, the system servers of the presently preferred embodiment provide and manage up to about twenty GigaBytes of addressable RAID 5 data storage, or the equivalent and support at least one mode of data transfer that will allow a Stress ECG Record transfer to complete in less than twenty minutes and which will also allow a Resting ECG Record transfer to complete in less than two minutes. The preferred CIS configuration also supports at least one mode of network data transfer that will allow a Stress ECG Record transfer to complete in less than twenty seconds and will allow a Resting ECG Record transfer to complete in less than two seconds. The preferred CIS system configurations further support at least one mode of data transfer via a floppy disk that will allow a Stress ECG Record transfer to complete in less than five minutes and will allow a Resting ECG Record to complete transfer in less than thirty seconds. The stand-alone system configuration is also preferably capable of executing parallel transfers of up to two data transfers simultaneously. The small network system configuration is preferably capable of executing up to about 25 data transfers simultaneously. The medium network system configuration is preferably capable of executing up to about 50 data transfers simultaneously.

In the preferred form of the present invention, the Resting ECG Reports and Stress ECG Reports are available to the customer as system options, and the CIS is designed to readily include additional system functions to be implemented on the CIS. These additional options include, an allow networked, integrated database option, touchscreen overlay, billing notification, CPT Coding and Management, Inventory Control, Scheduling, Advanced Database Query, HIS Interface Configuration, E-mail, Fax Polling, Merged Reports,Cath-lab Procedure Reports, Electrophysiology Reports, Imaging Reports, Holter Reports, Rehabilitation ECG Reports, Pulmonary Reports, Resting ECG Analysis, Advanced Scanned and Faxed Report Analysis, Tool Bar customization, Work Forwarding, Acronym Macros, Auto-Lead-Size Sensing and Outcomes Reporting.

Figure 9:
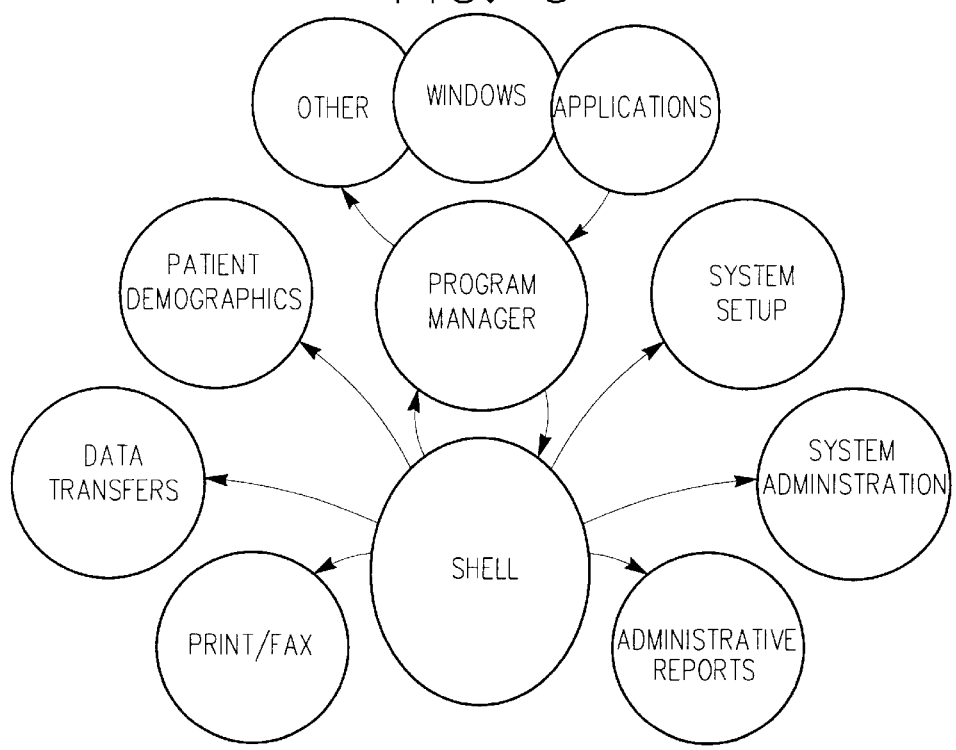
FIG. 9 is a diagrammatic view illustrating the preferred functional components of the workstation portion of the CIS of the present invention.

As mentioned briefly above, the CIS includes workstation systems that are made up of one or more PC-based workstations connected together, accessing one or more databases. Each workstation provides the user with a set of functions that will perform data processing, and in some cases data acquisition. Multiple functions can be open on a workstation at one time. Users at separate workstations are able to use the same functions and view the same data without interfering with each other (although only one user at a time will be able to edit a particular record). The workstation shell provides the basic platform from which all other workstation functions operate. Access to the shell is secured. The workstation shell essentially operates as a "Program Manager." Once properly logged onto the shell, the user has access to various standard features, such as viewing customized lists of patient/procedure records on the database, system setup, system administration, including user/group setup, backup, and archive, patient data and demographics entry and management, administrative reports generation and review and scheduled and on-demand transfer of patient and procedure records to/from other systems, including download of patient information records to instruments. In addition to the standard features, products based on the Workstation may add additional features, such as report generation and editing, data acquisition, and inventory. Functions such as data transfer may be performed in the background while the user is performing other tasks such as reviewing reports. FIG. 9 shows the interface between system functions within each workstation.

It is anticipated that workstation product use will vary. For instance, the hospital administrator will use a CIS workstation more frequently than a specialized workstation. The biomedical technician is a technically trained staff member, familiar with most details of medical instrumentation hardware and will typically be familiar with the principles of computer-based system operation. The clinical technicians or nurses are the typical operators of medical instrumentation. Their training varies widely, from assistants with a high school education to CCVTs or registered nurses. Their exposure to standard, current computer system operation will also vary widely. Physicians and/or physiologists are usually in attendance during medical procedures. They are well-educated staff members with exposure to current computer technology. Departmental administrators are rarely in attendance during medical procedures. They are also well educated and are well acquainted with current computer systems and operation. The hospital administrator typically has a four year or graduate degree and is usually familiar with current computer systems operation.

Figure 10:
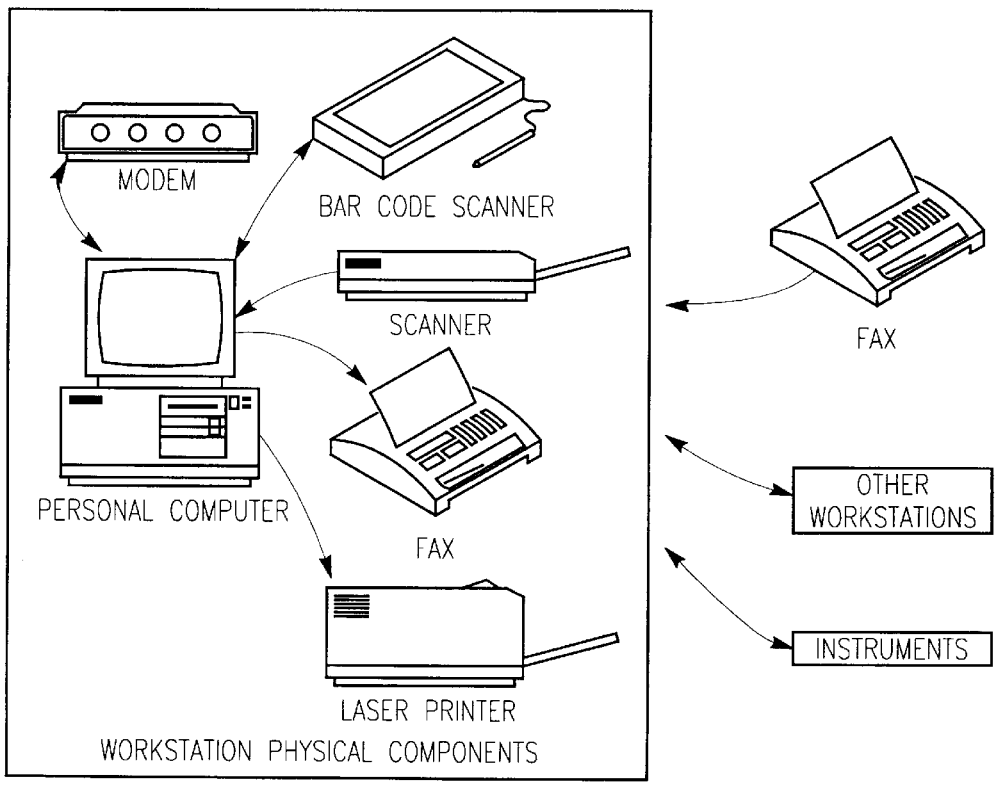
FIG. 10 is a diagrammatic view illustrating a single client or workstation functional configuration of the CIS system of the present invention.

The workstation systems are preferably capable of supporting the basic configurations briefly mentioned above. FIG. 10 shows the physical structure of a stand-alone workstation. In this product configuration, the system consists of a single workstation and a local database is maintained within the workstation. The system setup information for this configuration is maintained on the workstation. Communication with any other systems is preferably via the data transfer function described below.

Figure 11:
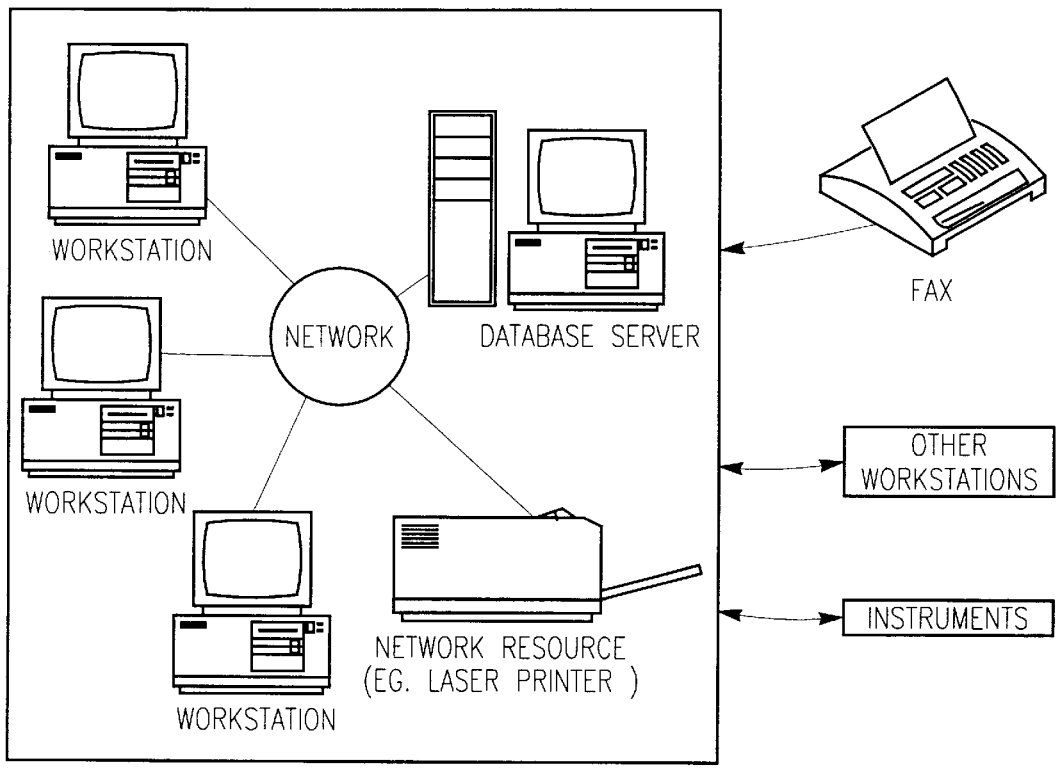
FIG. 11 is a diagrammatic view illustrating the small network or multiple workstation functional configuration of the CIS system of the present invention.

FIG. 11 shows the physical structure of workstations in a networked product configuration featuring an isolated database (small network). In this product configuration, the system preferably consists of one or more workstations and one or more database servers, networked. This configuration supports database server configurations which are dedicated database servers and/or database servers resident on client workstations. The system setup information for this configuration is preferably maintained in a single location on the network and therefore all workstations on the network use the same system setup regardless of which database server they are attached to. In a multi-database environment, such as the medium network configuration shown in FIG. 12, the user may view the list of databases and query any of the databases from any workstation on the network.

In the present invention, database queries associated with viewing lists of patient/procedure records may operate on only a single database at a time, and database queries associated with administrative reports are able to operate on all databases on the network. The results of cross database queries are typically reconciled in this configuration. For instance, if 30 patients are stored on database A and 50 patients are stored on database B, but seven of those entries represent the same patient (seen at both hospitals), a query requesting the number of patients seen would return 80, even though only 73 were actually seen. Finally, the multi-database user is preferably able to copy data from one database to another easily (such as using "drag and drop") and communication with any other systems not connected to the network shall be via the data transfer function described below. Common network resources will typically include optional printers, fax routers, modem routers, scanners, etc.

The physical structure of the workstations of the present invention in a networked product configuration featuring integrated database (medium network) is the same as that for isolated databases (small network). In the medium network product configuration, the CIS consists of one or more workstations and two or more database servers, networked. Dedicated database servers and/or database servers resident on client workstations are supported. The system setup information for this configuration is maintained in a single location on the network and therefore all workstations on the network use the same system setup regardless of which database server they are attached to. In a multi-database environment as contemplated by this configuration, the user is able to configure the presentation to view the data as a single logical database or use separately visible databases. The user is also able to query any of the databases and the queries are operable on multiple databases at a time. the user may also copy data from one database to another via "drag and drop". In this configuration, communication with any other systems not connected to the network is via the data transfer function described below.

Access to the CIS may occur via the initiation of the workstation application from the program manager (or its equivalent) on a local client workstation. The user may also initiate the workstation application from the program manager (or its equivalent) on a remote client workstation. The system administrator may also access the database server and third-party software packages are able to access the database via mechanisms supplied by the database. All access to the system is secured so that a valid user name and password is required. The system provides security to ensure that data is accessed only by authorized users. The system administrator may setup a default user to support automatic logins and an error will logged in the event log for each failed login attempt. The system administrator is able to select a maximum number of allowed login retries and if the number of consecutive failed user login attempts exceeds the maximum number of login retries, logins shall be suspended at that workstation for ten minutes. Once the user has gained access to the workstation application via one of these methods, the workstation shell will allow the user to access the functionality described below as well as product specific functionality delineated in the appropriate product specification. Finally, only one local client is allowed to run on each system node.

The system supports both background and foreground processing. Background processing (such as scheduled record transfer or administrative report generation) is allowed to proceed as required whenever a database server is active and does not require the presence of any logged in users. Foreground processing occurs in response to user commands from an active workstation. All client applications running on the system are able to simultaneously execute the same client functions subject to the user privilege levels, administrative user restrictions, and data integrity requirements as described below.

Only one client at a time is preferably allowed to edit an element of the database. Other clients will not be prevented from viewing data being edited by another client, but their view of the data will indicate that the data is locked for editing. The system will also not allow data in use by multiple clients to be deleted. The system will also preferably prevent loss or corruption of data due to system crashes or power failures. The workstation shell provides the user access to the system functions described below.

The user is able to view lists of the patient/procedure records contained on the database and is able to use standard and user-customized list filters to control what information is displayed. Standard filters include, all patients, all procedures, all conflicting procedures, deleted records and received scans/faxes. The user is also able to control the presentation of the list (column content, column order, and sort order) by sorting the list and printing the list. The user may also select records in the list and initiate their review (the procedure report functional specifications provide the requirements for review) using the keyboard or a mouse. The user may initiate creation of a new record and associate faxed/scanned records with new or existing patients.

With the present system, the user is able to access a broad range of administrative functions from the workstation shell, depending on the user's privilege level. These administrative functions include posting system messages, disabling and enabling logins, viewing logged-in system users and group and user setup, such as privileges to change passwords, perform event log management and system backup/archive.

The user is also able to access a broad range of system setup functions from the workstation shell. The functions listed below may be available to the user, depending on the user's privilege level include identification of default point-of-contact for system-recognized users (e.g., entry of a physician's pager number), data format setup, including country code, date and time format, units of measure, name format selection, and time zone identification, institution configuration setup, including site list management, fiscal calendars, department list management, location list management, and technician list management, list management, such as reviewing/editing the system lists, including the physician list, race list, comments list, and procedures list.

Various communication paths, interface protocols, and operational scenarios are provided by the system for transferring patient information and procedure records to/from the Workstations. The system supports record transmission and receipt for on-demand record transmission, including target selection, transfer timing, and record selection, requested and unsolicited record receipt from permitted sources and scheduled record transmission management, including target selection and transfer timing. The system also provides transfer status information to the user on request.

The user may also review, edit, and print the current patient demographic information associated with a new or existing patient. If the user has installed one or more of the optional procedure reports applications, the system will provide the user with the means to produce formatted resource utilization analysis reports, including such information as the volume of records handled by the institution, department, or physician, the volume of records overread by specific physicians and the volume of records produced internal and external to the institution. Specifically, the user will be able to perform report review, serial presentation report review, report editing, report scheduling, report distribution, report printing, setup of multiple report formats and automatic report scheduling.

The system will always allow a logged-in user access to the print and/or fax function to support the printing requirements of the various functional specifications discussed more fully below. The contents of printouts will vary depending on the active system function and appropriate privileges as may be required. For system functions where printing is allowed, the user will be able to print, fax or print-preview the selected data and specify a time and target resource for delayed printing and faxing. Delayed or background printing and faxing does not require interaction with the user. Context-sensitive on-line help related to the currently available functions are available to the user. Help information available to the user is correlated to the structure and level of detail found in the product Operator's Manual.

The system response time to user functions requiring access to the system database is preferably less than three seconds, and system response time to user functions not requiring access to the system database are preferably less than about 500 ms. The preferred system requirements for system response time to user functions do not apply while system backup or archive operations are in process and do not apply to workstations engaged in data transfer operations. The preferred requirements for system response time to user functions also do not apply to a specific workstation if minimum memory availability requirements are not met on that workstation. On a Hewlett-Packard LaserJet IIIsi brand printer, text-only documents preferably print at a minimum rate of 15 pages per minute, and mixed text and graphics documents will print at a minimum rate of four pages per minute. The mixed text and waveform documents also print at a minimum rate of three pages per minute, and the user is able to establish priority queues for system printers. Performance requirements for printing preferably only apply to top-priority queues. These requirements do not apply while system backup, archive or data transfer operations are in process or if minimum memory availability requirements cannot be met.

In the preferred form of the present invention, the workstation system clients and servers include a minimum amount of RAM and hard disk storage to operate properly. The specific preferred requirements for memory availability are determined as part of the overall system architecture. If memory availability requirements cannot be met, the system preferably notifies the user that system performance will be degraded if memory is not made available. The system software is developed as a standard commercially available WINDOWS software type application, and the system complies to this type of user interface standards. The system also provides the user with access to other standard applications and includes standard clipboard type cut/copy/paste functionality which is supported for editing all reports. An "Undo" function is also supported for at least the most recent editing action since the last save performed on the record. The workstation design also supports both full menus and short menus, and specific products are able to restrict presentation to full menu only. When more document windows are open concurrently than can be listed in the numbered list under the standard menu, an alternate display method is provided to allow the user to select from open windows. The user is also able to configure all text searches and comparisons performed by non-third-party software to be case-insensitive or case-sensitive. The workstation shell includes a tool bar containing icons for commonly used functions. Other functions working with the shell (such as report management functions) shall have the option of adding additional toolbars or toolbar icons. It is also anticipated that the user may edit multiple records at a time (not required to save before moving to next record), and the system is then able to recover changes lost due to unexpected shutdowns. The system software or added software options may be accomplished through the use of auto-install programs, and all system clients and servers shall be upgradable via the system network. Installation of workstation software and options is preferably accomplished through the use of auto-install programs described more fully below.

Figure 12:
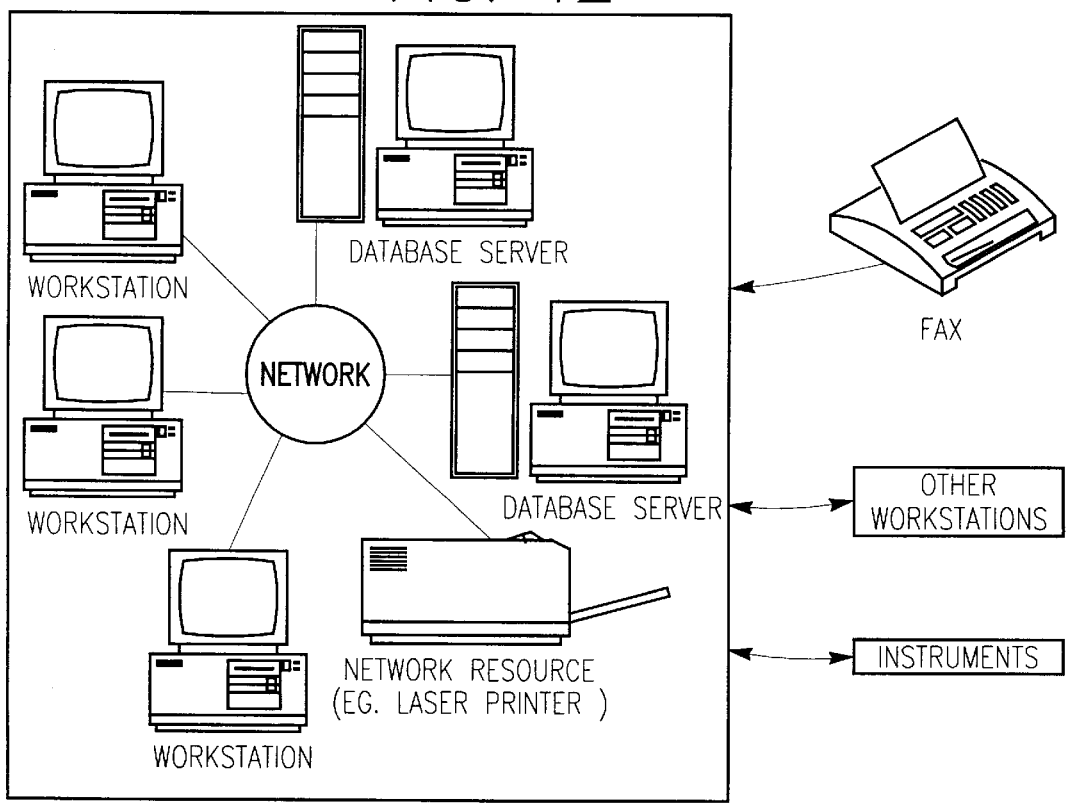
FIG. 12 is a diagrammatic view illustrating the medium network or multiple server functional configuration of the CIS system of the present invention.
Figure 13:
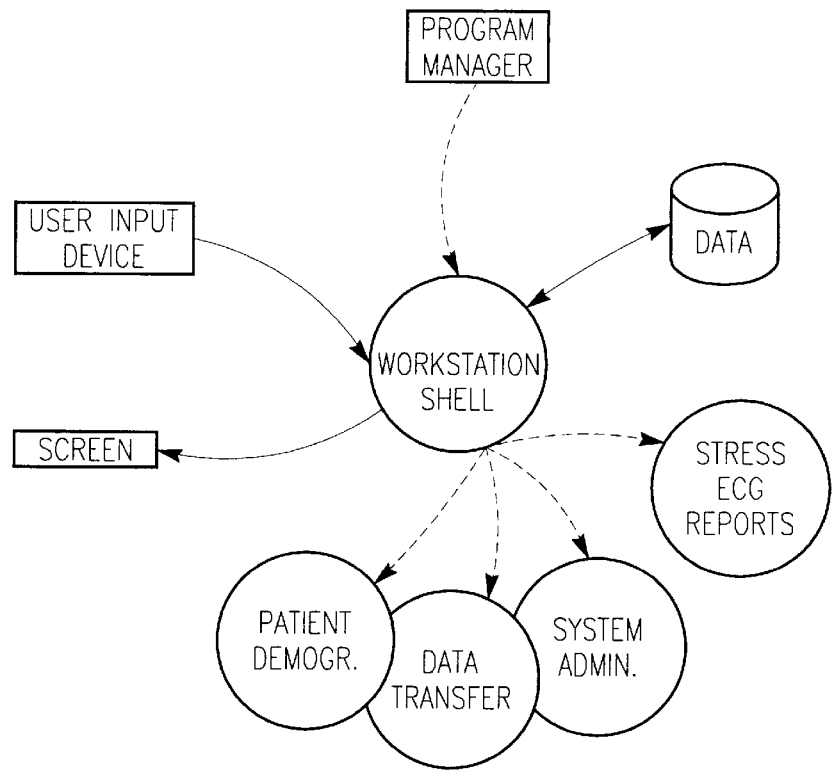
FIG. 13 is a diagrammatic view illustrating the workstation shell functions and the other functional components in the context of the shell portion of the present inventions.

In the preferred form of the present invention, workstation systems are made up of one or more PC-based workstations connected together accessing one or more databases as generally illustrated in FIGS. 10–12. Each workstation forms the basic functionality of the present invention and will provide the user with a set of functions that will perform data processing and, in some cases, data acquisition. Users at separate workstations are able to use the same functions and view the same data simultaneously without interfering with each other. The shell function of the present invention provides the basic platform from which all other workstation functions operate. The shell provides basic system functionality (including viewing lists of patient and procedure records and launching appropriate functions based on user commands). FIG. 13 shows the interface between the shell function and the other functions of the present invention. Upon startup of the application, the CIS logo and product copyright are displayed. The shell function determines which workstation functional entities are present and available, and diagnostics are performed on each available functional entity to determine operability. If any functional entity fails the diagnostics, the user is notified of the failure. If any functional entity fails the diagnostics, the user may be prompted to exit to the application or continue with limited functionality. The database contains a patient folder for each unique patient. Each patient folder includes a current demographics record which represents the most recent patient demographics information for the patient and zero or more procedure records associated with the patient. Each procedure record contains demographic data representing the patient's information at the time the procedure occurred.

The user is able to view a variety of lists of patient/procedure records resident on the database. The user may view various types of lists, including the patient list which consists of a list of all patient folders that meet the filter criteria, the procedure list which consists of a list of all procedures that meet the filter criteria and the patient folder which consists of a list of all of a specific patient's procedures that meet the filter criteria. Each list is associated with a filter allowing the user to limit what database entries will be included in the list, and how the data will be presented. The user is also able to display the lists by selecting a list filter or by using the "find" control. User access to specific records may be limited by the system administrator by selecting various privilege levels which function to limit access to records by filtering the availability to data and records. For example, if user JOE is only allowed to access group filters, and the only filters available for his group are RESTING records with attending physician of DR. CARL or DR. DRAB, other patient records are protected from JOE.

The user may display an initial list of patient information or records by selecting from a list of filters. The list of filters available for selection varies based on what filters have been created and what the user has access to. A patient filter, procedure filters, conflicting records filter, scanned or faxed images filter and deleted records filter are initially provided with the system. The patient filter list includes all patients, without displaying any of the associated procedures. The procedure filters include a list of all procedures on the database, a procedure list for each available procedure and a list for unconfirmed reports for specific procedure. The conflicting records filter includes all records that have been marked as conflicting. The faxed and/or scanned images filter includes all faxed/scanned images that have not been associated with a patient/procedure. The deleted records filter includes all records marked for deletion. Although the user is not able to change the filter criteria for these lists, the user is able to change the presentation of the lists.

The user of the CIS system is able to create a list by searching for records matching a specified criteria. For example, the user may choose the search fields for patient last name, MRN, social security number, or billing number. The user may also choose a search filter from the list of patient filters described above and the user is able to enter a string of characters to be matched. At the user's command, the system searches for any records in the database that meet the filter criteria and contain a value in the specified field that wholly or partially matches the input string. If multiple matching records are found, a patient list is displayed showing all patient folders containing matching records. If only a single matching record is found, the patient folder containing the record will be displayed with the matching record(s) highlighted. If no matching records are found, the user is so notified.

The following preferred system requirements identify the preferred method of how a list will be displayed. Entries in a patient list will represent patient folders of patients in the database meeting the list criteria. Entries in a procedure list will represent procedure records in the database meeting the list criteria. Patient folder lists preferably consist of the specified patient's current demographics record and each of the patient's procedure records meeting the list criteria. The patient's name and MRN are displayed in the title bar of the window and because patient folders always originate from patient lists, the filter criteria is defined in the patient list filters. The conflicting records list displays a list of all records that are currently marked as conflicting. The faxed and/or scanned images list displays a list of all images stored on the system that have not been assigned to a patient/procedure. This list displays the date/time image was received and image file size for each image. The deleted records list displays a list of all records that are currently marked for deletion. The column setup associated with the selected filter will dictate what data is displayed for each entry. The displayed list is initially sorted based on the field in the left most column in the order (ascending/descending) selected in the filter. If a record has been marked as conflicting (the system was unable to determine whether the record matched another record), the list will indicate the conflict via a visual cue. FIGS. 14A-C illustrate examples of some of the possible list views with the present invention.

The user can edit existing filters or create a new filter. A filter is defined by initially selecting a list type, selecting the criteria used to determine which entries will be included, selecting which columns of data will be included in the view and activating the filter (which may or may not include saving). List filters are defined by selecting either the patient list or procedure list. The filter criteria is selected by selecting qualifying fields to selectively view a subset of the entries on the database. In the present system, the user may only change the filter criteria for the patient, procedure, and patient folder lists. The user may not change the criteria for the conflicting records, faxed and/or scanned images, and deleted records lists. Although it is obvious why both patient and procedure data is used in procedure lists, it is not so obvious why procedure data is used in patient lists. The reason is twofold: 1) the user may want to view "All patients with unconfirmed rest records;" and 2) the user may open a patient folder (containing procedure records) from the patient list; and, therefore, the user must have filter criteria for the patient folder.

In the preferred form of the system, the fields preferably default to "any value" criteria and the user may then narrow down the criteria for the fields of interest. If the field is a text field, the user may enter a string of characters to be matched. If the field is a list field, the user is able to select one or more entries from the appropriate system list. For example, the user may use the field "Attending Physician" as a criterion and select "Dr. Jones" and "Dr. Hall" from the physician list as legal matches.

If the field is a date field, the user may select a date range from the custom choice where the user provides a start date and an end date, earliest entries to current date, year to date (calendar or fiscal), quarter to date (calendar or fiscal), month to date (calendar or fiscal), week to date (calendar or fiscal), previous year (calendar or fiscal), previous quarter (calendar or fiscal), previous month (calendar or fiscal), previous week (calendar or fiscal) or previous day.

The column setup for each patient or procedure list determines what data will be displayed for each entry and in what order the data will be displayed. For patient list filters the user is able to select the column data for the patient folders associated with the patient list.

The user may select one or more of the following fields for display of patient column data. The column data may be selected according to patient last name, patient first name, patient middle initial, patient medical record number (MRN), patient status (e.g., In-patient, deceased, etc.), patient birth date, patient gender, patient billing number, social security number (standard nine digits plus one character extra) and record status (e.g., deleted, archived, conflicting, etc.). The user may select one or more of the following fields for display in procedure lists. These fields include procedure type (e.g., Resting, Stress, etc.), procedure date, procedure time, record priority (e.g., normal/STAT), procedure status (e.g., confirmed/unconfirmed), procedure diagnosis (e.g., normal/abnormal), acquiring site, attending physician, referring physician, ordering physician, overreading physician, technician or procedure record size.

The user is able to determine the order of display of the selected fields and the first column is designated as the initial sort key. The user is able to choose ascending or descending sort. The user may also adjust the column width for each selected field.

Once the user has completed the setup of the filter, the user may activate it, resulting in the creation of a list meeting the filter criteria. Prior to activation of the filter, the user may save the filter so that it will appear in the filter list. If the user does not save the filter, it shall be lost once the user closes the window. If the user chooses to save the filter, the user is required to select the access level for the new filter. One access lead is private which is visible only to the User, and only up to five private filters are preferably supported per user. The user always has the privilege to access private filters. Another possible access level is the group access level. This access level is visible only to users within the user's group. If the user belongs to multiple groups, the function will prompt the user to select which group(s) will have access. Up to ten group filters are preferably supported per group. Global is another type of access level. With this type of access level, the filter is visible to all users on the system, and up to ten global filters are preferably supported by the present system. The user will also be required to assign the filter a name. If the name is not unique at the selected access level, the user shall be required to choose a new name or overwrite the existing filter.

Users with appropriate privilege levels, such as system administrators, are able to delete any of the filters to which they have access, regardless of ownership, with the exception of the conflicting records filter, the faxed and/or scanned images filter or the deleted records filter. The user is able to change which field the list is sorted on to override the initial setting (left-most column) and may choose one of the fields included in the display of the list. This type of selection will not change the display order. The user shall be able to enter text related to the left-most column to search the list. As text is entered, the display window is updated so as to place the first matching or partial matching entry in the window, highlighted. If a character is entered which does not match any entry, the display window will remain unchanged, the user will be notified, and that character won't be accepted.

The shell function of the workstation product allows the user to create a new patient folder by adding a new current demographics record to the database. For each type of procedure function available on the system, the shell function will allow the user to add a new procedure record to the database. The user is required to select an existing patient folder to associate with the new record or indicate that the procedure is for a new patient.

The user may select one or more entries in the list, and the system of the present invention supports both contiguous and disjoint selections. Once one or more entries are selected, the user is able to initiate the actions described below. The user shall be able to initiate printing of the selected entry(s). If the entry represents a current demographics record, the printing without viewing requirements of the patient demographics function will apply. If the entry represents a procedure record, the printing without viewing requirements in the applicable procedure reports function will apply. If the entry represents a patient folder, the patient summary report containing the current patient address, the patient information fields enabled for viewing in the list filter and each of the patient's procedures that meet the filter criteria, are printed as defined in the filter's column setup with one procedure per line. If the entry represents an image, the user may print the image as a BLOb (Binary Large Object). If the image has been assigned to a patient/procedure, the attached information will also be printed.

The user may initiate review of the selected entry(s) but may not edit archived entries. If the entry represents a patient folder, the patient folder list will be displayed. If the entry represents an image that has been assigned to a patient/procedure the user may view information attached to the image as well as the image itself (viewed as a BLOb), edit the procedure type, patient folder association, site, and comment attached to the image and confirm the report represented by the image. If the entry represents an unassigned image (faxed or scanned into the system), the user may view the image as a BLOb or assign the image to a patient/procedure by editing the information related to the procedure type of image, the patient folder to which the image belongs, the site the image was received from, the comments and confirmation status of the image. This information is then stored with the image and the image will disappear from the faxed and/or scanned image list. The image will then appear in any list views in which it meets the filter criteria.

A record is determined to be conflicting if the system cannot clearly determine which patient folder the record belongs. The criteria for how a record is determined to be conflicting is described more fully below. If the entry is a record marked as conflicting, the user may request conflict resolution support for the record. The following information is preferably displayed for the selected record and for each record which conflicts with the record. This information includes patient MRN, patient name, date of birth, gender, social security number, site from which the record was received, location from which the record was received, date the record was received or last edited and the nature of conflict (same MRN/different name, same MRN and name/different gender, etc.).

The user is also allowed to perform editing of the displayed fields of the conflicting record to resolve the conflict, to accept the conflicting record as a new patient if the record's MRN is unique within the MRN model for the record's site, to accept the conflicting record as an alias for the patient with which it conflicts if the MRN/MRN model and date of birth match, but name or gender are different, or if the MRN model is different (same patient, different hospital using different MRN model) to resolve record conflicts. If the conflict is resolved (and no new conflict is generated), the conflict marking is removed from the record. The user may mark the priority of a record by marking a procedure record as STAT or Normal. STAT indicates that a record needs immediate attention. The user may delete selected entries but is unable to delete records that are currently being viewed or edited by another user. The user is also required to verify deletions of records. If the selected entry is a patient folder or a current demographics record, all associated procedure records will also be deleted. The user may not be allowed to delete archived entries. As a safeguard, it is important to note that records are not really deleted from the database until an authorized user instigates a purge. Before the purge is instigated records are only marked as deleted, which removes them from any lists that don't include deleted records.

If the selected entry has a status of "deleted," the user may be able to restore the selected record(s) to the database (removing the deleted status) or purge the selected record(s) from the database. Once a record has been purged, it cannot be recovered. The shell function specifically requires user verification of the purge function.

The user is able to print the list currently being viewed as described below. If the list being viewed represents a patient folder, the user may print the patient summary report.

In the preferred form of the present system, the functions available to the user via the menus and toolbar will be dynamically altered to reflect which workstation functions are present. The user is able to access the available functions (system setup, administrative reports, etc.) if the user's group/user rights permit access to that function. A selected function will automatically transition to visible mode and become the active function.

The procedure functions provide the ability to "mask" reports by aliasing the patient MRN and obscuring the patient name and billing number and the user is able to enter an aliased MRN. The function preferably responds with the original MRN and patient name. If there has been no activity on the client for more than the time specified by the system administrator, the workstation shall automatically be secured. The user will be able to return to processing by reentering the password. Upon entry of the valid password, the user will be returned to the previous screen.

The user will be able to exit the application. Unanticipated shutdowns (e.g., due to power loss) may also occur. Under either of these conditions, a controlled shutdown is performed if possible. If the shutdown affects system services and other clients on the system are currently operational, the user will be notified and not allowed to exit. If the shutdown is user initiated and any records or setup fields are currently open for editing, the user will be required to save or abandon the changes or cancel the shutdown. If the user chooses to save changes, the changes are saved and the record closed. If the user chooses to abandon changes, the record will be closed. If the user chooses to cancel the shutdown, the shell function may return to the previous shell screen, canceling the exit command. If the shutdown is not user initiated (e.g., power loss), changes to records or setup fields may be lost. Additionally, all visible functions shall be made non-visible, and all client functions on the workstation shall be closed. The application will also be closed, returning the user to the Program Manager (or its equivalent).

The user of the system is able to access the shell function via application initiation wherein the application is initiated. Upon successful initialization, the shell proceeds to the active state, allowing the user access to the system functionality. The shell function will also exhibit the state behavior indicated by the idle state which is the initial state for the application. Once the user has logged onto the workstation, the application waits to be opened. During the active state, user can access the application functions via the shell component of the workstation product. The requirements specified below apply to the active state of the shell function.

Figure 15:
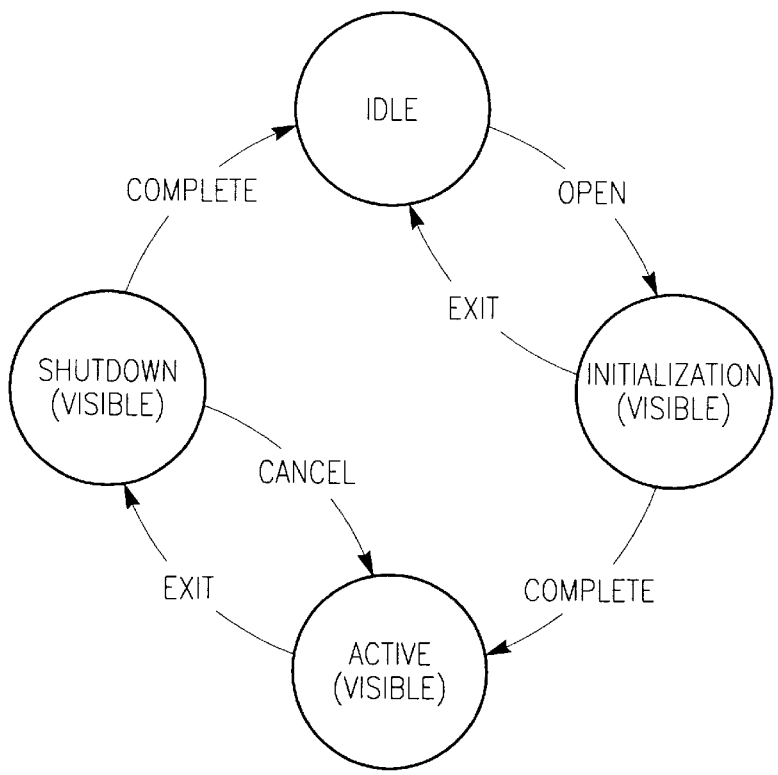
FIG. 15 is a diagrammatic view illustrating the shell transition states upon initiation of the application.

The shell function may be entered in response to the user initiating the application. FIG. 15 shows the state transition diagram for this scenario. As shown, once the user opens the application, the function transfers from the idle state to the initialization state in visible mode. Upon entering the initialization state, the shell function preferably remains in the initialization state for a minimum of three seconds (required for display of copyright notice). If the diagnostics pass, the function transits to the active state. If the diagnostics fail, the user may choose to continue with limited functionality, and the function will transit to the active state. If the user chooses to exit the function, the system will transit to the idle state. Upon entering the active state, a status window will be displayed to the user indicating system notifications which have occurred since the user's last login. If a default display has been selected by the user for initial display, the shell function will trigger the appropriate function. If the user exits the application, the function will transit to the shutdown state. If the user chooses to cancel the shutdown when being prompted to save or discard changes to records, the function will transit back to the active state.

In addition to the above described features, it is anticipated that the Shell function may also incorporate an "Encounter" or grouping concept (where a single encounter may contain several different types of procedures). Additionally, a feature such as Soundex may be incorporated to the list search capabilities so that user may enter the approximate spelling of the name and the function will show close matches. A further feature such as ordering Physician information and procedure coding may be added to the list views options, and optical character recognition (OCR) features for faxed or scanned images may be incorporated into the CIS product. The shell function may also preferably determine if any data recovery activities need to be performed (because an unexpected termination of the application occurred, either through remote shutdown by the system administrator or through a crash or power down of the workstation). If data does need to be recovered, each record that was open for edit will be reviewed to determine if a database record matches the recovered record, and the user will be notified. If the records do not match and the database record has been edited since the termination, the user will be notified and the record from the database shall be opened in edit mode. Additionally, the recovered record may be opened in view mode, and the display will clearly show that this is a recovered copy only. The user may then manually compare the two versions and make the desired changes to the database record. If the records do not match and the database record has not been edited since the termination, the database record will be locked for editing and the changes retrieved. The user will then be notified of the recovery of the record. The list entries will also be sorted based on the column order and the left-most column will represent the primary sort key, the next column to the right will represent the secondary sort key, and so on. Less significant sort keys represent sorts done "within" the previous column, without disturbing the order of the more significant sorts. Patient name will preferably always be sorted based on last name, first name, then middle name. Sort depth of the present embodiment preferably does not exceed five levels. Use of the search function will also not result in deselection of current selections. If a patient information record or procedure record is currently being edited by another user, the list will preferably indicate via a visual cue that the record is being edited. A preferred form of the present invention will also include an automatic screen secure mechanism so that, if a different user returns, the user will be required to logout and login. The present invention also preferably allows the user to set duplicate procedure records to conflicting status, and the user will be allowed to replace the current procedure record with the conflicting record, change the association of the conflicting record to a different patient, or delete the conflicting record.

Figure 16:
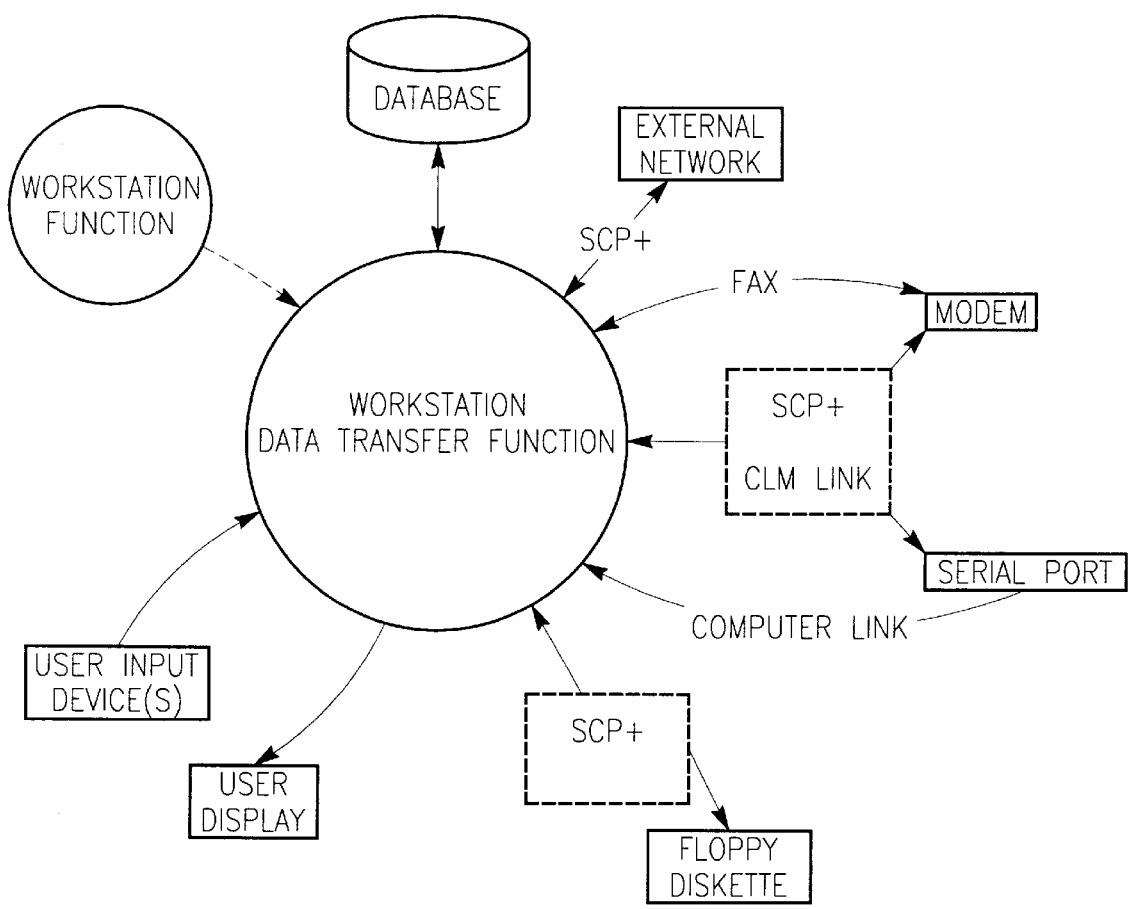
FIG. 16 is a diagrammatic view functionally illustrating the various data transfer functions of the present invention.

An integral component of the preferred form of the present invention relates to the transfer of data between the workstation component of the CIS and various physiological signal acquisition devices or instruments. The functional components for data transfer in the CIS includes the communication paths, interface protocols and operational scenarios which are supported for transferring patient information and procedure records to/from a workstation in accordance with the present invention. FIG. 16 shows the interface between the data transfer function and other devices. The data transfer function of the present invention supports several physical pathways for communication with external devices and instruments. For example, the data transfer may occur via RS-232 serial ports, RJ-11 interfaces, inter-network interfaces, floppy disk interfaces, and an SCSI interface. An RS-232 serial port is supported for the serial transfer of records. An RJ-11 interface is supported for modem and fax transfer of records. Record transfer between other compatible network systems will be supported. Record transfers to or from 5¼" and/or 3½" floppy diskettes (in DOS format) is supported. A SCSI interface is also supported for receipt of digital images of records from external scanners.

The data transfer function of the present invention includes use of the SCP (Standard Communications Protocol) which defines a protocol for transferring 12-lead ECG test records. This protocol allows for proprietary extensions for other record types as used in the present invention. The term "SCP+" denotes the extended SCP protocol which supports both Resting and Stress records. The SCP+ protocol is supported for communication with various physiological signal acquisition instruments along the modem, serial, inter-network and floppy disk transmission and receipt communication paths.

The present invention also supports the transmission and receipt of data transfer from "open" and "closed" physiological signal acquisition instruments along the modem and serial communication paths. In certain formats, data will simply be stored as a "BLOb." Another communication protocol supported by the present invention is the CLM link (Communications Link Manager). This is a protocol which defines the serial transfer of data for Stress ECG test records. In the present invention, the CLM protocol supports modem and serial communication paths for the transmission and receipt of data. In the preferred embodiment of the present invention, only data received in the CLM format may be transmitted in the CLM format. Computer Link is another protocol defined and supported for the serial transfer of Stress ECG test records. This protocol requires a real-time response, and the test record is transmitted as the Exercise Stress Test progresses. The Computer Link protocol is preferably supported for the receipt of data via modem and serial communication paths. The present invention also supports the diskette transfer of a Stress procedure record from a currently available stress testing product marketed by Quinton Instrument Company of Bothell, Wash., U.S.A., as the Q5000. Only unabridged data received in the Q5000 format may be transmitted and received in the Q5000 diskette format. The present invention also supports the diskette transfer of a Stress procedure record from a currently available stress testing product marketed by Quinton Instrument Company of Bothell, Wash., U.S.A., as the Q4500. The transfer of a Q4500 Stress procedure record is supported for the diskette transfer and receipt of data. In the preferred embodiment, only unabridged data received in the Q4500 format may be transmitted and received in the Q4500 diskette format. Data is also supported and accepted in a standard FAX format for the transmission and receipt of the data in the modem, inter-net and floppy disk communications paths. Additionally, data is also supported and accepted in a scanned format for the serial receipt and inter-net and floppy disk transmission and receipt communication paths.

The user of the present invention is allowed to enter up to about 1000 possible system connections. For each entry in the list, the user is queried for the connection name, type of connection from a list of protocols supported and the method of connecting from a list of modem and com port resources. If the method of connecting is a modem resource, the fields for country code, area code and phone number will apply. The user may also modify delete or print entries in the list.

As described briefly above, patient information records and procedure records may be transmitted to other instruments or networks. When a record is transmitted, the appropriate communication protocol to be used is determined from the Connections List. The data transfer function translates the record to the appropriate format for the transfer and sends the translated record, using retries or other error-correcting techniques as appropriate.

With the system of the present invention, patient information records and procedure records may also be received from other instruments or networks. When a record is received, the communication protocol to be used is be determined from the connections list. The data transfer function receives the record, using retries or other error correcting techniques as appropriate and verifies the integrity of the record. If no errors are detected, the data transfer function translates the record to the system database format and the data transfer function initiates the appropriate record workflow actions. If the device transferring the record requests a serial record transfer, the data transfer function transfers the most recent record (if any) associated with the same patient as the received record.

The system of the present invention also allows the user to transfer record(s) on request. This may be accomplished by target selection where the user chooses a source (for reception) or destination (for transmission) location from the connection list or may manually enter a source/destination connection. This may also be accomplished by transfer timing where the user specifies that the transfer is initiated immediately or deferred to some later time. If the transmission is deferred, the user is requested to select a day of the week and a time of day for the transfer, and the transfer is scheduled for the requested time and day. If the transmission is not deferred, the transfer is initiated immediately in background mode if the resource is available; otherwise, the transfer is queued. The user may also perform a record transfer based on record selection with certain devices or protocols that support it. In the record receipt situation, a list of the records available on the target device will be obtained and presented to the user. The user may then select record(s) from this list for transfer from the device. The user may also transfer records selected in the patient list or procedure list to an external device.

With the present invention, a transfer request from an external device may be received at any time. Only requests to receive data into the system are presently supported, and unsolicited requests to transmit data out of the system are not presently supported. When an unsolicited request to transfer data into the system is received, the data transfer function will attempt to perform the transfer. A record transfer schedule is used in the system as a user-defined timetable for a periodic, recurring, automatic transfer of selected record types. In this system, the user may schedule up to 100 different transfers per system. For each transfer schedule, the user is queried for the name, record type, source or destination, direction, period and time of day. The name is required to be unique for the schedule and up to 24 characters. The user is allowed to select patient records or any installed procedure record type for the scheduled transfer. The user is allowed to select the source or destination for the record transfer from the Connection list. If feasible, the list should be further qualified to offer only those locations which are appropriate for the type of transfer selected. The user shall be able to select whether the transfer is to send, receive or both. If the direction is send, the user is queried for the record status and/or patient status. The user is allowed to establish the desired time frame for the transfer, such as annually, quarterly, monthly, calendar date, as last day of month, 1st, 2nd, 3rd or 4th, and by the day of the week (e.g., the first Tuesday of each month), weekly or daily. The user is further requested to select the time of day (hour/minute) at which the scheduled transfer is to be initiated. The user may modify, delete or print existing transfer schedules. The data transfer function initiates the scheduled transfers as described above at the scheduled times.

The user may review the status of scheduled, in-progress and completed transfers by selecting any connection from the connection list. The system will respond to the inquiry by identifying the records which have been queued for transfer, but not yet initiated, the record currently being transferred, and some indication regarding the current status of the transfer and a list of transfers that have occurred and some indication of their completion status (successful, error, cancelled). This view is dynamic; as a transfers progress, the view will be updated to reflect the current disposition of the transfers for the chosen resource. The user is able to select a transfer in the list, so that if the selection is a queued transfer, the user shall be able to cancel it. If the selection is an in-progress transfer, the user is able to terminate it. If the selection is a transfer that did not complete successfully, the user may re-initiate it. Each of the above actions requires user verification.

The user may access the data transfer function by performing an on-demand record transmission, performing an on-demand record reception, performing an unsolicited record reception, performing a scheduled record transfer, schedule transfers or by viewing the status of transfers. The idle state is the initial state for the data transfer function. The function is not visible to the user and awaits external initiation. In the initiate transfer state, a transfer is begun, if the resource is available, or queued if the resource is busy. In the select target state, a source or destination is selected for a transfer. In the select record(s) state, the record(s) to receive from an external device is selected. In the select transfer timing state, the user elects to initiate a transfer immediately or to defer the transfer. In the review transfer status state, the status of past, current and scheduled transfers are displayed for a selected resource. The user may also terminate scheduled/in-progress transfers and restart failed transfers. In the schedule transfers state, scheduled transfers may be created, edited or deleted. In the print schedules state, scheduled transfers may be previewed, printed, or faxed.

Figure 17A:
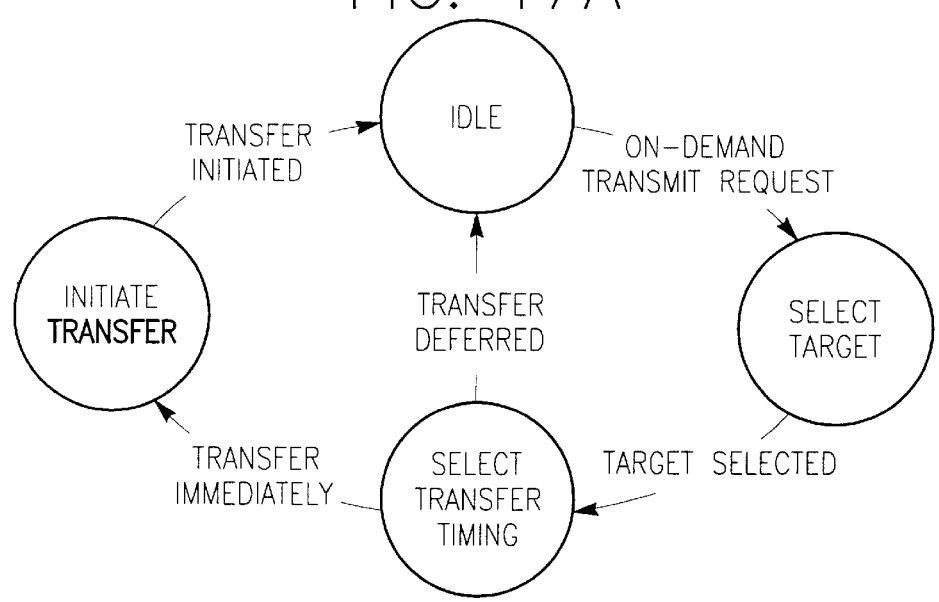
FIGS. 17A–F diagrammatically illustrate the state transition diagrams for the various scenarios of data transfer function of the present invention.

As discussed above, the data transfer function may be entered in response to a user request to perform an on-demand transmission. FIG. 17A shows the state transition diagram for the on-demand transmission scenario. This scenario assumes that the patient/procedure records to be transmitted have already been selected. Under this scenario, the idle state occurs when the user initiates an on-demand transmission. The function then transits to the "select target" state in the visible mode. The select target state occurs when a target has been selected. The function then transits to the "select transfer timing" state. The select transfer timing occurs when transfer timing has been selected. The function then transits to the "initiate transfer" state (in background mode) if the transfer is initiated immediately. The select transfer timing state function will transit to the "idle" state (in non-visible mode) if the transfer is deferred. The initiate transfer state occurs when the transfer has been initiated. The function then transits to the "idle" state in non-visible mode.

Figure 17B:
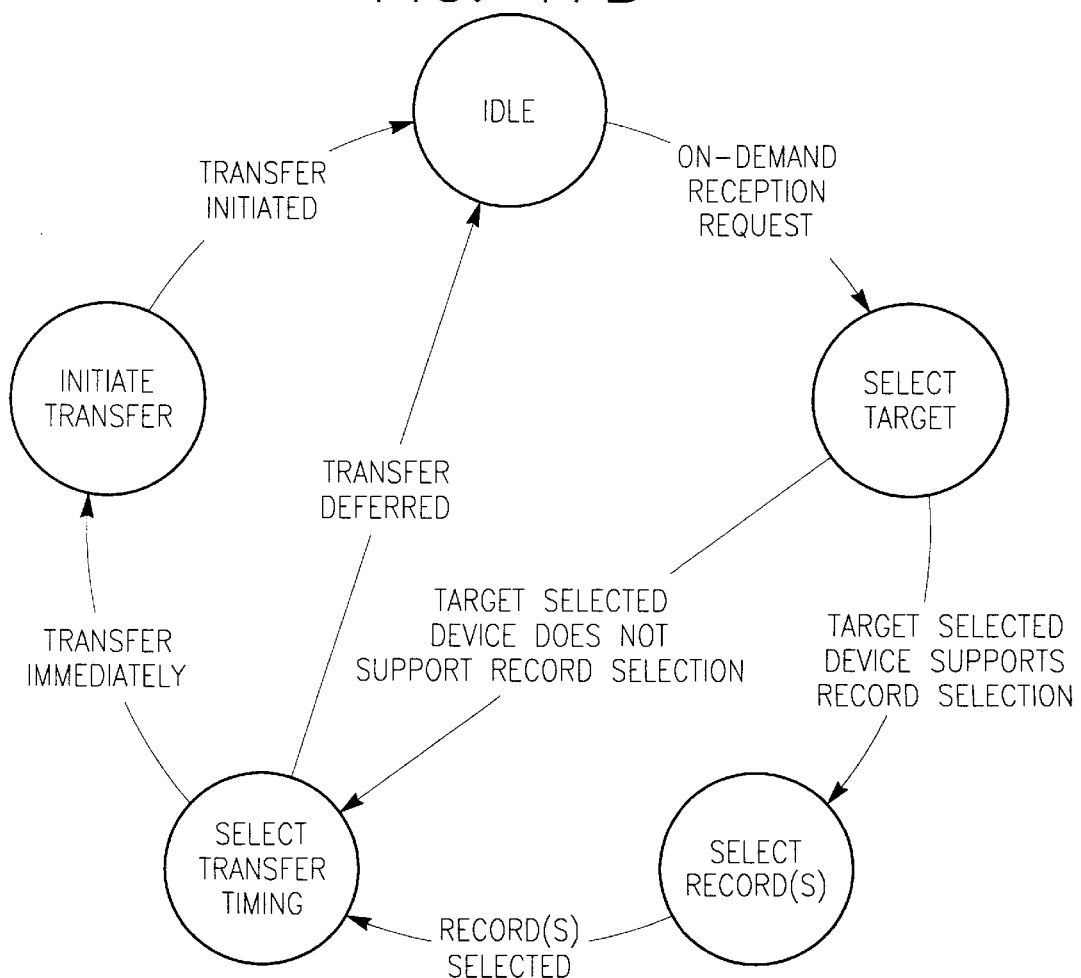

The data transfer function may also be entered in response to a user request to perform on-demand reception. FIG. 17B shows the state transition diagram for the on-demand reception scenario. Under the present scenario, the idle state occurs when the user initiates an on-demand reception. The function then transits to the "select target" state in visible mode. The select target state occurs when a target has been selected. The function transits to the "select record(s)" state if the target device provides a "directory" of its records. The select target function transits to the "select transfer timing" state if the device is unable to support the selection of records. When the records from the target device have been selected for transfer, the function transits from the select records state to the "select transfer timing" state. The select transfer timing state is activated when transfer timing has been selected. The function transits from the select transfer timing state to the "initiate transfer" state if the transfer is to be initiated immediately. The function transits from the select transfer timing state to the "idle" state (in non-visible mode) if the transfer is to be deferred. The initiate transfer occurs when the transfer is initiated, the function then transits to the "idle" state in non-visible mode.

Figure 17C:
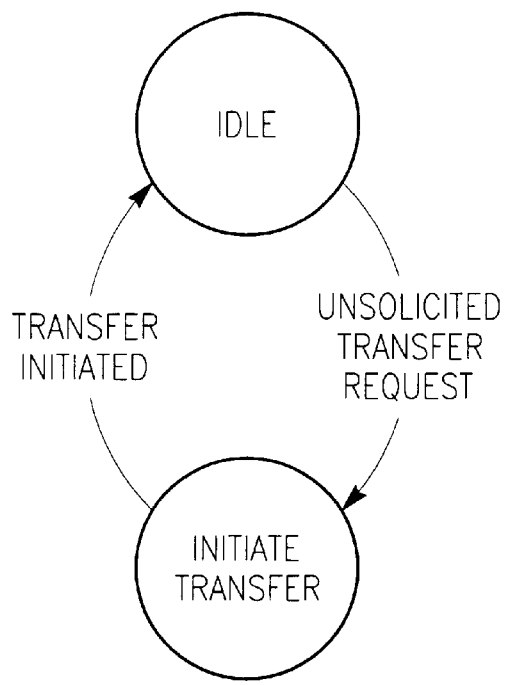

The data transfer function may also be entered in response to an unsolicited request for a transfer from some external device in an unsolicited data transfer scenario. FIG. 17C shows the state transition diagram for the unsolicited data transfer scenario. In this scenario, the idle state occurs when an unsolicited transfer request is received. The function then transits from the idle state to the "initiate transfer" state in a background mode. The initiate transfer state occurs when the transfer is initiated and the function then transits to the "idle" state in non-visible mode.

Figure 17D:
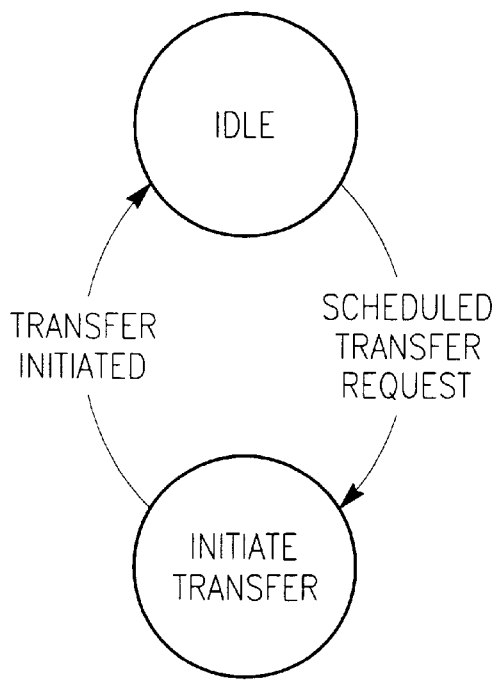

The data transfer function is also entered in response to a scheduled request to perform a data transfer in accordance with a scheduled data transfer scenario. FIG. 17D shows the state transition diagram for the scheduled data transfer scenario. Under this scenario, the idle state occurs when the time for a scheduled data transfer arrives. The function then transits from the idle state to the "initiate transfer" state in a background mode. The initiate transfer state occurs when the transfer is initiated. The function then transits from the initiate transfer state to the "idle" state in non-visible mode.

Figure 17E:
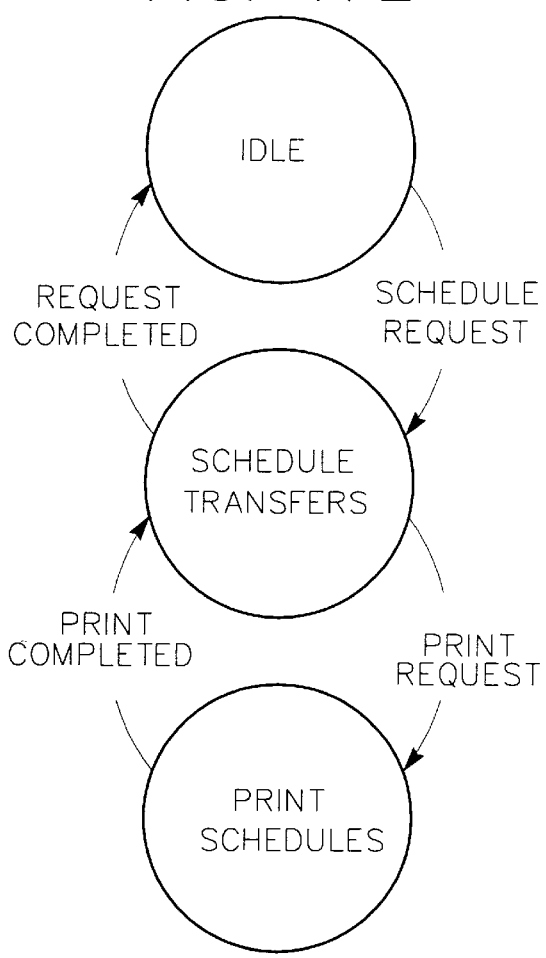

The data transfer function is also entered in response to a user request to schedule transfers in accordance with a schedule transfer scenario. FIG. 17E shows the state transition diagram for the schedule transfers scenario. In accordance with this scenario, the idle state occurs initially; and then when a user indicates a desire to schedule transfers, the function transits from the idle state to the "schedule transfers" state in visible mode. From the schedule transfers state, the function transits to the "print schedules" state if the user elects to print the transfers which have been scheduled. The function transits from the schedule transfers state to the "idle" state (in non-visible mode) if the user indicates completion of the scheduling activities. When the print or preview is complete, the function transits from the print schedules state to the "schedule transfers" state.

Figure 17F:
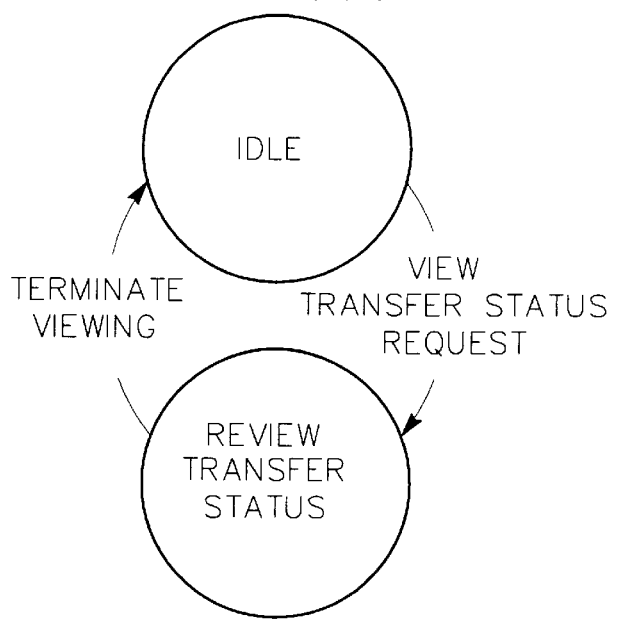

The data transfer function is further entered in response to a user request to view the status of transfers for a resource in accordance with the view transfer status scenario. FIG. 17F shows the state transition diagram for the view transfer status scenario. As shown in FIG. 17F, the function is initially in the idle state. When the user initiates view transfer status, the function transits from the idle state to the "review transfer status" state in a visible mode. The function transits from the view transfer status state to the "idle" state (in a non-visible mode) if the user elects to cease viewing the transfer status.

In addition to the features of the data transfer function described above, it is anticipated that the data transfer function may be enhanced to accept records from third-party devices so that those additional records may be stored in the system database format and manipulated. Additionally, the ability to automatically detect the protocol to use on unsolicited transfers is an anticipated enhancement. Similarly, the ability to perform external device initiated transfers by supporting unsolicited requests for transmitting data out of the system with some type of criteria/security requirement to make sure that data is only transmitted to approved sites is a desirable addition.

Figure 18:
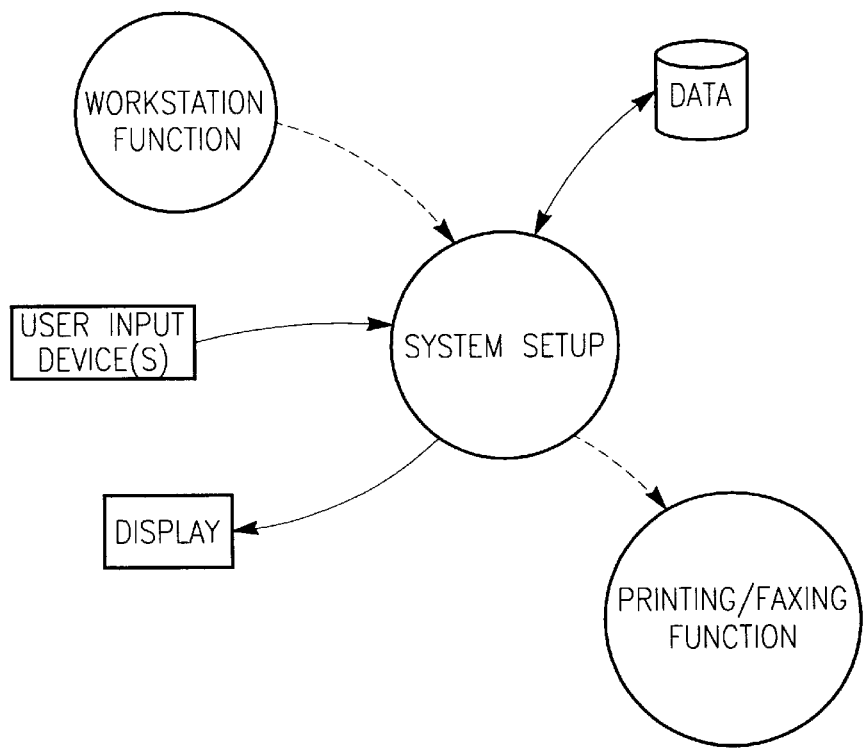
FIG. 18 is a diagrammatic view illustrating the system setup functions of the present invention.

The system setup function of the present invention provides the with user with the ability to define the environment and system lists for a particular CIS as shown in FIG. 18. This schematic drawing illustrates the system setup context of the present invention. The following functionally describes both system wide parameters; i.e., setup by the system administrator and user specific parameters. In the present invention, the physicians, technicians and administrators that are identified by the system each have an assigned "notification path." This allows them to be used as "destinations" in the system distribution list, as it provides the system information on how to notify the person. To indicate the means by which the system is to communicate with hospital personnel, the system administrator may be offered the choice of "None," which indicates that the system has no means of communicating with this person; "Print/FaxResource," which indicates the resource (selected from the available printers and faxes in the resource list) used to print the message, report or record; "Connection," which indicates the connection used to store/send the message, report or record; "Notify," which indicates that the person is to be notified with a system message and the system administrator is required to enter the system user name; "Message," which indicates that the system administrator is required to enter a user-defined or default message (up to 40 characters); or "Pager," which indicates the person is to be notified via a telephone pager. In order to select this notification path, the system administrator enters the phone number of the pager and a user-defined or default message (up to 10 characters) or "None."

The system of the present invention provides several broad system lists of data for use in query definition and record editing. The user may print any of the system lists which are described more fully below. System defined lists are created by the system, allowing little or no editing by the user. The system administrator cannot add or delete procedures from the procedure list (since the list represents the procedures currently installed on the system) but may rename procedures to accommodate institution conventions. For each procedure in the procedure list, the system administrator may view a list of common aliases for the procedure. For example, Resting ECG procedures may also be referred to as resting, resting ECG, resting EKG, resting 12-Lead, ECG, EKG, or 12-Lead procedures. The system administrator may also add an alias to the list, delete an alias from the list, or select an alias to represent the procedure. There must always be at least one alias in the list; therefore, the user may not delete the last alias in the list. Thereafter, the selected procedure name will be used by the system whenever the procedure is referenced. Each procedure is also provided with a default alias during manufacture.

The system distribution list represents all entities in the system that can be considered a source or destination. It is used by other functions for both intrasystem and external communications. This list is generated automatically by the system and includes the choices for all printer and fax resources in the resource list, all connections in the connection list, all technicians from an all site technician list and who do not have "none" selected for notification path, all physicians from the physician list who do not have "none" selected for notification path, all administrators from the administrator list who do not have "none" selected for notification path, and all system users.

Extensible system defined lists are those lists provided by the system which allow additional entries to be created by the user. These lists allow the user to add, modify or delete entries to the list. The user may also disable standard list entries (deleted from the user's point of view but still available to support records containing the standard entries). Additionally, each entry in the list is preferably qualified by the installed procedures to which the entry applies, and the default is preferably "all installed procedures." The system administrator may also assign acronyms to commonly used list entries so that, when users enter these acronyms in free text fields, the system automatically expands the acronym to the associated text. The system administrator may also choose any of the fields in the list on which to sort. The specific list requirements identify the default sort key.

In the present invention, the extensible system defined lists provided by the system may include a list such as a Race List in which the system administrator shall be able to remove all references to patient race from the system. The extensible system may also include a diagnosis list wherein diagnoses (sometimes called "Bottom Line Statements" in resting procedures) are used to provide a brief description of the procedure result. A standard set of statements is provided by the system (normal, abnormal, etc.). The system administrator may also enter up to 50 user-defined statements. For each diagnosis, the system administrator is queried for a statement which is a text string and a code which is a unique identifier. The default sorting key is preferably the statement text field.

The extensible system defined list also includes a standard list of medications provided by the system. The system administrator may enter up to 50 user-defined medications. For each medication, the system administrator is queried for the name, as a text string, and the code, which is a unique identifier. The default sorting key is the medication name field. The extensible system defined list also includes an indications list, which is a statement describing a patient condition that indicates a potential medical problem (such as "chest pains"). A standard list of indications is provided by the system. The system administrator may also enter up to about 50 indications. For each indication, the system administrator is queried for the name in a text string. The default sorting key is the indications name field.

In addition to the system defined lists and the extensible system defined lists, the system also includes various user defined lists, which are created by the user. These lists allow the user to add, modify or delete entries to the list. Each entry in the list is qualified by the installed procedures to which the entry applies, and the default is the "all installed procedures." The system administrator may also assign acronyms to commonly used list entries; and, when users enter these acronyms in free text fields, the system automatically expands the acronym to the associated text. The system administrator may also choose any of the fields in the list on which to sort. The specific list requirements identify the default sort key.

The user defined lists provided by the system include the physician list, administrator list, comment list and interpretation statement list. As part of this system, the system administrator is allowed to identify up to about 1000 physicians who have some association with the system. For each physician, the system administrator is requested to provide the physician name, the unique physician number and the notification path. The notification path is the means for communicating with the physician, as described above. The physician list is always sorted based on physician name. The system administrator is able to identify up to about 250 administrators. This list is intended to represent "clinical administrators" rather than "system administrators." For each administrator, the system administrator is requested to provide the administrator name, the unique administrator number and the notification path. The administrator list is always sorted based on administrator name. The comment list allows the operator a means of entering frequently used text by choosing from a list rather than having to type the text each time. The system administrator is allowed to enter up to about 1000 comments. For each comment, the system administrator will be requested to provide the comment which consists of an alphanumeric text string of up to about 255 characters. The default sorting key is preferably the comment field. The Interpretation Statement list consists of frequently used textual interpretive statements common to multiple procedures. The system administrator is allowed to enter up to about 1000 interpretive statements. This list is not the resting ECG interpretation code list that is used for editing resting ECG interpretations. For each statement, the system administrator is queried for the interpretation which is an alphanumeric text string of up to 255 characters. The default sorting key is the interpretation text field.

Figure 19:
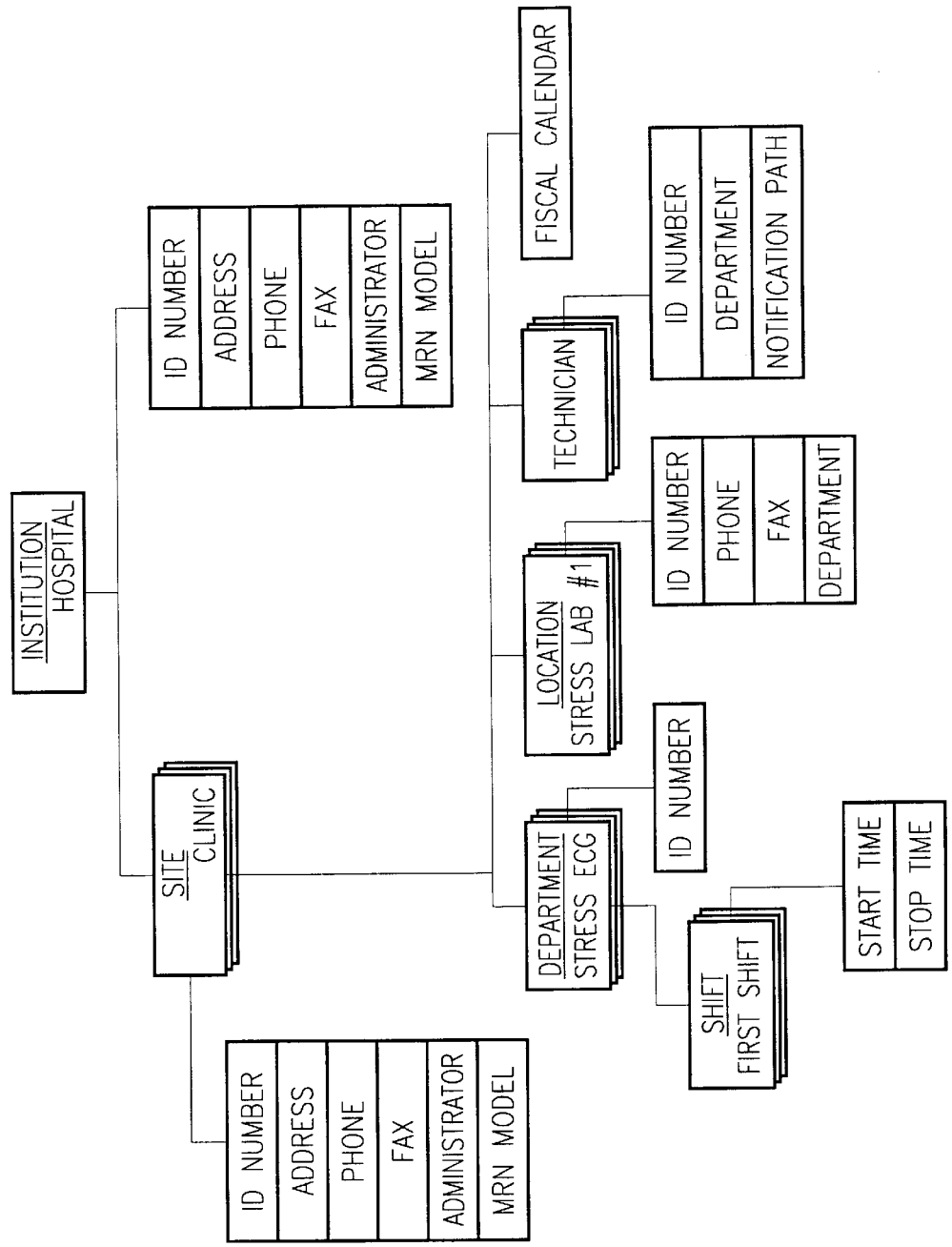
FIG. 19 is a diagrammatic view illustrating a sample institution configuration tree created using the system setup function of the present invention.

With the present invention, the system administrator also has the opportunity to describe the institutional configuration or environment of the system. A rudimentary example of how an institution might use the structure provided by this feature is shown schematically in FIG. 19. This structure is designed to represent a situation where the system supports an institution made up of various subordinate sites. The structure does support other configurations, although the terms may be misleading. For instance, the system may belong to an institution that contracts out record storage and/or overreading functions to peer institutions. In this configuration, the peer institutions are represented in the system as subordinate sites. The system administrator is able to enter information defining the institution such as institution name, institution ID number, institution address, institution MRN model, two institution phone numbers, two institution fax numbers, and the name and telephone number of the primary contact for the institution. The system administrator is allowed to print the institution information as generally described below. The system administrator is also allowed to identify up to 250 sites of the institution in a site list. The list is preferably always sorted based on site name. The system administrator may also enter the information which defines a site, such as a unique site name, the unique site ID number, the site address, two site phone numbers, two site fax numbers, and the name and telephone number of the primary contact for the site. The system also allows the system administrator to enter the site time zone and the fiscal calendar used at the site. The default site time zone is preferably the same as the system time zone. The site list may also include the MRN model used by the site. The site MRN model defaults to the institution MRN model. The system administrator is allowed to enter up to 50 departments for each site. For each department, the system administrator is requested to supply the unique department description, the unique department number, and the name and telephone number of the department administrator. The system also allows the system administrator to enter shift information for the particular site. The system administrator is allowed to enter up to 1000 locations per site. For each location, the system administrator is requested to supply the unique location description, the unique location number, the location phone number, the location fax number and the department associated with this location (or "none").

The site list may also include a technician list of up to about 250 technicians per site. For each technician, the system administrator is requested to supply the technician name, the unique technician number, the notification path and the department (from the department list defined above) with which the technician is associated (or "none"). The system administrator may also control the hardware configuration of the system utilizing standard system services provided by the operating system. This application uses the system time and date and resource list (local and network, including identification of clients and servers). If the system contains multiple databases, the system administrator will be able to define what information is stored on each database. One database may be designated as the primary container of system data (all user-defined parameters specified in the functional specifications), and each site/procedure type combination is assigned to one of the databases. For example, in a procedure based organization, resting records from site A may be stored on the Resting Database; resting records from site B may stored on the Resting Database; stress records from site A may be stored on the Stress Database, and stress records from site B may be stored on the Stress Database. In a site based organization, the resting records from site A may be stored on Database A; the stress records from site A may be stored on Database A; the resting records from site B may be stored on Database B, and the stress records from site B may be stored on Database B.

The system administrator may also set the pediatric cutoff age (in years) so that any patient equal to or less than the pediatric cutoff age will be considered pediatric, while any patient older than the cutoff age will be considered an adult. The system allows the system administrator to select the desired format to be used when entering or displaying a person's name. The options available to the system administrator include order such as last, first, middle or first, middle, last names and titles such as Mr., Mrs., Ms., etc. or M.S., DDS, Ph.D., etc.

The system also allows the user the capability to set up user specific data formats and screen saver timeouts. These formats are for display and entry purposes only, and they do not imply a format to be used for internal storage. The functions provided by the operating system may be used to perform these tasks where practical, and the system administrator is responsible for setting up the formats for the user on the server that performs background processing such as report distribution. The user is able to select a default country code for the system which is based on the two-digit international telephone dialing codes. The selected country code governs the entry and display of the address and phone number. The user may select date entry and display as mm/dd/yy, dd/mm/yy, yy/mm/dd, dd.mm.yy or dd-mm-yy. The user may select time entry and display format as either 12-hour with AM/PM indicators or 24-hour. The user is able to select units of measure display format as metric or English. The user may enter a time value ranging from one to 60 minutes for a screen saver. The users may determine the initial function launched at application initiation from a list of displays available at application initiation. The user may also enter any additional data required for a particular initial display.

As described above and shown in FIG. 16, the user is able to access the system setup function via the edit setup function. The system setup function exhibits the functional state behavior indicated by the idle state, which is the initial state for the system setup function. The function is not visible to the user and awaits external initiation. The user may enter the system setup function through the setup state in which the user may edit the setup data. The user may also enter the system setup function via the printing state where the setup data is printed, faxed and/or previewed.

Figure 20:
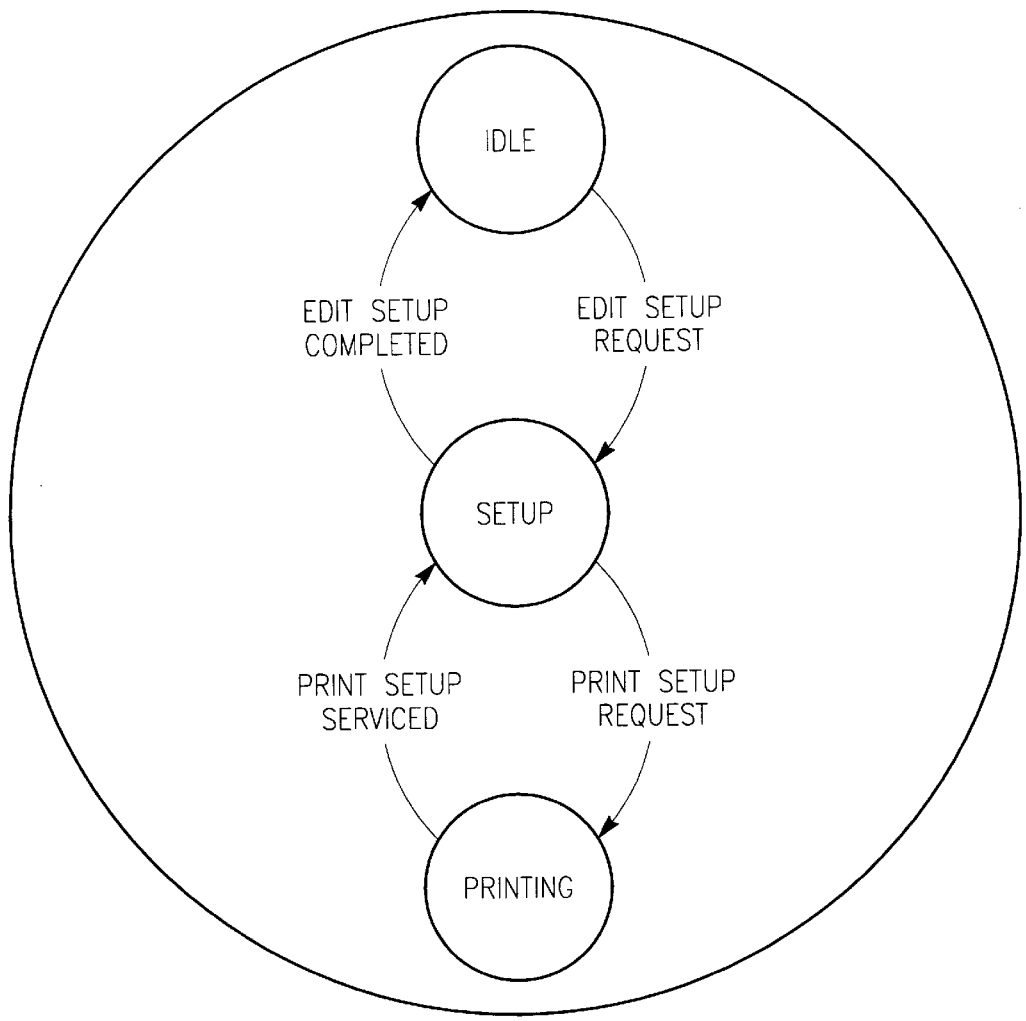
FIG. 20 is a diagrammatic view illustrating the transition states of the system setup function.

The system setup function may be entered in response to a user request to edit the system or institution configuration or any of the system lists. FIG. 20 shows the state transition diagram for the initial edit setup scenario of the system setup function. In this scenario, the idle state occurs when the user initiates the setup function for editing. The function transits from the idle state to the setup state in visible mode. In the setup state, the function transits to the printing state when the user indicates a desire to print, and the function transits to the idle state in non-visible mode when the user indicates that editing is complete. In the printing state, the printing is serviced, and the function transits to the edit setup state.

In addition to the above, the system setup function may include features such as "Personal Digital Assistants" (PDAs) and other emerging communication technologies in the notification path capabilities. The setup function also preferably includes the ability to transfer system lists (race, comments, interpretations) to instruments which are capable of receiving them. It is further anticipated that the system setup function may incorporate in-out status with forwarding information for each physician and confirmation schedules for physicians so that "confirming physician" can be a selection for distribution of reports. Additional lists, such as for identification of complications and allergies, may also be incorporated.

Figure 21:
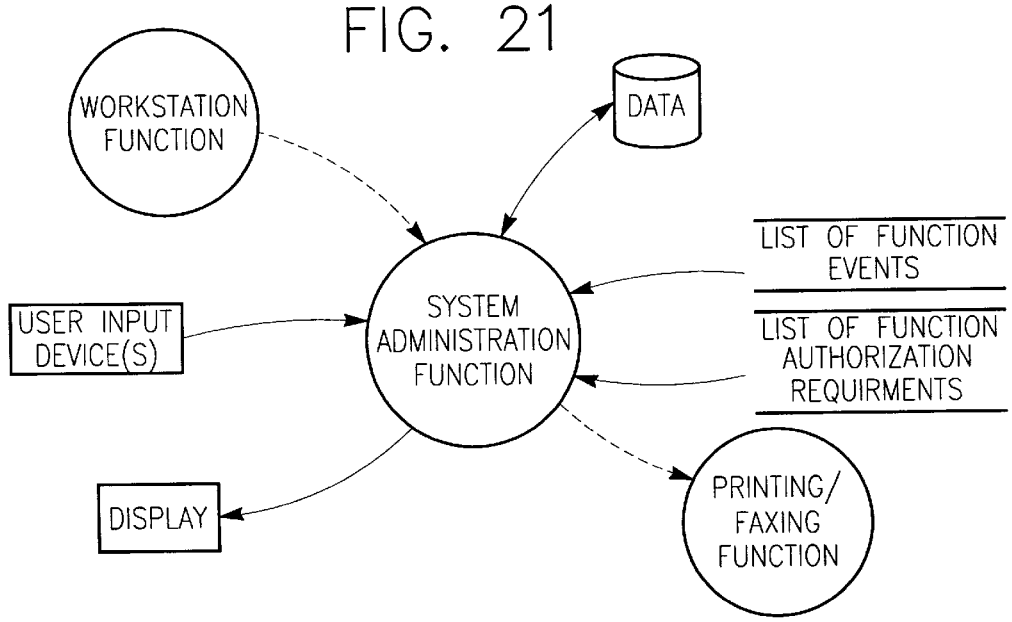
FIG. 21 is a diagrammatic view functionally illustrating the various system administration functions of the present invention.

The system administration function of the present invention controls the system level administrative functions. To ensure that these functions are only used by the appropriate user, each function requires access privileges. FIG. 21 shows the interface between the system administration function and the other functions in the environment. The system administrator may enter a message on the system of up to 240 characters. The system administrator is able to post the message to specific users or specific groups. The system administrator may choose a specific user(s) to notify from a list of users. The system administrator may also choose a specific group(s) to notify from a list of the currently defined groups containing logged in users, and all users in the specified group(s) who are currently logged in to the system will be notified. The message from the system administrator will be displayed on each receiver's screen, and the receiver will be required to acknowledge reception of the message to clear the message from the screen. The system will allow at least 16 unacknowledged messages per receiver. When a receiver acknowledges a message, a subsequent message (if available) shall be displayed in the order received. Unacknowledged messages will not persist if the receiver logs out. The system administrator will be able to view a list of users currently logged in. For each user, the user name, user network name and groups to which the user belongs are listed for review by the system administrator. The system administrator may print the user list.

The system administrator may define groups which consist of a class of users that share a set of system privileges. changes made in group setup which modify user privileges will not take effect until the next time the user logs into the system. The system will be provided with a default system administration group. Members of the system administration group have all of the system administration privileges. The group setup functions supported include create group, delete group, assign group privileges, set default group and print. The system administrator may create up to about 250 groups. The system administrator is able to create a new group based on an existing group and its privileges and is required to assign a unique group name to the new group. The system administrator may also delete a selected group except for the system administration group. Any group deletion will require verification. The system administrator is be able to assign functional privileges to the selected group which may be selected from a list of each function's access privileges. A list of initial access privileges will be built based on the privileges for the functions installed on the system. The system administrator may not assign privileges to the system administration group. The system administrator may select a default group for newly created users and may select any group from the group list or "none." The system administrator is able to print the group list, group members and group privileges.

The system administrator is be able add unique users to the user list. The system will support up to about 500 users. When adding a user, the system administrator is be able to initialize the groups and privileges of the new user to that of an existing user; and for each user, the default password for a new user is no password. The system administrator may also delete or disable an active user from logging in to the system. This action requires a verification; and if a user to be deleted is currently logged in, the system administrator will be notified, and the user will not be deleted. The system administrator may also re-enable logins for an inactive user.

In the preferred form of the present invention, the system administrator may edit the user's password or name, assign a user to a group, edit a user's privileges, or print a list of user's or user's characteristics. To change a user's own password, the user must enter the new password and enter the new password again for verification. If the password verification fails, the old password will remain in effect. The system administrator may also edit the user name, and any new name is required to be unique. The system administrator is able to assign a user to a group; and when the user is assigned to a group, that user will automatically inherit the privileges of the group. The system administrator is also able to edit user privileges by choosing from a list of privileges from which privileges to modify may be selected. The system administrator may enable or disable user-level privileges for a selected user. If a user has been granted a privilege as part of a group, that privilege may not be denied by changing the user privileges in this function. The system administrator is able to grant a user-level privilege even if that privilege has already been granted to the user through group membership; doing so enables the privilege to the user even if the user is later removed from the group or the group's privilege is revoked. Changes to a user's characteristics will take effect the next time the user logs onto the system. The system administrator may print a list of the currently defined users and the group assignments and personal privileges for one or more selected users. All users may change their own password as described above.

The system administrator of the preferred form of the present invention also has access to event log which is used to track events which have occurred on the system. Each logged event includes a time stamp, event type, event identifier, workstation identifier and user identifier. The event type is the type or class of event (user-related, data transfer, etc.), and the event identifier is the event that occurred. The workstation identifier is the place where the event occurred, and the user identifier is the identifier of the current user or "scheduled" or "unsolicited." The system administrator may enter a maximum event log size. Once the maximum event log size is exceeded, the logged events will be deleted on a first-in-first-out basis. The system administrator may also save a copy of the current event log by entering a unique event log name. The system administrator may purge a saved event log by selecting from a list of saved event logs and verifying the desired deletion. The system administrator may also clear the event log upon verification of the system administrator's desire to clear the event log. The system administrator is able to review the event log by selecting the event log to review from a list of active and/or saved event logs. The system administrator is be able to query the event log based on the event types, time period, user and/or workstation. The system administrator may also print the events in the selected event log based on the events and/or the results of a query.

Various system events dictate that system messages are generated to notify specific system users. This system message differs from posted messages. System messages are displayed on the selected receiver's screen. If the system message is sent to a logged out user, the system message will be displayed upon user login. The receiver is required to acknowledge reception of the message to clear the message from the screen. The system allows at least 16 unacknowledged messages per receiver. When a receiver acknowledges a message, a subsequent message (if available) is displayed in the order received. Unacknowledged messages persist even if the receiver logs out.

The system administrator is able to display memory and disk utilization and/or fault status for all nodes on which a server or system client is active. The system administrator will also have limited access to standard network and database server maintenance and tuning features. The system administrator is also able to perform system backups and restores and may backup the system database, system applications and the system configuration. In the present invention, the system database includes the patient records and other data within the system database.

The system applications consist of the system software. The system configuration includes user lists, group definitions, system lists, report format definitions, etc. If more than one backup device is available, the system administrator is able to select the device on which the backup or restore is to occur. The system administrator may perform a total or incremental backup and may request that a manual backup be performed on the system database, system applications and/or the system configuration. The system administrator is able to establish times at which scheduled backups are to be performed based on days between incremental backups or total backups. The system will automatically perform scheduled backups at the scheduled intervals. If incremental and total backups are scheduled on the same day, only the total backup will be performed (e.g., days between total backups=5, days between incremental backups=1; on the fifth day, both total and incremental backups are scheduled, but only the total backup is performed). The system administrator may also restore previously backed up data in a total or partial backup. If any of the data to be restored will result in overwriting existing data on the database, the system administrator will be warned prior to restoring the data, and the system administrator will be required to verify the command prior to restoring data. If an error occurs while executing a backup or restore operation, the system administrator will be notified of the problem and will be required to decide whether or not to continue, restart or abort the backup or restore procedure.

The system administrator may also perform system archival and/or retrieval of patient information records and procedure records. Archival may be scheduled as part of a specific record workflow. Additionally, the system administrator is able to create up to 16 scheduled archives, or modify/delete an existing schedule. For each archive schedule, the system administrator must provide a name for the archive schedule, the archival device, the record types to be archived, the acquiring sites, the minimum age of the records to be archived and the period and time of day for the archive to be initiated. The system administrator may also request an on-demand archival by selecting the records to be archived and specifying the archival device.

When a procedure record is archived, the system shall maintain an entry in the system database with a reference to the archival media to support retrieval of the record, sufficient data to allow for conflict detection with other records, sufficient data to support patient/procedure lists, sufficient data to support administrative reports, a request to archive a patient folder or current demographics records shall be satisfied by archiving all unarchived procedure records for that patient. If an error occurs while attempting to archive a record, the record in the system database will remain unchanged. The system administrator is able to retrieve a selected archived record; and, if the archive media which holds the selected record is not on-line, the system administrator shall be notified that the record is unavailable and will be prompted to install the required archive media. The system administrator is able to establish a database memory utilization threshold as a whole number from 50–90%. When the percentage of database memory in use exceeds the utilization threshold, all members of the system administration group will be notified with a system message.

As described above, the system administration function consists of a group of capabilities used by the system administrator. Most of these functions have one entry point and have basic temporal requirements. The system administrator is able to access the system administration function via the general system administration functions, perform on demand backup or archive, or perform scheduled backup or archive modes. As described below and shown diagrammatically in FIG. 22A, the general system administration functions scenario occurs when the user wants to perform a system administration function. This is done in a visible mode. As described below and shown diagrammatically in FIG. 22B, the perform on demand backup/archive scenario occurs when the user wants to perform backup or archive functions. This is performed in a visible mode. As described below and shown diagrammatically in FIG. 22C, the perform scheduled backup or archive mode occurs when the user has scheduled backup or archive functions. This is performed in a background mode.

The system administration function exhibits the functional state behavior described herein. The idle state is the initial state for the system administration function. The function is not visible to the user and awaits external initiation. The system administrator performs the system administration setup functions. The generated report(s) is printed, faxed and/or previewed in the printing state. The backup or archive setup state prepares for the backup or archive functions. The backup or archive setup state executes the backup or archive as requested or scheduled.

Figure 22A:
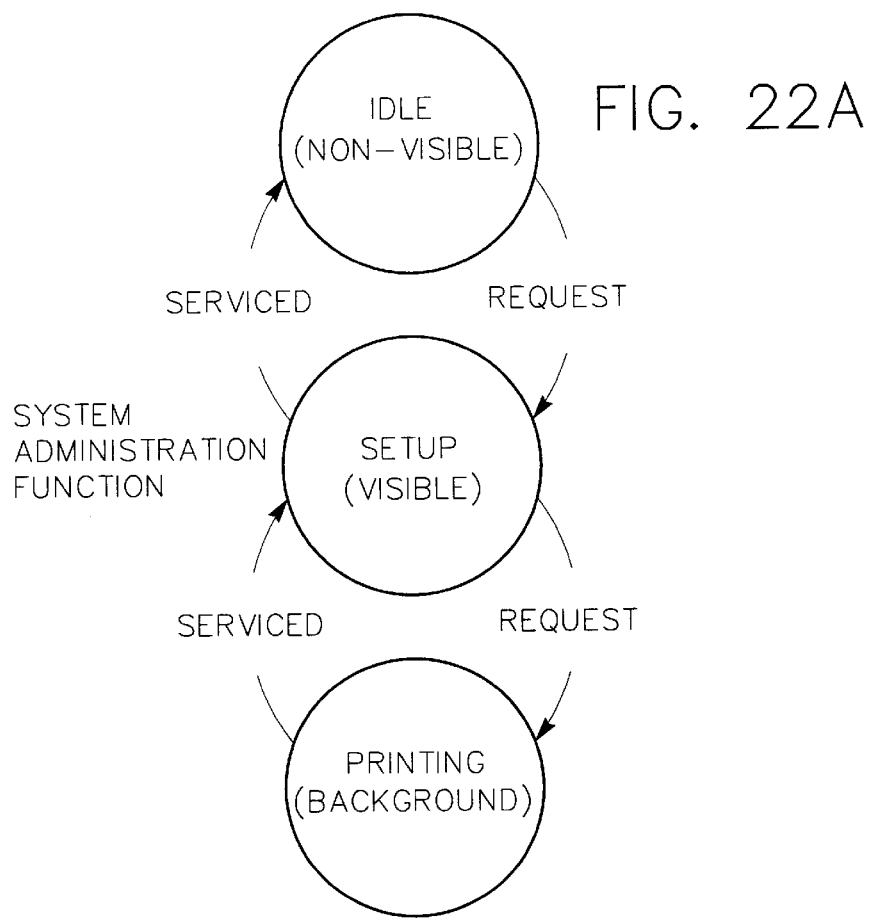
FIGS. 22A–C diagrammatically illustrate the state transition diagrams for the various scenarios of the system administration function of the present invention.

The system administration function will be entered whenever a user requests to perform general system administration functions. FIG. 22A shows the state transition diagram for the general system administration functions scenario. Under this scenario, the idle state occurs prior to a request to perform general system administration functions, the function then transits from the idle state to the setup state in a visible mode. When the user chooses to print a report, the function transits from the setup state to the printing state. When the user chooses to close the system administration function, the function transits from the setup state to the idle state in a non-visible mode. When the print request has been serviced, the function transits back to the setup state.

Figure 22B:
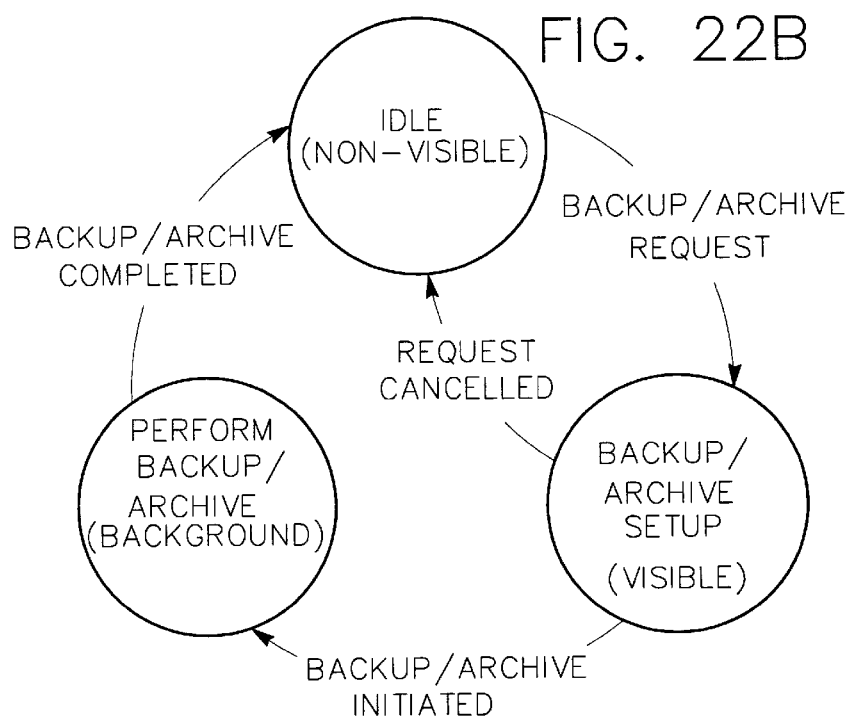

The system administration function is entered whenever a user requests to perform on demand backup or archive in accordance with the perform on demand backup or archive scenario. FIG. 22B shows the state transition diagram for the perform the on demand backup or archive scenario. In accordance with this scenario, the idle state occurs initially; and when a request to perform backup or archive occurs, the function shall transit to the backup or archive setup state in a visible mode. When the user initiates the backup or archive, the function transits from the backup or archive setup state to the perform backup or archive state in a background mode. If the user cancels the backup or archive, the function transits from the backup or archive setup state to the idle state in a non-visible mode. When the backup or archive request is serviced, the function transits from the backup or archive state to the idle state in a non-visible mode.

Figure 22C:
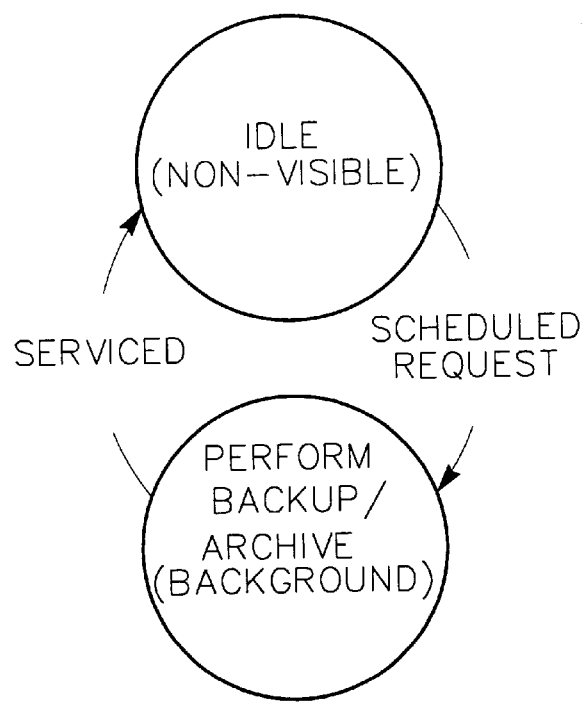

The system administration function is also entered when it is time to service a scheduled request for backup or archive functions in accordance with the perform scheduled backup or archive scenario. FIG. 22C shows the state transition diagram for the perform scheduled backup or archive scenario. When the time arrives to perform a scheduled backup or archive activity, the function transits from the idle state to the backup or archive state in a background mode. When the backup or archive request has been serviced, the function transits from the perform backup or archive state to the idle state in a non-visible mode.

In addition to the system administration functions set forth above, it is anticipated that the following capabilities may be included as part of the system administration function. For example, events may be prioritized to allow filtering and masking during a query. Transparent user login may be enabled for users of instruments that want to be able to turn on the machine and immediately have waveforms start scrolling across the screen without having to login. The posting messages capability may be expanded to include full e-mail capabilities. The system administrator may also be able to view a list of the system events for which logging may be enabled or disabled. The system list will be enlarged to include information relating to all optional events for all functions installed on the system and will be expanded to indicate the logging status of each event. The system administrator may also enable, disable or print any of the events in the list.

Figure 23:
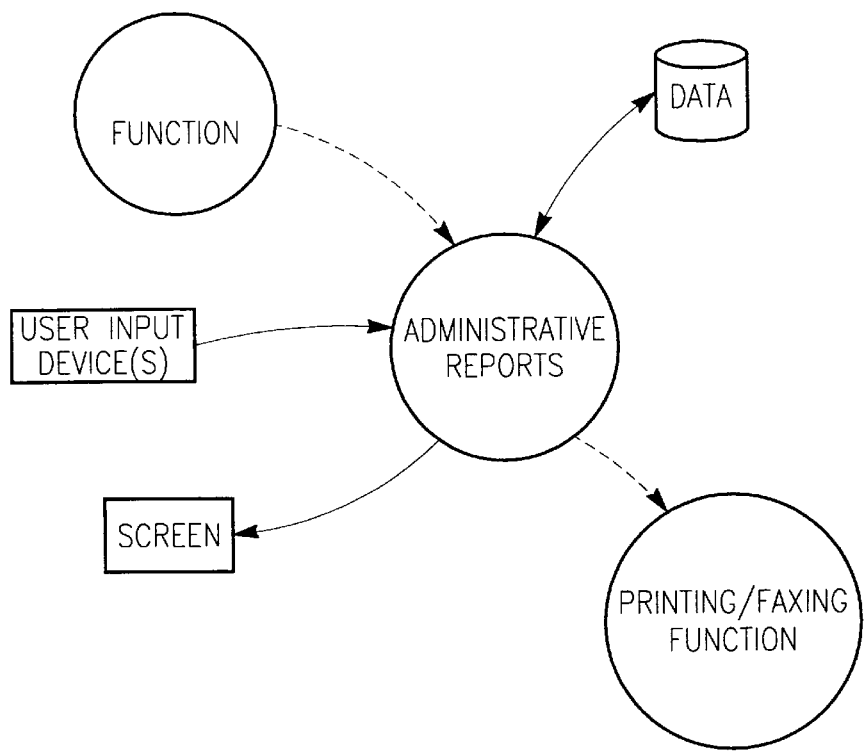
FIG. 23 is a diagrammatic view functionally illustrating the various administrative reports functions of the present invention.

The administrative reports function of this present invention is preferably responsible for the setup, scheduling, generation, editing, and printing of management reports. These reports summarize various aspects of departmental work flow, productivity and efficiency. FIG. 23 shows the context diagram for the administrative reports function. The administrative reports function will typically be operated by system administrators. This section describes the preferred features of the administrative reports function. Administrative reports are typically generated from report formats created by the user. The format specifies the content and layout of the report. There are preferably about four types of segments—cover page segment, tabular segment, data graph segment and trend graph segment—initially available for use by the user. Each administrative report is made up of one or more segments, appended in a specific sequence. The following sections define the preferred report generation requirements for each segment. Several representative administrative report formats will be shipped with the system, and the hospital administrator of the institution may select one or more of these reports as the institution standard. These initial report formats are representative of standard administrative views and may be modified or deleted by the user.

Figure 24:
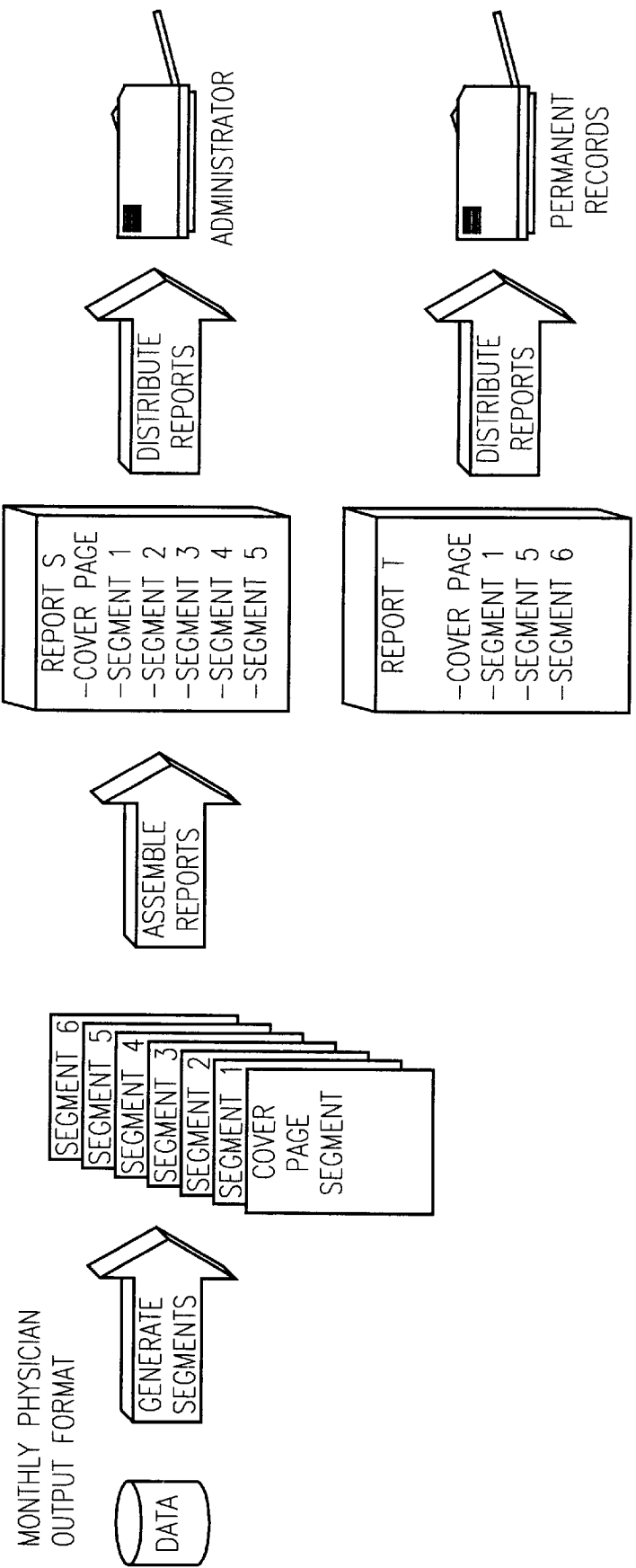
FIG. 24 is a diagrammatic view illustrating the assembly of a sample administrative report using the administrative reports function of the present invention.

A report format defines one or more segments. Reports are viewed one segment at a time. If the user has the appropriate privileges, the various segments may be edited. Editing of a report segment does not affect the system database. At the user's discretion, reports may be exported, distributed, and printed. The user may schedule automatic generation and distribution of reports based on a selected format. The example shown in FIG. 24 is included generally to illustrate how finished reports are constructed from the various generated report segments. In this example, report generation is requested for the Monthly Physician Output format, which defines Report S for printing at the administrator's desk and Report T for permanent records. The report generation function generates all report segments as defined in the Monthly Physician Output format and makes them available for review. Upon user request, the function assembles the segments into two reports (as defined by the format) and distributes them to the specified locations: Permanent Records printer and the administrator's printer.

An administrative report format defines the segments, layout, schedule and distribution of administrative reports. The user may create new administrative report formats which are based on existing formats or modified from the existing formats. The user may also delete various undesired formats. The modifiable elements of an administrative report format include the format name, cover page definition, segment page layout, segment queries, segment date range, tabular segment definition, data graph segment definition, trend graph segment definition, report scheduling, report distribution and notification lists, serial presentation layout and printing administrative report setup. The user may save a new or edited report format and will be required to provide a name unique to the administrative report formats. The user may select landscape or portrait orientation for the cover page. The user may also select and position zero or more of the following elements for inclusion on the cover page. These selectable elements include institution logo, institution text, report format name, report date, report time, number of pages in the report or free text. The user may define the header and footer for all tabular, data graph and trend graph segment pages. The user may select and position zero or more of the following elements for inclusion in the segment page header or page footer. These selectable elements include institution logo, institution text, report format name, report date, report time, number of pages in the report or free text. For each tabular, data graph and trend graph segment, the user may also select landscape or portrait mode.

The information in tables and graphs is obtained by querying the system database to produce the desired tables or records. This section defines the basic queries available to the user, and the options available for each of those queries. The requirements in this section specify the options available to the user, but not the means of expressing those options. The defined queries are built of query elements. This section describes each of these elements. The "How many" or "Which" element distinguishes between counting the number of records which match the rest of the query (How Many) and listing the records which match the query (Which). This choice is available when defining a tabular segment. only the "How many" option is available (or meaningful) when defining graphs.

The record type list is a predefined list which allows the user to indicate which record type(s) to include in the query. The list includes "Patient Information Record" and identifies all of the installed procedure types.

The activity list is another predefined list and is used to define the event of interest related to the record type. For each record type selected, the user is allowed to select one or more activities. This list is dynamic and changes to reflect the current record type.

The qualifier list is yet another predefined list. This list may be used to further qualify a record type or activity pair. It refines the query by allowing the user to select a status or condition. For each record type or activity which has been selected, the user may select one or more qualifiers (if available). This list is dynamic and changes to reflect the current record type or activity. The "From" or "From Each Of" element is typically followed by the site list. The "from" or "from each of" choices distinguish between grouping the sites (from) or treating each site as a separate entity (from each of) when performing the query. The "By" or "By Each Of" element is typically followed by the physician list. The "by" or "by each of" choices distinguish between grouping the physicians (by) or treating each physician as a separate entity (by each of) when performing the query. The "At" or "At Each Of" element is typically followed by the client workstation list. The "at" or "at each of" choices distinguish between grouping the workstations (at) or treating each workstation as a separate entity (at each of) when performing the query. When forming groups, the user is prompted to provide a name for each group. For example, if there are seven system sites defined (sites A, B, C, D, E, F and G), then the user might create three named site groups; i.e., sites A, C, and D may be named "Sally's area;" site B may be "Jon's area;" and sites F and G may be "Jane's area." The user may also create a site list, physician list, technician list, department list, shift list, client workstation list, time options list and an activity pair list. The activity pair list is typically coupled with the time options list. For each record type selected, the user is allowed to select one or more activity pairs. Therefore, this list is also dynamic and may change to reflect the current record type. Additionally, the time of the second activity of the activity pair may be used when qualifying records for the selected date range. The query elements as described here are examples which are designed to be combined with each other so as to form a sentence which defines the query.

The Record Throughput query is another predefined component of the administrative reports function. This query is intended to provide the system administrator with the answers to how quickly records in the system are being handled. A predefined Physician Throughput query is intended to provide the system administrator with the answers to how quickly records in the system are being handled by specific physicians. A Record Handling query is intended to provide the system administrator with information regarding the workstations being used to perform work. A Record Status query provides the system administrator with the ability to determine the status of records in the system database.

A Physician Activity table is also provided. This table is intended to provide the system administrator with the ability to determine which physicians are handling the various types of records. The Technician Activity table is intended to provide the system administrator with the ability to determine the activity of the technicians. For each segment in the segment date, the user may indicate a time period for the query. This date range will restrict the inclusion of records to only those whose selector occurs within the date range. For tabular and data graph segments, the user will be requested to indicate a single date range. For a trend graph segment, the user will be requested to indicate a trend date range. The user may select a date range from a variety of choices including custom where the user provides a start date and an end date to daily, monthly or yearly or month to date or year to date for the desired time period. If a fiscal calendar has been selected, then the user may be requested to select a site from which the fiscal calendar data is to be obtained. The user may also be requested to indicate the number of time periods to use to generate the graph (how many "bars" on the graph). The user is also able to define each time period (which reflects the date range for a single "bar" of the trend graph) from a variety of choices including custom where the user provides a start date and an end date to daily, monthly or yearly or month to date or year to date for the desired time period. The user may also select either record acquisition (at the instrument) or record reception (by CIS) as the marker for selecting the records which fall within the date range described above.

In the preferred embodiment, a Tabular Segment preferably consists of a matrix of columns and rows relating to the patient records in the system database. The row and column contents are defined by the queries. In the present invention, the user may specify up to about 99 tabular segments for the current format. The modifiable elements of a tabular segment include the tabular segment name, tabular segment date range, tabular segment record identification or tabular segment definition. The user is preferably required to provide a unique (within the report format) name for each tabular segment. The user must indicate the time period over which data for the tabular segment will be searched. When presenting a detailed tabular display (using the "Which" query), the patient information or procedure records are included in the table. The user is able to select patient name, patient MRN, record type, record date, record time, reception date and reception time for inclusion in each Record Identification row. The user may also select the sort order for the record identifiers, choosing any of the elements selected above.

Any of the report queries referred to above may be used to generate a tabular segment. The section below refers to the illustrative choices which are available to the user for each of the queries. For example, the user is able to request a Record Throughput table segment based on the results of a Record Throughput query. The user may also request a Physician Throughput table segment based on the results of a Physician Throughput query. The user may further request a Record Status table segment based on the results of a Record Status query or a Physician Activity table segment based on the results of a Physician Activity query. Finally, the user is also able to request a Technician Activity table segment based on the results of a Technician Activity query.

Once the user has defined a table, the user may use a totaling or paging feature. With the totaling feature, the user may enable or disable row or column totals for each row or column tier. With the paging feature, the user is allowed to request a page break following the table or within tiers of the table (if appropriate).

A data graph may also be created to present a view of the distribution of data over several categories for a specific data element. This view may be presented as a bar graph (relative distribution) or as a pie graph (percentage distribution). The user will be required to provide a unique (within the report format) name for each data graph segment. The user will indicate the time period over which data for the data graph will be searched from the choices referred to above. The options for selecting the data element for the data graph segment are based on the record handling query, record status query, physician activity query or the technician activity query. For this graph, the "Which" option is not available (only the "How many" option), and one and only one of the multiple-choice query elements of the selected query must be multiply selected (the graph is capable of demonstrating distribution over one and only one data element). The user may select the type of graph to be presented as a Horizontal Bar graph, a Vertical Bar graph or a Pie Chart. The user may also request that the graph be placed on a new page or remain (if it fits) on the current report page.

With the preferred embodiment, a Trend Segment is available for selection by the user as another predefined view. This view illustrates a single data element over time. The information is presented as a graph. The data element and time frame for the trend segment may be defined by the user. The user is able to specify up to about 99 trend segments for the current format. The trend segment may be modified by trend graph segment name, trend graph date range, trend graph data element, trend graph type or trend graph segment options. The user is required to provide a unique (within the report format) name of up to about 64 characters for each trend graph segment. The user is also required to indicate the time period over which data for the trend graph will be searched. The options for selecting the data element for the trend graph segment are based on the record handling query, record status query, physician activity query or the technician activity query, and the "Which" option is not available (only the "How many" option). At most, one of the multiple-choice query elements of the selected query may be multiply selected (the graph is capable of demonstrating a trend for one and only one data element). The user shall be able to select the type of graph to be presented from, at a minimum, a Bar graph or a Line graph. The user may request that the graph be placed on a new page or remain (if it fits) on the current report page.

In the preferred embodiment, the user is also allowed to establish a schedule by which the administrative report will be generated and routed. The user may select report generation to be conducted annually, quarterly, monthly, weekly or daily on selected dates. The user is able to establish at least two routing lists for each report: a scheduled routing list and a manual routing list. When a report is generated automatically as per schedule, the report is routed according to the scheduled routing list; the user may then manually route the report using the manual routing list. This scheme allows an administrator the ability to route the original report to himself, review/edit the report, then manually route the polished report to others. Each of the two routing lists preferably consists of up to about 20 destinations chosen from the system distribution list. For each destination, the user may include or exclude any of the defined segments, and the user may also select the number of serial presentation reports to include with the report (zero or more). The user is able to select tiled or full screen for display of serial presentation reports and may print the current report format in the manner described below.

The requirements for generating each of the administrative reports segments are described herein. Report generation involves performing the necessary queries of the system database to produce the records and numbers of interest, formatting the information as specified in the administrative report format, and (if performing a scheduled report generation) distributing the report(s) as dictated by the format. The user of the present system may select any saved report format as the basis for generating the report and may generate an administrative report manually. The user may also route any manually generated administrative report. The segments are generated based on the selected report format and are generated in the orientation specified in the format (landscape or portrait). The tabular, data graph and trend graph segments include a header and footer as defined in the format for each page of the segment, and each segment is titled with the segment name. For each of the tabular segments which include a multi-page table, the table headings shall appear on each page, and each tier of a multi-tier table is indented to reflect the tier level.

The user may retrieve any saved report using the administrative reports function. For the current report, the user is able to view and edit all segments as defined in the report format and may initiate manual report distribution and notification. If serial presentation reports are requested in the report format and appropriate serial reports are available, the user is able to initiate serial presentation. The user may edit any of the free text or table entries in a report, and changes to the report will not affect the CIS system database. If the user edits automatically generated query results, totals on the generated reports will be updated. The user is also able to export the report in the ASCII format as desired. In the preferred form of the present invention, tabular segments are exported in tabular form and data will be converted to tabular form prior to export for graphical segments. The user may save the current report; if the user exits without saving the report, any changes which were made are lost. The user is also able to delete any report which has previously been saved.

The user may elect to have previous reports based on the same format printed/displayed with the current report. The system offers other saved reports which are based on the same administrative report format for serial presentation. While the user is reviewing a current report, the user is able to select a serial presentation report from those that match the criteria above and having selected a serial presentation report, the user may concurrently view any segment of the current report and corresponding segment of the serial presentation report. The serial presentation report is clearly marked as a serial presentation report to distinguish it from the active report. If the current or serial presentation reports are tiled, the user may make either the window for the current report or the window for the serial presentation report full screen. If the user closes the serial presentation window, the window for the current report will go to full screen. If the current/serial presentation reports are already full screen, the user may tile the windows. If the user closes the serial presentation window, the window for the current report will be viewed, and the serial presentation report will be closed if the current report is closed. When a report is printed and serial presentation reports have been requested, the function includes the number of serial presentation reports indicated in the distribution list, starting with the most recent report which matches the criteria above and working backwards in time. Each serial presentation report is clearly marked as a serial presentation report to distinguish it from the active report.

When a report is to be routed (either automatically due to a scheduled request or manually by operator request), the report will be distributed as indicated in the report format. The user is able to print the selected report using the facilities defined below in the section relating to the Print, Fax and Preview functions of the system. When printing, the user is able to include or exclude any of the defined segments. The user may also select serial presentation reports to include with the report.

Figure 25A:
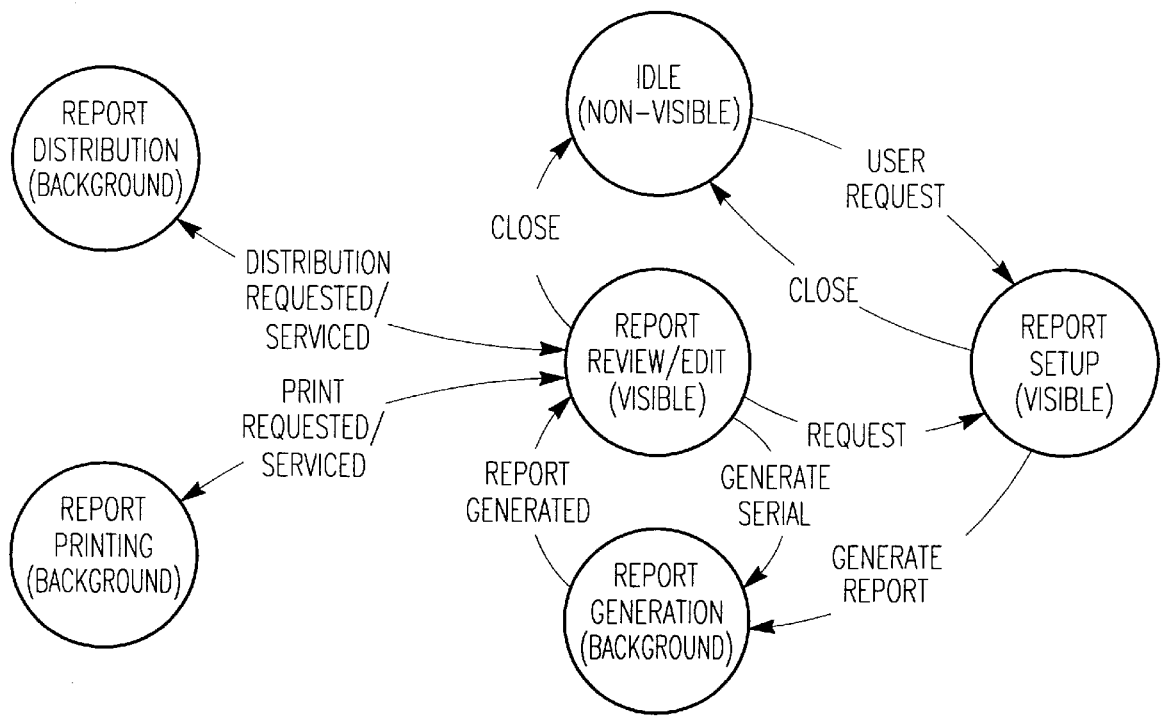
FIGS. 25A and 25B diagrammatically illustrate the state transition diagrams for the various scenarios of the administrative reports function of the present invention.
Figure 25B:
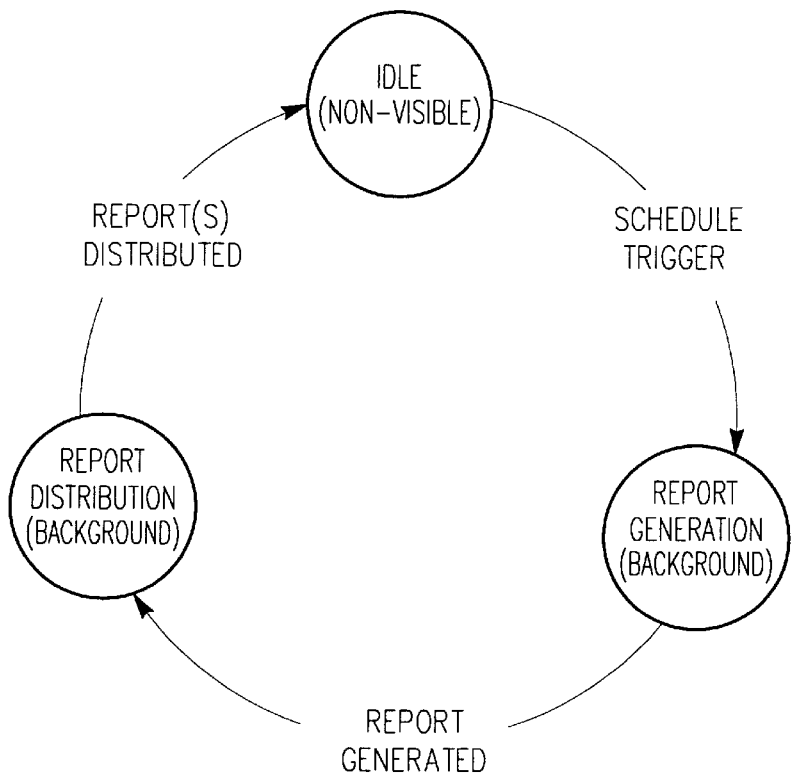

In the preferred form of the present invention, the user is able to access the administrative reports function via the administrative report setup or review scenario and the scheduled administrative report generation scenario. As shown in FIG. 25A and described below, in the administrative report setup or review scenario, the user creates or edits report formats or generates, reviews, edits and/or prints administrative reports. As shown in FIG. 25B and described below, in the scheduled administrative report generation scenario, scheduled administrative reports are generated and distributed.

The administrative reports function exhibits the state behavior indicated by the idle state, report setup state, report generation state, report review or edit state, report distribution state, or report printing state. The idle state is the initial state for the administrative reports function. This function is not visible to the user and awaits external initiation. In the report setup state, report formats are created, modified and/or deleted. In the report generation state, a report is generated based on the selected format. In the report review or edit state, the report segments are displayed on the screen, and the user may edit the values in the report. In the report distribution state, the report is routed to the locations specified in the distribution list. In the report printing state, the generated report(s) is printed, faxed and/or previewed.

The administrative reports function may be entered in response to a user request to generate and/or schedule administrative reports. FIG. 25A shows the state transition diagram for the administrative report setup and/or review scenario. When the user requests to enter the administrative reports function, the function transits from the idle state to the report setup state in a visible mode. If the user requests generation of a report or selects a saved report, the function transits from the report setup state to the report generation state. If the user closes the administrative reports function, the function transits from the report setup state to the idle state in a non-visible mode. If changes were made which have not been saved, the user is prompted to save/discard the changes before the function is closed. Upon completion of a report, the function transits from the report generation state to the report review and/or edit state. If the user requests to select a new report format, the function transits from the report review and/or edit state to the report setup state. If the user initiates serial presentation, the function transits from the report review and/or edit state to the report generation state. If the user initiates report distribution, the function transits from the report review and/or edit state to the report distribution state. If the user initiates printing of a report, the function transits to the report printing state. If the user closes the administrative reports function, the function transits from the report review and/or edit state to the idle state in a non-visible mode. If changes were made which have not been saved, the user is prompted to save or discard the changes before the function is closed. When the routing is complete, the function transits from the report distribution state to the report review and/or edit state. When the print request is serviced, the function transits from the report printing state to the report review and/or edit state.

Another feature of the present invention is that the administrative reports function may be initiated when it is time to generate a scheduled administrative report. FIG. 25B shows the state transition diagram for the scheduled administrative report generation scenario. When it is time to generate a scheduled report, the function transits from the idle state to the report generation state in a background mode. Upon completion of the report generation, the function transits from the report generation mode to the report distribution state. Once the report is routed, the function transits back to the idle state in a non-visible mode.

In addition to the features described above for the administrative reports function, it is also anticipated that this function may add billing support and additional overread services.

Figure 26:
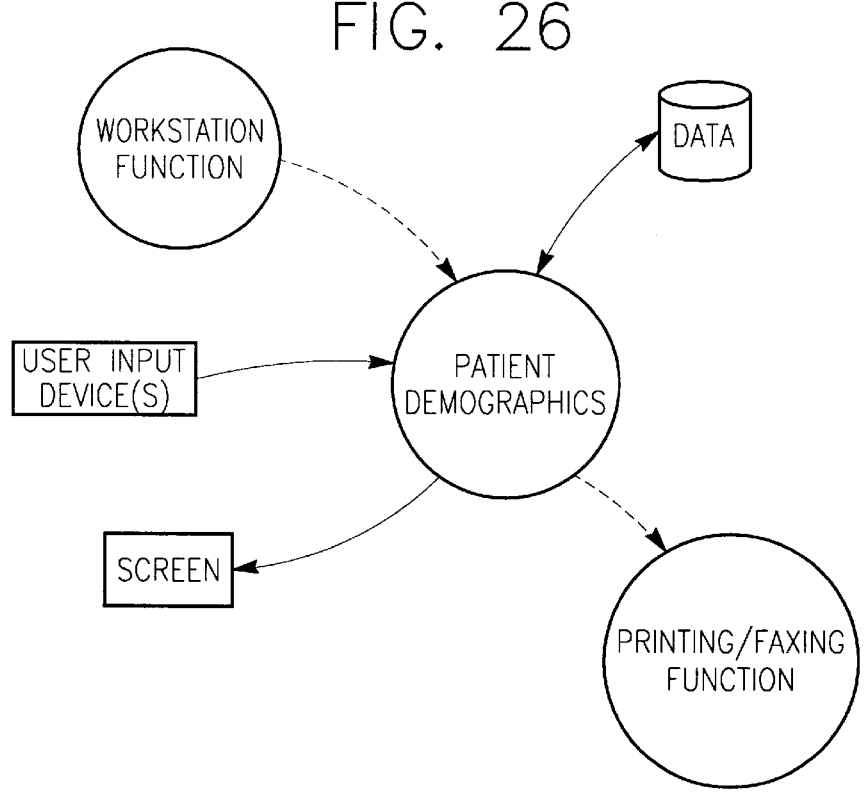
FIG. 26 is a diagrammatic view functionally illustrating the various patient demographics functions of the present invention.

The patient demographics function of the present invention provides for the viewing, printing and editing of current demographics for existing patients and the addition of new patient records. FIG. 26 shows the context diagram for the patient demographics function. The "current demographics" associated with a patient represents the most recent information on that patient. This is updated automatically when new records are received, or it may be updated manually by the user via the patient demographics function. The active current demographics are displayed on the screen for review/editing by the user. A particular patient may be represented by multiple MRN numbers if the patient has had tests run at different sites that are represented by different MRN models. Therefore, all MRNs associated with the patient along with each of the sites for which the particular MRN is valid are automatically displayed to the user. If the user has edit access to the record, the user may edit the fields of the record. Elements of the demographics which have been edited during the current session are prominently displayed (i.e., highlighted or bolded), and each element will preferably indicate the date/time data was last entered or modified. If date of birth is undefined in the record of a patient, age will automatically be incremented by one year if more than one year has passed since the demographics have last been updated. If multiple current demographics records are selected, the user may change which of the open records is the active (viewed) record, and the user is required to save or discard changes to the active record. The user may also add a new current demographics record, and the field values of the new record will be initialized to the defaults specified. The user has the option to either save the edited current demographics record to the system database or cancel any changes that were made to the record. If the user has edited any of the MRN fields or the date of birth field, the user will be notified that the change will affect all procedure records associated with the patient. If a patient MRN field does not contain a unique identifier for the associated MRN model, the user will be informed that a unique patient MRN is required before saving, and the record will not be saved if the unique MRN is not provided. If the user accepts the changes, any changes to the MRN and date of birth fields are saved to the current demographics record and all procedure records associated with the patient. Any changes to fields other than MRN and date of birth will affect only the current demographics record. If the user cancels changes to a new current demographics record, the record is discarded. The user may export the current demographics record to a specified repository, and the ASCII format will be supported for transfer of all of the demographic records. The user may also print the current demographics record(s) currently being viewed; and, if more than one current demographics record is open, the user will be given the choice of printing the active record or all open records. The user may also print multiple copies of the selected record(s) as desired.

In the preferred form of the present invention, the user is able to access the patient demographics function via the patient demographics review function when the user wants to view, edit and/or print one or more current demographics records or add a new record. The user may also enter the patient demographics function for printing without viewing when the user wants to print selected current demographics records without visibly entering the patient demographics function. This function is performed in the background mode. The patient demographics function operates in the idle state, and the function awaits external initiation in the non-visible mode. The patient demographics function operates in the review state wherein the user may view and/or edit the data associated with the selected patient(s). In this function, the user may also add a new patient record. The patient demographics function also operates in a printing state so that the specified current demographics record(s) may be printed, faxed and/or previewed as desired.

Figure 27B:
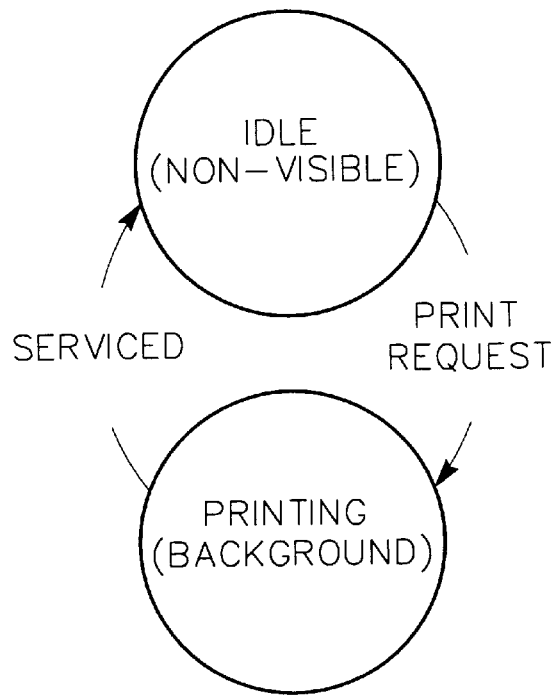
FIGS. 27A and 27B diagrammatically illustrate the state transition diagrams for the various scenarios of the patient demographics functions of the present invention.
Figure 27A:
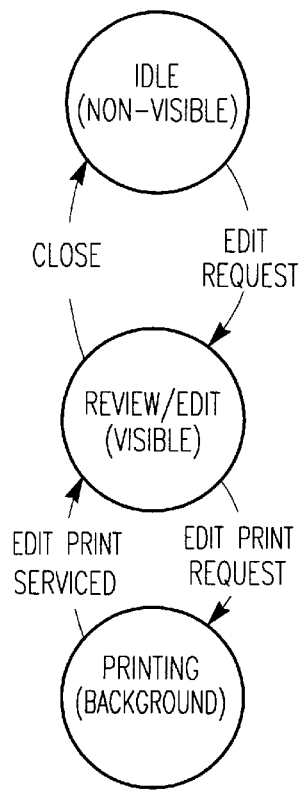

In the patient demographics review scenario of the preferred embodiment, the patient demographics function may be entered in response to a user request to view and/or edit a current demographics record or add a new record. FIG. 27A shows the state transition diagram for the patient demographics review scenario. In this scenario, the function transfers from the idle state to the review state whenever the user opens one or more current demographics records or adds a new patient. In the review state, if multiple current demographics records were selected, the first patient, as determined by the sort order selected by the user, shall be initially viewed in the review state. If the user does not have edit privileges, the user may only view the records. If the user does have edit privileges and any of the selected records are already locked for edit by another user, the current user will be notified that another user is editing the record and the current user will be restricted to view access to that record. If any of the selected records are archived, the user may only view them. All selected records not already locked by another user are then locked for edit by the current user; and, if the user initiates printing of the record(s), the review function will transit to the printing state. If the user closes the patient demographics function, the function requires the user to save or discard changes to the active record, and the function will then transit to the idle state in non-visible mode. The patient demographics function also operates in the printing state; and once a print request is serviced, the function transits back to the review state.

In the present invention, the patient demographics function may also be entered in response to a user request to print one or more current demographics records without viewing them. FIG. 27B shows the state transition diagram for the printing scenario where the user elects not to view the record. The printing patient demographics without viewing function operates initially in the idle state; and once the user selects one or more patients and initiates the function to print the associated current demographics record(s), the function transits to the printing state in background mode. Once the print request is serviced, the function transits to the idle state in non-visible mode. It is anticipated that in addition to the functions described above, the following features may be included in the patient demographics function. These additional features include expansion of the user notification of editing to identify the user name of the person editing the record, as well as the location from which it is being edited, and providing the user with the ability to adjust the field templates and specify field widths and embedded characters (such as parenthesis and dashes for phone numbers).

Figure 28:
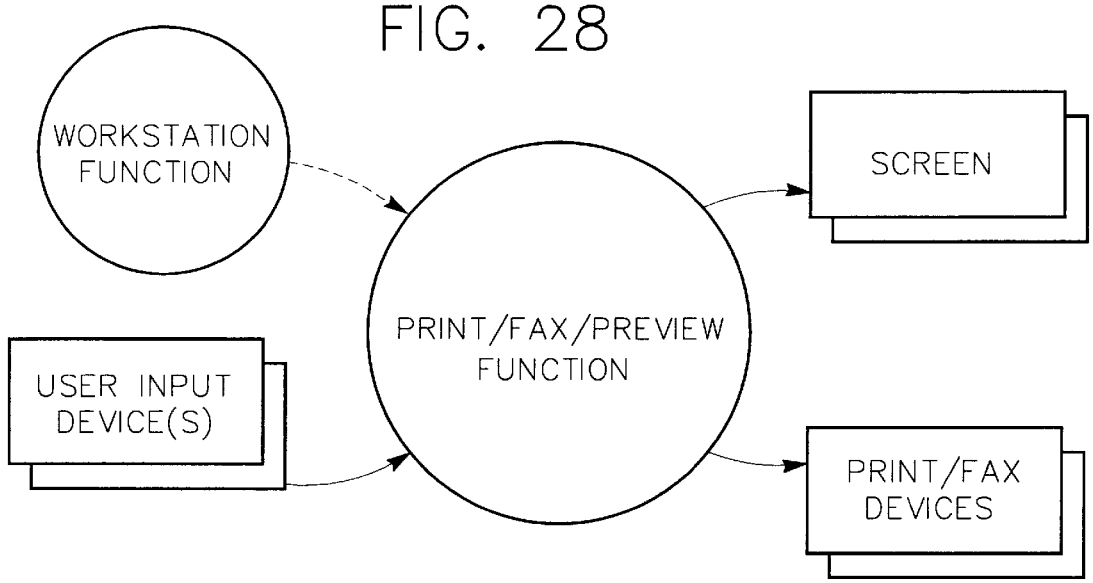
FIG. 28 is a diagrammatic view functionally illustrating the various print, fax and/or preview functions of the present invention.

The print, fax and/or preview function is responsible for the printing, faxing and previewing of textual or graphic material (including waveforms) in the system. It is assumed that the external function which invokes the print/fax/preview function provides this material. FIG. 28 shows the context diagram for the print, fax and/or preview function. This function will typically be operated by all users of the system and provides the user with the ability to print or fax textual, graphical and/or waveform data. The material to be printed or faxed is provided and delineated prior to the invocation of this function. A "preview" function is provided that allows the user the opportunity to view the material on the screen as it would appear if printed or faxed. The user is able to choose a printer or a fax from the list of all networked or local printers and faxes, except that devices under time restriction or in use at the time of selection are not be available for selection. The default device will be the last device selected.

The user is allowed to modify the parameters that apply to the selected device. If the selected device is a fax, the user is requested to provide a phone number for the destination. Initially, the default fax number is blank. The user is allowed to select a member of the system distribution list who has a fax number or manually enter a fax number. The length of time to defer retries and the number of retry attempts are user selectable from one to 10 minutes or attempts. The default parameters for a given device will be the previous parameters used for that device. The system architecture described above for the present invention product will initially identify the printers and faxes that will be supported by the system.

The user may specify that the printing/faxing be performed immediately or deferred to some later time. If printing or faxing is deferred, the user is allowed to indicate when the request is to be initiated by selecting a day of the week and/or a time of day (in hours and minutes). If the deferred printing time falls within the time restriction for the selected printer, the user will be notified and required to select a new deferred print time or cancel the request. If the printing or faxing is not deferred, the printing or faxing will be initiated immediately in a background mode. The user is able to have the selected material printed or faxed at the selected device. If the selected device is currently engaged, this request is queued and serviced when the device is available. If the selected device is a printer, the user may indicate that this material is to be printed before any other print jobs which are queued without this option. If the selected device is a fax and a busy signal is received, the fax request will be deferred and re-tried according to the parameters set during device setup.

The preview capability provided by the print, fax and/or preview function allows the user to view the material on the screen as it will appear when printed or faxed. The user may view the data presented as a single full page. If the material being previewed cannot be viewed within a single screen, the user will be allowed to scroll through the material.

The user is able to access the print/fax/preview function via the scheduled print and/or fax request, print request using defaults, user print or fax request, or print or fax preview modes. A scheduled print and/or fax request occurs when the time to perform a scheduled or deferred print and/or fax request has arrived. In this situation, the print and/or fax device has already been selected, and the device setup parameters have been established (at the time the request was scheduled or deferred). This scenario operates in a background mode. The print request using defaults mode occurs when the user requests that something be printed using the default printer and printer setup. The user print and/or fax request mode occurs when a user has manually requested that something be printed or faxed. The user may select the print and/or fax device and device parameters or may choose to use predetermined default values. The print and/or fax preview mode occurs when a user has requested that the material be displayed on the screen as it would appear if faxed or printed. While viewing the preview display, the user may elect to fax or print the material. The print, fax and/or preview function exhibits the functional state behavior indicated by the idle, print and/or fax setup, print and/or fax and preview functional states. The idle state is the initial state for the print, fax and/or preview function. This function is not visible to the user and awaits external initiation. In the print and/or fax setup state, the user is allowed to select a print and/or fax device, establish the operational parameters for that device, and select the timing of the print and/or fax operation (immediate or deferred). This state operates in a visible mode. In the print and/or fax state, the print and/or fax image is transmitted to the selected print and/or fax device. This state operates in a background mode. In the preview state, the user is allowed the opportunity to view the material on the screen as it would be printed or faxed. This state operates in a visible mode.

Figure 29A:
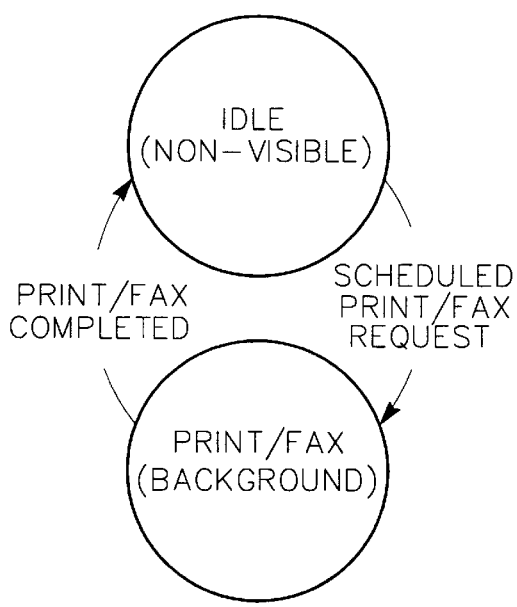

The print, fax and/or preview function may be entered in response to a scheduled or deferred request to print or fax in accordance with the scheduled print and/or fax request scenario. The printer or fax device is determined when the function is entered, so no operator intervention is required; this scenario operates in a background mode. FIG. 29A shows the state transition diagram for the scheduled print, fax and/or preview scenario. In the idle state, the function awaits initiation in a non-visible state. When the time arrives for a scheduled print or fax to occur, the function will automatically transit to the print and/or fax state in a background mode. The print and/or fax state ends when the print and/or fax request is completed. The function will then transit to the idle state in a non-visible mode.

Figure 29B:
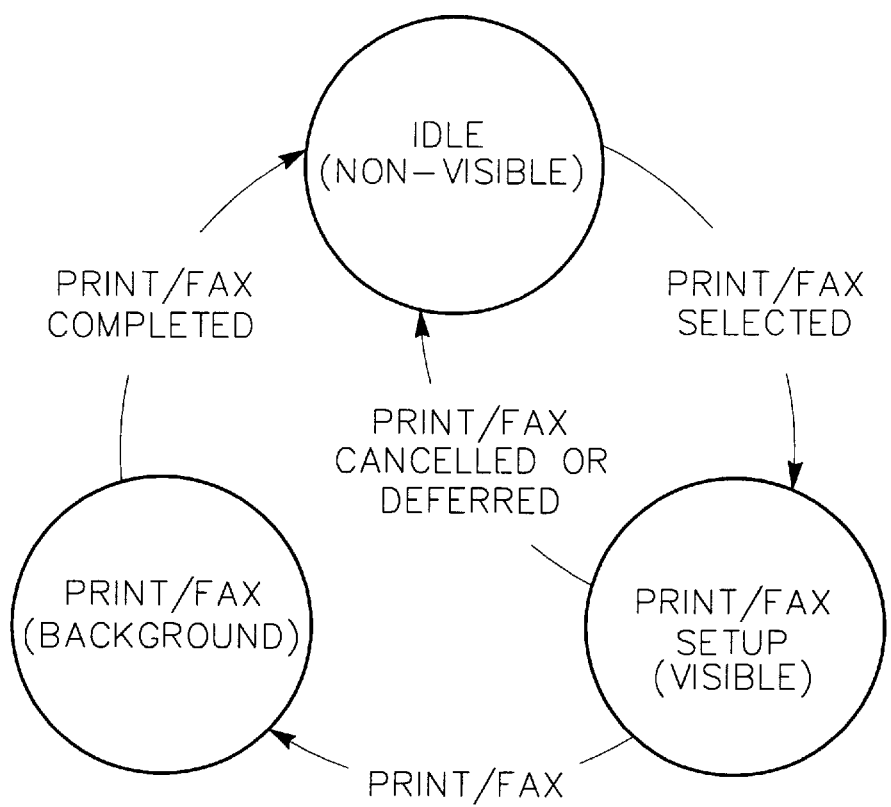

The print, fax and/or preview function may be entered in response to a user request to print something using the default printer in accordance with the print request using defaults scenario. FIG. 29B shows the state transition diagram for the print request using defaults scenario. In the idle state, the function awaits initiation in a non-visible state. When the user requests printing with defaults, the function transits to the print and/or fax state in a background mode. When the print and/or fax request is completed, the function will transit from the print and/or fax state to the idle state in a non-visible mode.

Figure 29C:
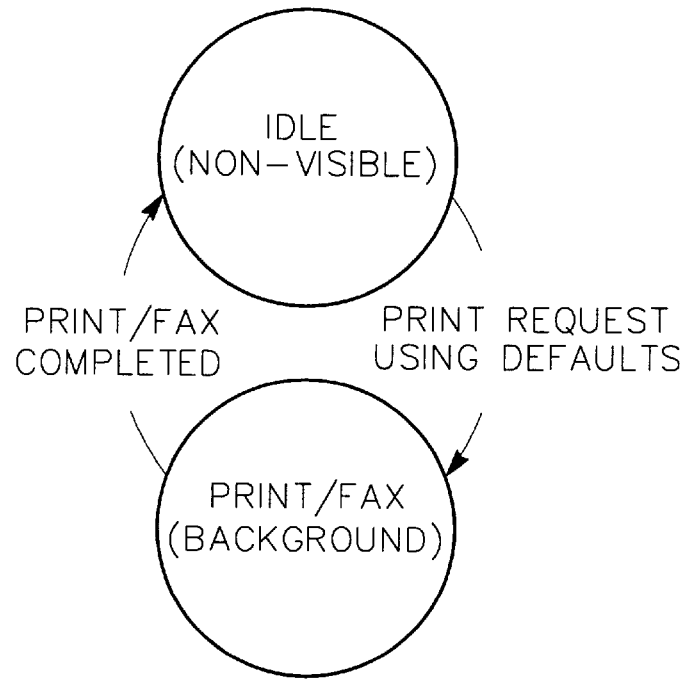

The print, fax and/or preview function may also be entered in response to a user request to print or fax in accordance with the user print and/or fax scenario. FIG. 29C shows the state transition diagram for the user print and/or fax request scenario. In the idle state, the function awaits initiation in a non-visible state. When the user initiates printing or faxing of something, the function shall transit to the print, fax and/or preview state in a visible mode. If the user elects to print or fax, the function transits from the print and/or fax setup state to the print and/or fax state in a background mode. If the user elects to defer or cancel the print and/or fax operation, the function will transit from the print and/or fax setup state to the idle state in a non-visible mode. When the print and/or fax request is completed, the function transits from the print and/or fax state to the idle state in a non-visible mode.

The print and/or fax preview scenario may also be initiated when the user elects to preview something that might be printed or faxed. FIG. 29D shows the state transition diagram for the print and/or fax preview scenario. In the idle state, the function awaits initiation in a non-visible state. When the user initiates print and/or fax preview, the function will transit from the idle state to the preview state in a visible mode. If the user elects to setup a printer or fax device, the function transits from the preview state to the print and/or fax setup state. If the user elects to print or fax what is being previewed, the function will transit from the preview mode to the print and/or fax state. If the user elects to end the preview session, the function transits to the idle state in a non-visible mode. The function will transit from the print and/or fax setup state to the preview state when the user has selected or setup the printer or fax device. When a print or fax request is completed, the function transits from the print and/or fax state to the idle state in a non-visible mode.

In addition to the features set forth above for the print, fax and/or preview function, it is anticipated that the print, fax and/or preview function may be expanded to allow the selection of multiple phone numbers for a single fax job. Additionally, if multiple faxes have been queued up to be sent to the same destination, the system may send them as a single session, regardless of their order in the queue.

Figure 30:
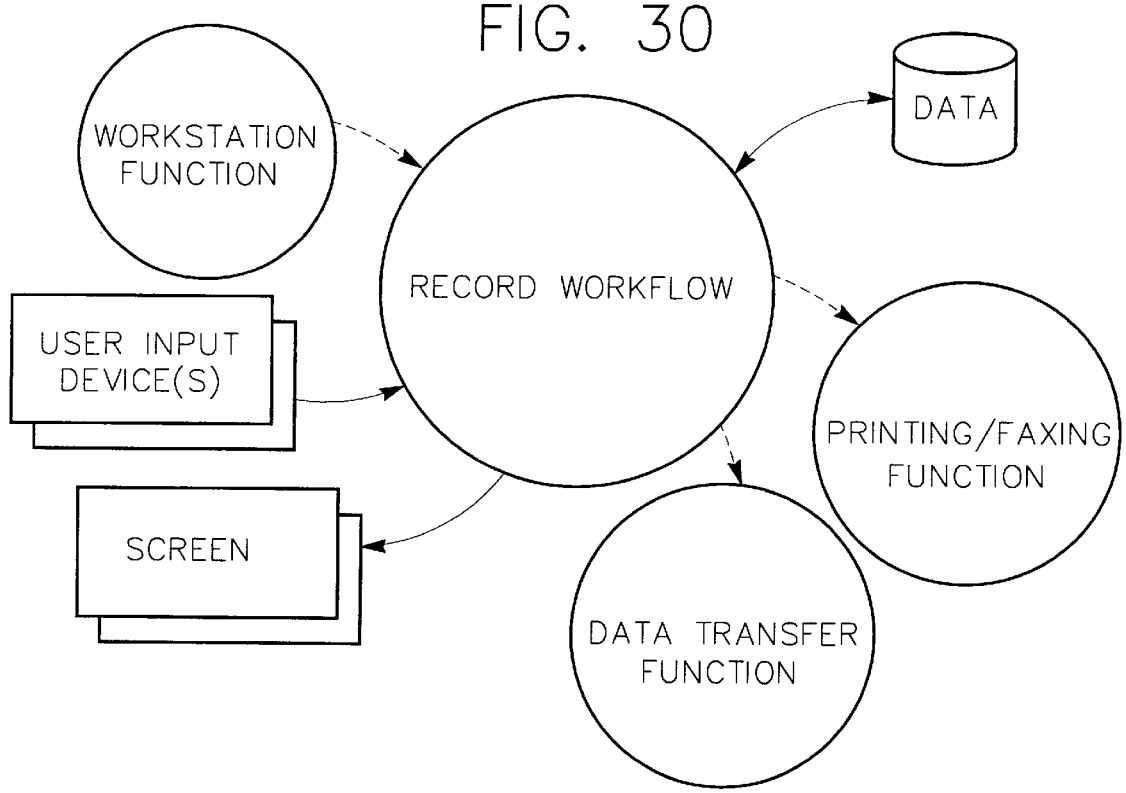
FIG. 30 is a diagrammatic view functionally illustrating the various record workflow functions of the present invention.

The following description of the record workflow function of the present invention describes the basic processing that occurs for all procedure records and the user setup which is allowed to control the process in the preferred embodiment. FIG. 30 shows the context diagram for the record workflow function. With this function, the user can set up a record workflow for each type of record received. This workflow will control how a record is distributed, abridged, etc. For instance, the user may set up the record workflows so that resting records received from a certain clinic will be distributed upon receipt to Dr. Jones for overreading, distributed to Medical Records upon confirmation, and abridged after 3 months. Stress records received from the clinic may be distributed upon receipt to Dr. Howell for overreading, distributed to Medical Records upon confirmation, and abridged and archived after 1 month. The user may also setup the record workflows so that Resting records received from another clinic are abridged upon receipt.

With the present invention, the workflow of each record is preferably tied to a specific procedure type, since procedure specific criteria can be used to qualify the workflows. When a record is received on the system, the appropriate workflow is selected based on certain key fields in the record. The present invention preferably includes the use of selected record fields to uniquely identify a workflow for the acquisition institution which corresponds to a site in the site list; the acquisition location which may correspond to a location in the site's location list; the acquisition department which may correspond to a department in the site's department list; the acquiring physician(s) which may correspond to a physician in the system physician list; the acquiring technician(s) which may correspond to a technician in the site's technician list; the patient MRN which may be combined with the site specific MRN model to create a unique patient identifier; the patient name; the patient gender; the patient date of birth; the procedure type and the acquisition date and time. Many acquisition instruments will not have site, location, department, physician, and technician lists that correspond to the system lists. Therefore, these fields are represented by free text entries. Depending on the workflow associated with the record, the system may or may not try to reconcile the text entries to system list entries. For instance, if Site A wishes that records from the ER be handled differently then ones from the hospital rooms, the location fields will have to be reconciled for records from Site A. If a Site B wishes the system to be able to run administrative reports querying on physician and technician activities from Site B, those fields will have to be reconciled for records from Site B. In order for the receiving system to correctly identify these fields in records, it forces the users to agree on the contents of the site, location, department, physician, and technician lists, update the workstation system lists accordingly, identify the MRN model used by each site and update each of the acquisition instruments that will be supplying records to the system. In the present invention, it is important that the institution name/ID exactly match an entry in the system site list. If the site wishes the system to support queries on the location, department, physician, and/or technician fields (e.g., to support administrative reports), those fields must also be updated to match entries in the system lists. Some sites (sites using the system only for storage) may select not to reconcile these fields. Fields that cannot be reconciled with entries in system lists will be reconciled to an "unspecified" or default. The input text strings are retained for the record workflows function.

With the record workflows function of the present invention, the user is able to review a list of record workflows. A default workflow is provided with the system for each installed procedure type. The default record workflows are the workflows that will be used for any records not covered by user-created workflows. The user is able to create new workflows. The new workflow may be based on the default workflow for the specified procedure unless another workflow is specified by the user. The user is also able to modify all workflows (including the certain of the defaults). The system is designed to prevent the user from creating overlapping workflows (where a single record qualifies for multiple workflows) and the user may delete all of the workflows except for the default workflows. The user may also print workflows as described above. For each new record workflow, the user is required to assign a unique name to the workflow. This name should preferably be descriptive, such as "Resting Procedures from A clinic".

In the preferred embodiment, various fields qualify which records will be handled by the workflow. For example, the user is preferably able to select one procedure type from the list of procedures supported by the system and one or more acquiring sites from the site list. For each site selected, the user may then select one or more acquiring locations from the site's location list (if the site has a location list). The user is preferably then queried for any procedure specific workflow qualifications because each procedure may add specific qualification fields. For instance, resting records may be qualified based on the diagnosis so that normal ECGs may be handled differently than abnormal ECGs. Once a workflow is identified, the user can define what actions will be performed on the record.

The fields relating to record reception actions will control what occurs upon record reception. For example, the user will be able to override the procedure status (e.g. records coming from the location "ER" may be set to "Stat") and the user may select a special distribution list identifying destinations to which unconfirmed records are to be distributed upon receipt. The user may then select a distribution list identifying destinations to which confirmed records are to be distributed upon receipt. Throughout this procedure, the user is able to enable or disable the fields of the record that will be reconciled to entries in system lists.

Upon record confirmation, the user may select a distribution list identifying destinations to which the record is to be distributed upon confirmation and also reconfirmation. The user is also preferably queried for any procedure abridgment rules and the may specify when the record is to be abridged (how long after it has been received on the system). Choices for automatic abridgement of the record include upon reception, a specified number of months after receipt, upon confirmation, upon archival, on demand(default) or never. The user is preferably able to override abridgment times for a particular record. For example, the normal resting ECG workflow may require that all resting ECG records be abridged after three months. However, if Dr. Jones considers Jon Doe's Mar. 24, 1992 resting procedure to be of particular interest, he can disable abridgment (set to "Never") for that particular record. The user may also specify when the record is to be archived (how long after it has been received on the system). These choices preferably include upon reception, a specified number of months after receipt or on demand (default).

The user is also be able to review a list of distribution lists and may create new distribution lists or edit or delete existing distribution lists. The user may also print distribution lists as described above. Each distribution list is preferably made up of up to about 20 routing destinations. For each routing destination, the user may select a destination from the system distribution list, select attending physician, if the record's attending physician field corresponds to a physician in the system physician, or select confirming physician if the record is confirmed and the record's confirming physician field corresponds to a physician in the system physician list. If the distribution method is not noted, the user may specify the number of copies to be sent and define which previous reports will be distributed with the current report (serial presentation). The search limit (in months prior) is preferably in a range of about 0–99 months and the number of most recent prior reports is in the range of about 0–9. Only records satisfying both parameters will be included in the distribution. The user will also be queried for any procedure specific information (such as format to be used).

When a record is received on the system, the institution name and ID will be reconciled with the corresponding system site. If no association can be made, the acquiring site shall be considered "unspecified". If enabled, the location, department, physician, and technician fields will also be reconciled. If reconciliation has been enabled for the field, an attempt shall be made to match the entry to an entry in the system list. If no association can be made, the field will be assigned to "unspecified". If reconciliation has been disabled for the field, the field will be assigned to "unspecified". In the present embodiment, assigning a field to "unspecified" does not result in the loss of the original text string. If the record does not meet the qualifications of any of the defined workflows, the default workflow for that procedure will be used. The database to which a record will be stored is determined by the record's acquiring site and procedure type.

The record will also be assigned to a patient folder and stored. If the system configuration is "Standalone" or "Networked, Isolated Databases", the record will only be compared to patient folders on the assigned database. If the system configuration is "Networked, Integrated Databases", the record will be compared to all patient folders on the system. The patient demographics portion of the record is compared to the current demographics of existing patients on the database(s). The record is then assigned to a patient folder according to various patient folder assignment rules. If the record is assigned to an existing patient folder or if a new patient folder is created, the demographics of the record and/or the current demographics of the patient folder are updated. The new record contains an acquisition date and time and each field of the current demographics will have the acquisition date/time of the data stored with the field. Each field in the current demographics will then be compared to the associated field in the new record. If the field in the new record is empty or older than the current demographics field and the current demographics field is not empty, the field in the new record is updated with the value from the current demographics. If the field in the new record is non-empty and newer than the current demographics field, the current demographics field and the associated date and time are updated with the value from the new record. If the procedure record does not already exist on the system, it is saved to the database identified for that procedure type and acquisition site. If the procedure record already exists on the system (same patient folder, procedure type, acquisition date, and acquisition time), the most recently edited record is saved to the assigned database and the older one discarded. If the system is unable to determine which record was most recently edited, both records are saved to the assigned database. If the workflow indicates that the procedure status should be updated, the record is updated to reflect the new status. If the record is unconfirmed, it is distributed as defined in the unconfirmed distribution list. If the record is confirmed, it is be distributed as defined in the confirmed distribution list. If automatic record abridgment was set up for "Immediately" the record will be abridged as specified in the appropriate procedure report. If automatic record archival was set up for "Immediately" or automatic record abridgment was set for "Upon Archival", the record is abridged as specified in the appropriate procedure report and the record is archived.

In the preferred embodiment, a record is assigned to a new or existing patient folder by initially evaluating whether or not there is a matching patient folder. If the user confirms that another record is not different, the record may be marked as conflicting and assigned to the patient folder with the matching MRN model and MRN. If the user indicates that the records are not conflicting, a new patient folder will be created for the record. When a record is saved, the conflict detection rules are automatically run. The record's conflict flag is set or cleared based on the results of the conflict detection. When a record is confirmed, the record is be distributed as defined in the workflow unless distribution is disabled by the user. If automatic record abridgment was set up for "Upon Confirmation" the record is also abridged as specified in the appropriate procedure report. When a record is reconfirmed, the record is be distributed as defined in the workflow unless distribution is disabled by the user.

Figure 31:
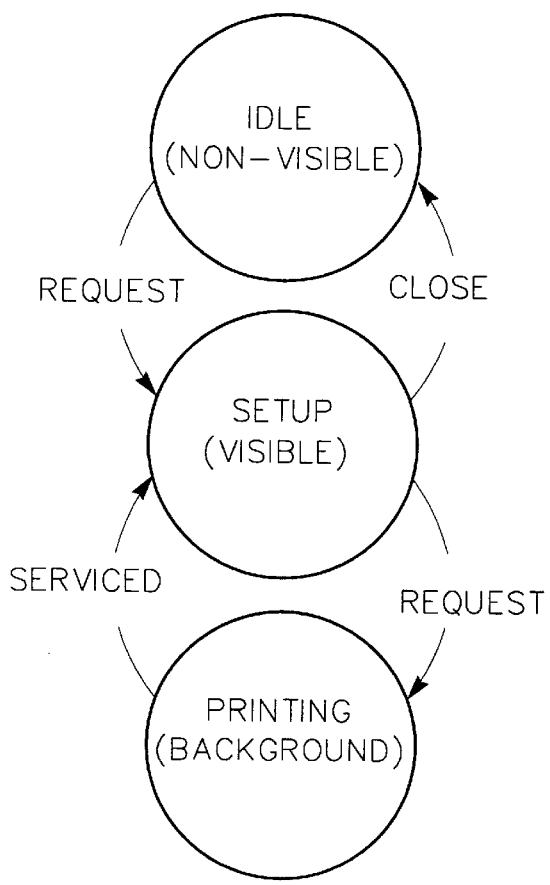
FIG. 31 is a diagrammatic view illustrating the state transition diagram for the record workflow scenario of the present invention.

Some activities can be set up to occur automatically when the record reaches a specified age (as measured in time since the record was received on the system). The record age shall be monitored and the appropriate functions triggered as specified in the workflow. For example, record abridgment may occur if specified in the appropriate procedure report functional specification. Record archival may also be set to occur if automatic record abridgment was set for "Upon Archival". The user may access the record workflow function via the workflow setup, record reception, record confirmation and timed activities scenarios. The record workflow function is initially in the idle state. The function is not visible to the user and awaits external initiation. In the setup state, the user reviews/edits workflows and/or distribution lists. The workflow execution state occurs when the workflow is executed. In the printing state, the data is printed, faxed and/or previewed. The record workflow function is entered whenever a user requests to review or edit the workflow or distribution lists. FIG. 31 shows the state transition diagram for the record workflow setup scenario. The idle state occurs whenever the user initiates the function, the function will then transit to the setup state in a visible mode. If the user initiates printing of the setup parameters, the function transits from the setup state to the printing state. If the user exits the setup function, the function will transit to the idle state in a non-visible mode. Once a print request is serviced, the function transits from the printing state back to the setup state.

The record workflow function will also be entered whenever a record is received on the system (e.g., an instrument transmitted the record to the system). When a record is received on the system, the function will transit from the idle state to the workflow execution state in a non-visible mode. Once all applicable workflow actions have been executed, the function transits from the workflow execution state to the idle state in a non-visible mode.

The record workflow function is also entered whenever a record is confirmed or reconfirmed. When a record is confirmed, the function will transit from the idle state to the workflow execution state in a non-visible mode. Once all applicable workflow actions have been executed, the function will transit to the idle state from the workflow execution state in a non-visible mode.

The record workflow function may also be entered whenever the age of the record surpasses the time limit set for an activity in the record workflow function. When the time since a record was received on the system surpasses one of the activity time limits set in the workflow, the function transits from the idle state to the workflow execution state in a non-visible mode. Once all applicable workflow actions have been executed the function will transit from the workflow execution state to the idle state in a non-visible mode.

In addition to the features set forth above, the record workflow functions may be expanded to include a feature which qualifies workflow by department so that for each site selected, the user may select one or more acquiring departments from the site's department list (if the site has a department list). Additionally, it may be desirable to provide the user with the ability to turn off conflict detection for certain records.

Figure 32:
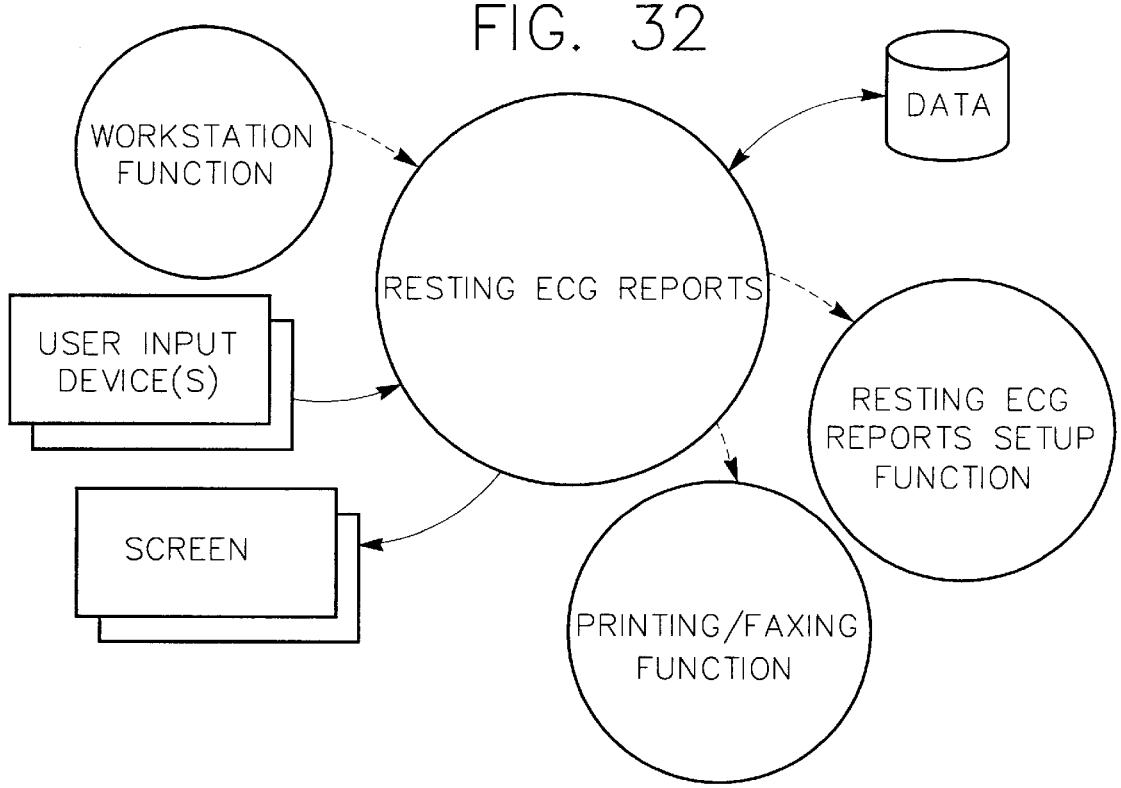
FIG. 32 is a diagrammatic view functionally illustrating the various resting ECG final report functions of the present invention.

The resting ECG reports function is responsible for the generation, editing, printing, and routing of resting ECG reports. It is triggered by an external system client function. This section describes the functional requirements for a single instantiation of this function. Depending on the system configuration, many users may be using instantiations of this function simultaneously. FIG. 32 shows the context diagram for the resting ECG reports function. In general, the requirements specified below describe functions performed on resting ECG records. One or more records are initially selected, and then this function is initiated. One report is generated for each selected record. For viewing and printing, each report will initially be displayed in the format associated with the current user. Copies of the report may then be distributed to different locations, using a different format for each copy. Each report preferably consists of up to two segments, a 12-lead segment and an extended measurements segment.

The user is allowed to view any of the reports one segment at a time. If the user is assigned the appropriate privileges, the 12-lead segment may be edited. Only one user at a time may edit a particular record. If a record is opened for edit by another user, it will only be available for viewing by other users. Editing is performed on data in the record; consequently, changes to a given data element will be reflected in all report segments that subsequently use the data element. At the user's discretion, reports may be confirmed, distributed and printed. The user may also change how the report looks by selecting a new format or changing the individual parameters of the current format. When the user is finished, the edited reports can be saved and any changes to the resting ECG record are then updated to the database.

Resting ECG reports are generated and reviewed as described below. If the acquisition site of the record belongs to a different time zone than the receiving institution, the acquisition date and time of the displayed or printed report will be adjusted to reflect the receiving institution time zone. The reports are displayed on the screen for review by the user, and the user may change the viewed report or change the report parameters, causing regeneration of the report. If the record is a new record, the patient demographics information for the new record will be initialized to the values from the current patient demographics for the selected patient. If date of birth of the patient is undefined in the record, the identified age will be updated if more than one year has passed since the demographics have been last updated. If the record is marked as conflicting, the display will indicate that it is conflicting and identify the patient with whom it is conflicting. The initial display of reports during a review session will be based on the predefined user specific parameters which govern the initial display mode and report format of the displayed reports. Serial presentation will be disabled for each open record and subsequent display of reports during a review session will return to the page/ segment last displayed. If the serial presentation window was previously open for that record, it will be displayed again (if split screen) or be available (if full screen), showing the last viewed serial presentation record. If the serial presentation window was not previously open for that record, no serial presentation window will be displayed. If multiple resting ECG records are open, the user may change which of the open records is the active (viewed) record, and the user will be required to save or discard changes to the active record. The user is also able to change the display mode of an active record.

In the patient demographics mode of the resting ECG reports function, the complete set of patient demographic information valid at the time of the test will be displayed. This includes some values which are not displayed on the printed report, such as address. In the test information mode portion of the resting ECG record, the textual information for the 12-lead segment as well as some patient demographics, basic measurements and interpretation will be displayed. In the waveforms mode, the waveform data of the 12-lead segment is displayed. At a minimum, the footer information (including patient MRN and test date/time) is also displayed with the waveform data. In the 12-lead report mode, the 12-lead segment of the report resembles a printed 12-lead report and contains both test information and waveforms. In the extended measurement report mode, the extended measurement segment of the report will resemble a printed extended measurement report. The user may initiate report setup to select a new format or change individual format parameters for the active record (waveform layout, print speed, etc.). If resting ECG records other than the active record exist for the patient, the display will also indicate that serial records exist. The user may also enable or disable serial presentation for the active report. The user is able to initiate report printing and may enable or disable abridgment for the active report. If abridgment is not disabled for the active record, the user is able to manually abridge the active record and also initiate manual report distribution or notification for the active report.

The user may also compare the active report to reports associated with other resting ECG tests run on that patient (if available) using serial presentation. When the serial presentation made is enabled, the report associated with the most recent resting ECG record prior to the active record for the active patient is displayed. If no prior record exists, the user is notified, and serial presentation is disabled for the active record. If the serial presentation layout selected in setup is "tiled," the screen will be split into two windows with the report representing the active (current) record in the top window and the report representing the serial record in the bottom window. If the serial presentation layout selected in setup is "full screen," the report representing the serial record is displayed on the full screen, and the user may toggle between the display of the current report and the serial report. The serial presentation report will be displayed in a manner that makes it obvious to the user that it is not the current report (e.g., different background) and the user cannot edit either of the reports in the serial presentation window.

The initial display of reports during a review session are governed by the predefined user specific parameters. Subsequent display of reports during a review session will cause the function to return to the page or segment last displayed. The user may then change which of the patient's resting ECG records (other than the current record) is currently being viewed in the serial presentation window and may also change the display mode of the serial record. The user is also able to initiate report setup to select a new format or change individual format parameters for the serial report independent from those of the current report. If the current or serial presentation reports are tiled, the user may make either the window for the current report or the window for the serial presentation report the full screen display. If the user closes the serial presentation window, the window for the current report will go to the full screen display. If the current or serial presentation reports are full screen, the user may tile the windows. If the user closes the serial presentation window, the window for the current report will be viewed and the serial presentation report will then be closed if the current report is closed.

The resting ECG reports function also allows the user to edit the header and interpretation section of the current record (serial presentation records cannot be edited). The record may then be saved, confirmed, or reconfirmed. The specific edit requirements vary based on the type of acquisition device the record was acquired on. Any changes made to a data element will be reflected in all segments in which that data element appears, and any data elements that have been edited during the current session will be displayed prominently (e.g., highlighted or bolded). The user may also save the resting ECG record to the system database identified for that record by overwriting the existing record. Additional actions, such as conflict detection, may be performed upon saving a record. If a conflict is detected, the user will be notified of the conflict along with an indication of the patient with whom the record conflicts and the nature of the conflict. The user will then have the option of completing the save (with the record marked as conflicting) or cancelling the save.

The user may also request record confirmation on unconfirmed records. In many institutions, resting ECG records may be overread by residents (without the ability to legally confirm a record) or a licensed cardiologist. If this feature is enabled in the resting ECG report setup, the user may mark a record as "overread" by entering the overreading physician's name from the physician's list, entering free text, or entering an acronym representing the physician. The user is also required to enter the name of the confirming physician by selecting from the physician's list, entering free text, or entering an acronym representing the physician. The physician list is filtered to include entries applicable only to the resting procedure. The record will then be marked as confirmed, and the user may enable or disable distribution of the confirmed record. The editing of confirmed records allow the user to save the changes to the system database without reconfirmation if the interpretation statements, diagnosis or basic statements were not changed during editing. If any of these items were changed, the user is required to reconfirm the report in order to save the changes. The user will also be notified that the report has already been confirmed, and any changes may affect the confirmed interpretation. If the user then chooses not to reconfirm, the changes will be abandoned. If the user chooses to reconfirm, the user is required to enter the name of the confirming physician by selecting from the physician list, entering free text, or entering an acronym representing the physician. The user may also enable or disable distribution of the reconfirmed record.

The abridgment function of the resting ECG reports function may be disabled by setting abridgment time to "Never." If abridgment is not disabled, the record can be abridged manually by the user. If abridgment is disabled for the current report, the record will not be abridged. To abridge a resting record, all extended measurements must be deleted. For manual abridgment, all waveform data not necessary to reproduce the report in the current format must be deleted. For automatic abridgment, all waveform data not necessary to recreate the report is automatically deleted.

Report distribution can be initiated manually for the active record or may occur automatically on record receipt, confirmation, or reconfirmation. If the active record is distributed manually, the user may select a distribution list which has been filtered to only include entries applicable to the resting procedure. The record and the serial presentation record(s) meeting the serial presentation criteria in the distribution list will be routed to each destination listed in the distribution list. The distribution list specifies the routing parameters (number of copies, serial presentation inclusion, etc.). If the destination is a physician, technician or administrator, the notification path for the physician, technician or administrator specifies the desired routing method. If the destination is a fax or a printer, copies of the report(s) will be faxed or printed according to the previously defined specifications. If the destination is a system user, the user will be notified with a system message. If the destination is a system connection, the report will be transmitted to the indicated location. If the destination is a pager, the specified pager number will be called and the specified message entered.

The user may also print the report(s) currently being viewed. If more than one record is open, the user will be given the choice of printing the active report or all open reports. The user may also specify which segment(s) of the report is to be printed. If the 12-lead segment is to be printed, the user is able to select diagnosis only; basic measurements only; basic measurements, diagnosis and interpretation statements; basic measurements, diagnosis, interpretation statements and reasons; or no interpretation for the interpretation section of the segment. The user may also enable or disable the masking of patient demographics on the printed report(s) and specify the number of copies to be printed. If the record is marked as conflicting, the report will indicate that it is conflicting and identify the patient with whom it is conflicting.

The resting ECG reports function also allows the user to export the record in the ASCII format. The user is able to enable or disable the masking of patient demographics on the exported record and select which fields of the record will be exported. Additionally, the user may select a new report format or change the parameters of the existing format for the active record. These changes will only affect the active record and will remain in effect for that record until the user closes the record. The user also has the option to change the global report setup parameters for the open record.

In the preferred form of the present invention, the user is able to access the resting ECG reports function via the report review scenario and the report printing without viewing scenario. The report review scenario occurs when the user wants to view, edit or print one or more resting ECG reports or create a new resting ECG record. The report printing without viewing scenario occurs when the user wants to print selected reports without visibly entering the resting ECG report function. The user may also access the resting ECG reports function via the report confirmation without viewing scenario, record reception scenario, or the timed activities scenario. The report confirmation without viewing scenario occurs when the user confirms a report without visibly entering the resting ECG report function (i.e., doctor overread and agreed with interpretation). The record reception scenario occurs when a resting ECG record is received from an external source. The timed activities scenario occurs when stored resting ECG records are automatically abridged or archived after residing on the system for a predetermined length of time.

The resting ECG reports function exhibits the state behavior for the idle state, report review state, printing state, report distribution and notification state and the report setup state. The idle state is the initial state for the resting ECG reports function. In this state, the function is not visible to the user and awaits external initiation. In the report review state, the user may view the report, view the serial presentation and edit the report. In this state, the user is able to switch between selected reports. In the printing state, the report(s) is printed, faxed and/or previewed. In the report distribution and notification state, the report is routed. In the report setup state, a new format may be selected, or the parameters associated with the active record may be modified.

Figure 33A:
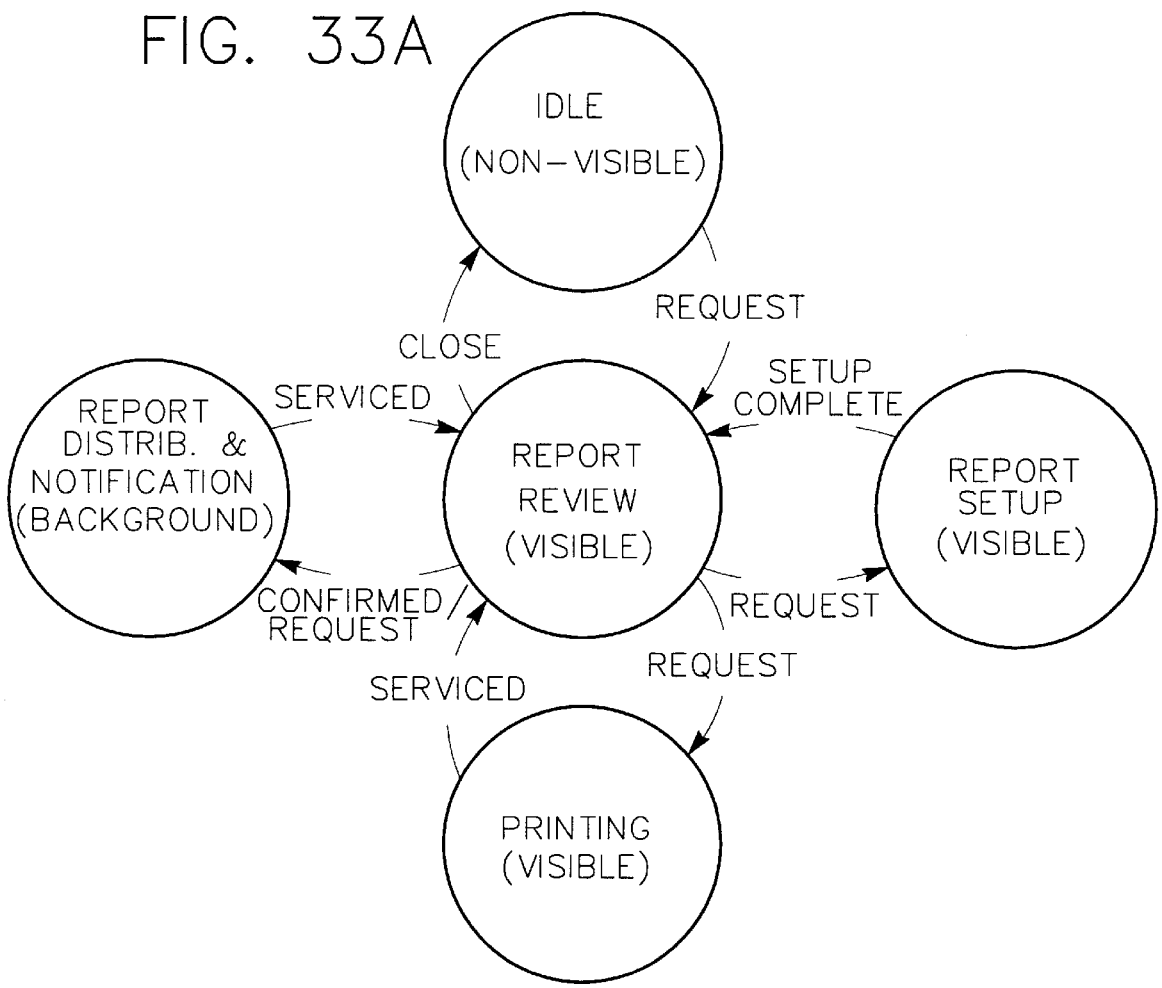
FIGS. 33A and 33B are diagrammatic views illustrating the state transition diagrams for the resting ECG final report functions of the present invention.

The resting ECG reports function may be entered in response to a user request to view/edit one or more resting reports or to create a new resting ECG record. FIG. 33A shows the state transition diagram for the report review scenario. In this scenario, the idle state is the initial state. When the user opens one or more resting ECG records or requests to create a new resting ECG record, the function transits to the report review state in a visible code. If multiple resting ECG records were selected, the first record as determined by the sort order previously selected by the user will be initially viewed. If the user does not have edit privileges, the user will only have view access to the records. If any of the selected records are already locked for edit by another user, the current user will be notified that another user is editing the record, and the current user will be restricted to view access. If any of the selected records are archived, the current user will only have view access to them. All selected records not already locked by another user will be locked for edit by the current user if the user has the appropriate edit privileges. When the user initiates printing of the report(s), the function will transit to the printing state. If the user initiates confirmation with routing or manual routing, the function transits to the report distribution and notification state. If the user requests to change the report format, the function transits to the report setup state. If the user closes the resting ECG reports function, the function requires the user to save or discard any changes the user has made to the active record. The function will then transit to the idle state in a non-visible mode. Once a print, fax or print preview request is serviced, the function will transit from the print state back to the report review state. When the routing is complete, the function transits from the report distribution and notification state to the report review state. When the user requests to exit the report setup state, the function transits from the report setup state to the report review state.

Figure 33B:
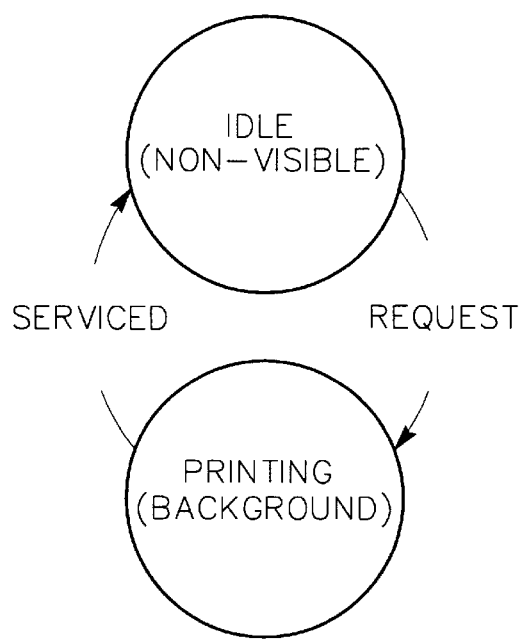

The resting ECG reports function may also be entered in response to a user request to print or fax one or more resting reports (without viewing the report). FIG. 33B shows the state transition diagram for this scenario. When the user selects one or more resting ECG records and triggers the function to print the report(s) without review, the function transits from the idle state to the printing state in a non-visible mode. Each enabled segment for each selected resting ECG record is generated based on the report format associated with the current user. Once a print request is serviced, the function transits from the print state to the idle state in a non-visible mode.

In addition to the features described above for the resting ECG reports functions, it is anticipated that the functionality may be expanded to accommodate various resting interpretation functions; allow generation of custom resting ECG reports; allow full serial comparison; provide the user with the ability to edit multiple records without saving between records; perform waveform zoom and use electronic calipers to aid in the measuring of waveforms on the screen. Additionally, it is anticipated that the desired functionality may further include side by side serial presentation display of about 10 seconds of waveform on each side, the addition of the Ordering Physician to reports, the addition of physician schedules to the routing of reports, and allowing the user to format extended measurements in the basic measurements area of headers.

Figure 34:
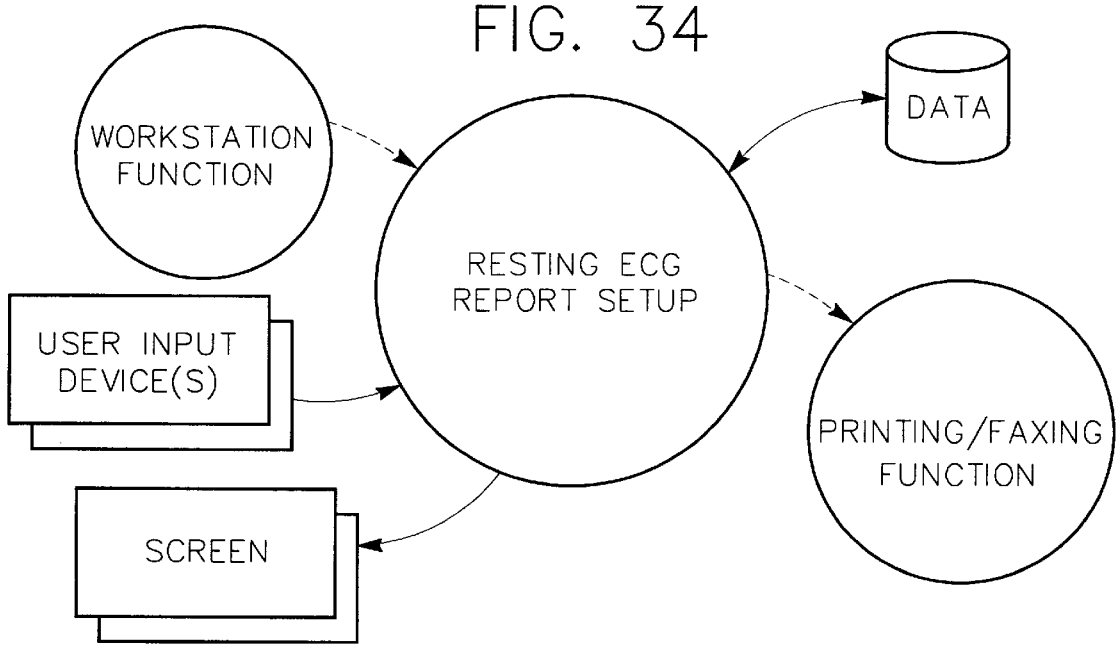
FIG. 34 is a diagrammatic view functionally illustrating the various resting ECG report setup functions of the present invention.

The resting ECG report setup function is responsible for the viewing, editing and printing of report formats, as well as user specific review settings and record workflow parameters. If resting ECG records are currently open, format changes will only affect that specific record. For example, while editing a resting ECG record, a user may decide to change the lead format from Standard to Cabrera 12-lead. This change will affect this record only. On the other hand, the user may also elect to establish the Cabrera lead format as the default for all reports and change the report distribution lists using the resting ECG report setup function. FIG. 34 shows the context diagram for the resting ECG report setup function.

Resting ECG report formats determine how the resting ECG report(s) will be generated upon entering the resting ECG reports function. A default format is typically shipped with the system, and the user is able to create new resting ECG report formats. The user may base new formats on an existing format or modify the existing formats (including the default format). The user may also delete any format except for the default format. If the deleted format was assigned as a user(s) initial report format, the affected user(s) initial report format will be reassigned to the default. With the resting ECG report setup function, the user is required to provide a name for the format that is unique to resting report formats and may not rename the default resting format. The user may also select standard 12-lead or cabrera 12-lead and choose the font (from a list of supported fonts) that will be used for printing the report.

The header of the resting report is typically made up of patient demographic information as well as some measurements and institution information. With the resting ECG report setup function, the user may select whether the report header will be located at the top of the report or the bottom of the report. The user may also customize the header by choosing which patient demographic fields will be included. The user may not eliminate the patient MRN field. The user may select various waveform layouts for the 12-lead report including 3×4 Sequential; 3×4 Sequential, 1Rhythm; 3×4 Sequential, 3Rhythm; 6×2 Sequential; 6×2 Simultaneous, 1 channel rhythm; 3 channel rhythm; 6 channel rhythm, and 12 channel rhythm for the 12-lead reports. For each of the available 12-lead waveform layouts set forth above which also include a rhythm portion less than the 12 channel rhythm layout, the user must also select a lead from a list of leads that are available with the selected lead format for each rhythm channel. The user may also enable or disable the filter on reports that are not abridged and have unfiltered data available and may select 25 mm/sec or 50 mm/sec as the waveform print speed. The lead sizes for displayed and printed waveforms may be selected as 5 mm/mV, 10 mm/mV or mm/mV; and, if the selected waveform gain is greater than 5 mm/mV, the user may set the size of the V leads to half or full of the selected gain setting.

The resting ECG report setup function also allows the user to enable or disable the display of interpretive statement codes or statements reasons. The user may also enable the deletion of hints upon confirmation. The user may also number the interpretive statement as desired.

The user of the preferred form of the present invention may modify the parameters which control the initial presentation of the resting ECG reports function to the user. In the initial display mode, the user may choose one of the patient demographics, test information, waveforms, 12-lead report or extended measurement report as one of the initial display modes. The user may also select a serial presentation layout with tiled or full screen for viewing of the serial presentation. The user may choose an initial report format which dictates how records opened by the user will be displayed and initially printed. This type of setting may be overridden during a review session. The user may save these settings as private where the settings only apply to the current user. The settings may also be saved as group so that the settings apply to all users in the group who do not have private settings defined. If the user belongs to more than one group, the user is required to select the group(s) that the assignment will affect. The user may also select system settings so that the saved settings apply to all users who do not have private or group settings defined.

When a user opens a resting ECG report for review, the system uses the defaults as defined by the following priorities. If the user has a private setting, it is used. If the user does not have a private setting but belongs to one or more groups with group settings, the system chooses one of the group settings for the user. If the user has no private or group settings, the system setting is used.

The present system allows some institutions to train residents by having the resident do a preliminary overread of ECG records. These records are then later confirmed by a staff physician. The user is able to enable or disable entry and display of the Resident Overread field. Coded interpretative statement lists (including codes and modifiers) are maintained by the system for each version of each resting interpretation algorithm supported by the system. With the system of the present invention, the user is able to review these lists and add new entries, modify user defined entries or delete user defined entries on the list.

The resting ECG report setup function allows the user to qualify the workflow of resting ECG records using the fields of diagnosis where the user is able to select one or more diagnoses from the system diagnosis list; i.e., it would be possible to select only normal reports for a particular diagnosis, as well as to select all reports classified as abnormal for the desired diagnosis. The diagnosis list is also filtered to display only entries which are applicable to the resting procedure. Another selectable field which may be initially set up by the user is the record priority field. In this field, the user is able to select "normal," "Stat," or "all." Patient age is another selectable field in which the user is able to select "Pediatric," "Adult," or "Both." The user can also set each destination in a distribution list and specify additional information for resting reports such as which segment(s) of the report is to be routed.

If the 12-lead segment of the report is to be routed, the user is able to select various information levels for the interpretation section of the segment, such as no interpretation; basic measurements only; diagnosis only; basic measurements, diagnosis and interpretation statements; or basic measurements, diagnosis, interpretation statements and reasons. As part of this selection, the user may select a specific report format from the list of report formats.

In the present system, the user may also define how a resting ECG record is abridged. For example, the user may be required to specify the lead format for abridged reports, the waveform layout for abridged reports and the filter setting for abridged reports.

The resting ECG report setup function allows the user to access the default setup where the user is able to view, modify and/or print the resting ECG report system formats and other setup parameters. The user also has access to the resting ECG report setup function via the report setup feature where the user is able to change report formats and change the current report format parameters for the active resting ECG record. These changes in the current report parameters do not affect the system formats.

Figure 35A:
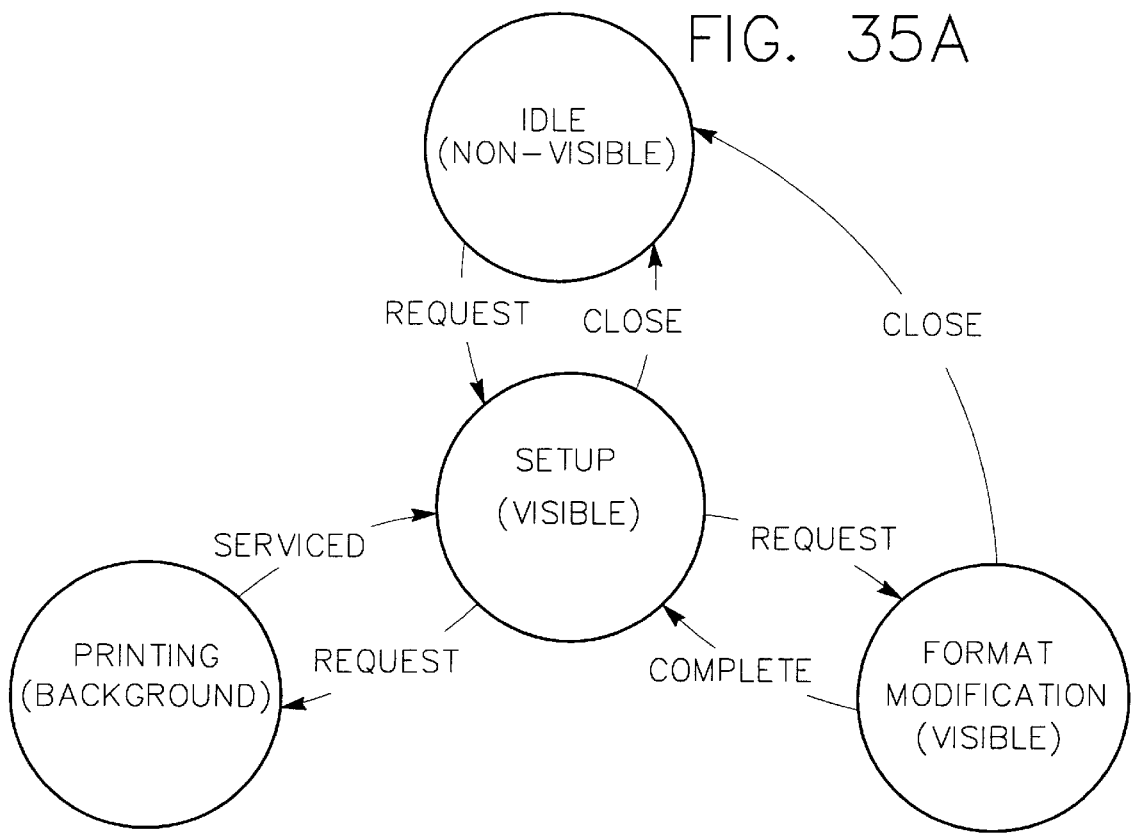
FIGS. 35A and 35B are diagrammatic views illustrating the state transition diagrams for the resting ECG report setup functions of the present invention.
Figure 35B:
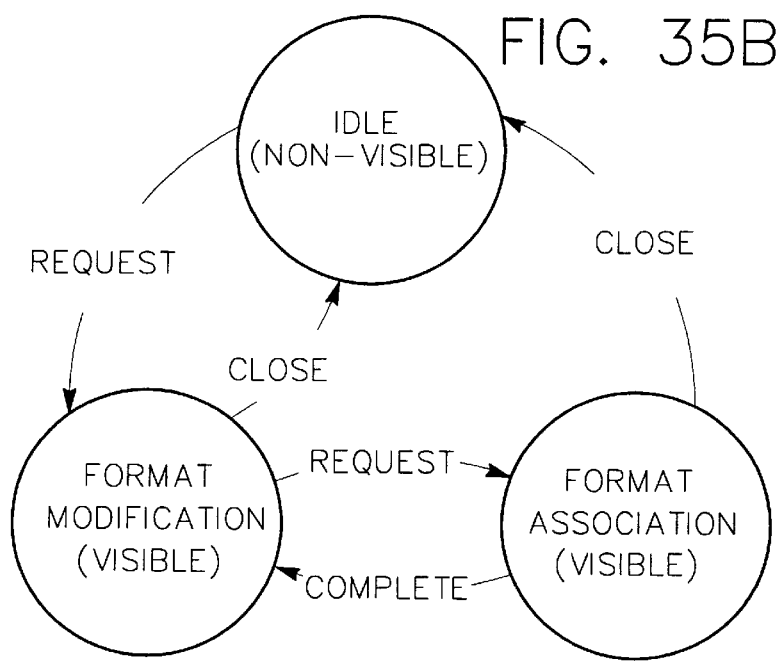

In the preferred form of the present invention, the resting ECG report setup function preferably exhibits the state behavior shown in FIGS. 35A and 35B. The initial state for the resting ECG report setup function is the idle state. This function is not visible to the user and awaits external initiation. During the setup state, the user selects report formats, establishes user specific settings, and modifies the coded interpretive statement lists. In the format modification state, the user views or edits the parameters associated with a particular format. In the format association state, the user may select a new resting ECG report format from a list of resting ECG report formats for the current or active resting ECG record. In the printing state, the parameters for the selected report format are printed, faxed and previewed. In the workflow definition state, the user defines the workflow for a resting record.

The resting ECG report setup function may be entered in response to a user request to view or edit the resting ECG setup parameters. FIG. 35A shows the state transition diagram for this scenario. In this scenario, the idle state occurs when the user initiates the function which then transits to the setup state in visible mode. In the setup state, if the user initiates modification or requests creation of a report format, the function transits to the format modification state. If the user initiates printing of the selected report format, the function transits to the printing state. If the user closes the resting ECG report setup function, the function transits to the idle state in non-visible mode. The format modification state ends when the user completes the modification of a report format. The function then transits to the setup state. If the user closes the resting ECG report setup function, the function will then require the user to save or discard any new changes to the format. The function will then transit to the idle state in non-visible mode. Once a print request is serviced, the function shall transit back to the setup state.

In the resting ECG report setup scenario, the ECG report setup function may be entered in response to a user request to edit the resting ECG report generation parameters for the active resting ECG record. FIG. 35B shows the state transition diagram for this scenario. Once the user initiates the resting ECG report setup function, the function transits to the format modification state in a visible mode. If the user requests to choose a new format, the function transits to the format association state. If the user closes the resting ECG report setup function, the function requires the user to save or discard any current changes to the format. Saving changes to the report format only affects the current view of the active resting ECG report, and the actual report format is not updated. The function then transits to the idle state in a non-visible mode. When the user completes the selection of a new format or cancels the action, the function transits from the format association state to the format modification state. If the user closes the resting ECG report setup function, the function transits to the idle state in a non-visible mode.

It is anticipated that in addition to the features of the resting ECG report setup function set forth above, the features may be expanded to include customization of resting ECG reports, rhythm reports greater than 10 seconds, fixed-length rhythm reports with and without rhythm analysis, and setup for serial comparison. Additionally, it is desirable to add the choice "auto sense" to Lead Size and V-Lead Size selections and report the font selection in a report section-by-section. Furthermore, a beneficial added feature is to allow the user to qualify workflows based on the Arrhythmia Indicator so that the user may select "on," "off," or "both" and to allow the user to disable abridgment of records containing arrhythmias by setting the abridgment time to "Never."

Figure 36:
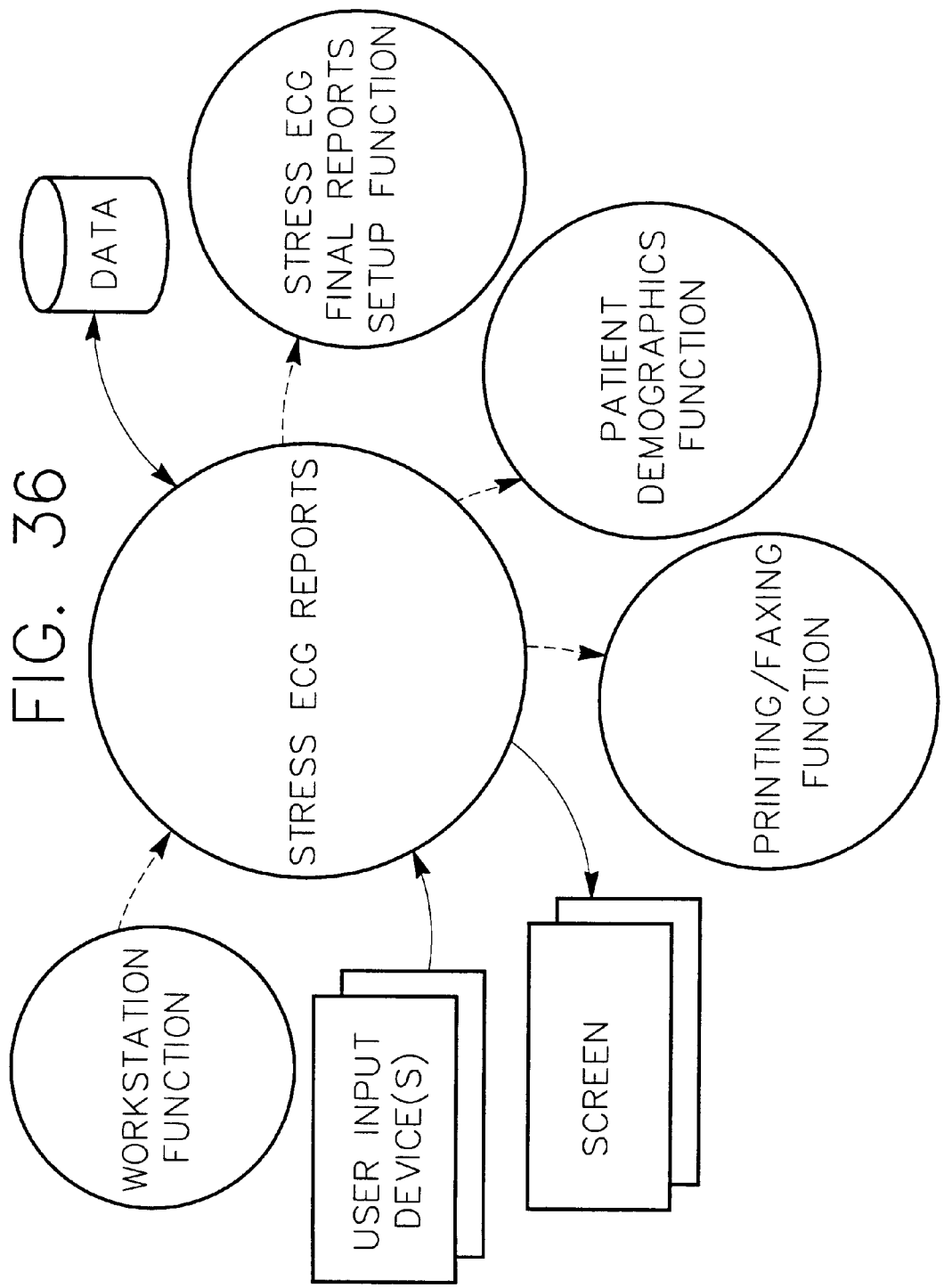
FIG. 36 is a diagrammatic view functionally illustrating the various stress ECG final report functions of the present invention.

The stress ECG final reports function is responsible for the generation, display, editing, printing, and routing of stress ECG reports. It is triggered by an external system client function. FIG. 36 shows the context diagram for the stress ECG final reports function. This section establishes the preferred requirements for the stress ECG final reports function. In general, the requirements specified in this section describe functions performed on stress ECG records. One or more records are selected, and this function is initiated. One report is generated for each selected record. The report is generated based on the final report format associated with the attending physician listed in the record. Each report consists of multiple segments which are appended in a specific sequence. The text document segments of a report are generated from pre-test data, event data and post-test data. The pre-test data may include data such as patient demographics and the reason for the test. The event data preferably includes information such as a ten-second ECG analysis and measurements, blood pressure data and comments. The post-test data preferably includes information such as the reason for ending test and test-maximal indications. The waveform document segments of a report are preferably generated from a combination of average-beat and ECG data. Typically, the textual information will also be included in the segment. The user may view any of the reports one segment at a time. If the user is assigned the appropriate privileges, the segments of the stress ECG may be edited. only one user at a time may edit a record; and, if a record is opened for edit by another user, it will only be available for viewing by additional users. Editing is performed on data in the record; consequently, changes to a given data element will be reflected in all report segments that subsequently use the data element. At the user's discretion, reports may be confirmed, abridged, distributed and printed. The user may change how the report looks by selecting a new format or changing the individual parameters of the current format. When the user is ready, edited reports can be saved, and any current changes to the stress ECG record are then updated to the database. In addition to the user initiated activities described above, many automatic activities such as report reception, distribution and abridgment may also occur.

Figure 37A:
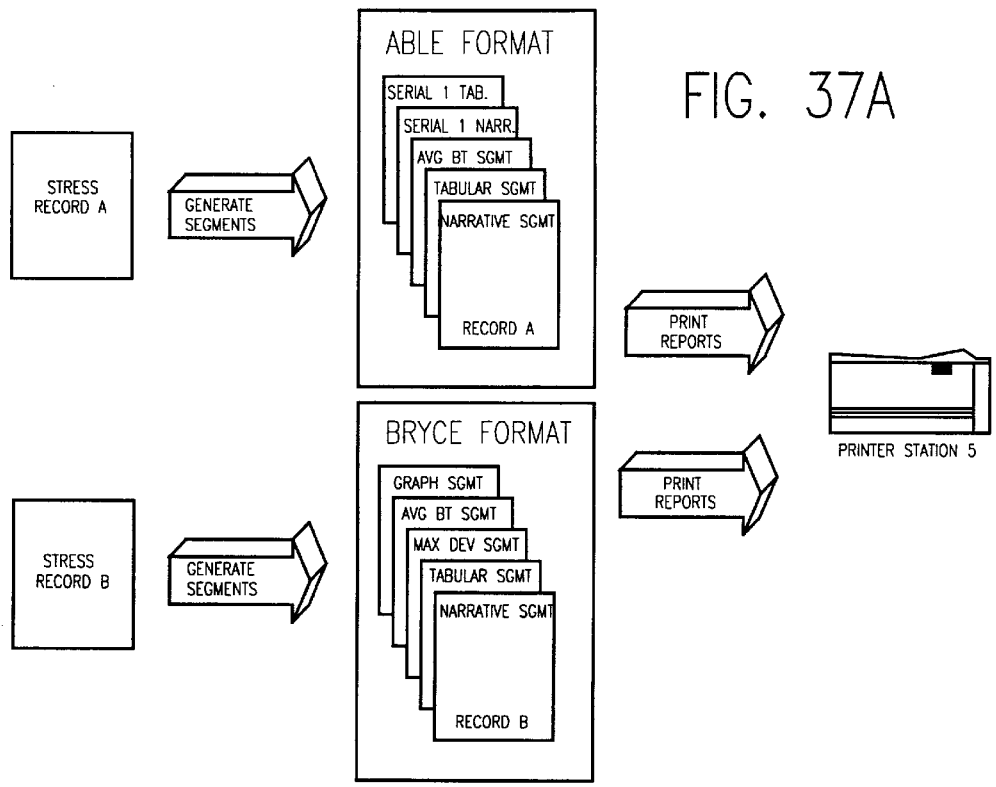
FIGS. 37A and 37B are diagrammatic views illustrating examples of report generation procedures using the stress ECG final report functions of the present invention.
Figure 37B:
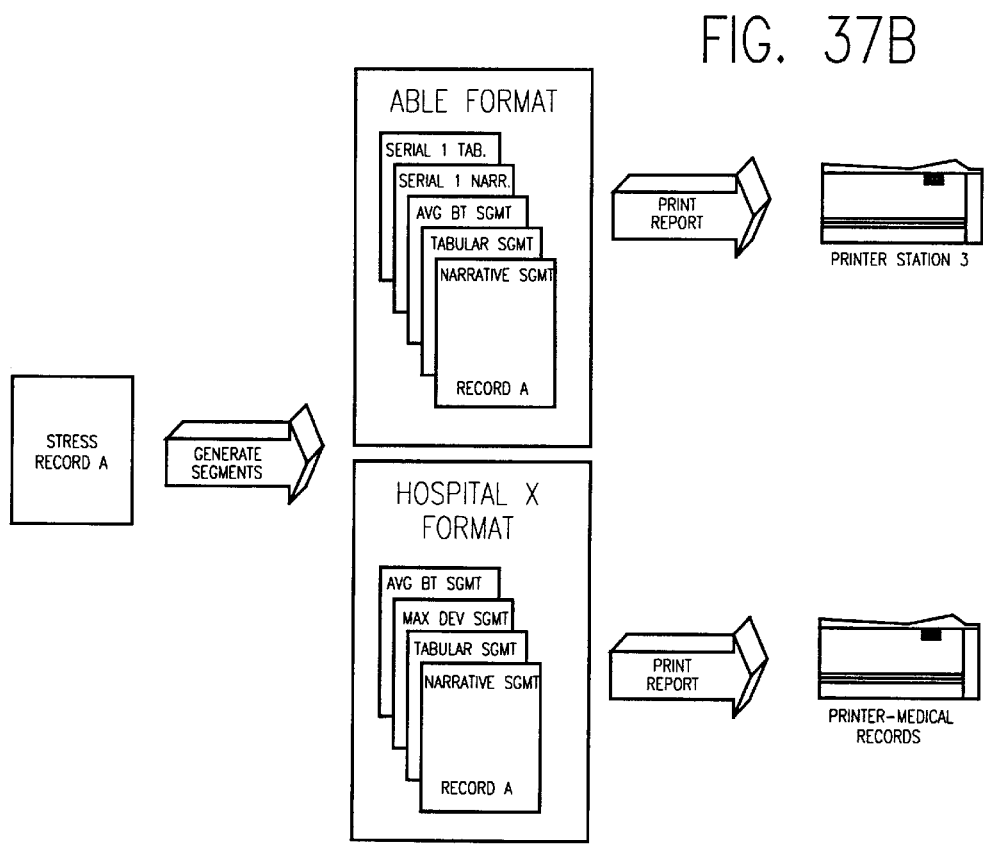

FIG. 37A illustrates how finished reports are constructed from the various generated report segments using the stress ECG final reports function. In this example, stress ECG records A and B have been received by the system from stress test room 1. The pre-defined workflow for stress records from room 1 requires that one copy of each report be printed in the attending physician's format at the printer at station 5 upon receipt. The attending physician for A is Dr. Able, who is associated with the Able Final Report Format. This format indicates that the Narrative Summary, Tabular Summary, and Average Beat Summary segments are printed with the most recent serial presentation report for that patient. The attending physician for B is Dr. Bryce, who is associated with the Bryce Final Report Format. This format indicates that the Narrative Summary, Tabular Summary, Maximum Deviation, Average Beat Summary and Trend Graphs segments are printed with no serial presentation reports. The reports are picked up at station 5 by Dr. Able and Dr. Bryce. They look them over, write in comments and hand them to an ECG technician for editing. The technician then logs onto the system and opens both records. All segments of each report and all serial presentation reports associated with those records will be available for the technician to view and/or edit. These segments are generated according to the format associated with the record's attending physician. Once the technician has completed the edit session, the technician requests the system to confirm and route the report for Record A. The workflow for stress records from room 1 requires that one copy be routed to station 3 for printing, using the attending physician's format for inclusion in the patient's charts, and one copy is routed to the medical records for printing, using the Hospital X format for inclusion in the patient's permanent records as shown in FIG. 37B.

Final reports representing stress ECG records include multiple segments. The requirements described below illustrate the preferred method of generating these segments. All final report segments will contain the same single-line footer format on each page. The patient MRN, patient name, billing number, acquisition date and time and edit date and time appear left to right and are left justified in the footer. If the acquisition site of the record belongs to a different time zone than the institution, the acquisition date and time of the displayed or printed report is adjusted to reflect the institution time zone. For printed report segments, the page number appears right justified in the footer. For viewed report segments, a page number does not appear. The footer appears as the last line at the bottom of the page in both landscape and portrait modes following the portrait or landscape orientation of each report segment. If the masking patient demographics feature is enabled, all occurrences of the patient MRN, patient name and billing number in the generated report are masked, and a false patient MRN will be generated. The false generated MRN is repeatable, and all other masked records for the same patient are matched, decodable and unique so that they match neither current nor future patient MRNs. The patient name and billing number are also obscured or blanked.

For stress ECG reports, average beat waveforms will be generated with the averages reflecting a gain of 10 mm/mV. These average beat waveforms are scaled according to the appropriate zoom factor, and the averages will reflect a print speed of 25 mm/sec, which is also scaled according to the appropriate zoom factor. The stress ECG reports also include TicK marks which are used to identify the isoelectric point and J point for each average beat. The stage and stage time identifications for data events are also included in several report segments. For the resting phase of the stress test, the event identification is the rest label effective at the time of the data event. For the exercise phase of the stress test, the event identification is the exercise stage number followed by stage time and exercise time or total elapsed time for the data event. For the recovery phase of the stress test, the event identification is a textual identification of the recovery phase, followed by the stage time of the data event.

If the narrative summary segment of the final report has not been previously edited, this segment will be generated by replacing the data place holders defined in the template for this segment with data values from the active stress ECG record. This report segment is preferably a single or multiple page text document generated in portrait mode, and no fixed header is included for this report segment. If the narrative summary segment of the final report has been previously edited, the edited segment is generated precisely as edited.

With the stress ECG final reports function of the present invention, the tabular summary report segment is generated by labeling the rows and columns of a table and inserting actual data values from the active stress ECG record into the table. A single-line header is centered at the top of the first page of the report segment to identify the type of report segment. The tabular summary report segment is a single or multiple page text document generated in a portrait mode. The table rows are generated for synchronous and asynchronous events. For synchronous events, such as 10-second data events and programmed stage changes, the total number of rows generated for the table is determined by the interval selection in the final report format for this segment. The intervals may be stage intervals only or stage intervals plus a selected timed interval. A row is created for each asynchronous event, such as a protocol change, comment entry or RPE entry, and rows are presented in temporal sequence from top to bottom. Table rows are labeled with data event time identifiers at the left end of the row. The rows are grouped by test phase and stage, and the test phases are separated by double horizontal lines. Stages within a test phase are separated by single horizontal lines. Table columns are generated as specified in the final report format for this segment, and table columns will be labeled according to the parameters specified in the report format for each column. The columns are filled in for the event in each table row so that, for synchronous event rows, each column in the table contains the indicated data value effective at the time of the synchronous event. For asynchronous event rows, the table columns are overwritten with a textual event description, such as "Changed to Bruce Protocol," or an entered comment, such as "Patient breathing heavily."

This function also allows a maximum deviation report segment to be generated by arranging data from the active stress ECG record. A single-line header is centered at the top of the first page of the report segment to identify the type of report segment. This report segment is a single-page text and waveform document which is generated in the landscape mode. For each lead in the stress ECG record lead format, resting and maximum ST depression average beats are displayed at 100% size. The average beats are grouped as pairs, side by side, and the pairs of average beats will be labeled and correspond left to right as Resting and Maximum. Average beat groupings also include a lead identifier with each maximum ST depression average beat having a data event time identifier above the baseline and to the right of the average. For each average beat, the corresponding ST level and slope data values are displayed with the associated labels below the baseline and to the right of the average. If the selected lead format is a standard or Cabrera 12-lead, the waveform layout will be as specified in the final report format. If the selected lead format is a 3-lead format, the waveform layout will be 3×1 with each lead pair on an individual waveform channel. A calibration pulse will also appear at the right end of each waveform channel used for the segment.

The stress ECG final reports function also allows the user to create a peak exercise comparison report segment which is generated by arranging data from the active Stress ECG record. This report includes a single-line header which appears centered at the top of the first page of the report segment to indicate the type of report segment. Below the header line, data event time identifiers for peak exercise and total recovery time will be listed. This report segment is preferably a single-page text with the waveform document generated in a landscape mode. The report is generated in 6×2 format for 12-lead formats and generated in 3×1 format for 3-lead formats. For each lead in the stress ECG record lead format, resting and peak exercise and final average beats are displayed at 100% size. The average beats are grouped side by side in trios, and the trios of average beats are labeled and correspond left to right as resting, peak and final. The average beat groupings include a lead identifier; and for each average beat, corresponding ST level and slope data values are displayed with the associated labels below the baseline and to the right of the average. A calibration pulse will also appear at the right end of each waveform channel used for the segment.

The stress ECG final reports function also allows the user to select an average beat summary report segment which is generated by arranging data from the active stress ECG record with a single-line header which is centered at the top of the first page of the report segment to identify the type of record segment. The report segment is also a single or multiple page text and waveform document which is generated in the landscape mode. The number of rows or channels and the leads each row represents will be as specified by the final report format. If the selected lead format is a 3-lead format, the number of rows or channels is three. A column is generated for each set of resting averages available, and columns are presented in temporal sequence from left to right. For exercise phase averages in this report, the columns generated will depend on the reporting interval specified in the final report format. If the reporting interval is "stage plus time," a column is generated for each multiple of the time interval specified in the format. At least one column is generated for each stage, following any timed columns generated, and the average displayed in this column represents the last average generated in that stage. A column is also generated for peak exercise averages if it is not already included in the report segment. For the recovery phase averages in this report segment, columns are generated at the interval defined in the current format. If the interval is defined as "Stage plus time," a column will be generated for each multiple of the time interval following peak exercise as specified in the defined format. At least one column is also generated for each minute interval, and the columns are appended in progressive time sequence from left to right to form full pages if possible. For each column, a data event time identifier is displayed at the top of the column which identifies the time the averages represent; and for each channel, the average beat(s) for the lead associated with the channel is displayed as well as the average beat corresponding to the data event time identifier for that column. If the type of averages specified in the format is "current and resting averages," the resting average will also be displayed to the left of the current average. For each average beat, the corresponding ST level and slope data values will be displayed with the associated labels below the baseline and to the right of the average beat. A lead identifier will appear above the baseline and to the left of the left-most average beat on each page of the segment. A calibration pulse will also appear at the right end of each waveform channel used on each page of the segment.

The user may also select a trend graphs report segment which is generated by plotting data from the active stress ECG record on specific two-axis graphs. In this report segment, a single-line header appears which is centered at the top of the first page of the report segment to identify the selected record segment. This report segment is formed as a single or multiple page text and graphics document which is generated in a landscape mode. The final report format specifies how many graphs are generated and which data parameters are plotted on each graph. Each graph plots a single data parameter, with the exception of blood pressure, which plots both diastolic and systolic pressures. For each graph identified in the final report format, a label will appear above the graph indicating the data parameter(s) being graphed. The X-axis is labeled with time units (e.g., "Minutes") ranging from zero to thirty minutes after start of the exercise phase, and the Y-axis is labeled with the units of measure for the graphed data parameter. Both axes have at least four major labeled numeric subdivisions corresponding to the X and Y-axis parameters. Minor subdivisions, if any, will not be labeled. All available data points for the graphed data parameter will be plotted and connected in temporal sequence by a continuous line. A visual marker is displayed above each graphed data line indicating peak exercise, and the diastolic and systolic pressure lines of the blood pressure graph are differentiated. A legend is included to indicate which line represents pressure. Up to nine graphs may be displayed per page, and the graphs are positioned as specified in the final report format.

The stress ECG final reports function also allows the user to select recordings segments which are generated from full disclosure data. All waveforms for the duration of the test are saved with the record or are generated from saved snapshots in certain acquisition devices. Not all stress ECG records contain data for the ECG recording segment, and the ECG recording segment is only generated if the record contains the required recording data. This report segment may be a collection of single or multiple page text and waveform documents which are generated in a landscape mode.

The reports for the stress ECG final reports function are displayed on the screen, one segment at a time, for review by the user. The user may change the viewed report or change the report parameters. If the report parameters are changed, the report will be regenerated. If the record is a new record, the patient demographics information for the new record will be initialized to the values from the current patient demographics for the selected patient. If the patient date of birth is undefined in the record, the age will be adjusted accordingly if more than one year has passed since the demographics have been lasted updated. If the record is marked as conflicting, the display will indicate that it is conflicting and identify the patient with whom it is conflicting. During the initial display of reports during a review session, serial presentation will be disabled for each open record, and the reports are generated based on the final report format associated with the attending physician listed in the record. If a default final report format cannot be identified for the attending physician, the system default format shall be used. For subsequent display of reports during a review session, the function will return to the page or segment last displayed; and if the serial presentation window was previously open for that record, it will be displayed (if split screen) or be available (if full screen), showing the last viewed serial presentation record. If the serial presentation window was not previously open for that record, no serial presentation window shall be displayed. If multiple stress ECG records are open, the user may change which of the open records is the active (viewed) record. The user will first be required to save or discard any current changes to the active record. The user is also able to change which report segment of the active record is currently being viewed; and if the new segment has not been reviewed during the current review session, the first page of the segment will be displayed initially. If the new segment has been reviewed during the current review session, the function will remember which page of the segment was displayed last and display that page. When the ECG recordings segment is displayed, the user may change which recording is currently being viewed. The user is also able to initiate the final report setup feature to select a new format or change individual format parameters for the active record. If stress ECG records other than the active record exist for the patient, the display will indicate that serial records exist. The user may enable or disable serial presentation for the active report. The user may also initiate report printing for the selected report segment and enable or disable abridgment for the active report. If abridgment is not disabled for the active record, the user may manually abridge the active record. The user may also initiate manual report distribution and notification for the active report.

The user may compare the active report to reports associated with other stress ECG tests run on that patient (if available) by using the serial presentation feature. When serial presentation is enabled, the report associated with the most recent stress ECG record prior to the active record for the active patient will be displayed. If no prior record exists, the user will be notified, and serial presentation is disabled for the active record. If a "tiled" serial presentation layout is selected in setup, the screen will be split into two windows with the report representing the active or current record in the top window and the report representing the serial record in the bottom window. If the serial presentation layout selected in setup is "full screen," the report representing the serial record is displayed full screen. The user may toggle between the display of the current report and the serial report. The serial presentation report is displayed in a manner that makes it obvious to the user that it is not the current report, such as with a different background. The user cannot edit the reports in the serial presentation window. During the initial display of reports during a review session, the first page of the segment will be displayed. Reports will be generated based on the final report format associated with the attending physician listed in the record. If a default final report format cannot be identified for the attending physician, the system default format will be used. For subsequent display of reports during a review session, the function will return to the page or segment last displayed. The user may also change which of the patient's stress ECG records, other than the current record, is currently being viewed in the serial presentation window, and the user is able to change which report segment of the serial presentation record is currently being viewed. If the new segment has not been reviewed during the current review session, the first page of the segment will be initially displayed. If the new segment has been reviewed previously during the current review session, the function will remember which page of the segment was displayed last and display that page. The user is able to initiate report setup to select a new format or change individual format parameters for the serial report independent from those of the current report. When the ECG recordings segment of the serial presentation record is displayed, the user may change which recording is currently being viewed. If the current or serial presentation reports are tiled, the user may make full screen either the window for the current report or the window for the serial presentation report. If the user closes the serial presentation window, the window for the current report will go to full screen. If the current or serial presentation reports are full screen, the user may tile the windows. If the user closes the serial presentation window, the window for the current report is viewed. The serial presentation report will be closed if the current report is closed.

With the stress ECG final reports function of the present invention, the user may edit the procedure and patient data for the active stress ECG record. The record may then be saved, confirmed or reconfirmed. Any changes made to a data element will be reflected in all segments in which that data element appears, and any data elements that have been edited during the current session will be displayed prominently (e.g., highlighted or bolded). The user is also able to edit the patient demographics for the active record and may edit stress ECG pre-test, post-test and event data. The user is also able to edit average beat measurement data and fully edit all generated narrative summary and tabular summary segments, using the data field, free text, acronym expansion and text cut, copy, move and paste text items and formatting operations of this report function. The user may also save the stress ECG record to the system database identified for that record by overwriting the existing record. The date and time of saving will be saved with the record.

The user may also request record confirmation on unconfirmed records so that the stress ECG record will be marked as confirmed. The date and time of confirmation will be saved with the record. The user may also enable or disable distribution of the confirmed record. Editing of confirmed records also requires that the user be notified that the report has already been confirmed, and any changes may affect the confirmed diagnosis. The user will be required to reconfirm the report or discard any new changes. If the user chooses not to reconfirm, the changes will be abandoned. If the user chooses to reconfirm, the stress ECG record will be marked as reconfirmed. The user may enable or disable distribution of the reconfirmed record, and the date and time of any reconfirmation is saved with the record.

Abridgment may be disabled by setting abridgment time to "Never" for a specific record. If abridgment is not disabled, the record may be abridged manually by the user or may occur automatically. If abridgment is disabled for the current report, the record will not be abridged. To manually abridge a stress record, all waveform data not necessary to reproduce the report in the current format must be deleted. For automatic abridgment of a stress record, pre-specified waveform data will be deleted.

Report distribution may be initiated manually for the active record or may occur automatically on record receipt, confirmation or reconfirmation. If the active record is distributed manually, the user is able to select a distribution list. The list of distribution lists are filtered to only include entries that are applicable to the stress procedure. The record and the serial presentation record(s) meeting the serial presentation criteria in the distribution list will be routed to each destination listed in the distribution list. The distribution list specifies the routing parameters (number of copies, serial presentation inclusion, etc.). If the destination is a physician, technician or administrator, the notification path for the physician, technician and/or administrator specifies one of the appropriate routing methods. For example, if the destination path is to a fax or a printer, copies of the report(s) will be faxed or printed according to the predefined specifications. If the destination is a system user, the user will be notified with a system message. If the destination is a system connection, the report will be transmitted to the indicated location. If the destination is a pager, the specified pager number shall be called and the specified message entered.

The user may print the report(s) currently being viewed as described above. If more than one record is open, the user will be given the choice of printing the active report or all open reports. The user is able to override which segment(s) of the report is to be printed (initially specified in the format) and limit printing to specific pages of the final report. Each included page of the report will be numbered consecutively with the first page starting at 1. The page number will also reflect both current page and total number of pages in the report (e.g., 1/5 for page 1 of a 5 page report). The user may enable or disable the masking of patient demographics on the printed report(s) and also specify the number of copies to be printed. If the record is marked as conflicting, the report will be marked to indicate that it is conflicting and will identify the patient with whom it is conflicting.

The user may also export the report in the ASCII format and may enable or disable the masking of patient demographics on the exported report. The user is also able to choose which fields of the record will be exported. The user may also select a new report format or change the parameters of the existing format for the active record. These changes will only affect the active record and will remain in effect for that record until the user closes the record. The user may also change global report setup parameters.

The user is able to access the stress ECG final reports function via the report review and report prating without viewing scenarios. The report review scenario is used when the user wants to view, edit and/or print one or more stress ECG reports or create a new stress ECG record. The report printing without viewing scenario is used when the user wants to print selected reports without visibly entering the stress ECG final reports function. In addition, the user may also access the stress ECG reports function via the report confirmation without viewing, record reception and timed activities scenarios. The report confirmation without viewing scenario is entered when the user wants to confirm a report without visibly entering the stress ECG final reports function (i.e., the doctor has no changes to make). The record reception scenario is entered when a stress ECG record is received from an instrument. The timed activities scenario is entered when stored stress ECG records are automatically abridged or archived after residing on the system a predetermined length of time.

The stress ECG final reports function exhibits the state behavior indicated by the idle, report review, printing, report distribution and notification and report setup states. The idle state is the initial state for the stress ECG final reports function. The function is not visible and awaits external initiation. The report review state occurs when the user views the report, views serial presentation and edits the report. In this state, the user is able to switch between selected reports. In the printing state, the report(s) is printed, faxed and/or previewed. In the report distribution and notification state, the generated report is routed. In the report setup state, a new format is selected or the parameters associated with the active record are modified.

Figure 38A:
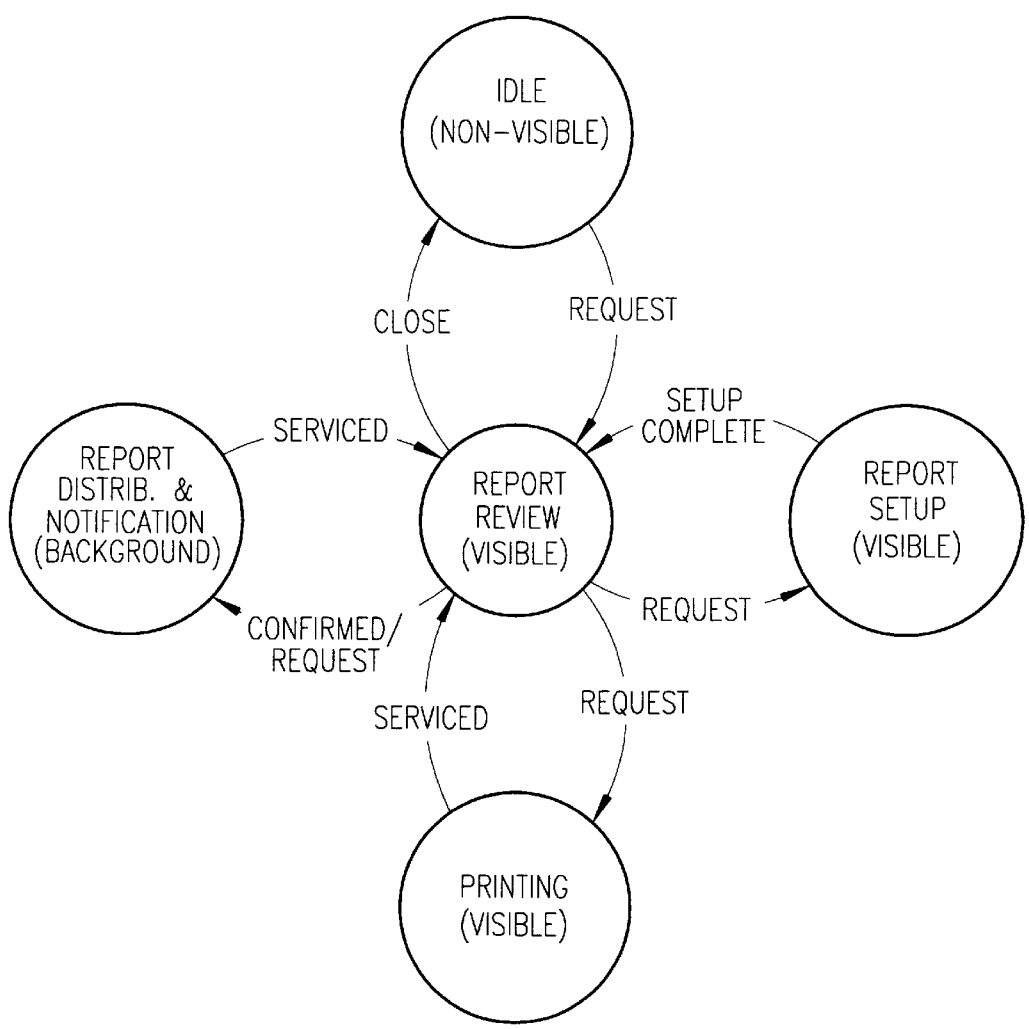
FIGS. 38A and 38B are diagrammatic views illustrating the state transition diagrams for the various stress ECG final report functions of the present invention.

The stress ECG final reports function may be entered in response to a user request to view and/or edit one or more stress reports or to create a new stress ECG record. FIG. 38A shows the state transition diagram for the report review scenario. In this scenario, the function leaves the idle state when the user opens one or more stress ECG records or requests to create a new stress ECG record. The function then transits from the idle state to the report review state in a visible mode. If multiple stress ECG records were selected, the first record as determined by the sort order previously selected by the user will be initially viewed. If the user does not have edit privileges, the user will only have view access to the records. If any of the selected records are already locked for edit by another user, the current user will be notified that another user is editing the record and will be restricted to view access to them. If any of the selected records are archived, the current user will only have view access to them, and all selected records not already locked by another user will be locked for edit by the current user. If the user initiates printing of the report(s), the function will transit from the report review state to the printing state. If the user initiates confirmation with routing or manual routing of the active report, the function transits from the report review state to the report distribution and notification state. If the user requests to change the report format, the function will transit from the report review state to the report setup state. If the user closes the stress ECG final reports function, the function will require the user to save or discard changes to the active record, and the function will then transit from the report setup state to the idle state in a non-visible mode. Once a print, fax or print preview request is serviced, the function will transit from the print state back to the report review state. When the routing of a report is complete, the function will transit from the report distribution and notification state back to the report review state. When the user requests to exit the report setup state, the function transits from the report setup state to the report review state.

Figure 38B:
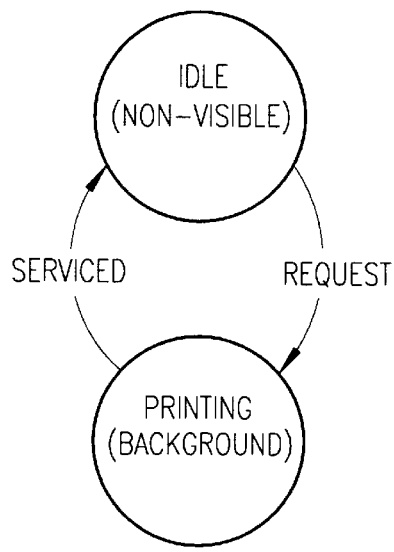

The stress ECG final reports function may also be entered in response to a user request to print and/or fax one or more stress reports (without viewing the report). FIG. 38B shows the state transition diagram for the report printing without viewing scenario. In this scenario, the idle state ends when the user selects one or more stress ECG records and triggers the function to print the report(s) without review. The function transits from the idle state to the printing state in a background mode. Each enabled segment for each selected stress ECG record will be generated based on the report format associated with the attending physician listed in the record. If the attending physician does not have an associated final report format, the system final report format shall be used. Once a print request is serviced, the function will transit from the print state to the idle state in a non-visible mode.

In addition to the functional features of the stress ECG final reports described above, it is also anticipated that the stress ECG final reports function may be expanded to include features such as full-disclosure, review and edit, arrhythmia review and analysis, and serial comparison as well as the ability to edit multiple records without saving between records. Further features such as waveform zoom and electronic calipers to aid in the measuring of waveforms on the screen are also contemplated. Additionally, it is anticipated that the user may adjust fiducial points to recalculate ECG measurements for each average beat or initiate a feature to automatically calculate predicted total exercise duration based on age, sex, and FAI, or automatically calculate the percent of predicted total exercise duration to actual total exercise duration for the patient. Similarly, it is anticipated that the stress ECG final reports functions may be expanded to include features such as merged graphs to enable the plotting of a single parameter for one or more tests and to allow ST/HR slope calculations and recovery loops. Furthermore, the ordering physician may be added to reports, and the routing of reports to physicians will accommodate physician schedules.

Figure 39:
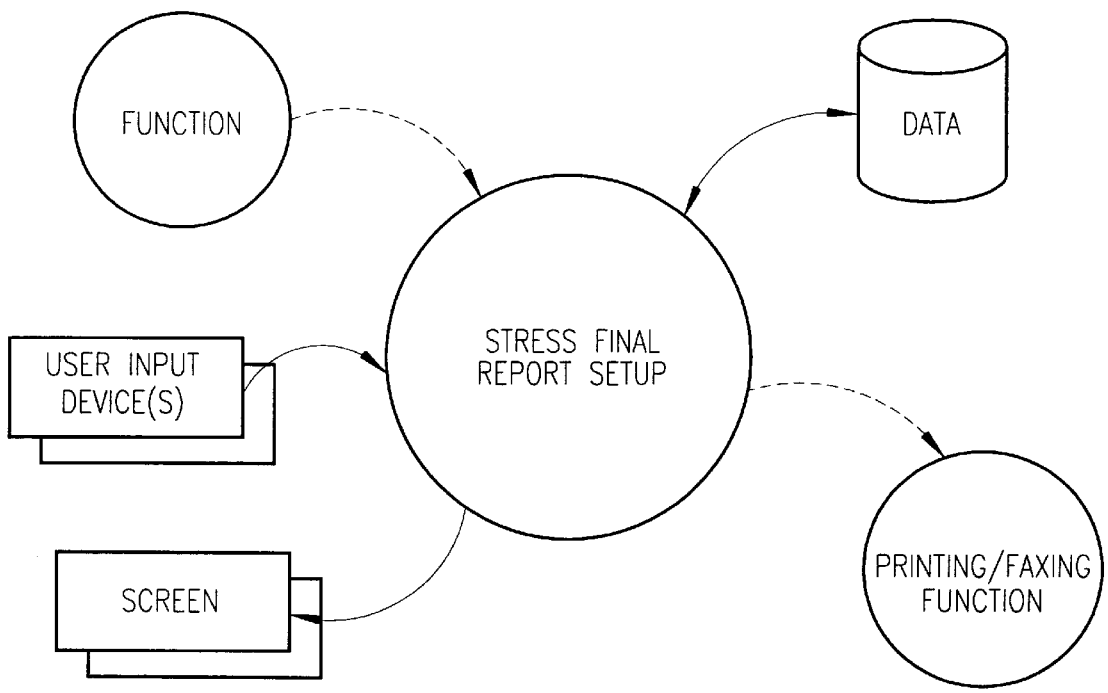
FIG. 39 is a diagrammatic view functionally illustrating the various stress ECG final report setup functions of the present invention.

The stress final report setup function is responsible for the viewing, editing and/or printing of the final report formats, user specific review settings and record workflow parameters. If a stress ECG record is currently open or active, the user can select a new format to associate with the record or modify the format currently associated with the record. FIG. 39 shows the context diagram for the stress final report setup function. The narrative summary and tabular summary segments of the final report are user-definable segments which allow the user extensive customization capabilities to produce "signature ready" final reports. Both a narrative summary template list and a tabular summary template list are available for review by the user. In the preferred embodiment of the present invention, a default narrative summary template and a default tabular summary template are shipped with the system. The user may create new templates which may be based on an existing template. The user may also modify the existing templates (including the default templates) or delete any templates except for the default templates. If the deleted template was contained in a final report format, the appropriate default template (either narrative or tabular) will be substituted for the deleted template. The user is required to provide a name for each template that is unique to the template list and may not modify the names of the default templates. The user may use free text or data fields, such as place holders for pre-test and post-test data and also conditional text which may be embedded as if-then-else type macros or keyed off the value of specific data elements, acronym expansion, logo insertion or a stress event table having 0–9 columns with a required data field type for each column desired, and the user is required to turn the stage interval on or off when creating and/or modifying a template. If the stage interval is "off," the user is required to select a timed interval. The user will be able to choose either landscape or portrait mode for the presentation of the segment as well as set and mix fonts in the segment and perform standard word processing operations (such as cut and paste) when creating and/or modifying a template.

The stress ECG final report formats determine how the stress ECG report(s) will be generated upon entering the stress ECG final reports function. A default format is shipped with the system. The user of the system may create new stress ECG final report formats which may be based on an existing format. The user may also modify the existing formats and the default format or delete any format except for the default format. If the deleted format were assigned to a physician, the default format will become the affected physician's final report format assignment. The user may also print the final report formats as described below.

In order to setup the final reports, the user is required to provide a name for the format that is unique to stress final report formats. The user may not rename the default stress format. The user may also select either standard 12-lead, Cabrera 12-lead, Frank or Canadian Bipolar formats for the final report. Different leads comprise the lead groups listed above. In some cases, a stress ECG record may have been generated using a different lead format from the one selected for the final report setup. Therefore, the user may view how the leads map from one lead format to another. The user may choose the font (from a list of supported fonts) that will be used for printing segments of the report other than in the narrative and tabular summaries. The user may also define the content and appearance for each final report segment using various functions for the narrative summary segment, tabular summary segment, maximum deviation report segment, average beat summary segment, trends graph segment, ECG recordings segment or segment selection and order functions. The user may select a narrative summary template from a list of summary templates. It is important to note that the narrative summary segment setup affects only the initial layout of the summary page. If a final report has already been edited for a procedure record, the summary page for that record will not change if the user changes final report formats.

The user may even select a tabular summary template from a list of summary templates. If the current lead format is standard or Cabrera 12-lead, the user may select a maximum deviation report in a 6×2 or 3×4 format. If the current lead format is a three lead format, a 3×1 format will be automatically be used. The user may then select stage only or stage+time wherein the time interval shall be specified in 10 second increments, ranging from 00:10 to 99:50 as reporting intervals for the Average Beat Summary. If the current lead format is standard or Cabrera 12-lead, the user may select the number of channels (three or six) and may select a lead for each channel from current lead format or none. The user will also be able to determine which types of averages will be included in the summary. These averages preferably include current averages only or current and resting averages. The trend graphs segment may be defined by using up to 36 graphs, and the user is required to select one data field type from the in-test tabular test data for the Y axis of each graph (the X axis is always time). If the data field type "blood pressure" is selected, both diastolic and systolic pressures are plotted. The user may also determine the position on the page in which selected graphs will be presented. Typically, users will also want to include representative recordings with their final report. The selections described below will act as filters to reduce the number of recordings included with reports by default. The user may override any of these selections during the report review process. The user is able to limit which ECG recording types will be included by enabling or disabling inclusion of the 12-lead, Exercise Set, Average Beats, Write Screen, Rhythm, Ectopic or Write Hold ECG recordings segments. The user may also limit which major recording events will be included by enabling or disabling inclusion of Resting (recordings corresponding to the resting averages), Peak (recordings occurring at time zero of recovery phase, or at the end of exercise if no recovery) or Final (the last recordings of recovery phase) major recording events. The user may also limit which mode of recordings will be included by enabling/disabling inclusion for programmed or manual modes. The user may also select which segments are present and the order of the segments in the printed final report. All segments are always present for review.

The user may modify parameters which control the initial presentation of the stress ECG reports function to the user by selecting one of the segments listed on a predetermined list as the initial segment for display or by choosing tiled or full screen for viewing the serial presentation. The user may save these settings at the following levels: user, group or system level. As described above, in the private level, the settings only apply to the current user. In the group level, the settings apply to all users in the group who do not have private settings defined; and if the user belongs to more than one group, the user is required to select the group(s) that the assignment will affect. In the system level, the settings apply to all users who do not have private or group settings defined. When a user opens a stress final report for review, the system uses various defaults for the levels. For example, if the user has a private setting, it is automatically used. If the user does not have a private setting but belongs to one or more groups with group settings, the system will choose one of the group settings. If the user has no private or group settings, the system setting will be used.

The rest labels list feature of the stress final report setup function contains text strings describing the patient's position when a resting recording was taken (supine, sitting, standing, etc.). The user of the system is able to add up to 1000 entries to the list. The user may also modify or delete the entries in the list and print the list as desired. The user nay also add a reason for ending a test by using a list which contains frequently entered text strings describing the reason the test was ended (maximum heart rate achieved, tightness in chest, etc.). The user may add up to 1000 entries to the list and modify or delete the entries in the list. The user may also print the list as desired. Another feature of the present invention is that the user may assign a report format to each physician in the physician list, and all stress ECG reports viewed are initially displayed in the default format assigned to the attending physician for that report. Additionally, all stress ECG reports are printed in the default format assigned to the attending physician for that report, unless the user has changed formats during the view and/or edit session, and all stress ECG records are distributed in the format selected in the report distribution and notification list. The user is also able to choose a format as a system default which is to be used on records containing physicians not associated with the system physician list.

The system of the present invention also defines how record workflows are defined and executed. The stress specific information provided in the record workflows includes workflow qualifiers, distribution requirements and abridgement requirements which are specific to stress records. For example, the user must be able to qualify stress ECG record workflows using the diagnosis, record priority and patient age fields. The user may select one or more diagnoses from the system diagnosis list, and it is also possible to select only normal reports, as well as to select all reports that are classified as normal for a selected diagnosis. The diagnosis list is preferably filtered to only include entries applicable to the stress procedure. The user may select "normal," "Stat," or "all" for record priority, and the user may select Pediatric, Adult, or Both for patient age. In addition to the general information a user may set for each destination in a distribution list, the user may also specify which segment(s) of the report is to be routed, select a specific final report format from the list of report formats or indicate that the attending physician's default format should be used. Unless otherwise specified, the default selection will be used as the attending physician's format. With the present invention, the user is able to select the waveform data to be abridged from the reports based on all average beats, all live ECG or all waveform data unused in the current final report.

In the system of the present invention, the user may access the stress final report setup function via default setup or report setup scenarios. The default setup may be used if the user wants to view, modify and/or print stress final report system formats and other setup parameters. In the report setup format, the user is able to change report formats and change the current report format parameters for the active stress ECG record. The changes in the report setup format do not affect the system formats. The stress final report setup function exhibits the state behavior indicated by the idle, setup, format modification, format association printing and workflow definition states. The idle state is the initial state for the stress final report setup function. The idle function is initially not visible to the user and awaits external initiation. In the setup function, the user selects templates, final report formats and user specific settings and assigns formats and defines the workflow. In the format modification state, the user views and/or edits the parameters associated with a particular template or format. In the format association state, the user is able to select a new final report format from a list of stress ECG final report formats for the active stress ECG record. In the printing state, the parameters for the selected final report format are printed, faxed or previewed. In the workflow definition state, the user defines the workflow for a stress record.

Figure 40A:
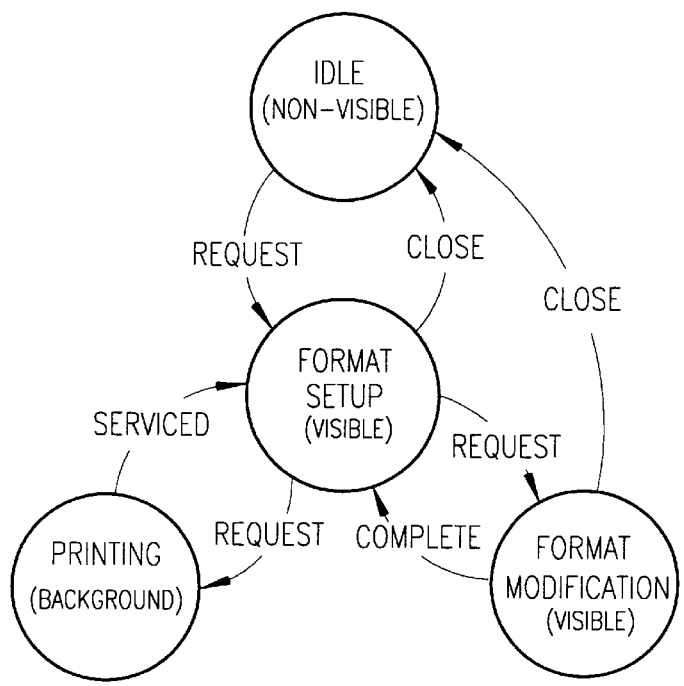
FIGS. 40A and 40B are diagrammatic views illustrating the state transition diagrams for the various stress ECG final report setup functions of the present invention.

In the default setup scenario, the stress final report setup function may be entered in response to a user request to view or edit the stress ECG final report formats. FIG. 40A shows the state transition diagram for this scenario. In this scenario, the idle state occurs when the user initiates the function, and the function then transits to the setup state in a visible mode. When the user elects to modify a final report format or template, the function will transit from the setup state to the format modification state. When the user requests printing, the function transits from the setup state to the printing state. When the user closes the stress final report setup function, the function transits from the setup state to the idle state in a non-visible mode. When the user completes modification of a report format or template, the function transits from the format modification state to the setup state. If the user closes the stress final report setup function, the function requires the user to save or discard changes to the format. This function then transits from the format modification state to the idle state in a non-visible mode. Once a print request is serviced, the function transits from the print state to the format setup state.

Figure 40B:
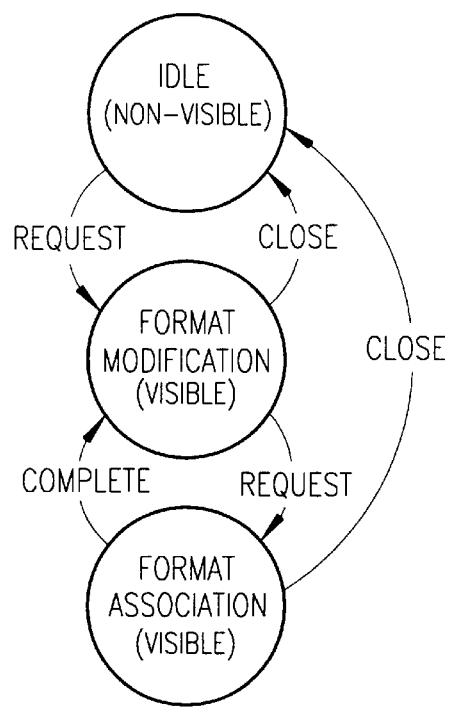

The stress final report setup function may also be entered in response to a user request to edit the stress ECG report generation parameters for the active stress ECG record using the report setup scenario. FIG. 40B shows the state transition diagram for this scenario. In this scenario, once the user initiates the function, the function transits from the idle state to the setup state in a visible mode. If the user requests to choose a new format, the function transits from the idle state to the format association state. If the user closes the stress final report setup function, the function requires the user to save or discard changes to the format. In this scenario, saving changes to the report formats only affects the current view of the active stress ECG report. The actual report format will not be updated. The function then transits from the format modification state to the idle state in a non-visible mode. When the user completes the selection of a new format or cancels the action, the function transits from the format association state back to the format modification state. If the user closes the stress final report setup function, the function transits from the format association state to the idle state in a non-visible mode.

In addition to the features set forth above for the stress final report function, it is anticipated that features relating to support for native report formats, setup for serial comparison and the ability to change lead size and V-lead size, including the choice of "auto sense," may also be added to the present invention.

The following section describes the framework of the preferred form of the workstation portion of the present invention from the software design perspective. This section also describes and establishes the basic abstract framework concepts and provides classes that can be used by workstations to implement the preferred implementation of these concepts. The workstation framework is not a product but rather a set of building blocks that can be used in the construction of the basic framework for a workstation. As described briefly, the preferred form of the software of the present invention is designed and constructed as part of the object oriented software program.

An important workstation framework concept is the abstract concept of records composed of fields and stored on data repositories (i.e., databases). Although portions of these concepts, such as fields, are substantially implemented within the workstation framework modules, the workstation framework primarily provides building blocks (classes) that can be used by the workstation products to implement these concepts. For instance, the workstation framework modules do not implement any records but do provide abstract base classes that can (and must) be used by workstation products to implement records.

Another important workstation framework concept is that of dynamic extensibility. There are two types of extensibility provided in the preferred embodiment of the present invention. The first concept of dynamic extensibility relates to the dynamic and automatic recognition of the presence of modules provided by the workstation. This is the ability of the workstation framework shell module to dynamically and automatically recognize the presence of non-framework modules and automatically reconfigure itself to satisfy the requirements of these modules. Another concept of dynamic extensibility relates to run-time registration of providers of additional services. This is the ability of the various workstation framework "factories" to support registration of providers of the specific services provided by a factory. For instance, the workstation framework implements a record factory. Other modules can register a record builder service with the framework-provided record factory. When any module needs to construct a record, it asks the record factory to construct this record, and the record factory will select the appropriate record builder from those that have been registered. A further important workstation framework concept is that of an Applet DLL. An Applet DLL, or Applet, is preferably a Win32 DLL that implements an additional interface, called the Applet Interface, as defined by the workstation framework. Most DLLs that are part of the workstation framework are Applet DLLs, or Applets. Some of the workstation framework modules assume that all other workstation modules are Applets. All modules that are part of workstations are expected to be Applets.

The workstation framework modules are designed to be used unchanged across multiple workstations. Each unique workstation consists of the workstation framework modules packaged with additional, product specific Applets. It is important to realize that the modules provided by the workstation framework do not implement a viable product. The workstation framework modules provide class definitions that serve as building blocks for the workstation specific Applets.

The following abstract workstation framework concept of records, composed of fields and stored on data repositories (i.e., databases), presents the abstract framework record concepts from multiple viewpoints. The Applet views a record object as being simply a collection of field objects. The record views itself as an accessor object capable of accessing field objects on some data repository. The Database Accessor views records as a collection of recordset objects to some database. The recordset views fields as a mapping of the database contents.

Figure 41:
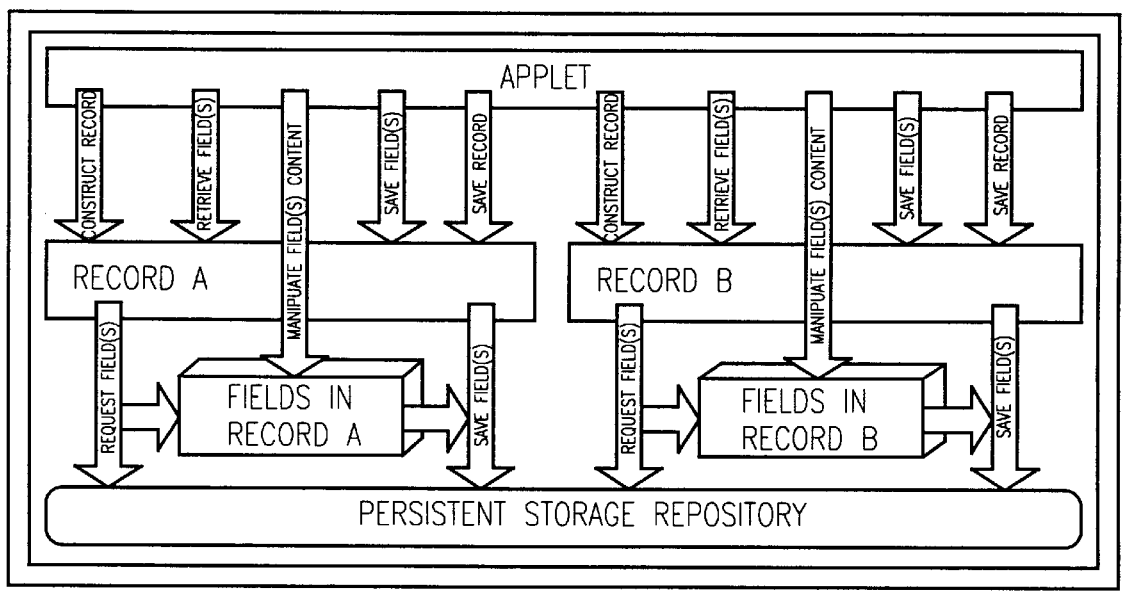
FIG. 41 is a diagrammatic view illustrating the Applet view of the field record framework of the present invention where the arrows show the calls made in the direction of the calls.

From an Applet's viewpoint, each record object consists of multiple field objects which appear to exist and appear to be available upon the construction of the record object. It appears to the Applet that the fields are retrieved from the persistent storage media when the record is constructed. An Applet can ask each record object for a selected field object(s) contained within that record object and receive a pointer to each requested field object. The Applet can manipulate that field object in any way allowed by the field object itself. It can save the changed record object to the persistent storage media. Multiple record objects can be accessed simultaneously by any Applet. These relationships are shown diagrammatically in FIG. 41 where the arrows show calls made, in the direction of the calls.

Figure 42:
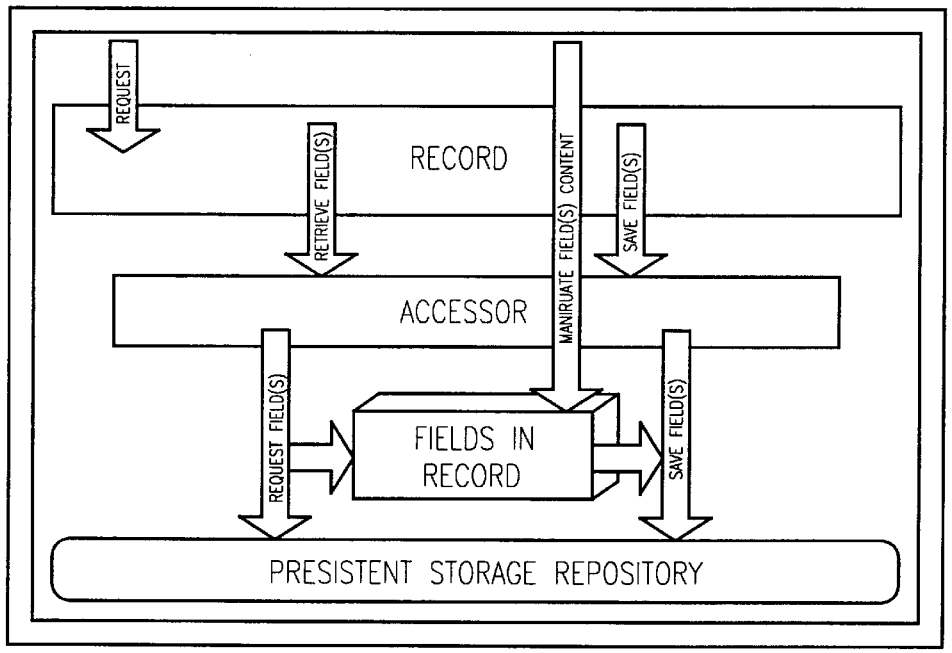
FIG. 42 is a diagrammatic view illustrating the record view of the accessor record field framework of the present invention where the arrows show the calls made in the direction of the calls.

As shown in FIG. 42, each record object contains an accessor object. In one form of the present invention, the only supported accessor type is the Database Accessor. From a record's viewpoint, the accessor object consists of multiple fields which are always available. It appears to the record object that the fields are retrieved directly from the accessor object. An accessor can be thought of as an abstraction of the persistent storage of a record. When a record object receives a request for a field object, it asks its accessor object to provide it. The accessor object appears to construct and return the requested field object if it is available. When a record object is told to save itself to persistent storage, it requests its accessor object to save each field object to persistent storage. These relationships are shown in FIG. 42 where the arrows show calls made, in the direction of the calls.

Figure 43:
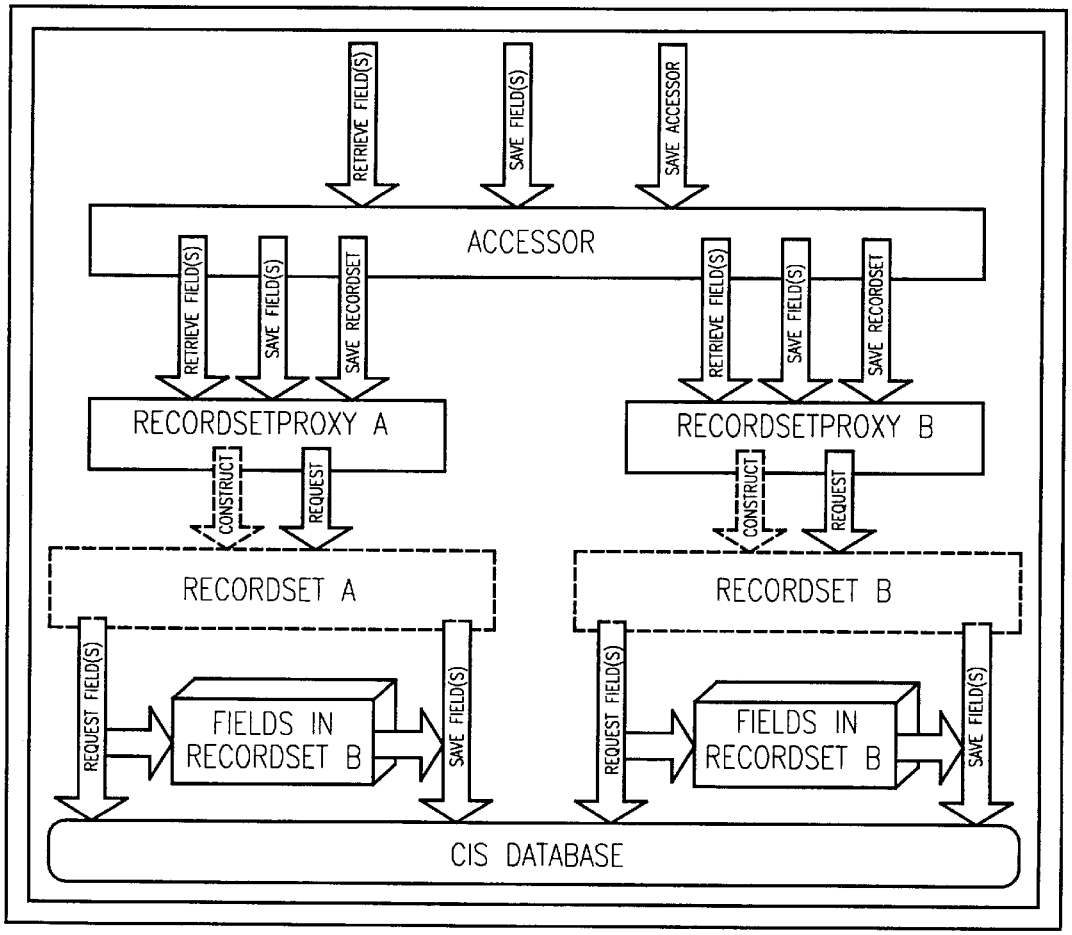
FIG. 43 is a diagrammatic view, illustrating the database accessor view of the recordset accessor field framework of the present invention where the arrows show the calls made in the direction of the calls.

As shown in FIG. 43, an example of an accessor type is the Database Accessor. Each Database Accessor object contains one or more recordset proxy objects. Each recordset proxy object exposes all the methods of a recordset object but constructs the associated recordset object only if access is requested to a field contained in that recordset object. Thus, the storage required for the data contained within a recordset object is allocated only if an Applet actually uses that data. This technique of constructing recordset objects only as fields are requested from them is called lazy construction. It has the potential of making significant reductions to database traffic and to the workstation's memory requirements. From the Database Accessor object's viewpoint, each recordset proxy object consists of multiple field objects which exist and are available upon the construction of the recordset proxy object. When a Database Accessor object receives a request for a field object, it asks each of its recordset proxy objects for this field until either the field object is constructed and returned by a recordset proxy object or all recordset proxy objects have been asked for the field object. Requests of the Database Accessor object to save a field back to persistent storage are forwarded to each recordset proxy object until either a request made to a recordset proxy object succeeds or all recordset proxy objects have rejected the request. When a Database Accessor object is asked to save itself to the database, it asks each recordset proxy object in turn to save itself to the database. Any recordset proxy object that does not yet contain a recordset object ignores these requests and returns successfully. These relationships are shown in FIG. 43 where the arrows show calls made, in the direction of the calls.

Figure 44:
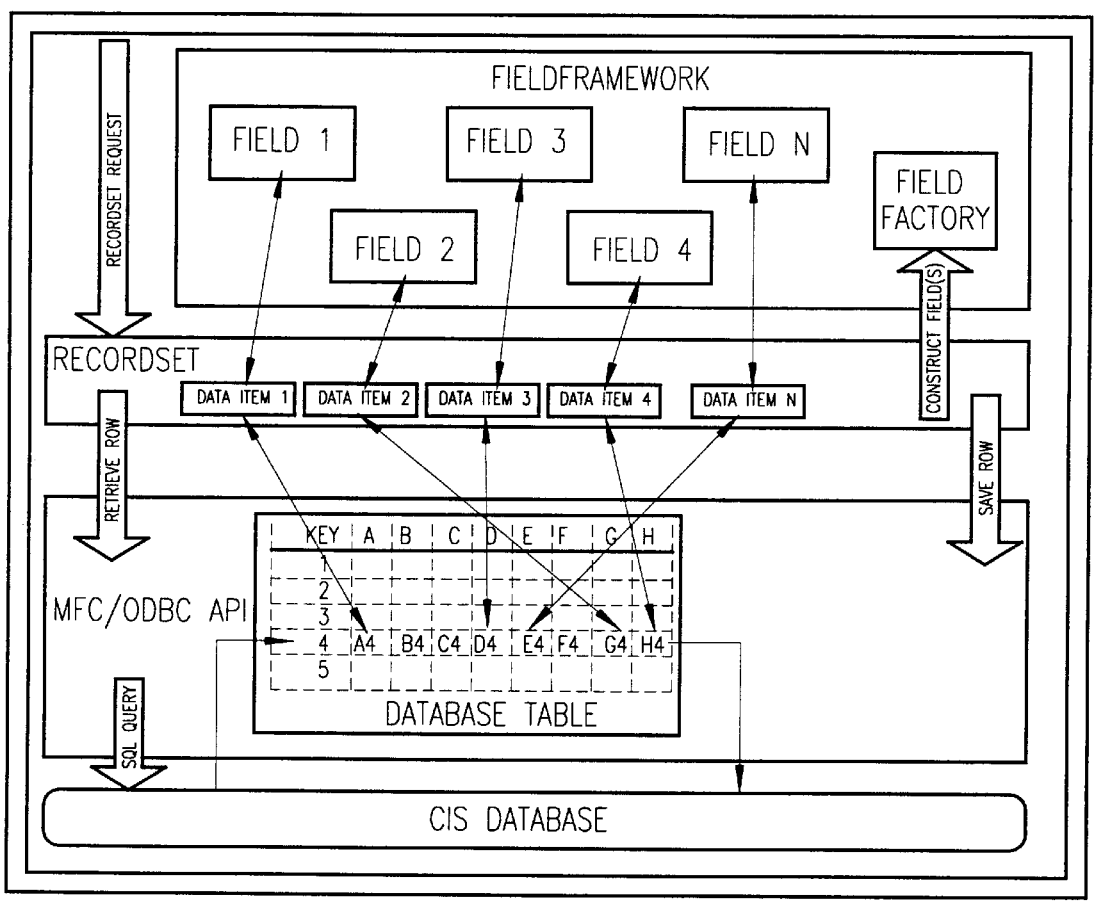
FIG. 44 is a diagrammatic view illustrating the recordset view of the recordset database field framework of the present invention where the white arrows show the calls made in the direction of the calls and the black arrows show the flow of data.

As shown in FIG. 44, each recordset object contains multiple member data items, including one distinct member data item for each and every field which a recordset object can process. From a recordset object's viewpoint, these member data items are the actual database data elements representing row-column intersections within a database table. Each member data item represents a unique column. All member data items are always in the same row of the database table. Any changes made to the individual member data items are automatically made back to the database, either immediately or when the database is asked to save the recordset object. When a recordset object is asked to construct a field, it calls the field factory within the FieldFramework module to construct an actual field object. It then initializes that field object with the appropriate member data item. Requests to save a field to the database cause the recordset object to retrieve the field object value and save it into the appropriate member data item. These relationships are shown in FIG. 44 where the wide white arrows show calls made in the direction of the calls, and the black arrows show data flow.

Figure 45:
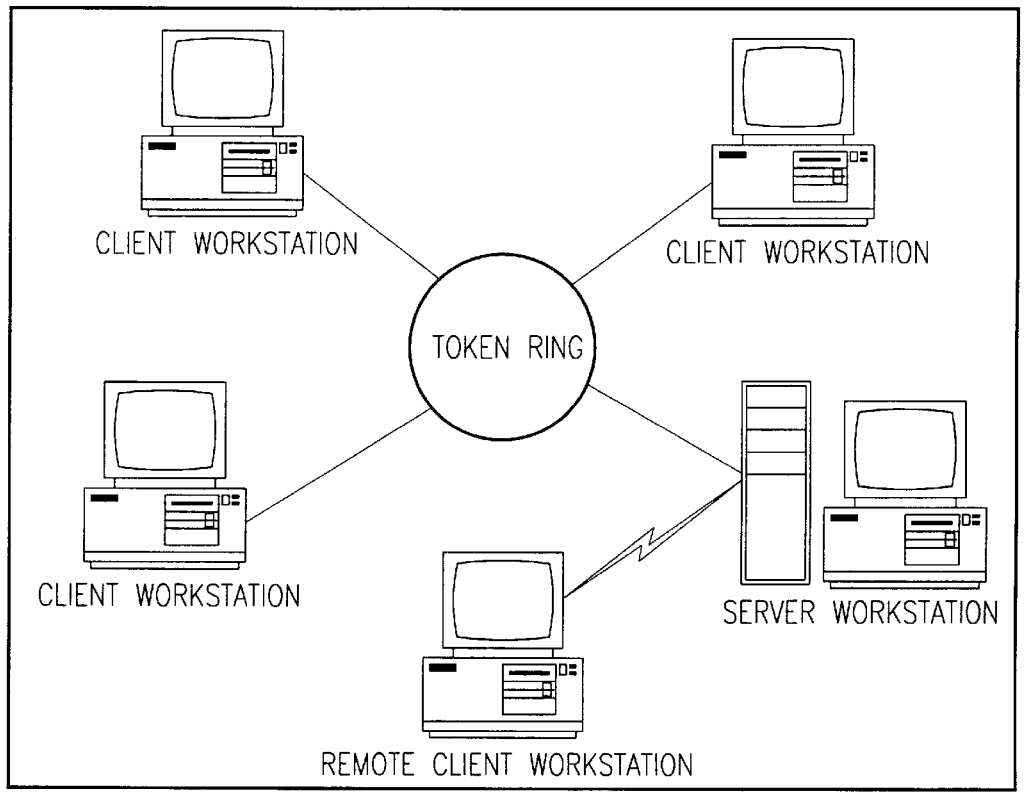
FIG. 45 is a schematic drawing of an example of the workstation framework for the client/server processes of the present invention.

In the preferred form of the present invention, the primary persistent storage repository for "records" may either be single sequel database servers or multiple sequel database servers depending on the configuration of the CIS. The preferred primary persistent storage repository for centralized configuration is a WINDOWS NT Domain Server Registry. Examples of centralized configuration information include definitions of users and groups, privileges assigned to individual users and groups, and system configuration settings such as name format. Additionally, directions on a WINDOWS NT file server may be defined to include ordinary disk files such as archived records, data transfer files, facsimiles or scanned images and saved administrative reports. FIG. 45 illustrates an example of the workstation framework for the client/server processes. In this example, multiple client workstations and a server workstation are connected to a Token Ring configuration, and a remote client workstation is remotely connected to the server workstation.

Figure 46:
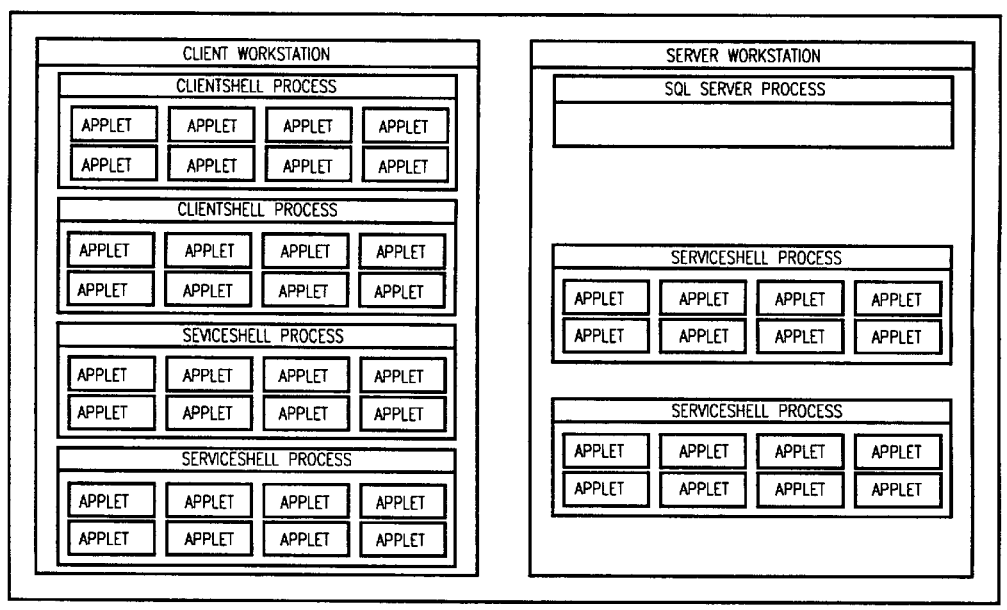
FIG. 46 is a diagrammatic view illustrating the client/server processes of the present invention.
Figure 47:
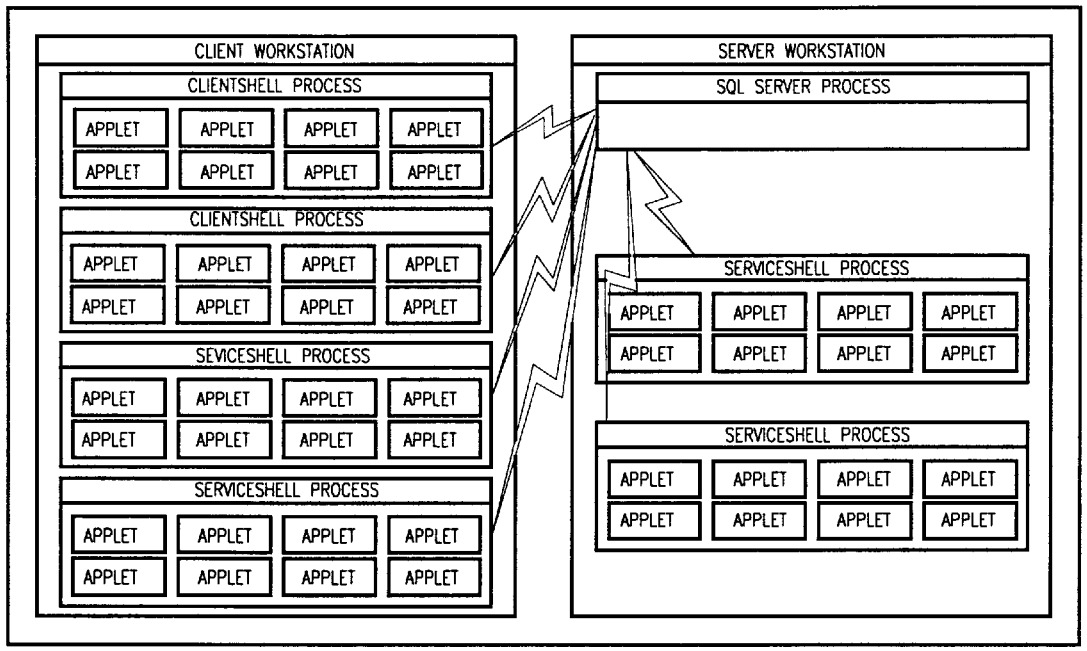
FIG. 47 is a diagrammatic view illustrating the database communication processes of the client/server of the present invention.
Figure 48:
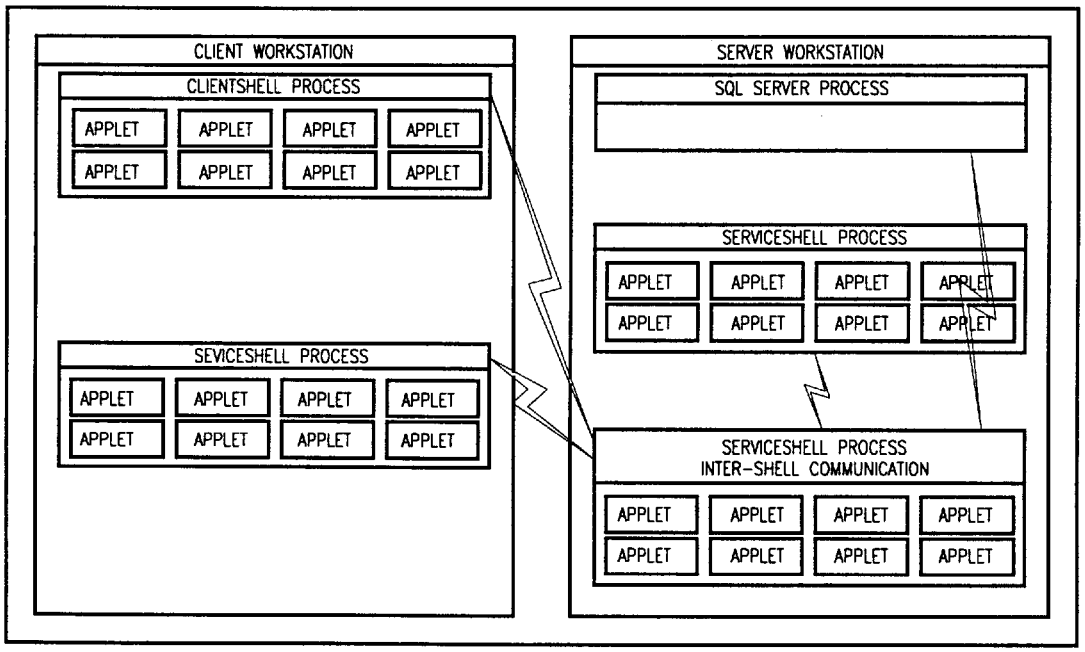
FIG. 48 is a diagrammatic view illustrating the inter-shell communication processes of the client/server of the present invention.

FIG. 46 illustrates the processes of the client workstation and the server workstation. As shown, the client workstation includes Applets for the Client Shell processes. The Service Shell processes and the server workstation include sequel server processes as well as Applets for the Service Shell processes. FIG. 47 is illustrative of the database communication processes of the client and server of the preferred embodiment. FIG. 48 is illustrative of the inter-shell communication of the client and server processes.

Figure 49:
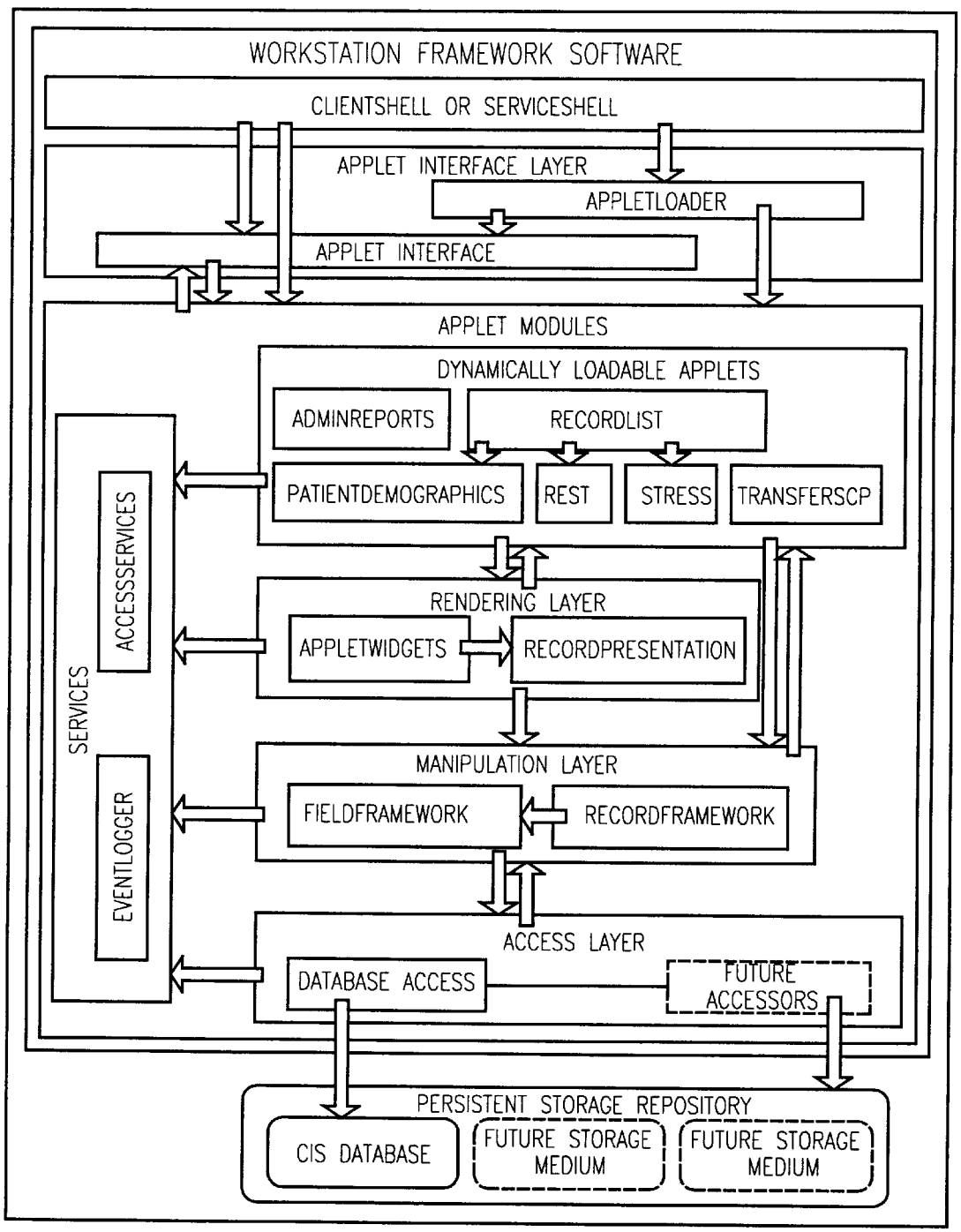
FIG. 49 is a block diagram illustrating the modules f the workstation framework of the present invention.
Figure 50:
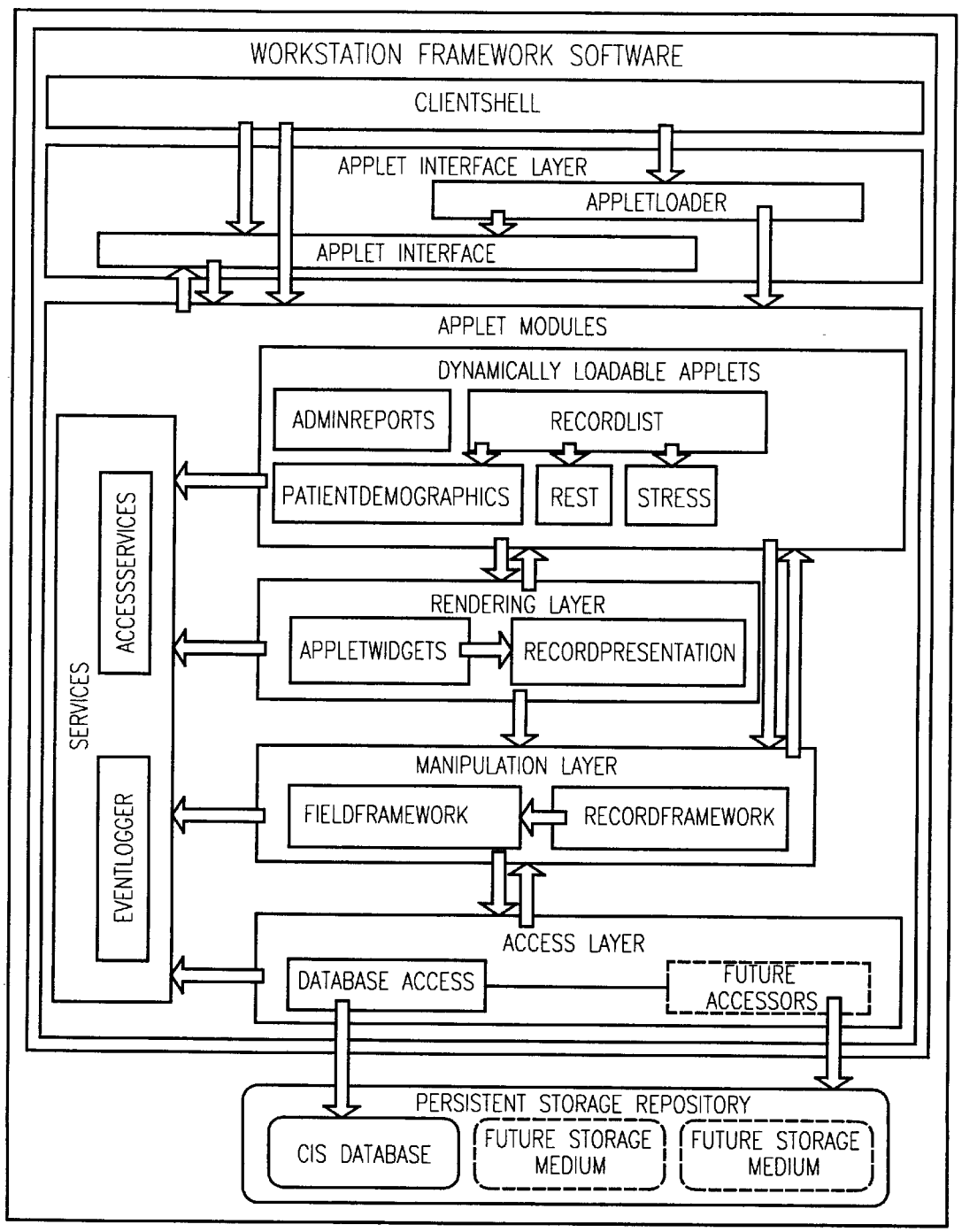
FIG. 50 is a block diagram illustrating the Client hell modules of the workstation framework of the present invention.
Figure 51:
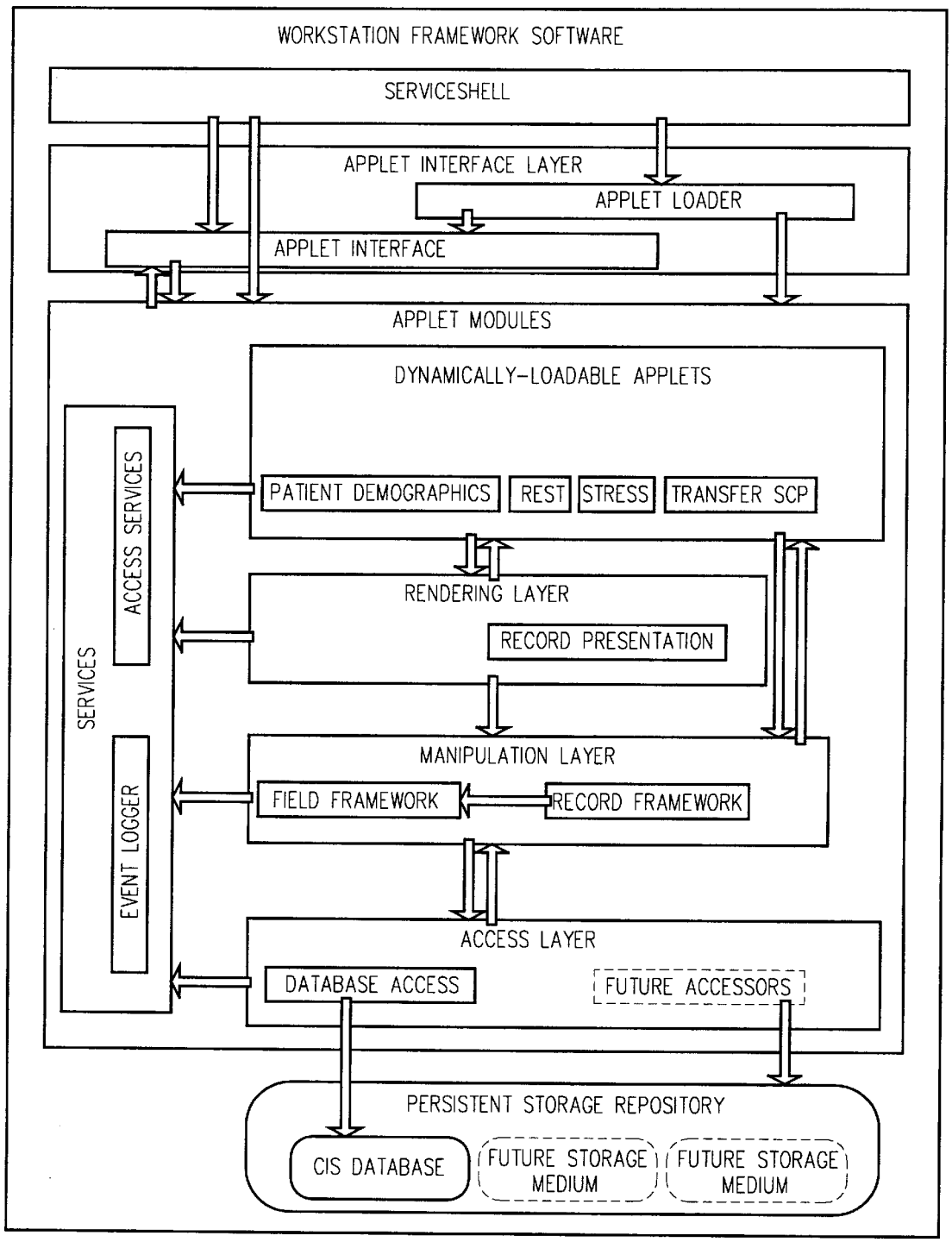
FIG. 51 is a block diagram illustrating the Service Shell modules of the workstation framework of the present invention.

The workstation framework preferably includes various modules therein. As shown in FIG. 49, the workstation framework includes software modules for the Framework Shell, Framework Applet, dynamically loadable Framework Applets and dynamically loadable CIS Applets. The Framework Shell preferably includes the Client Shell or Service Shell and an Applet interface layer consisting of the Applet interface and Applet loader modules. The Framework Applet further consists of the services layer, the rendering layer, the manipulation layer and an access layer. The services layer preferably includes the Event Logger Applet and Access Services Applet modules. The rendering layer preferably includes record presentation Applet and Applet Widgets Applet modules. The manipulation layer preferably includes Field Framework Applet and Record Framework Applet modules. The access layer preferably includes a Database Access Applet module. The dynamically loadable Framework Applet preferably includes the Admin Reports Applet, Patient Demographics Applet, Record List Applet and transfer SCP Applet modules. The dynamically loadable CIS Applet includes the Rest Applet and Stress Applet modules. FIG. 50 illustrates the modules of the workstation framework software which preferably are run within the Client Shell environment. FIG. 51 illustrates the modules of the workstation framework software which are preferably run within the Service Shell environment.

All modules of the workstation framework preferably run together as a single process under WINDOWS NT. In the preferred form of the present embodiment, the ClientShell module is the sole executable module of this WINDOWS NT process. The remaining modules are all preferably WINDOWS NT DLLs. Within this single process, all modules run as a single WINDOWS NT thread. It is anticipated that some of these modules or future modules may be modified or added to run partially or completely under additional threads. Likely candidates for such additional threads are requests made to Persistent Storage by the DatabaseAccess module.

As described briefly above and shown in the drawings, the workstation framework is divided into Framework Shell modules, Framework Applet modules, and Dynamically-Loadable Applet modules. The Framework Shell modules and Framework Applet modules together comprise the base functionality of the workstation product line. The Dynamically-Loadable Applet modules provide each product's unique functionality. The Dynamically-Loadable Applet modules may also become part of all products within the entire workstation product line.

The Dynamically-Loadable Applet approach is intended to allow additional Dynamically-Loadable Applets to be installed on top of a running workstation in a hospital environment. The existing product will preferably recognize the newly installed Applets and also make the additional functionality of these new Applets available to the user. In this way, a customer using the CIS could have installed either an Applet(s) to provide support of Resting ECG records, or an Applet(s) to provide support of Stress records, or both. Similarly, an existing CIS installation could be upgraded to the future product by adding Applets for the future product.

In the top level design of the workstations framework, the ClientShell is the main WINDOWS NT application program for the workstation framework. The ClientShell is designed to be a building block for all workstations. Since it is preferably an executable shared by all products within the workstation family of products, it cannot be modified and customized for each individual product. In fact, a single ClientShell executable could simultaneously be used for multiple versions of the workstations. To resolve this apparent ambiguity, the ClientShell is designed to be self-modifying. Individual workstation products implement the new product-specific Applet DLLs using the APIs provided by the Applet Interface and by other framework Applets. During initialization, the ClientShell will modify itself to incorporate all individual Applet UI requirements. The ClientShell is preferably capable of modifying its Menus and Submenus to reflect individual Applet requirements. Additionally, the ClientShell may also be capable of modifying its main window title to properly reflect the title(s) of the mix of workstation products installed. The ClientShell may also add support for Applet additions of Popup Submenus, product-specific "Options" dialog pages, product-specific banner screens and product-specific "About Box" dialog pages. The banner screen is designed to display which of the various possible products the user has currently installed. The ClientShell banner may be much more generalized but similar in flavor. Since the ClientShell will have no knowledge of the possible products that might be installed, the banner will not be pre-configured with commercially available products like the Microsoft Developer Studio. Rather, a method to add completely independent Applet-defined banners to a generic, product-independent workstation banner will be used. The Applet-defined banners will fit general Applet banner rules, but these are sufficiently flexible to provide for the anticipated needs of all future workstation products. The ClientShell uses the AppletLoader to load and initialize all Applets and then configures itself to Applet specifications using the Applet Interface to communicate with the loaded Applets. The ClientShell makes no distinction between statically-loaded and dynamically-loaded Applets. The ClientShell is preferably a Win32 application program, loaded by the Win32 program loader.

The Applet Interface Layer preferably consists of two modules, an AppletLoader and an Applet Interface. The AppletLoader preferably loads all Applets and provides the shell with a list of all loaded Applets. The Framework Applets are preferably loaded statically using a list of Applets specified in the AppletLoader source code. These statically loaded Applets may be automatically loaded by the Win32 program loader during the loading of the Applet-Loader module. Additional Dynamically-Loadable Applets are found by and loaded by AppletLoader. Preferably, the Dynamically-Loadable Applets are found only if they reside in the same directory on disk as the shell. The mechanism for identifying Dynamically-Loadable Applets may also be extended to allow for the searching of a different directory or limiting the loading to a subset of the Dynamically-Loadable Applets available. In the present embodiment, the AppletLoader module is preferably a Win32 DLL, loaded by the Win32 program loader, and the shell is statically linked to AppletLoader.

The Applet Interface provides a defined API to allow communication between Installable Applets and the shell. This interface is used by the AppletLoader to initialize and terminate the Applets. This interface is also used by the shell to request services from available Applets and is used by the Applets to request services from the shell. The Applet Interface module provides a mechanism for extending the shell to include additional behaviors and functionality provided by Applets and a mechanism for the shell to communicate with Applets. Additionally, the Applet Interface Module provides a mechanism for Applets to communicate with the shell and an extension to the Applets of common services normally provided to the executable by MFC. In the present embodiment, the Applet Interface module is preferably a Win32 DLL loaded by the Win32 program loader, and the shell, AppletLoader and all Applets are statically linked to the Applet Interface.

The Services Layer preferably consists of the AccessServices and EventLogger modules. The AccessServices layer is preferably an AccessServices Applet which provides an API for use by other Applets to establish whether or not a user has been granted specified privileges. The AccessServices Applet is preferably a statically-loaded Applet DLL, and other Applets are typically statically linked to the AccessServices Applet. The EventLogger Applet preferably provides an API used for logging events and program traces to the WINDOWS NT event logs. In debug builds, program traces are logged both to the WINDOWS NT event log and to the debug trace log. The debug trace log is typically a window provided by the Microsoft Developer Studio when running an application under the Developer Studio program debugger. A mechanism is provided to dynamically enable and disable the writing of program trace records both to the NT event log and to the debug trace log. The EventLogger Applet is preferably a statically-loaded Applet DLL, and other Applets are typically statically linked to the EventLogger. The EventLogger services are preferably used by the shell and by all Applets.

The Rendering Layer preferably consists of the AppletWidgets and RecordPresentation modules. The AppletWidgets Applet provides screen design elements with behavior and appearance that is preferably common across all of the workstation products. The Applets use these AppletWidgets screen design elements. In this way, the AppletWidgets can assure a common look across all Applets. The AppletWidgets interacts with the Workstation Client Shell to provide limited messaging capabilities between ClientShell and Applets. An example of such messaging is the notification of pending shutdown sent by the Workstation Client Shell to all active Applet Frame windows. The AppletWidgets Applet preferably provides various features such as specialized MDI child frame services, limited messaging from ClientShell to Applet-defined MDI child frame windows, singleton MDI child frames, a Button Bar Widget providing horizontal groups of buttons located at the bottom of an Applet Frame window, Button Bars which dynamically re-size to fit into the Applet Frame window, a Button Bar providing groups of buttons located within an Applet-defined view window, an Information Block Widget typically providing a horizontal group of labeled fields located at the top of an Applet Frame window, and/or a Tab Control Widget typically providing a horizontal group of labeled folder tabs located near the top of an Applet Frame window. Additionally, Applet Widgets may also provide color schemes which determine the colors used for various screen elements or the ability to edit color schemes. The AppletWidgets Applet is preferably a statically-loaded Applet DLL, and other Applets are typically statically linked to the AppletWidgets. The AppletWidgets Applet services are preferably used by the RecordList and RecordPresentation modules.

The RecordPresentation Applet provides for the display and handling of individual record objects within a managed list of record objects. Provisions are made for the user to select a record for editing or viewing from this list of managed record objects. This list of managed record objects is initially established outside the RecordPresentation Applet. For instance, the RecordList Applet builds a list of record objects corresponding to the records selected by the user within the RecordList Applet. The RecordPresentation Applet services are used by the PatientDemographics Applet to manage the presentation of current patient demographics records. The RecordPresentation Applet itself is designed to handle both current patient demographics records and procedure records (a.k.a., encounter records or test records). The RecordPresentation Applet may also provide additional services for managing and displaying serial records (or associated records) associated with a selected procedure record. The RecordPresentation Applet is preferably a statically-loaded Applet DLL, and other Applets are typically statically linked to RecordPresentation. In the preferred embodiment, the RecordPresentation services are typically used by the RecordList and PatientDemographics modules.

The Manipulation Layer preferably consists of the FieldFramework and RecordFramework modules. The FieldFramework Applet provides services which encapsulate data-specific knowledge about a specific data element and which format that data element for display. Each data element on the database can be represented as a field object which knows how to format and manipulate the data element contained within it. The FieldFramework may also be enhanced to support compound fields containing multiple, closely related data elements (such as a name or address) and to support array fields containing arrays of like data elements. The FieldFramework services are preferably used by all Applets which need information representing database data elements. This includes the RecordFramework and DatabaseAccess Applets as well as the dynamically-loadable Applets. The FieldFramework Applet is preferably a statically-loaded Applet DLL, and the other Applets are typically statically linked to the FieldFramework Applet. The FieldFramework services are used by the RecordList, PatientDemographics, RecordFramework and the DatabaseAccess modules.

The RecordFramework Applet provides an abstract definition of all records. It contains a Record Factory which can dynamically construct any record type using unique Applet-provided record constructors. During initialization, PatientDemographics registers a Record Builder capable of constructing current patient demographics records with the Record Factory. RecordList uses RecordFramework services to construct and process operations on current patient demographics records. Additionally, other Applets may supply the Record Factory with Record Builders for procedure records (a.k.a., encounter records or test records). The RecordList may then use the RecordFramework services to construct and process operations on these procedure records. Applets besides the RecordList may also provide RecordFramework services to construct records and process operations on these records. Other RecordFramework services may also be provided and used by various other Applets. The RecordFramework Applet is preferably a statically-loaded Applet DLL, and the other Applets are typically statically linked to the RecordFramework. The RecordFramework services are used by the RecordList, PatientDemographics and DatabaseAccess modules.

The Access Layer preferably provides access to various persistent storage media. It implements the transfer of data between a record object and a specific persistent storage medium. In the present embodiment, the Access Layer consists of the DatabaseAccess Applet. In the preferred embodiment, the DatabaseAccess Applet provides access to the CIS database which is implemented using the Microsoft SQL Server. The MFC database classes, which internally use ODBC, are used for communication with the SQL Server. The DatabaseAccess Applet is preferably a statically-loaded Applet DLL, and the other Applets are typically statically linked to DatabaseAccess. The DatabaseAccess services are used by the RecordList, RecordFramework and PatientDemographics modules.

In the preferred embodiment, all Dynamically-Loadable Applets are dynamically loaded by AppletLoader, and Dynamically-Loadable Applets are found only if they reside in the same directory on disk as shell. It is anticipated that the mechanism for identifying Dynamically-Loadable Applets may be extended to allow for the searching of a different directory or additional directories or by limiting the loading to a subset of the Dynamically-Loadable Applets available. In the present embodiment, there are preferably three Dynamically-Loadable Applets. The AdminReports Applet provides administrative reporting and is a Dynamically-Loadable Applet DLL. The RecordList Applet is a Dynamically-Loadable Applet DLL which provides windows containing lists of records on the database. The PatientDemographics Applet is a Dynamically-Loadable Applet DLL which provides patient demographics related records. The records in these lists can be selected for processing, and operations can be performed on these selected records. An explorer-like window is provided which displays available Record Filters. This window allows the selection of a Record Filter and displays the results of a database query represented by the selected Record Filter.

In the preferred form of the present embodiment, two Record Filters are provided. One Record Filter displays all procedure records on the database, and the other Record Filter displays all patient records on the database. Submenus are provided on the ClientShell Lists menu to activate the explorer-like window or to directly activate a selected Record Filter within an independent child window. In the present embodiment, patient records and current patient demographics records may be processed. Selected patient records may be opened, creating a patient folder window for each selected patient record. Selected current patient demographics records within patient folders can be selected for editing or viewing by PatientDemographics. Doing so causes RecordList to request the Record Factory to construct the selected current patient demographic record object. The Record Factory in turn calls the registered Record Builder provided by the PatientDemographics Applet to construct the actual record object. The record object, once constructed, is asked by RecordList to edit or view itself, causing the edit or view request to be processed by the PatientDemographics Applet. The PatientDemographics Applet is a Dynamically-Loadable Applet DLL which provides a Record Builder, registered with the Record Factory (within RecordFramework), that is capable of constructing record objects representing current patient demographics records on the database. The PatientDemographics Applet builds upon RecordPresentation and AppletWidgets to provide editing and viewing of patient demographics fields contained within current patient demographics records, and changes made during edit are saved to the database.

Figure 52:
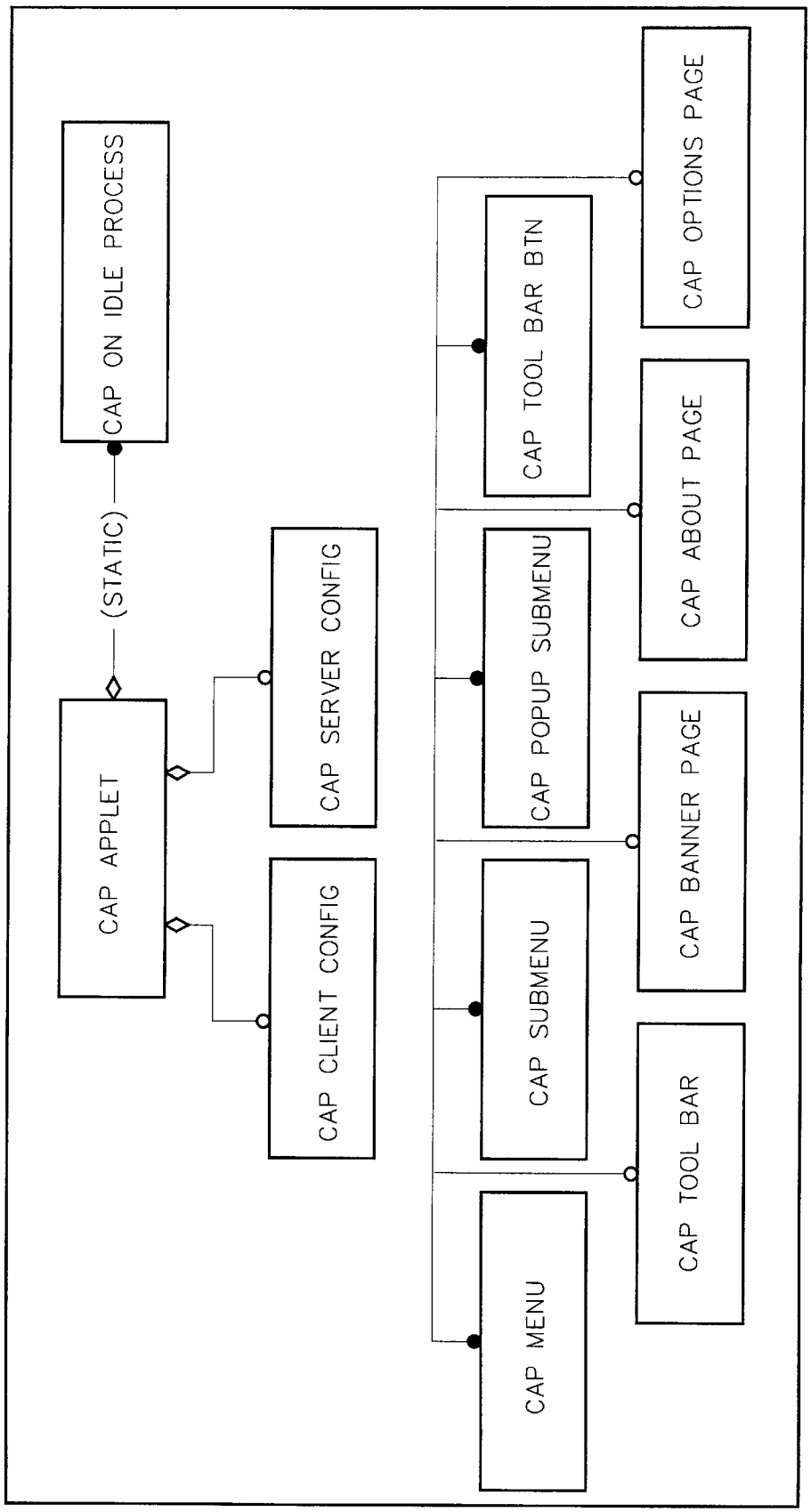
FIG. 52 is a diagrammatic view illustrating an overview of the Applet interface classes of the present invention.
Figure 53A:
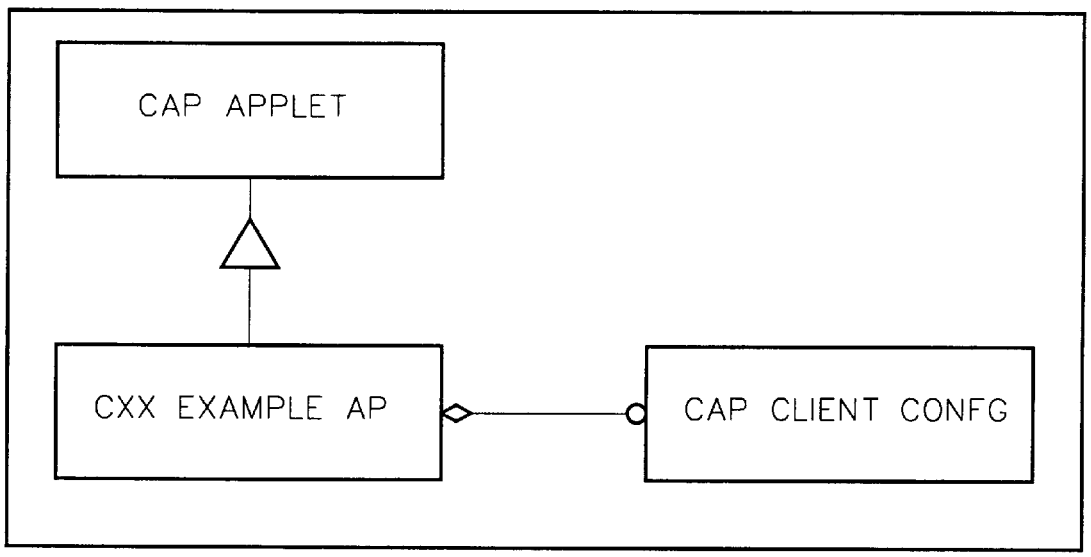
FIG. 53A and 53B are diagrammatic views illustrating the interactions between the Applet Interface and a typical Client Applet DLL of the present invention.
Figure 53B:
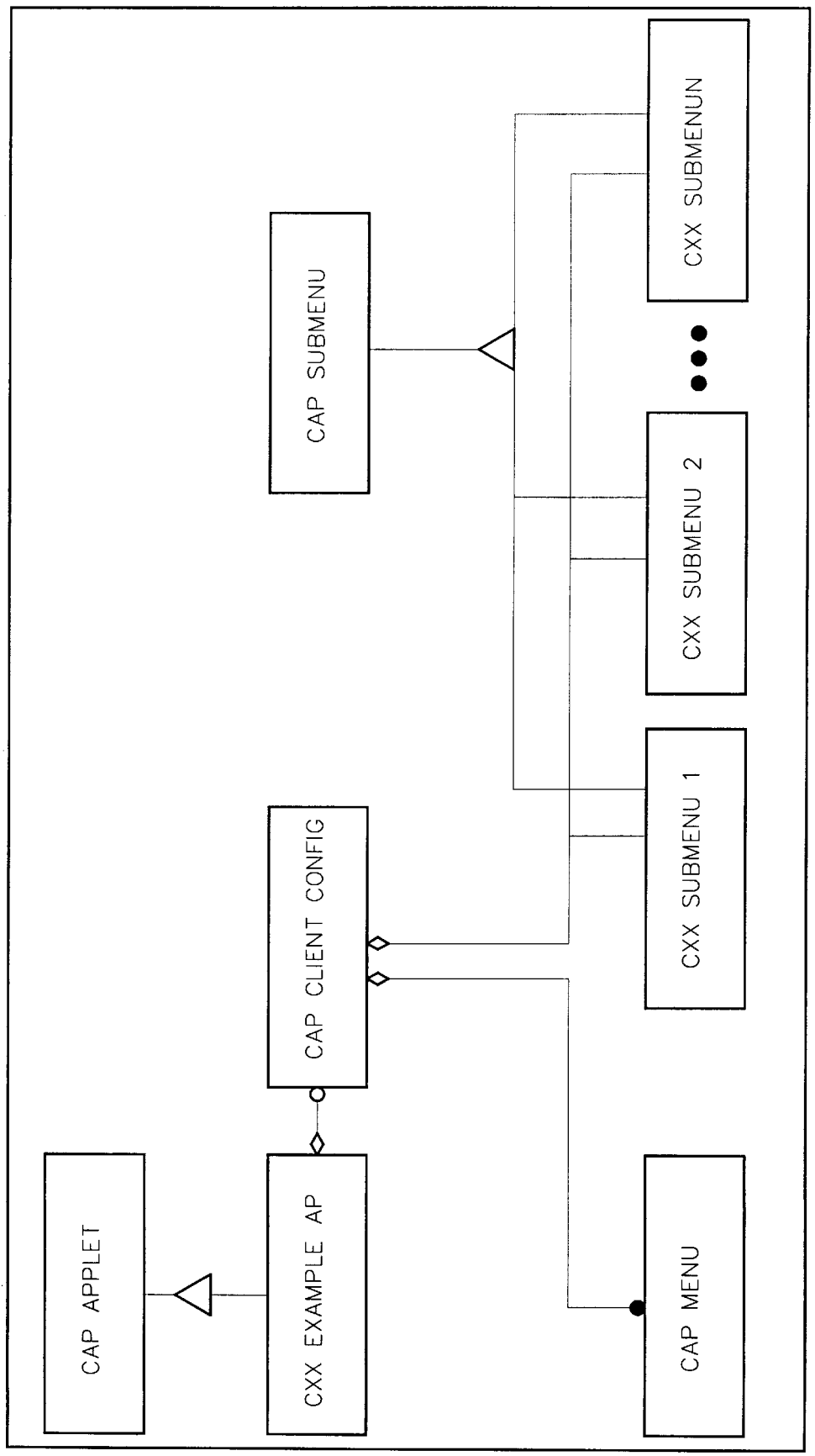

The following section describes the relationships between the classes defined in the Applet Interface module as well as the relationships between classes within the Applet Interface module and classes within other workstation framework modules. FIG. 52 shows an overview of the various Applet Interface classes of the preferred embodiment. The shaded (colored) classes are part of the Applet Interface module. Classes in other modules are shown in white. FIGS. 53A and 53B show the typical interactions between the Applet Interface classes, shown shaded, and the classes of a typical Client Applet DLL module, shown white. Preferably, a Client Applet DLL module contains an object of a class which inherits from class CapApplet. A method of this subclass provides a pointer to a subclass owned CapClientConfig object used by the workstation Client Shell as shown in FIGS. 53A and 53B.

The CapClientConfig object which is owned by the Client Applet DLL module contains the information the workstation Client Shell uses to reconfigure itself and also provides the interfaces needed by the Client Applet DLL. In the present embodiment, class CapClientConfig provides the workstation Client Shell with CapMenu and/or CapSubmenu objects. Preferably any CapSubmenu objects contained within the Client Applet DLL CapClientConfig object will actually be objects of a class derived from class CapSubmenu, typically a class provided by the Client Applet DLL. Examples of these relationships are shown in FIG. 53B.

Figure 54:
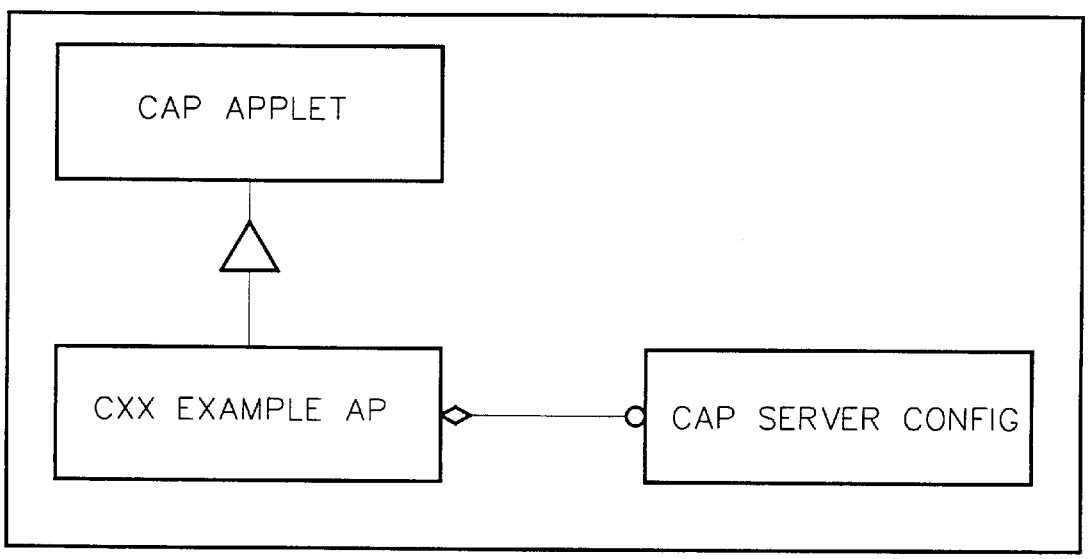
FIG. 54 is a diagrammatic view illustrating the typical interactions between the Applet Interface classes and the classes of a typical Server Applet DLL module of the present invention.

FIG. 54 shows the typical interactions between the Applet Interface classes, shown shaded, and the classes of a typical Server Applet DLL module, shown white. In the present embodiment, a Server Applet DLL module preferably contains an object of a class which inherits from class CapApplet. A method of this subclass provides a pointer to a subclass owned CapServerConfig object used by the workstation Server Shell. The CapServerConfig object is preferably owned by the Server Applet DLL module and contains information which is used by the workstation Server Shell to reconfigure itself and also provide the interfaces needed by the Server Applet DLL.

Figure 55:
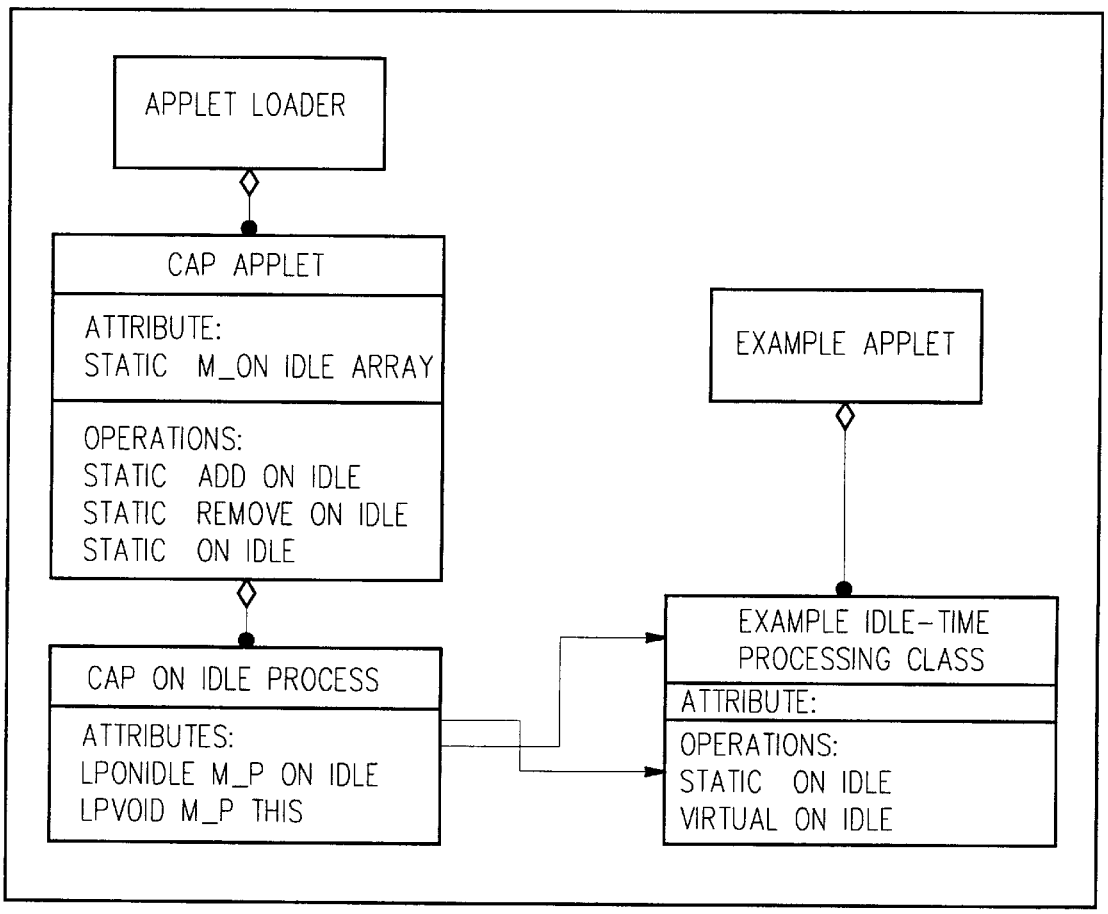
FIG. 55 is a diagrammatic view illustrating additional Applet Interface interactions with a Client or Server DLL in the present invention.

In the preferred embodiment, any class within either a Client Applet DLL or a Server Applet DLL can provide idle-time processing routines. The class CapApplet provides a mechanism for a class to register idle-time processing routines. These idle-time processing routines will be called by CapApplet during the idle-time processing of the workstation shell. As shown in FIG. 55, class "Example Applet" registers idle-time processing routines for each object of class "Example Idle-Time Processing Class" by calling the static AddOnIdle method of class CapApplet. For each call to AddOnIdle, the CapApplet builds an object of class CapOnIdleHandler, recording the static OnIdle routine to be called during idle-time processing. During idle-time processing, the workstation shell calls the DoOnIdle method of class CapApplet which then steps through its list of CapOnIdleHandler objects and calls the registered idle-time processing routines. In the example below, the static OnIdle method of class "Example Idle-Time Processing Class" is called. As shown, the static OnIdle method of class "Example Idle-Time Processing Class" can call a non-static OnIdle method, which is typically virtual, using the m_pThis value passed from the CapOnIdleHandler object to identify a specific target object. This is further described below in reference to the CapApplet and CapOnIdleHandler classes.

Figure 56:
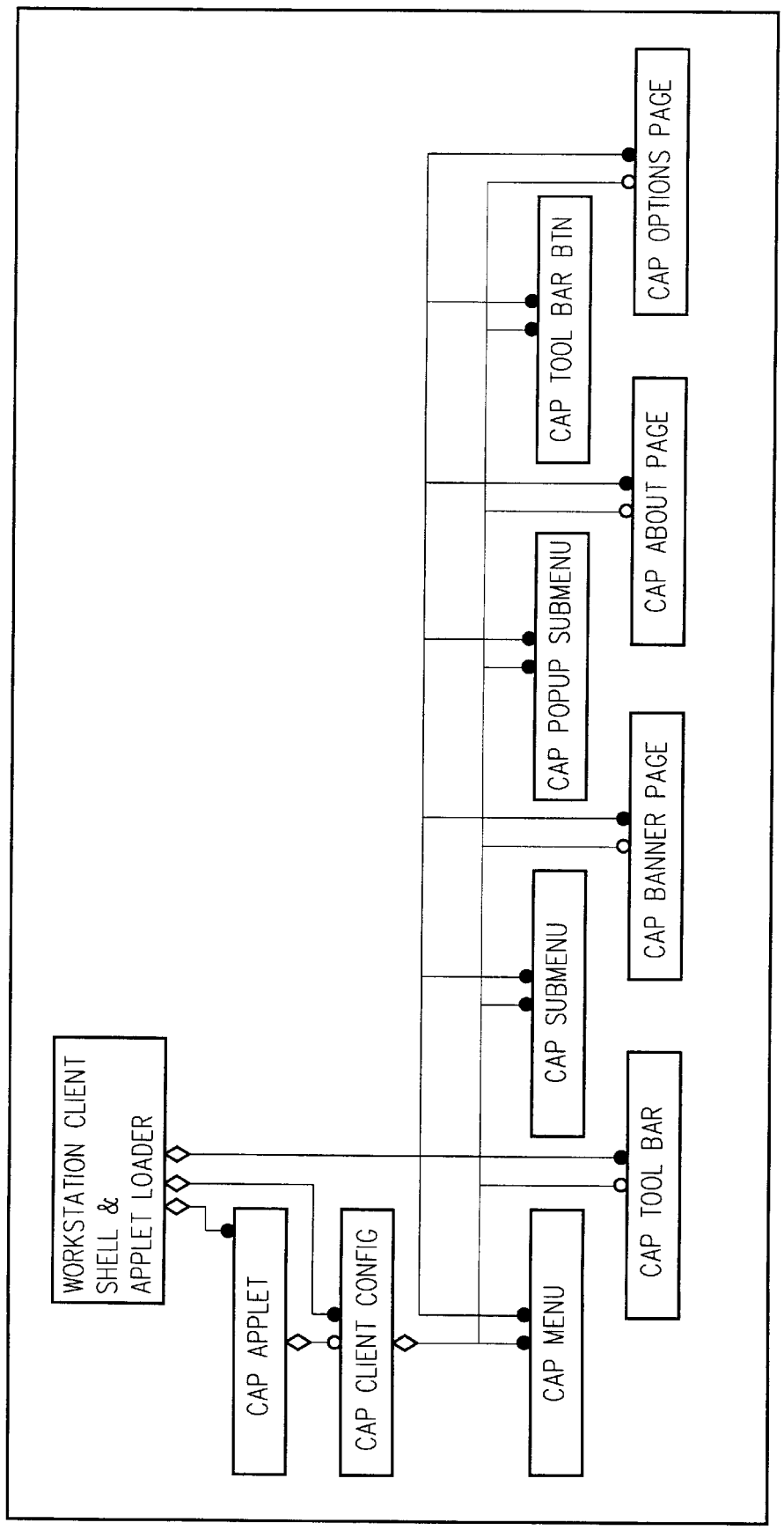
FIG. 56 is a diagrammatic view illustrating the Applet Interface interactions with the Workstation Client Shell of the present invention.

FIG. 56 shows as bold lines the associations established at run-time by the workstation Client Shell to objects within Client Applet DLLs of classes provided by the Applet Interface module. The actual use of these objects by the workstation Client Shell varies by the object's class and is described in further detail below. FIG. 56 shows the applet interface interactions with the workstation client shell.

Figure 57:
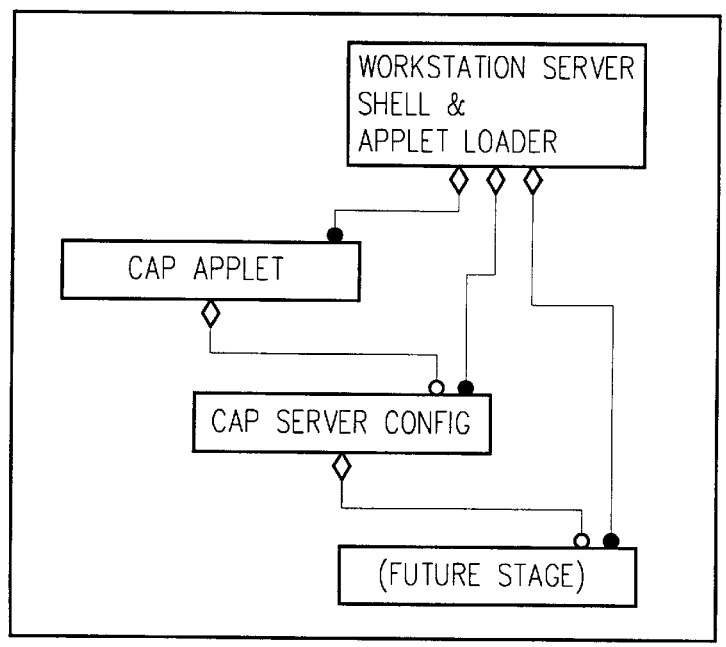
FIG. 57 is a diagrammatic view illustrating the Applet Interface interactions with the Workstation Server Shell.

FIG. 57 shows the Applet interface interactions with the Workstation Server Shell and Applet Loader. As with the interface interactions with the Workstation Client Shell, the Workstation Server Shell utilizes the class CapApplet as the primary interface between the Workstation Shell application and various installable DLLs.

The class CapApplet provides the primary interface between the Workstation Shell application and various Installable DLLS, called Installable Client Applet DLLs. The CapApplet is preferably designed to be the functional equivalent of the MFC CWinApp class to the extent needed by Applet DLLs. The CapApplet provides interfaces that are also preferably functionally equivalent to those provided in CWinApp by MFC. The CapApplet also provides a message routing mechanism causing messages received by the Workstation Shell CWinApp to be sent to each CapApplet object. Each Installable Applet implements a method which supplies Applet unique configuration changes which must be made by the Workstation Shell. These configuration changes are specified in the CapClientConfig class object returned by the GetClientConfig methods, and specify such things as additional menus and additional tool bars to be added to the Workstation Shell.

One of the primary benefits to the Client Applet interface of the preferred embodiment is that Applets are initialized in a defined order, after the initialization of MFC and during the initialization of the Workstation Shell. This is different from Win32 DLL initialization which occurs in an unpredictable order. The Applets are also terminated in a defined order. The termination of the Applets occurs in the exact reverse order as initialization. This ordering of Applet initialization and termination is controlled by a unique Applet ID within the Workstation Shell which is assigned to each Applet at compile time. The uniqueness of this ID is verified by the AppletLoader which builds an ordered list of all available Applets. In the preferred form of the present invention, the class CapApplet preferably has two friend classes, CapApplet Loader and CapApplet Proxy, both of which are defined in the Applet Loader module.

As mentioned above, the preferred embodiment of the present invention is designed using the object oriented approach to software design. Therefore, the preferred form of the present invention includes various public definitions, private definitions, public methods, protected methods and private attributes for the class CapApplet of the Applet Interface. For example, the class CapApplet of the Applet Interface preferably includes various public definitions which are referred to as "enum ExitType," "Enum ShutdownType," "LPapOnIdle," "LPapOnExitApplet," "LPapOnQueryShutdown" and "LPapOnShutdown." These public definitions are used for various termination, idle time processing, pre-termination and pre-shutdown processes for the class CapApplet of the Applet Interface. Examples of public methods used by the preferred form of the class CapApplet for the Applet Interface include "CapApplet," "BeginShutdown," "GetAppletID,"" "GetAppletName," "GetAppletTitle," "SetApplicationTitle," "GetUserName," "GetUserFullName," "GetComputerName," "GetStartStatus," "GetRunStatus," "GetStartTime," "GetRunTime," "GetApplPath," "GetApplet," "AddOnIdle," "RemoveOnIdle," "AddOnExitApplet," "RemoveOnExitApplet," "AddonQueryShutdown," "RemoveOnQueryShutdown," "GetProfileInt," "WriteProfileInt," "GetProfileString", "WriteProfileString", "GetPrivateProfileInt," "WritePrivateProfileInt," "GetPrivateProfileString," "WritePrivateProfileString," "GetClientConfig," "GetServerConfig," "OnInitComplete," "OnQueryShutdown," "OnShutdown," "OnIdle" and "OnServerMessage." These public methods are designed to retrieve certain information from various portions of the Applet Interface and CIS and to perform certain functions for the class CapApplet of the Applet Interface. Examples of the protected methods in the preferred form of the class CapApplet of the Applet Interface include "InitApplet," "ExitApplet" and "GetPrivateRegistryKey." These private methods are used by the class CapApplet of the Applet Interface to perform initialization, cleanup and termination and specify a private registry to be used by the Applet.

Figure 58:
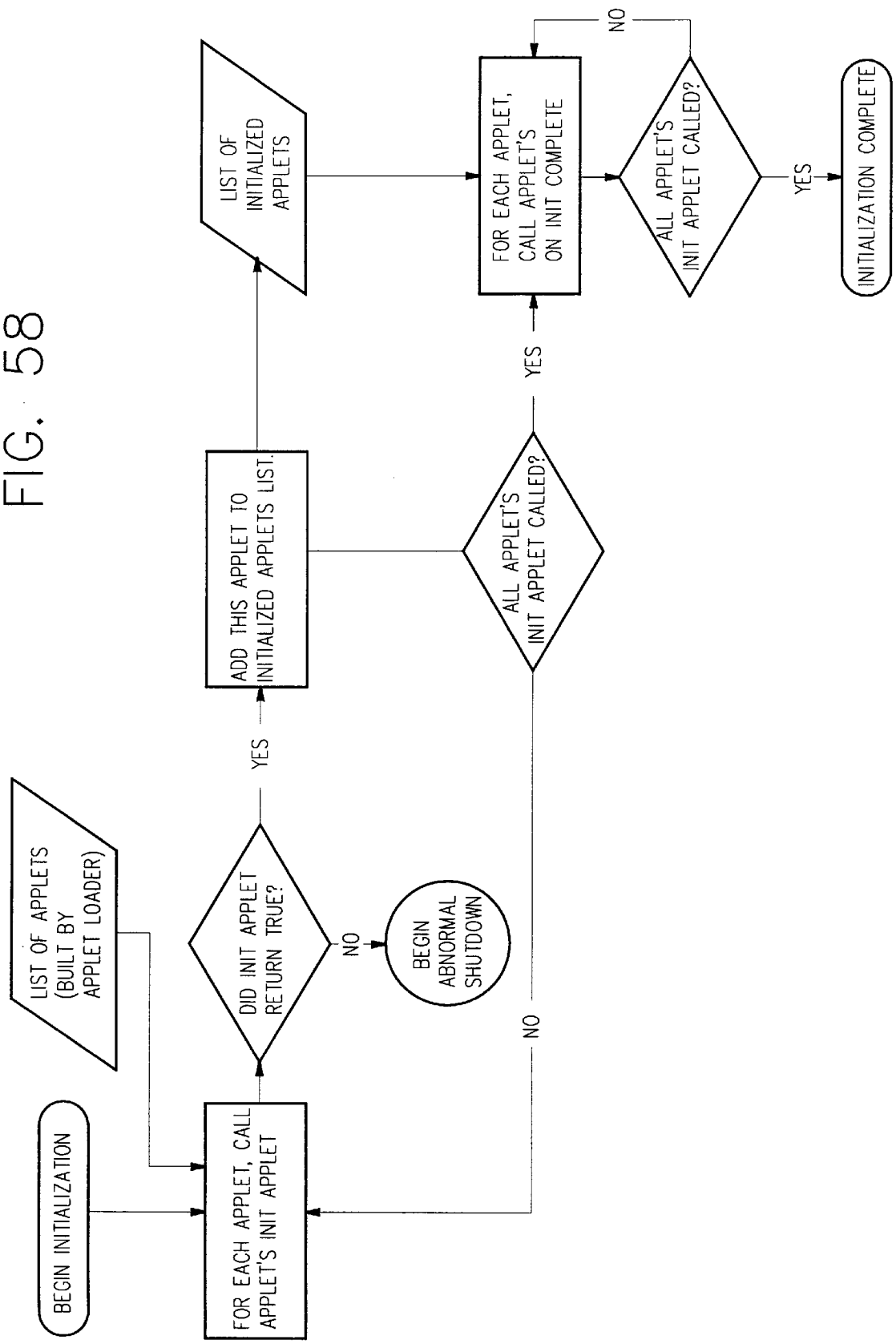
FIG. 58 is a flow diagram showing the process of initializing the Applets of the present invention.
Figure 59:
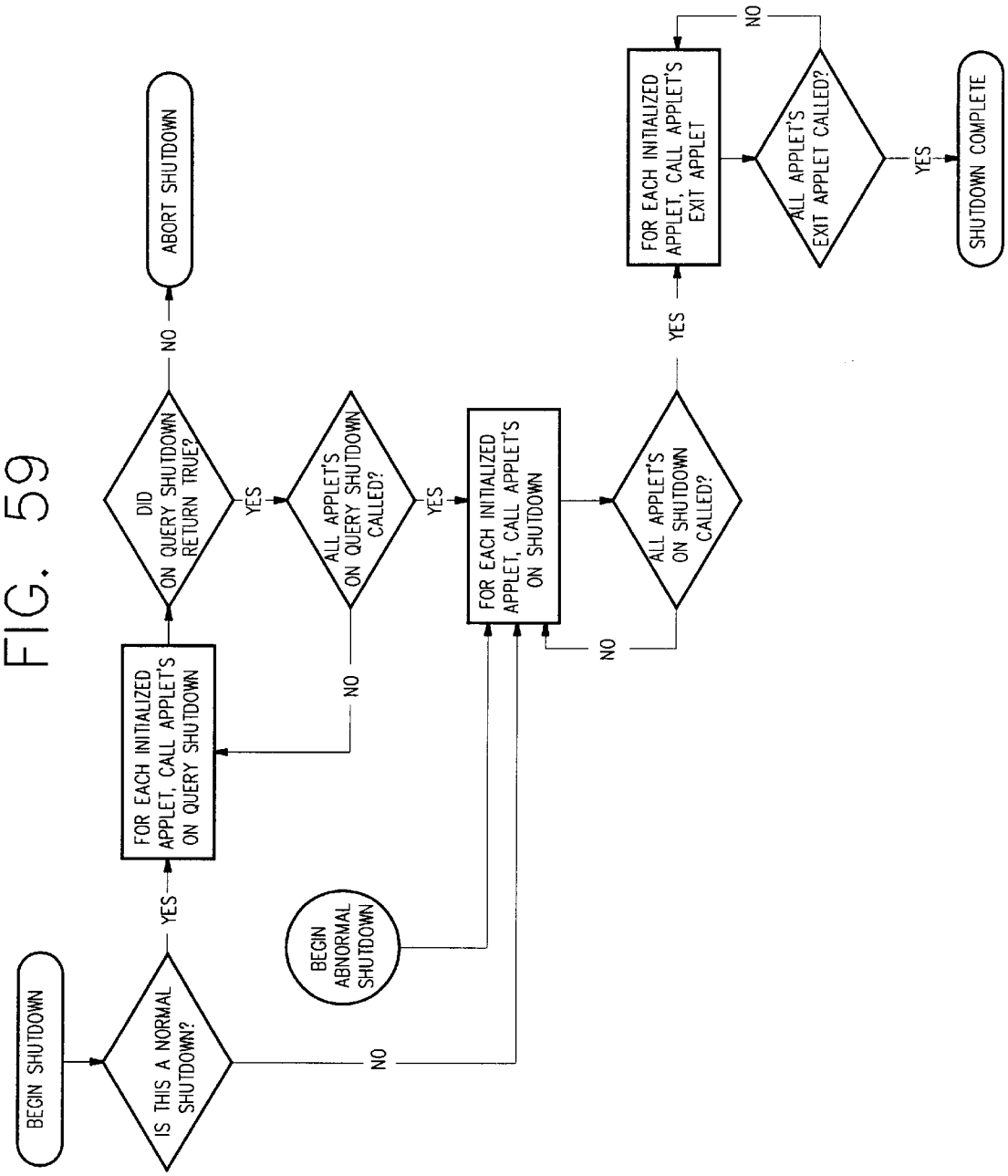
FIG. 59 is a flow diagram showing the process of shutting down the Applets of the present invention.

FIG. 58 is a flow diagram which illustrates the steps which are performed during the initialization of Applets. FIG. 59 is a flow diagram which illustrates the steps which are performed during the shutdown of Applets. During shutdown, if the "Abort Shutdown" exit is taken, the Workstation Shell continues running as if "Begin Shutdown" had never been entered. If an Applet contains OnQueryShutdown, OnShutdown or OnExitApplet handlers, these are called prior to calling the respective Applet's OnQueryShutdown, OnShutdown and ExitApplet methods.

The class CapOnIdleHandler is defined privately within class CapApplet. The class CapOnIdleHandler preferably exists solely for internal use by the class CapApplet and is unavailable for reference or use outside of the class CapApplet. Each object of class CapOnIdleHandler represents a single idle time processing routine supplied to the AddOnIdle method of the class CapApplet. Each successful call to AddOnIdle causes a new object of class CapOnIdleHandler to be constructed for recording the parameters passed on to AddonIdle. These CapOnIdleHandler objects are kept in the gm_OnIdleArray member of class CapApplet. This class is preferably made normal and is made a publicly accessible class so it can inherit from CObject and be made dynamic to facilitate finding memory leaks involving objects of this class.

The class CapOnExitAppletHandler is preferably privately defined within the class CapApplet. The class CapOnExitAppletHandler preferably exists solely for internal use by the class CapApplet and is unavailable for reference or use outside of class CapApplet. Each object of the class CapOnExitAppletHandler represents a single OnExitApplet function supplied to the AddOnExitApplet method of the class CapApplet. Each successful call to AddOnExitApplet causes a new object of class CapOnExitAppletHandler to be constructed for recording the parameters passed on to AddOnExitApplet. These class CapOnExitAppletHandler objects are kept in the m_OnExitAppletArray member of the class CapApplet. As with the class CapOnIdleHandler above, this class is also preferably made normal and is made a publicly accessible class so it can inherit from Cobject and be made dynamic to facilitate finding memory leaks involving objects of this class.

The class CapOnQueryShutdownHandler is preferably defined privately within the class CapApplet. The class CapOnQueryShutdownHandler exists solely for internal use by class CapApplet and is unavailable for reference or use outside the class CapApplet. Each object of class CapOnQueryShutdownHandler represents a single OnQueryShutdown function supplied to the AddOnQueryShutdown method of the CapApplet. Each successful call to AddOnQueryShutdown causes a new object of class CapOnQueryShutdownHandler to be constructed to record the parameters passed to AddOnQueryShutdown. These class CapOnQueryShutdownHandler objects are kept in the m_OnQueryShutdownArray member of the class CapApplet. As with the class CapOnIdleHandler above, this class is also preferably made normal and is made a publicly accessible class so it can inherit from CObject and be made dynamic to facilitate finding memory leaks involving objects of this class.

The class CapOnShutdownHandler is preferably defined privately within the class CapApplet. The class CapOnShutdownHandler preferably exists solely for internal use by the class CapApplet and is unavailable for reference or use outside of the class CapApplet. Each object of the class CaponShutdownHandler represents a single OnShutdown function supplied to the AddonShutdown method of the class CapApplet. Each successful call to AddOnShutdown causes a new object of class CaponShutdownHandler to be constructed to record the parameters passed to AddInShutdown. These class CapOnShutdownHandler objects are preferably kept in the m__OnShutdown Array member of the class CapApplet. As with the class CapOnIdleHandler above, this class is also preferably made normal and is made a publicly accessible class so it can inherit from CObject and be made dynamic to facilitate finding memory leaks involving objects of this class.

The class CapClientConfig preferably defines all the modifications which the Workstation Client Shell must make to provide the necessary interfaces for an Applet. It is preferably a simple collection of objects of other classes which define the actual Workstation Client Shell configuration changes. An Applet will typically contain a private member attribute of class CapClientConfig which may be named m__pClientConfig. The Applet's GetClinetConfig will preferably return the address of m__pClientConfig. The class CapClientConfig preferably includes various public methods, such as "CapClinetConfig," "GetMenuCount," "GetMenu," "GetSubmenuCount," "GetSubmenu," "GetPopupSubmenuCount," "GetPopupSubmenu," "GetToolBarBtnCount," "GetToolBarBtn," "GetToolBarCount," "GetToolBar," "GetBannerPageCount," "GetBannerPage," "GetAboutPageCount," "GetAboutPage," "GetoptionsPageCount" and "GetOptionsPage". Each of these public methods return a variety of pointers, numbers or data or add information to or from the CapApplet and other portions of the CIS.

The Menu Locations interface provides definitions to the framework defined menu and submenu locations. These values are used when defining the objects of the classes CapMenu and CapSubmenu to define the desired Menu and Submenu positions. This interface includes a variety of global definitions such as "apSubmenuOffset," "apMenuOffset," "apSubmenuMin," "apSubmenuMax," "apSubmenuFirst," "apSubmenuLast," "apFileSubmenuLocation," "apMenuLocation," "apEditSubmenuLocation," "apViewSubmenuLocation," "apListsSubmenuLocation," "apToolsSubmenuLocation," "apAdminSubmenuLocation," "apHelpSubmenuLocation" and "apDebugSubmenuLocation" to provide definitions for various menu and submenus features. This interface also preferably includes a global attribute such as "dwMenuLocations" to provide an array of the framework defined menu location values and is preferably only used by the Applet and ClientShell modules.

The class CapMenu preferably defines a new menu which the Workstation Client Shell must add to its menus to provide a necessary interface for an Applet. This class includes various public methods such as "CapMenu," "~CapMenu," "GetMenuLoc" and "GetMenuName".

The class CapSubmenu preferably defines a new submenu which the Workstation Client Shell must add to its menus to provide a necessary interface for an Applet. This class preferably includes various public definitions such as "apSubmenuType" and various private definitions such as "ApIsSubmenuShared," "ApIsSubmenuCalled" and "ApIsCmdRoutingCalled". The public definition for this class preferably specifies the complete characteristics of a Cap-Submenu Object. The private definitions of this class preferably define single bit values used within an apSubmenuType value. The public methods of this class include "CapSubmenu," "~CapSubmenu," "GetSubmenuType," "GetMenuLoc," "GetSubmenuLoc," "GetCommandID," "GetSubmenuName," "GetSubmenuShared," "GetSubmenuCalled," "GetCmdRoutingCalled," "IsSubmenuShared," "IsSubmenuCalled," "IsCmdRoutingCalled," "OnUpdateSubmenu" or "OnSubmenu" to perform various features for or on behalf of the class Submenu.

The class CapPopupSubmenu defines a new submenu popup menu which the Workstation Client Shell preferably must add to its menus to provide a necessary interface for an Applet. This class preferably includes various public methods such as "CapPopupSubmenu" and "~CapPopupSubmenu."

The class CapToolBarBtn preferably defines a new toolBar Button which the Workstation Client Shell must add to its ToolBar to provide a necessary interface for an Applet. This class preferably includes various public methods such as "CapToolBarBtn" and "~CapToolBarBtn."

The class CapToolBar preferably defines a new ToolBar which the Workstation Client Shell must enable to provide a necessary interface for an Applet. The characteristics of the ToolBar and the conditions under which it is enabled are also defined by this class. This class includes various public methods such as "CapToolBar" and "~CapToolBar."

The class CapBannerPage preferably defines a new Banner Page which the Workstation Client Shell must display within its normal Banner Page. Multiple Applet Banner Pages are preferably displayed sequentially in Applet ID order. This class preferably includes various public methods such as "CapBannerPage" and "~CapBannerPage."

The class CapAboutPage preferably defines a new about page which the Workstation Client Shell must display within its "About Box" dialog. This class preferably includes various public methods such as "CapAboutPage" and "~CapAboutPage."

The class CapOptionsPage preferably defines a new options page which the Workstation Client Shell must display within its "Options" dialog. This class preferably includes various public methods such as "CapOptionsPage" and "~CapOptionsPage."

The class CapServerConfig preferably defines all of the modifications which the Workstation Server Shell must make to provide the necessary interfaces for an Applet. This class is preferably a simple collection of objects of other classes which define the actual Workstation Server Shell configuration changes. An Applet will typically contain a private member attribute of class CapServerConfig which may be named m__pServerConFIG. The Applet will typically initialize m__pServerconfig within its InitApplet. The Applets GetServerConfig would then return the value of the m__ServerConfig. This class preferably contains various public methods such as "CapServerConfig" and "~CapServerConfig."

Figure 60:
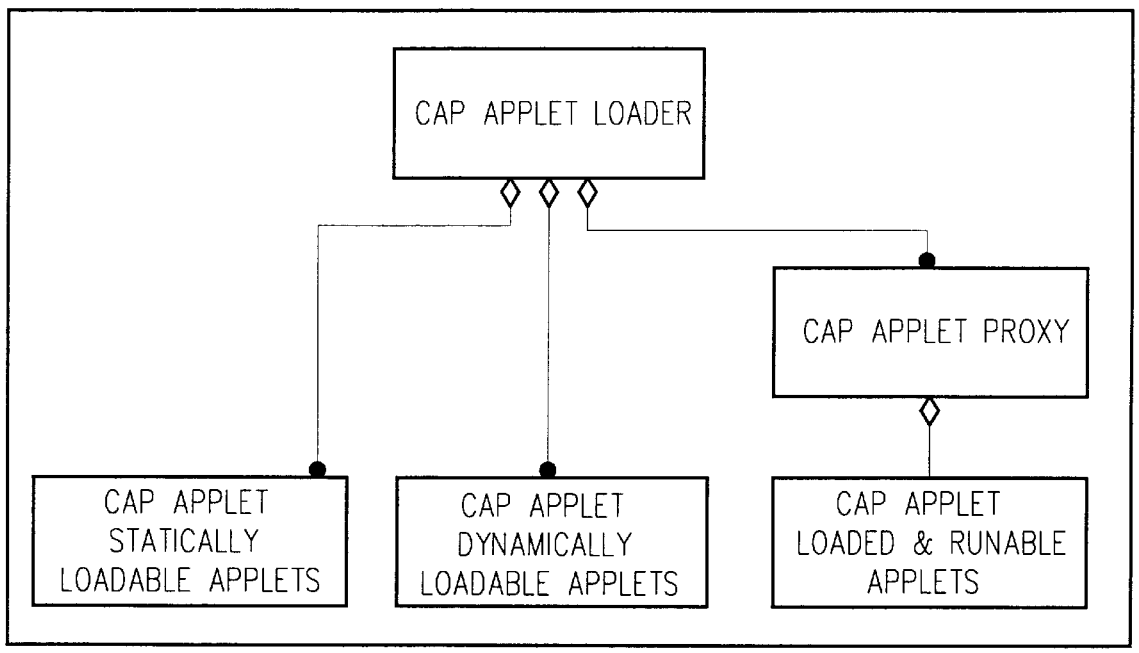
FIG. 60 is a diagrammatic view illustrating an overview of the Applet Loader class of the present invention.

FIG. 60 shows the preferred relationships between all classes defined in the Applet Loader module as well as the relationships between classes within the Applet Loader module and classes within other workstation framework modules in the present invention. The Applet Loader module class CapAppletLoader contains a list of statically loadable Applets (class CapApplet). These Applets have been statically linked into the Applet Loader module and automatically loaded into memory by the Win32 program loader.

Figure 61:
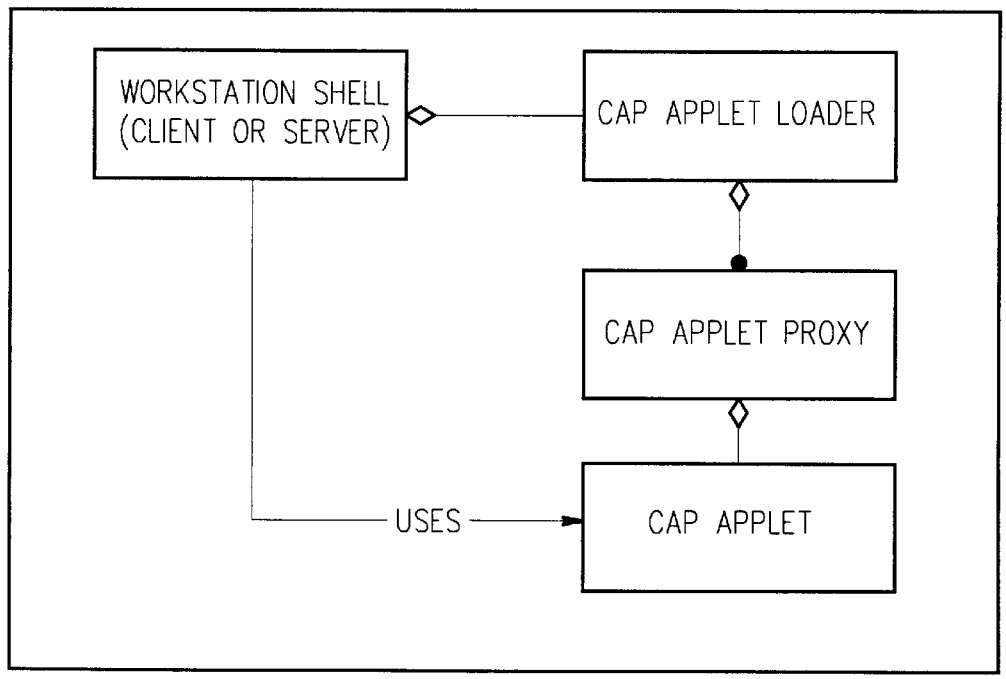
FIG. 61 is a diagrammatic view illustrating the interaction between the Applet Loader and the Workstation Shell.

When initialized by the Workstation Shell, CapApplet-Loader builds a list of dynamically-loadable Applets. The lists of statically and dynamically-loadable Applets are merged and sorted into unique Applet ID order and placed in the list of loaded Applets. Each loaded Applet is contained in a CapAppletProxy object which maintains Applet Loader information and Applet initialization status pertaining to an individual Applet. CapAppletLoader provides static methods which can be used to access individual Applets contained in the list of all loaded Applets. FIG. 60 shows these relationships. Both the Workstation Client Shell and the Workstation Server Shell preferably construct and initialize a single CapAppletLoader object. The Workstation Shell obtains addresses of CapApplet objects, as needed, from this CapAppletLoader object. FIG. 61 shows these relationships.

Figure 62:
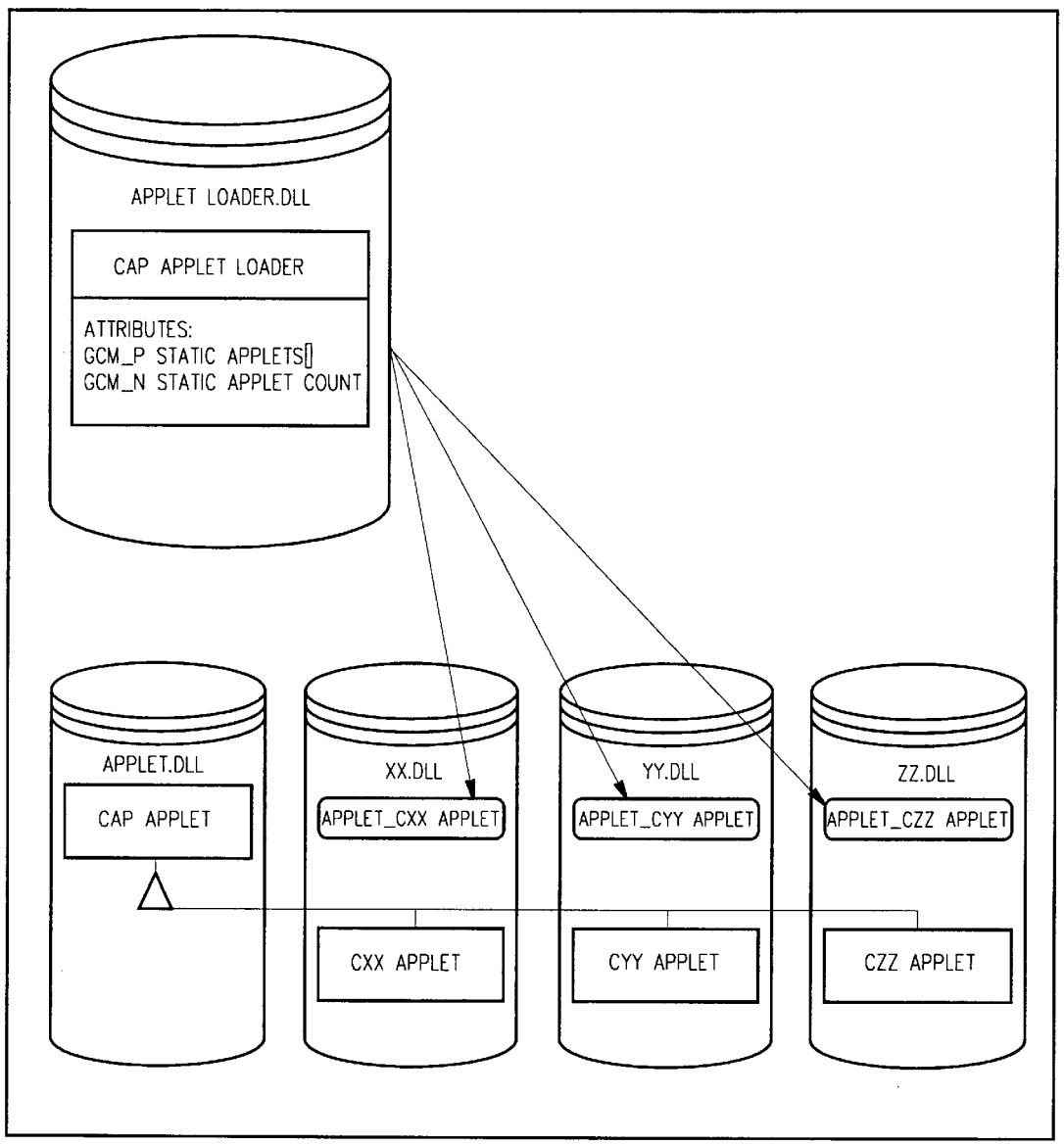
FIG. 62 is a diagrammatic view illustrating the loading relationships between the Applet Loader and statically-loaded Applets of the present invention.

In the present embodiment, the list of available Applets was defined statically, and all Applets were statically constructed within the Applet Loader. It is anticipated that the static construction of each Applet object may be moved from the Applet Loader to each Applet DLL. All statically loaded Applets are still preferably statically defined within the Applet Loader. The Applet Loader keeps a static list of pointers to Applet objects using the naming conventions described above for these Applet objects. FIG. 62 shows the loading relationships between the Applet Loader and statically-loaded Applets.

A further embodiment of the present invention adds dynamic Applet loading capabilities to the Applet Loader. This allows run-time detection and loading of Applets that are not included in the list of statically defined Applets within the Applet Loader. Each dynamically-loadable Applet must be explicitly enabled for dynamic loading. If an Applet has not been explicitly enabled for dynamic loading, that particular Applet can only be loaded statically. However, any Applet that has been enabled for dynamic loading can still be loaded statically (instead of dynamically) by including it in the list of statically defined Applets within the Applet Loader. Dynamic loading enabling of an Applet requires additional Applet program code. Although each Applet DLL is allowed to define and contain multiple Applets, it is anticipated that typically each Applet will be contained in its own DLL. In other words, typically each Applet DLL will define and contain only a single Applet. In addition to the required coding changes, the Applet DLL file type must be .QDA rather than .DLL. The Applet Loader of the present embodiment will preferably only attempt to dynamically load DLLs with a file type of .QDA.

The Applet Loader, when attempting to dynamically load an Applet DLL, will verify that a .QDA file is a dynamically-loadable Applet by the presence of both exported symbols __pDynamicApplets (the exported name of the symbol pDynamicApplets) and __wDynamicAppletCount (the exported name of the symbol wDynamicAppletCount). If both symbols are found in a DLL of file type .QDA, the Applet Loader assumes that __pDynamicApplets is an array of pointers to statically constructed CapApplet derived objects and that __wDynamicAppletCount is a word containing the number of CapApplet derived object addresses contained in the __pDynamicApplets array. This mechanism allows a single Applet DLL to define more than one Applet.

Figure 63:
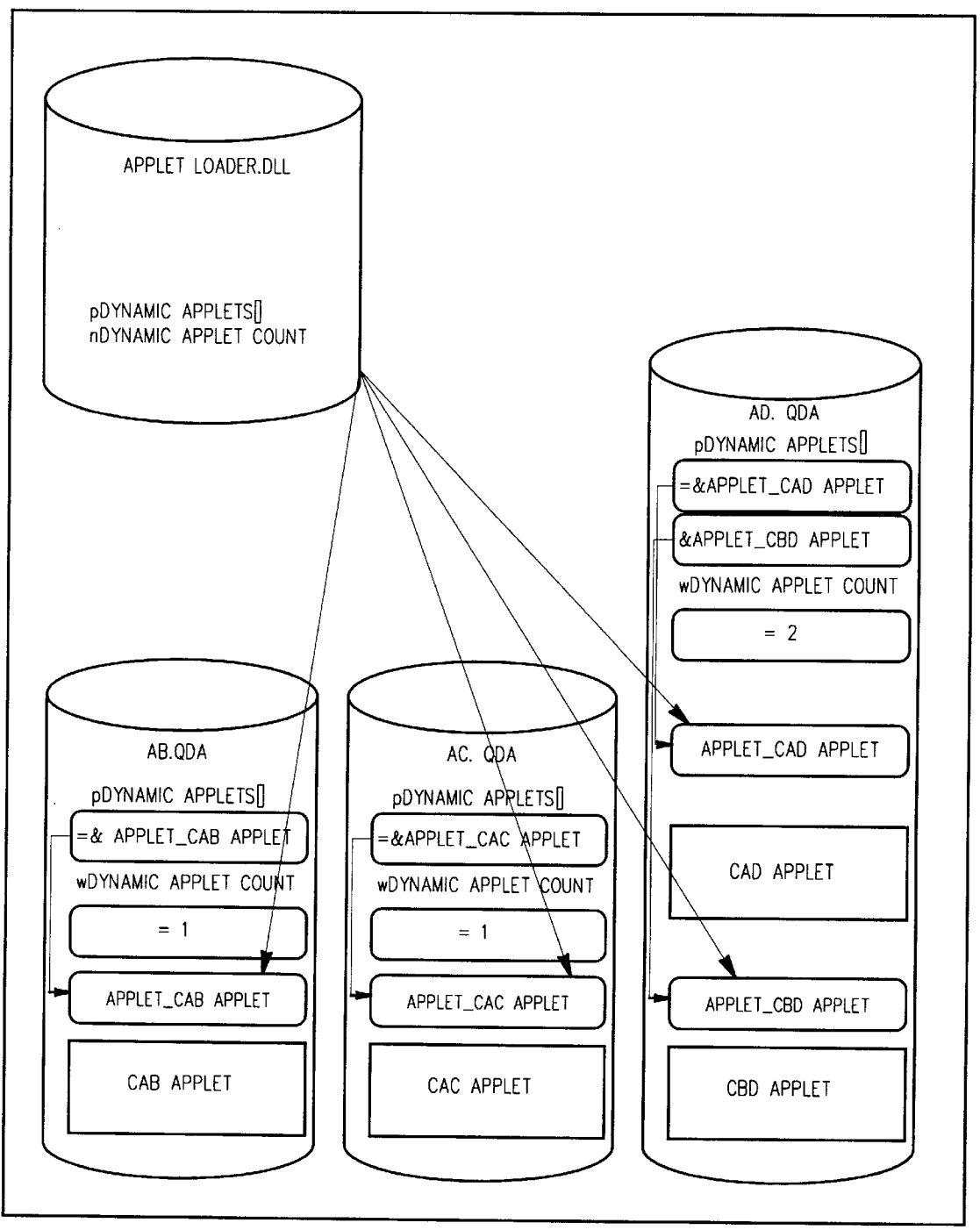
FIG. 63 is a diagrammatic view illustrating the loading relationships between the Applet Loader and the dynamically-loaded Applets of the present invention.
Figure 66A:
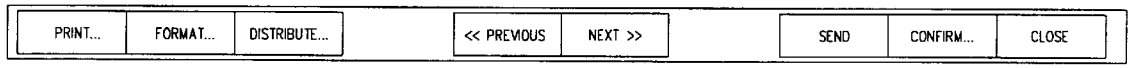
FIGS. 66A–C are diagrammatic views illustrating button bar widgets as formed by the present invention.
Figure 66B:
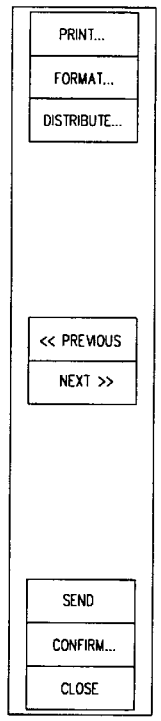
Figure 66C:
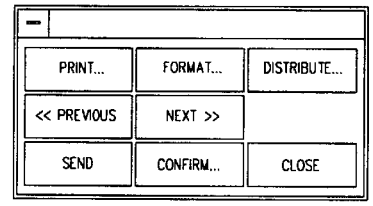

The list of Applet DLLs that are candidates for dynamic loading can come from several sources, including the registry, an INF file on disk, or the directory listing of all DLL files contained in any chosen directory. In another embodiment of the present invention, the list of Applet DLLs used as candidates for dynamic loading may be the directory listing of all files of file type .QDA contained in the same directory as the Workstation Shell executable. FIG. 63 shows the loading relationships between the Applet Loader and dynamically loaded Applets. In the examples in FIG. 63, both ab.QDA and ac.QDA represent typical Applet DLLs, each containing a single Applet class implementation along with an instantiation of an Applet object of that Applet class. In contrast, ad.QDA represents a DLL containing multiple Applet class implementations along with an instantiation of an Applet object of each Applet class.

The class CapAppletLoader provides various mechanisms to identify and load into memory all of the available Applets. It performs initialization and termination of the loaded Applets on behalf of the Workstation Shell. It also maintains the status of individual Applets as well as the status of the entire Workstation. In the preferred embodiment, only a single object of class CapAppletLoader is allowed. This object is expected to be constructed and owned by the Workstation Shell. This class preferably includes various public definitions such as "InitStatus." This definition is used for querying the initialization status of other than an individual Applet. This class also preferably includes various public methods such as "~CapAppletLoader," "InitApplets," "OnInitComplete," "OnQueryShutdown," "ExitApplets," "GetAppletLoader," "GetAppletCount," "GetApplet" and "GetInitStatus."

The class CapAppletProxy object serves as a repository for load status and the initialization status of the contained Applet. Each object of class CapAppletProxy preferably represents and contains a single Applet. The class CapAppletProxy preferably exists solely for internal use by class CapAppletLoader and is unavailable for reference or use outside of the Applet Loader module. This class preferably includes various public methods such as "CapAppletProxy," "~CapAppletProxy," "DoInitApplet," "IsStatic," "IsInitialized," "IsInitOK," "operator CapApplet&" and "operator CapApplet*."

As discussed above, the workstation framework is designed to be a building block for multiple workstation products. All these products are intended to run within the common Workstation Client Shell executable. It is highly desirable that all such products have a similar look and feel, similar screen layout characteristics and common communications capabilities between networked Workstation Client PCs and Workstation Server PCs. These traits are provided by the Workstation Client Shell executable and the Applet Widgets module. The Applet Widgets module provides screen design elements with behavior and appearance that is common across all workstation products. The Applet Widgets module interacts with the Workstation Client Shell to provide messaging capabilities between the Client Applets, between Workstation Client PCs, and between a Workstation Client PC and the Workstation Server PC(s). An example of such messaging is the notification of pending shutdown sent by the Workstation Client Shell to all active Applet Frame windows. FIGS. 64–70 are examples of how the various screen design elements might appear. These examples are intended to assist in the understanding of the Applet Widgets design by showing a general idea of what selected widget classes produce on the screen.

The Frame Widget, CawAppletFrm, is displayed as a normal MDI child window as shown in FIG. 64. The information block widget, CawFrameInfoBlock, is displayed as a horizontal group of labeled fields located at or near the top or bottom of a CawAppletFrm window as shown in FIGS. 65A and 65B. The fields automatically re-size to fit within the available space on the screen. Optionally, this screen element can be dragged off the CawAppletFrm, becoming a floating Widget. This screen element can be placed within the CawAppletFrm window at a program controlled location, or optionally the user can move this screen element to a new horizontal location at the top or bottom of the CawAppletFrm window. In a preferred form of the present invention, non-floating and floating Information Block Widgets may be supported.

The Button Bar Widget, CawFrameBtnBar, may be displayed as a horizontal or vertical group of labeled, horizontally oriented buttons located at or near a border of a CawAppletFrm window. Buttons are preferably grouped horizontally when located at or near the top or bottom borders and vertically when located at or near the left or right borders. The buttons automatically re-size to fit within the available space on the screen. Optionally, this screen element can be dragged off the CawAppletFrm, becoming a floating Widget. This screen element may also be placed within the CawAppletFrm window at a program controlled location, or optionally the user can move this screen element to a new location within the CawAppletFrm window. Buttons may optionally include an icon which will be positioned immediately to the left or the right of the button text. A Button Bar Widget containing three groups of buttons might appear similar to the example, shown in FIGS. 66A–C and include various icons.

The Tab Control Widget, CawTabCtrl, may be displayed as a horizontal group of labeled folder tabs located at or near the top border of a window. A CawTabCtrl may appear within a CawAppletFrm (instead of a CView object) or within a CawTab contained within another CawTabCtrl (instead of a CView object). The tabs are preferably horizontally oriented and grouped horizontally and located at or near the top border of the client area of their parent window. The tabs are also preferably a fixed size but can be scrolled when the Tab Control is wider than the parent window. In the preferred form of the present invention, the user is not able to move this screen element within the CawAppletFrm window nor is the user able to drag it off the CawAppletFrm window. The Tab Control Widget may appear similar to the examples shown in FIGS. 67A–H.

Figure 67A:
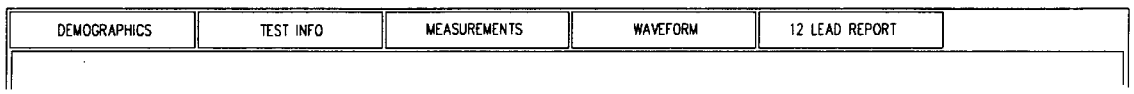
FIGS. 67A–H are diagrammatic views illustrating tab control widgets as formed by the present invention.
Figure 67B:
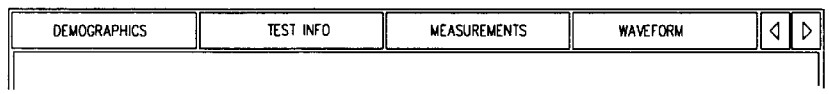
Figure 67C:
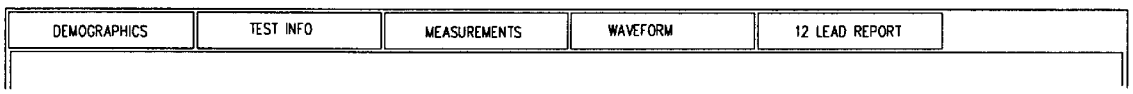
Figure 67D:
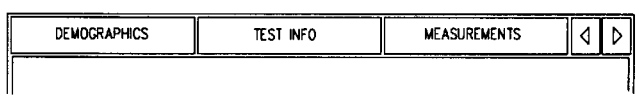
Figure 67E:
Figure 67F:
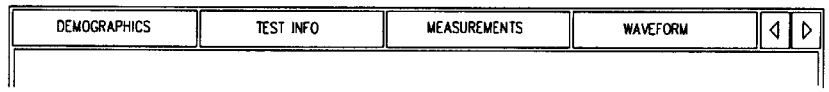
Figure 67G:
Figure 67H:
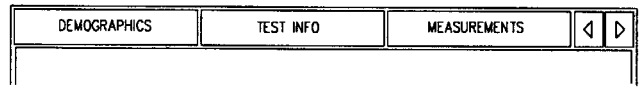

As shown in FIGS. 67A and 67B, the Applet Widgets may include a tab control widget to form a button style tab control. FIGS. 67C and 67D are illustrative of button style tab controls with icons. FIGS. 67E and 67F are illustrative of tab control widgets that form tab style tab controls, and FIGS. 67G and 67H add icons to the tab style tab controls.

As shown in FIG. 68, a CawTabCtrl may appear within a CawTab contained within another CawTabCtrl (instead of a CView object). Such a nested CawTabCtrl might appear similar to the example, showing selection of the "Stress" tab on a Tab Control contained within the "Demographics" tab of a different Tab Control. A Tab Combo Box Widget, CawTabComboBox, is displayed in FIG. 69 as a combo box containing a list of folder tabs. The combo box overlays the right-most or bottom-most portion of an Information Block Widget. A CawTabComboBox may appear within a CawTab contained within a CawTabCtrl (instead of a CView object), behaving similarly to a nested CawTabCtrl. This will appear similar to the example shown in FIG. 69, which shows the "12-lead simultaneous" tab selected on the CawTabComboBox contained within the "Demographics" tab (a truly contrived example) selected on a CawTabCtrl.

Figure 70B:
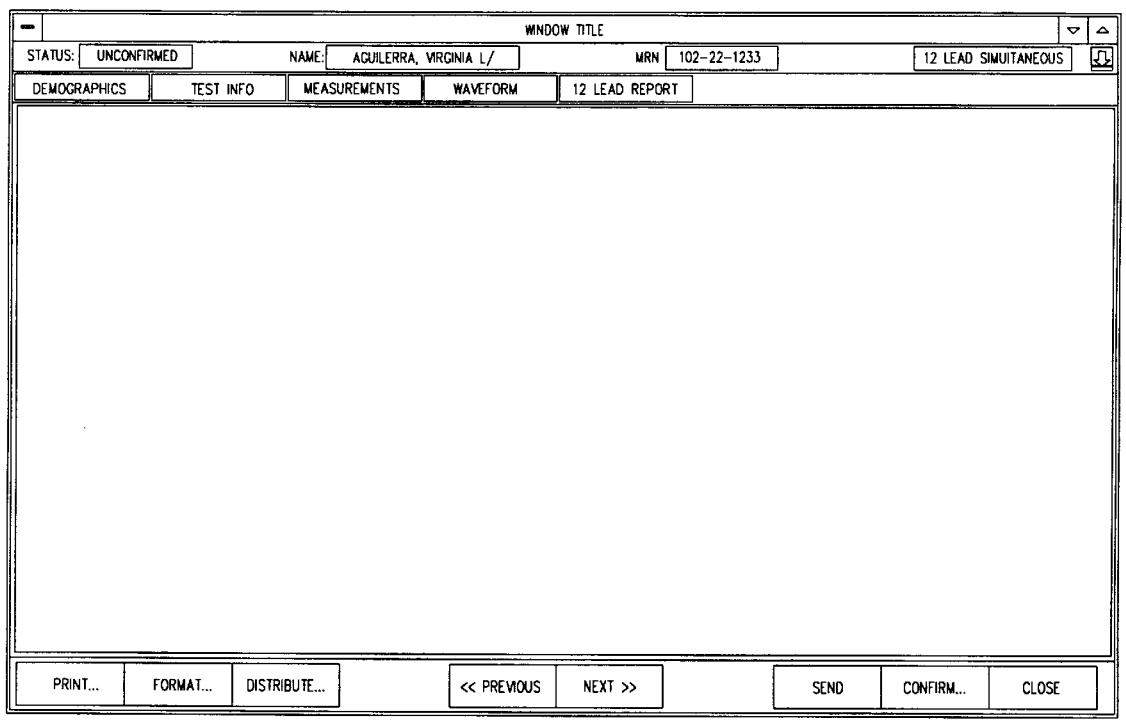

Examples of the use of multiple widgets are shown in FIGS. 70A and 70B. In FIG. 70A, a CawAppletFrm containing a CawFrameInfoBlock at the top, a horizontal CawFrameBtnBar at the bottom and a CawTabCtrl containing a nested CawTabCtrl is shown. As shown in FIG. 70B, multiple widgets are used to provide a CawAppletFrm containing a CawFrameInfoBlock at the top, a horizontal CawFrameBtnBar at the bottom and a CawTabctrl containing a CawTabComboBox.

Figure 71:
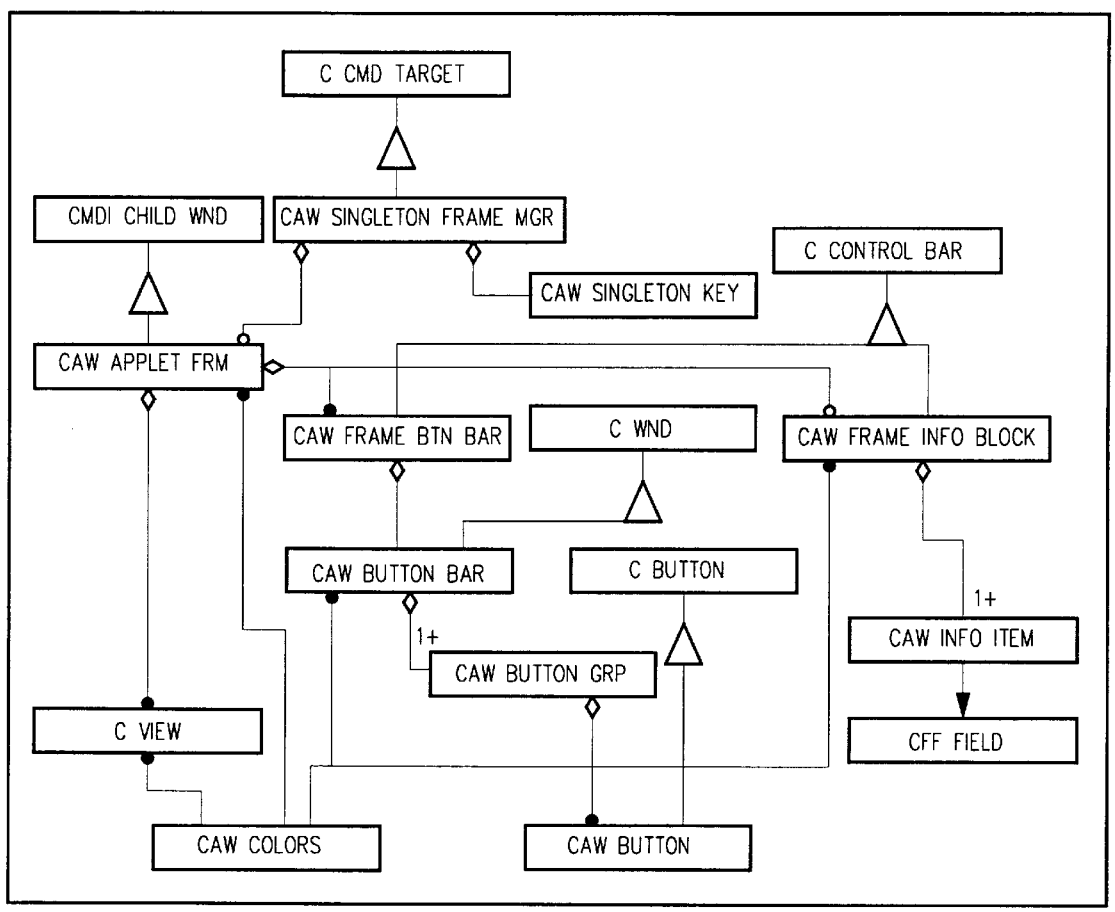
FIG. 71 is a diagrammatic view illustrating an overview of the Applets Widgets classes of the present invention.

Each Applet creates a frame window on the screen and uses a class derived or directly from CawAppletFrm to create this frame window. If the frame is to exhibit singleton behavior; that is, if an attempt to open a second copy of an existing frame window is disallowed and instead activates the existing copy, the frame can be created through class CawSingletonFrameMgr which provides and enforces this singleton behavior. CawSingletonFrameMgr can enforce singleton behavior either based on a specific instance of a CawSingletonFrameMgr object (keyed to the address of this object) or based on the specific Applet specified value of a CawSingletonKey object (using static CawSingletonFrameMgr methods). Each CawAppletFrm object can optionally contain a single CawFrameInfoBlock object (containing one or more CawInfoItem objects) and/or one or more CawFrameBtnBar objects. Both the CawFrameInfoBlock and the CawFrameBtnBar are MFC CControlBar objects which are allowed to be made into floating control bars which float above the CawAppletFrm window. They can also be dragged to different positions within the CawAppletFrm window. An Applet may include a CawButtonBar object within any Applet defined view. This provides a button bar, similar to the button bar provided by CawFrameBtnBar, that may not be dragged or floated. The buttons contained on button bars are grouped with space left between button groups. The CawButton defines an individual button bar button, and the CawButtonGrp serves as a container of those buttons which comprise a specific group of buttons. Colors of various screen elements are customizable. CawColors provides static methods used by widgets and optionally by Applet views to obtain the specific color value to be used for a particular screen element. These relationships are shown in FIG. 71.

Figure 72:
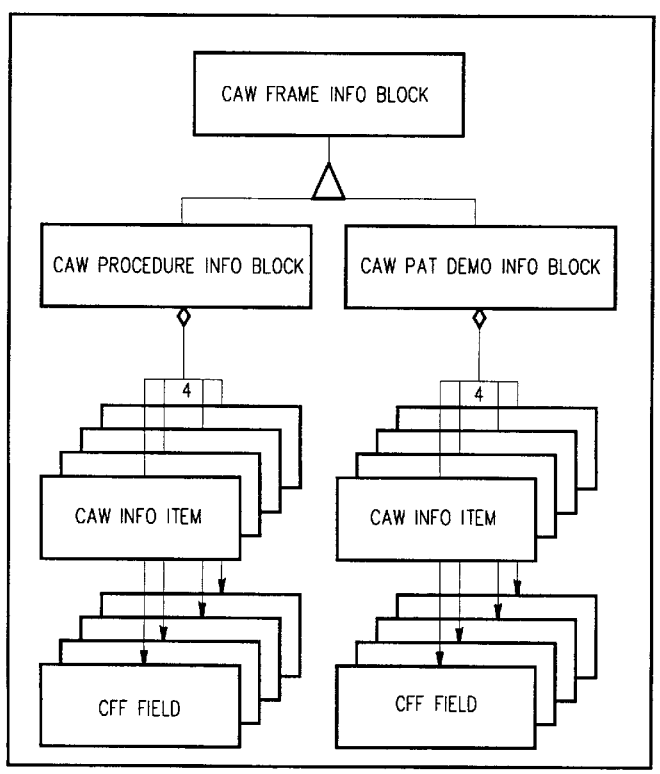
FIG. 72 is a diagrammatic view illustrating the class relationships used for a pair of predefined information block widgets in the present invention.

As shown, each CawFrameInfoBlock object preferably contains one or more CawInfoItem objects which supply specific CffField objects for display in the CawFrameInfoBlock window. Two commonly used Information Block Widget configurations are predefined within Applet Widgets. The CawProcedureInfoBlock defines an Information Block Widget used for viewing and editing procedure records. The CawPatDemoInfoBlock defines an Information Block Widget used for viewing and editing patient demographics records. These relationships are shown in FIG. 72. In the preferred form of the present embodiment, the CawProcedureInfoBlock contains four CawInfoItem objects specifying Procedure status (i.e., confirmed, unconfirmed, reconfirmed, etc.), Patient name, Patient MRN, and Procedure acquisition date and time. Also in the preferred embodiment, the CawPatDemoInfoBlock preferably contains four CawInfoItem objects specifying Patient status (i.e., In-Patient, Out-Patient, etc.), Patient name, Patient MRN, and Last demographics modification date and time as shown in FIG. 72.

Figure 73:
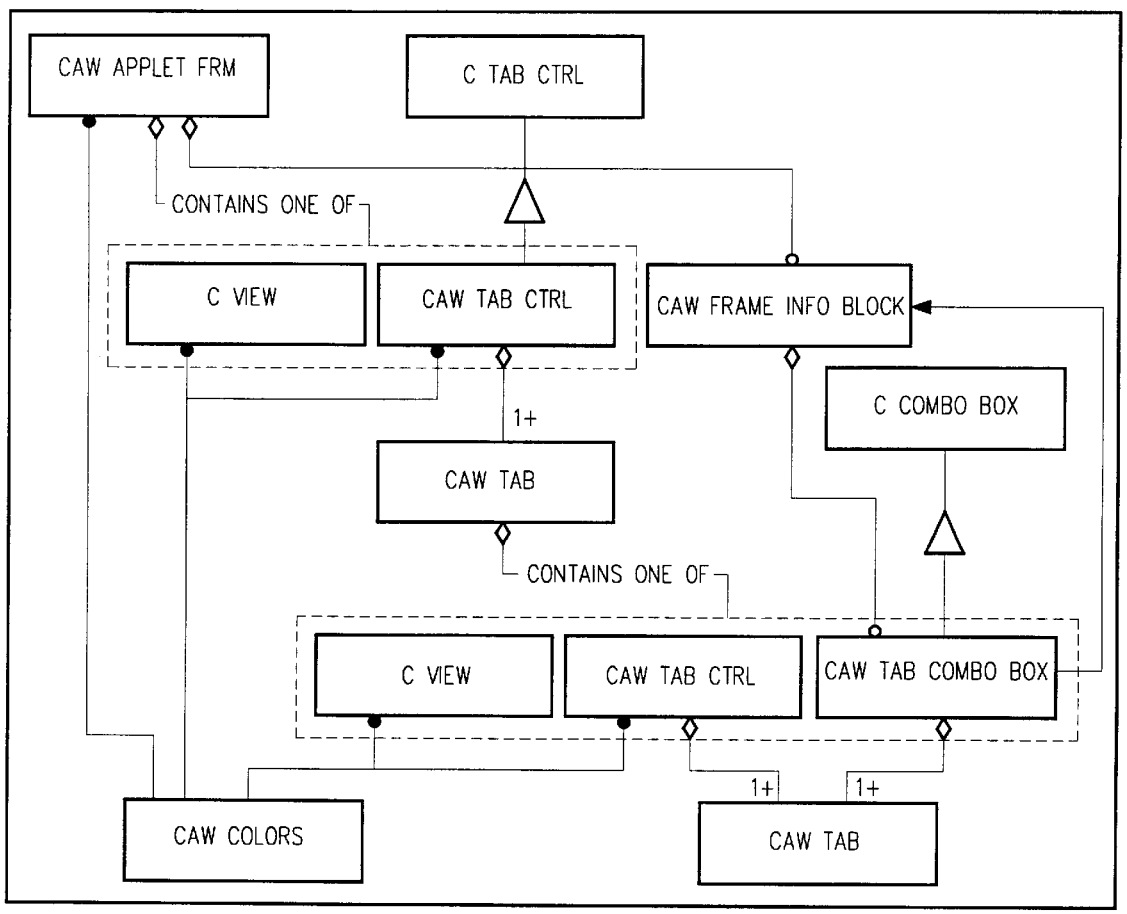
FIG. 73 is a diagrammatic view illustrating the class relationships used to form a multiple widget view similar to that which is shown in FIGS. 70A and 70B.

Typical MFC frame windows contain a single view window. Alternatively, the CawAppletFrm may include a CawTabCtrl object rather than a view window. In the present embodiment, each CawTabCtrl contains multiple tabs, each specified by a CawTab object which typically contains a view window. Alternatively, a CawTab object may contain either a CawTabCtrl object or a CawTabComboBox object instead of a view window. Each CawTabComboBox contains multiple tabs, each specified by a CawTab object. Each CawTabComboBox must be contained in a CawTab object contained in a CawTabCtrl object. These relationships are shown in FIG. 73.

In the present embodiment, the CawTabCtrl has been designed to be fully interchangeable with the MFC class CSplitterWnd. The CSplitterWnd may be used in place of a CView within a CFrameWnd and in turn may contain one or more CView objects or other CSplitterWnd objects containing CView objects, etc. The CawTab objects can also contain CSplitterWnd objects instead of a CView. The CSplitterWnd objects may contain CawTabCtrl objects instead of CView or CSplitterWnd objects. Conceptually, both CawTabCtrl and CSplitterWnd are similar. They can be used in place of a CView object anywhere a CView object would normally be used and normally contain CView objects (contained within tabs or panes, respectively), and any contained CView object may be replaced with a CawTabCtrl or CSplitterWnd object containing more CView objects.

Figure 74:
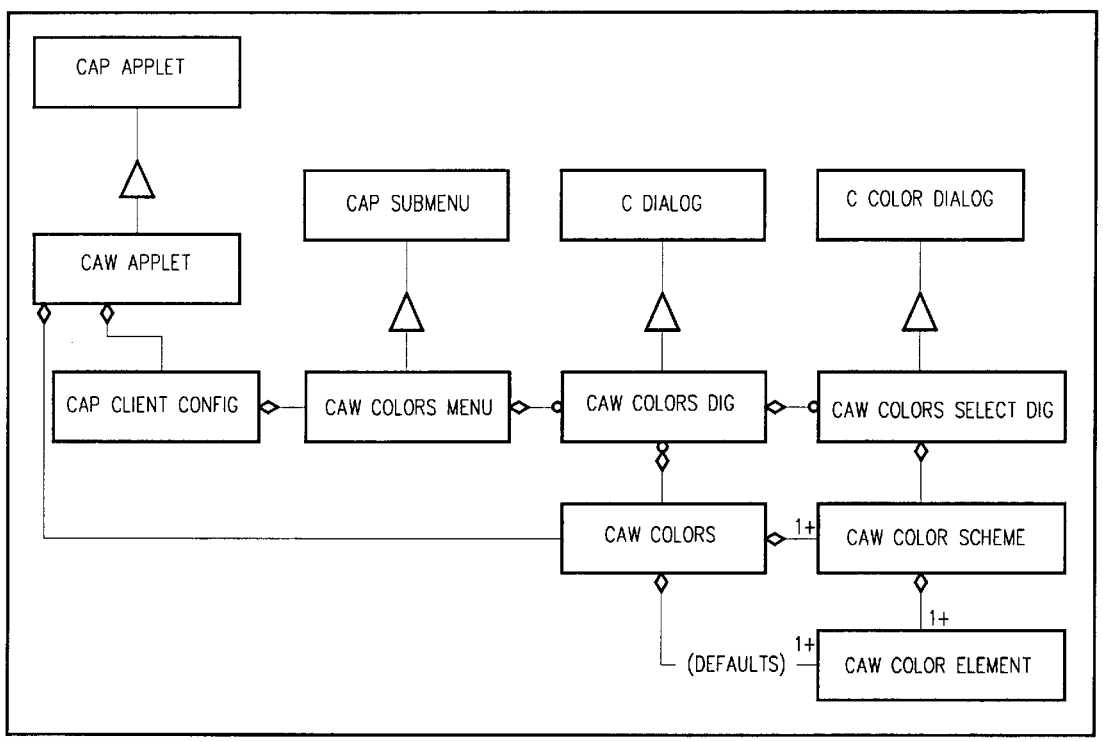
FIG. 74 is a diagrammatic view illustrating the class relationships which are used to enable the user to manipulate the color values used in the present invention.

The Applet Widgets provide classes which allow the user to manipulate the specific color values used. The class CawColorsMenu defines a Workstation Client Shell submenu which, when chosen, activates a CawColorsDlg color selection dialog. The CawColorsDlg allows the activation, creation, modification and deletion of color schemes (CawColorScheme objects) consisting of multiple color elements (CawColorElement objects). The CawColorsDlg also provides a means to activate the CawColorSelectDlg for a selected CawColorScheme object. The CawColorSelectDlg allows the selection of a specific CawColorElement object and customization of the color value assigned to the selected CawColorElement. FIG. 74 shows the color classes provided by Applet Widgets. Although it may appear that CawColorsDlg and CawColorSelectDlg would be better implemented as CPropertyPage objects within a CPropertySheet dialog (this would indeed provide a more friendly, easier to use user interface), this would preclude using the common color dialog (implemented with CColorDialog) and would require considerable additional code.

The class CawApplet of the Applet Widgets module provides the Applet Interface between the Workstation Shell and the Applet Widgets. This class includes various public methods such as "CawApplet," "~CawApplet," "GetClientConfig," "GetServerConfig," "GetAppletName," "GetAppletTitle" and "GetColors." The class CawApplet also includes protected methods such as "InitApplet" and "ExitApplet."

The class CawAppletFrm preferably provides the frame widget described above, an example of which is shown in FIG. 64. This class of the Applet Widgets module includes various public definitions such as "WidgetPos" and various protected definitions such as "FrameBehavior". The public definition WidgetPos describes the position of an attached Widget within the frame window. The private definition FrameBehavior, specifies the initial window size and position and color changes made to the background of any views contained within the frame window. This class also includes various public methods such as "CawAppletFrm," "~CawAppletFrm," "AttachWidget," "UpdateInfoBlock," "HasInfoBlock," "HasTabCtrl," "GetInfoBlock," "GetTabCtrl," "ReplaceWidget," "SetMinViewSize," "GetMinViewSize," "SetPlacementToMax," "SetPlacementToUpperHalf," "SetPlacementToLowerHalf," "RestoreToMax," "RestoreToUpperHalf," "RestoreToLowerHalf," "Addownedobject," "RemoveOwnedObject," "AddCmdTarget," "RemoveCmdTarget," "AddOwnedCmdTarget," "RemoveownedCmdTarget," "IsOwnedTarget," "IsCmdTarget," "IsOwnedCmdTarget," "PrecreateWindow," "LoadFrame," "OnCmdMsg," "Create" and "RecalcLayout." The class CawAppletFrm of the Applet Widget module may also include protected methods such as "SetChildListView," "OnQueryShutdown," "OnShutdown," "OnServerMessage," "PreCreateWindow," "OnWindowPosChanging," "OnClose," "OnDestroy" and "OnWindowPosChanged."

The class CawSingletonFrameMgr preferably provides singleton behavior for an object class of CawAppletFrm. This singleton behavior guarantees that for any one object of class CawSingletonFrameMgr, at most, one corresponding CawAppletFrm object will exist. The singleton behavior is tied to the memory address of each specific CawSingletonFrameMgr object. An alternative method of singleton behavior tied to a key behavior is also provided in the preferred form of the present invention. This alternative method uses a CawSingletonKey object to provide a unique frame key. The class CawSingletonFrameMgr uses this unique key value to establish singleton behavior of a CawAppletFrm object. The class CawSingletonFrameMgr preferably includes various public methods such as "CawSingletonFrameMgr," "~CawSingletonFrameMgr," "ActivateFrame," "CloseFrame" and "IsFrameopen."

The class CawSingletonKey preferably provides a mechanism for creating a string representing a unique entity. The value of a CawSingletonKey object is a string built up from string values, numeric values, address values and class names. The class CawSingletonFrameMgr may be used to control the singleton creation of a CawAppletFrm object based on the value of a CawSingletonKey object. The class CawSingletonkey preferably includes various public methods such as "CawSingletonKey," "~CawSingletonKey," "GetKeyValue," "operator=" and "operator<<."

The class CawFrameInfoBlock from the Applet Widgets module preferably provides the information block widget described above, examples of which are shown in FIGS. 65A and 65B. The class CawFrameInfoBlock preferably includes various public methods such as "CawFrameInfoBlock," "~CawInformationBlock," "Create," "UpdateInfoBlock," "GetItemCount," "GetItem," "SetTabBox," "OnUpdateCmdUI" and "CalcDynamicLayout." This class also preferably includes various protected methods such as "OnWindowPosChanged" and OnCtlColor."

The class CawInfoItem from the Applet Widgets module preferably provides a data item displayed within a CawFrameInfoBlock object. Each CawInfoItem data item preferably contains two windows which will be displayed in a parent window. The first window is preferably an optional window that is simple (CStatic object) and which contains right justified label text. The second window is preferably an edit control (CEdit object) containing left justified field value text which specifies the value of the current CffField object associated with this CawInfoItem object. The CawInfoItem windows are similar to those shown in FIGS. 65A and 65B. The class CawInfoItem preferably includes various public methods such as "CawInfoItem," "~CawInfoItem," "SetWidth," "Create," "UpdateInfoItem," "EraseInfoItem," "GetMinWidth," "GetMaxWidth," "GetHeight" and "MoveWindow."

The class CawProcedureInfoBlock from the Applet Widgets module preferably provides a common definition of the information block widget used for editing and viewing procedure records. The CawProcedureInfoBlock preferably contains four CawInfoItem objects which specify procedure status (i.e., confirmed, unconfirmed, reconfirmed, etc.), patient name, patient MRN and procedure acquisition time and date. The CawProcedureInfoBlock preferably includes various public methods such as "CawProcedureInfoBlock" and "~CawProcedureInfoBlock."

The class CawPatDemoInfoBlock from the Applet Widgets module preferably provides a common definition of the information block widget used for editing and viewing procedure records. The CawPatDemoInfoBlock preferably contains four CawInfoItem objects which specify patient status (i.e., In-Patient, Out-Patient, etc.), patient name, patient MRN and last demographics modification time and date. The CawPatDemoInfoBlock preferably includes various public methods such as "CawPatDemoInfoBlock" and "~CawPatDemoInfoBlock."

The class CawFrameBtnBar from the Applet Widgets module preferably provides the Button Bar Widget described above, examples of which are shown in FIGS. 66A–C. Each CawFrameBtnBar object contains a single CawButtonBar object implementing the actual Button Bar. Each CawButtonBar object contains one or more CawButtonGrp objects representing groups of buttons within the Button Bar. Each contained CawButtonGrp object contains one or more CawButton objects representing the actual buttons within the Button Bar. The CawButton objects which are contained by the CawButtonGrp objects are contained by the CawButtonBar object within a CawFrameButtonBar object and can be referenced by a zero based index, starting from the left-most or top-most button. This button indexing ignores the bottom groupings. The class CawFrameBtnBar preferably includes a variety of public methods such as "CawFrameBtnBar," 1 "~CawFrameBtnBar," "AddBtnGrp(s)," "CawButtonGrp," "GetButtonCount," "GetButton," GetButtonByCommand," "OnUpdateCmdUI" and "CalcDynamicLayout." The protected methods of the class CawFrameBtnBar includes "OnWindowPosChanged."

The class CawButtonBar from the Applet Widgets module preferably provides a window containing the buttons within a Button Bar Widget. It may also be used to implement a Button Bar within an Applet defined view, such as might be needed by the Record Lists Applet. The Button Bar Widget is preferably implemented by class CawFrameButtonBar, which contains a CawButtonBar object. Each CawButtonBar object contains one or more CawButtonGrp objects representing groups of buttons within the Button Bar. The CawButton objects contained by CawButtonGrp objects contained by a CawButtonBar object may be referenced by a zero based index, starting from the left-most or top-most button. The button indexing ignores the button groupings. The class CawButtonBar preferably includes a public definition for aworientation and public methods for "CawButtonBar," "CawButtonBar," "AddButtonGrps," "Create," "GetButtonCount," "GetButton," "GetButtonByCommand," "GetOrientation," "SetOrientation," "DefaultWidth," "defaultHeight," "MinVertWidth," "MinHorzHeight" and "OnCmdMsg." This class also preferably includes various protected methods such as "CalcBtnPositions," "BtnWidth," BtnHeight," "SepWidth," "SepHeight," "DefaultBtnWidth," "DefaultBtnHeight," "DefaultXOffset," "DefaultYOffset," DefaultSepWidth," "DefaultSepHeight," "OnWindowsPosChanged," "OnIdleUpdateCmdUI" and "OnCtlColor."

The class CawButtonGrp from the Applet Widgets module is preferably a container of CawButton objects which are used by CawFrameBtnBar objects to provide the Button Bar Widget as described above and shown in FIGS. 66A–C. This class preferably includes various public methods including "CawButtonGrp," "~CawButtonGrp," "AddButton(s)," "GetButtonCount," "GetButton" and "GetButtonByCommand."

The class CawButton from the Applet Widgets module preferably provides buttons held in CawButtonGrp containers used by CawFrameBtnBar objects to provide the Button Bar Widgets described above. The CawButton objects optionally support the display of an icon immediately to the left or right of the button text. The CawButton class preferably includes a public definition for IconPos and public methods for "CawButton," "~CawButton," "GetBtnCommand," "GetBtnName," "GetBtnIcon," "SetBtn," "SetBtnCommand," SetBtnName" and "SetBtnIcon."

The class CawTabCtrl from the Applet Widgets module preferably provides the Tab Control Widget described above, examples of which are shown in FIGS. 67A–H. The CawTabCtrl class inherits privately from class CTabCtrl so that it can extend and use the CTabCtrl common control while providing a different interface. The class CawTabCtrl preferably includes various private methods such as "CawTabCtrl," "~CawTabCtrl," "Addtab(s)," "Create," "GetTabCount," "SelectTab," GetSelectedTab," "GetTab," "RemoveTab," "DeleteTab" and "RedrawTabs." This class also preferably includes protected methods such as "OnSelChange" and "OnSize."

The class CawTabComboBox from the Applet Widgets preferably provides the Tab Combo Box Widget described above and shown in FIG. 69. The CawTabComboBox class preferably inherits privately from the class CComboBox so it can extend and use the CComboBox common controls while providing a different interface. The CawTabComboBox class preferably includes public methods such as "CawTabComboBox," "~CawTabComboBox," "AddTabs," "Create," "GetTabCount," "SelectTab," GetSelectedTab," "GetTab," "RemoveTab," "DeleteTab" and "RedrawTabs." This class also preferably includes a protected method for at least "OnSelChange."

The class CawTab from the Applet Widgets module preferably provides the tabs contained in the CawTabCtrl objects and the CawTabComboBox objects as described above. The class for CawTab preferably includes public methods such as "CawTab," "~CawTab," "GetTabName," "GetTabIcon," "SetTabName," SetTabIcon," "Activate," "ShowWindow," "MoveWindow" and "SetWindowPos." This class also preferably includes various protected methods such as "OnInitialActivate" and "OnActivate."

The class CawColors from the Applet widgets module preferably provides a static mechanism for supplying colors of various screen elements. It also serves as a container of multiple color schemes and default color elements. In the preferred embodiment, only a single object of class CawColors is allowed, and it is preferably constructed and owned by class CawApplet. The class CawColors preferably includes a global definition such as "enumawColoIDs" and public methods such as "~CawColors," "Initialize," "GetColorCount," "AddColor," "GetColorElement," "GetColor, "GetDefaultColor," "GetColorSchemeCount," "AddColorScheme," "RemoveColorScheme," "DeleteColorScheme," "GetColorScheme" and "SelectColorScheme."

The class CawColorScheme from the Applet Widgets module preferably provides a named collection of color elements which are used together as a unit. The class CawColorScheme preferably includes various public methods such as "CawColorScheme," "~CawColorScheme," "GetColorSchemeName," "GetColorCount," "GetColorElement," "GetColor" and "SetColor."

The class CawColorElement from the Applet Widgets module preferably provides a specific color value for a specific screen element. The class CawColorElement preferably includes a public definition for "enum StandardColors" and public methods for "CawColorElement," "~CawColorElement," "GetColorID," "GetColorName," "GetColor," "SetColor," "operator=" and operator "COLORREF."

The class CawColorsMenu from the Applet Widgets module preferably specifies a Client Shell submenu interface which, when selected, activates the color configuration dialog, CawColorsDlg. The class CawColorsMenu preferably includes various public methods such as "CawColorsMenu," "~CawColorsMenu" and "OnSubmenu."

Figure 75:
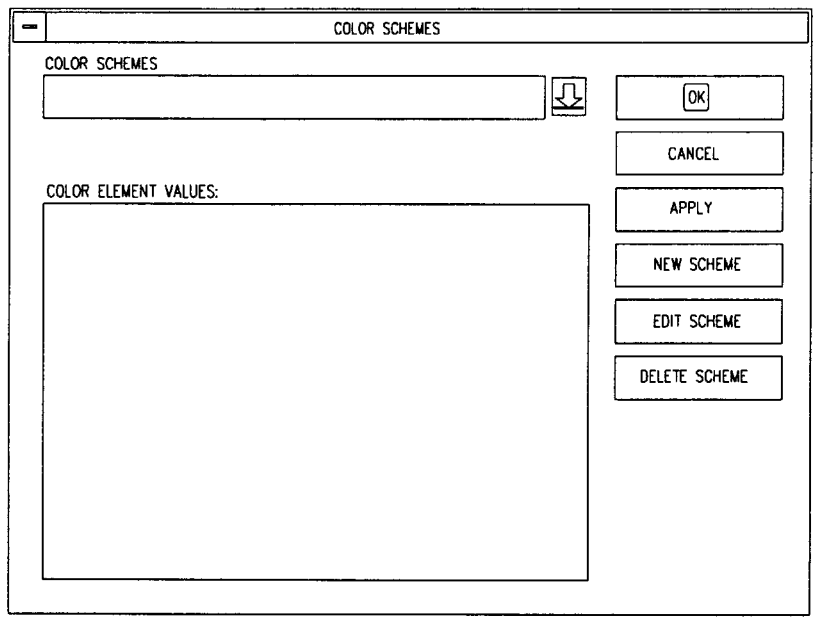
FIG. 75 is a diagrammatic view of a dialog for the class CawColorsDlg of the present invention.

The class CawColorsDlg from the Applet Widgets module preferably provides a colors configuration dialog which is used to select a specific color scheme, display current color values for the selected color schemes and change the color of a color element within a selected color scheme with the color selection dialog, CawSelectColorDlg. An example of the dialog produced by the CawColorsDlg is shown in FIG. 75. The "Color Scheme" which is selected becomes the active color scheme when either the "OK" or "Apply" selections are pushed. The "Color Element Values" selection displays the current colors of each color element for the selected Color Scheme. These color values can be edited by pushing the "EditScheme" selection, which activates the CawColorSelectDlg dialog. New color schemes can be created, and existing color schemes can be deleted. The class for the CawColorsDlg preferably includes public methods such as "CawColorsDlg" and "~CawColorsDlg."

Figure 76:
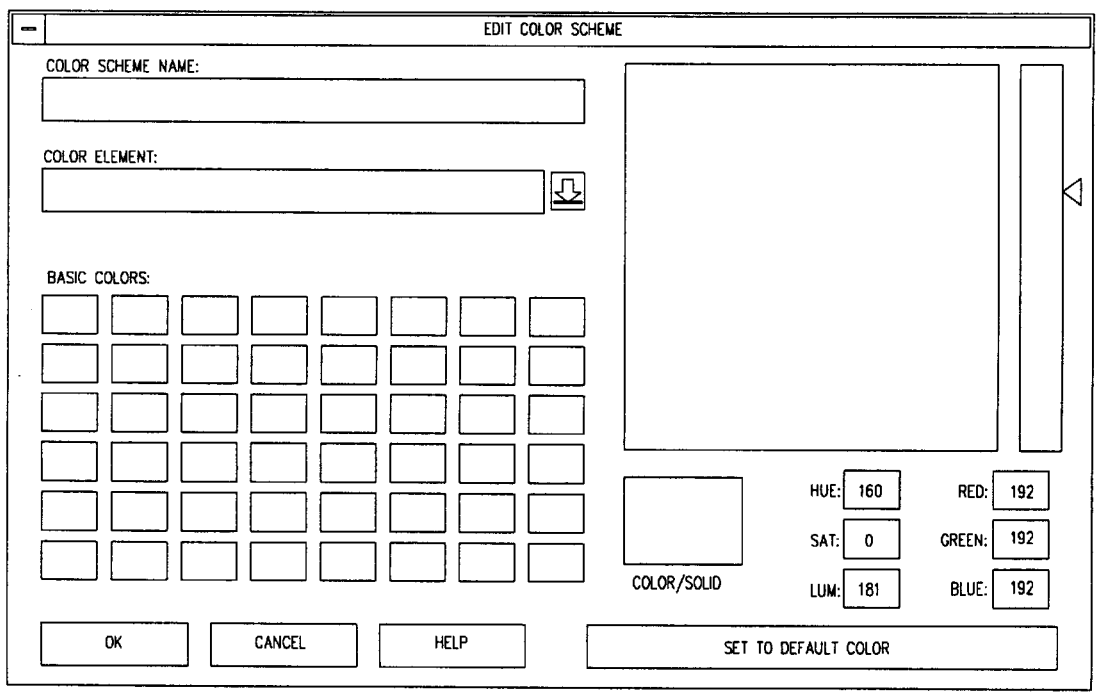
FIG. 76 is a diagrammatic view of a dialog for the class CawColorSelectDlg of the present invention.

The class CawColorSelectDlg from the Applet Widgets preferably provides a dialog which is activated by CawColorsDlg to edit a selected color scheme. An example of the dialog produced by the CawColorSelectDlg is shown in FIG. 76. The current color scheme name may be edited, and any "Color Element" may be selected for display or editing. Pushing "Set to Default Color" will change the currently selected "Color Element" to the default color value. It is anticipated that an "Apply" button may be added to the dialog. The class for the CawColorSelectDlg preferably includes public methods such as "CawColorSelectDlg" and "~CawColorSelectDlg."

The Workstation Client Shell is a part of the workstation framework and is designed to be a building block for other products. The class CcsClientShell provides the main application interface between MFC and the Workstation Client Shell. Since it is an executable shared by all products within the workstation family of products, it cannot be modified and customized for each individual product. In fact, a single Workstation Client Shell executable could simultaneously be used for multiple workstations. To resolve this apparent ambiguity, the Workstation Client Shell is designed to be self-modifying. Individual workstation products implement new product-specific Client Applet DLLs, using the APIs provided by the Applet Interface and the Applet Widgets Interface. During initialization, the Workstation Client Shell modifies itself to incorporate all individual Applet user interface requirements. In the preferred form of the present invention, the Workstation Client Shell is capable of modifying its Menus and Submenus to reflect individual Applet requirements. The Workstation Client Shell is also capable of modifying its main window title to properly reflect the title(s) of the mix of workstation products installed. It is also anticipated that further embodiments of the Workstation Client Shell may add support for Applet additions of Popup Submenus, product-specific banner screens and product-specific "About Box" dialog pages. The banner screen is designed to display each of the four or more possible products the user has currently installed. The Workstation Client Shell banner is intended to be much more generalized but similar in flavor. Since the present embodiment of the Workstation Client Shell will have no knowledge of the possible products that might be installed, the banner is not pre-configured. Rather, a method is used to add completely independent Applet-defined banners to a generic, product-independent Workstation banner. The Applet-defined banners preferably fit the Applet banner rules which are sufficiently flexible to provide for the needs of future workstation products.

Many applications designed for windows exhibit a singleton behavior. If the user attempts to start a new copy of an already running application, the existing copy is activated. The Workstation Client Shell implements such singleton behavior. It is anticipated that in the future, it may be desirable to actually run multiple copies of the Workstation Client Shell on the same PC, each implementing a different mix of Workstation based products and Applets. Each one of these product specific instances of the Workstation Client Shell would preferably still exhibit singleton behavior for that specific product while allowing other product specific instances of the Workstation Client Shell to run independently as separate Windows/NT processes. To facilitate this apparent conflict, each Workstation Client Shell process of the present invention may be optionally named. If no process name is supplied to the Workstation Client Shell, it will run as an unnamed process. Only a single instance of the unnamed Workstation Client Shell process is allowed. Attempts to start a new unnamed Workstation Client Shell process when an existing unnamed Workstation Client Shell process is already running will simply activate the existing unnamed Workstation Client Shell process. Each named Workstation Client Shell process is totally independent of both the unnamed Workstation Client Shell process, if any, and other named Workstation Client Shell processes, if any. However, for a given Workstation Client Shell process name, the singleton behavior is maintained. Attempts to start a named Workstation Client Shell process when an existing named Workstation Client Shell process of the same name is already running will simply activate the existing named Workstation Client Shell process of the same name as that being activated.

The Workstation Client Shell of the preferred embodiment does not provide any mechanism for communication between these potentially multiple Workstation Client Shell processes. Each uniquely named Workstation Client Shell process, if any, and the single unnamed Workstation Client Shell process, if any, run totally independently from each other as if the other processes were not running. In the present embodiment, the Workstation Server Shell is aware of the multiple Workstation Client Shell processes running on each PC. It is also possible that other workstation framework components will establish cross-process communication with similar workstation framework components running within other Workstation Client Shell processes on the same PC.

Figure 77:
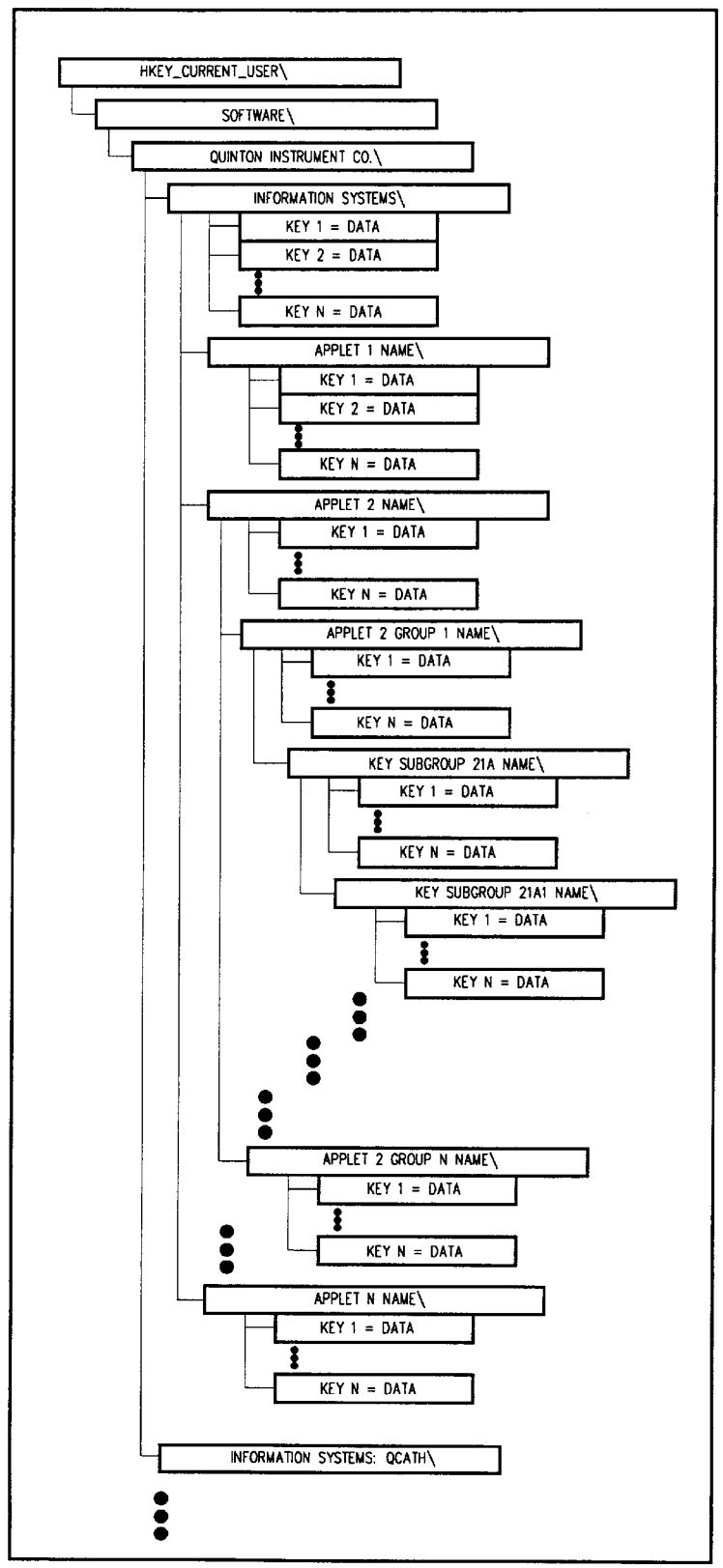
FIG. 77 is a diagrammatic view of the main workstation products registry structure of the present invention.

The Workstation Client Shell of the present invention extends the registry access mechanisms provided by MFC by providing a custom registry structure that preferably may be common to all workstation products without the risk of collision between products. Following the company name, the next key is generally either a product name or a product family name. The Workstation Client Shell sets a product name key of "Information Systems" for use by the unnamed Workstation Client Shell process. The Workstation Client Shell sets a product name key of "Information Systems: name" for use by named Workstation Client Shell process (es), where "name" is replaced by each unique process name. Beneath the product name key, Client Applets can define their own Applet key group or can define keys directly within the product family key. Client Applets define their own subgroups beneath their Applet key group. These subgroups can continue to any level needed by a Client Applet. An example is shown in FIG. 77 beneath the Client Applet key "Applet 2 Name." FIG. 77 is illustrative of the main workstation products registry structure.

Figure 78:
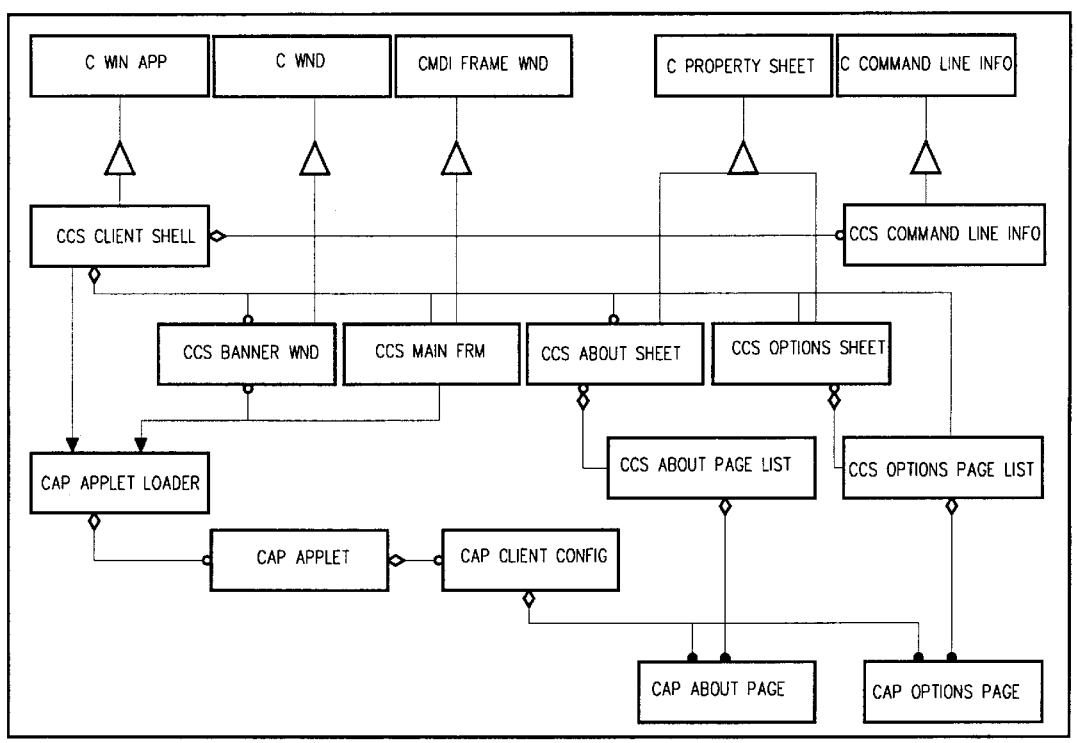
FIG. 78 is a diagrammatic view of an overview of the Workstation Client Shell classes of the present invention.
Figure 79:
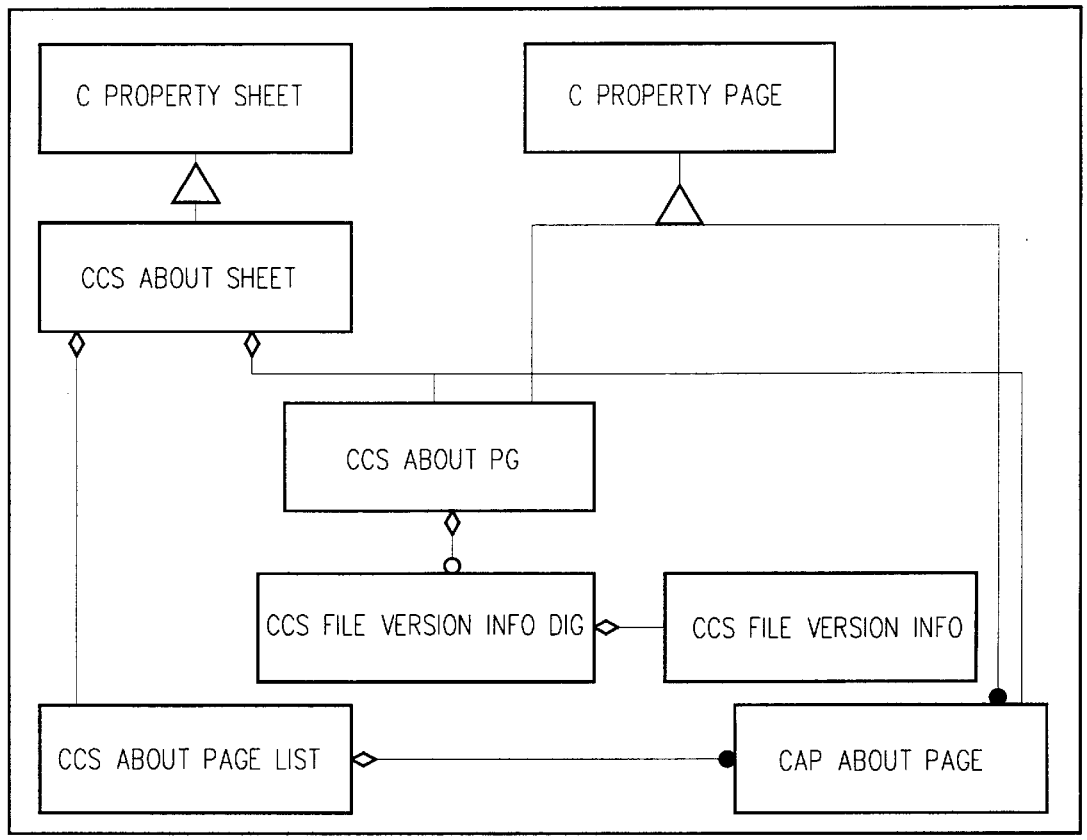
FIG. 79 is a diagrammatic view of the Workstation Client Shell "About Box" dialog class of the present invention.

This section describes the relationships between all classes defined in the Workstation Client Shell module as well as the relationships between classes within the Workstation Client Shell module and classes within other workstation framework modules. In FIGS. 78 to 82, all the Workstation Client Shell classes are shown shaded. The classes in other modules are shown in white. The primary classes which make up the Workstation Client Shell are shown in FIG. 78. During initialization, the CcsClientShell first constructs a CcsCommandLineInfo object to parse the Workstation Client Shell command line. Next, the CcsMainFrm object is constructed but not yet initialized. Next, a CcsBannerWnd object is constructed, causing display of the Workstation Client Shell banner for the duration of initialization, unless this banner display is suppressed by CcsCommandLineInfo. The CapAppletLoader is then initialized, causing initialization of all the Applets. The CcsMainFrm is then initialized, modifying itself to reflect the configuration requirements of the Applets. The CcsBannerWnd and CcsCommandLineInfo objects are both automatically destroyed when initialization is complete. Following destruction of the initial CcsBannerWnd and CcsCommandLineInfo objects, no objects of these classes are again constructed or used. The objects of classes CcsAboutSheet and CcsoptionsSheet are created and destroyed by user selections. The CcsAboutSheet class provides display of an "About Box" dialog. The CcsOptionsSheet class provides display of an "Options" configuration dialog. The classes that make up the "About Box" dialog are shown in FIG. 79. As shown, the "About Box" dialog is preferably a tabbed dialog consisting of a property sheet and multiple property pages. In the present embodiment, only a single property page exists, CcsAboutPg. It is anticipated that further support for additional property pages supplied in Client Applet DLLs may also be added.

Figure 80:
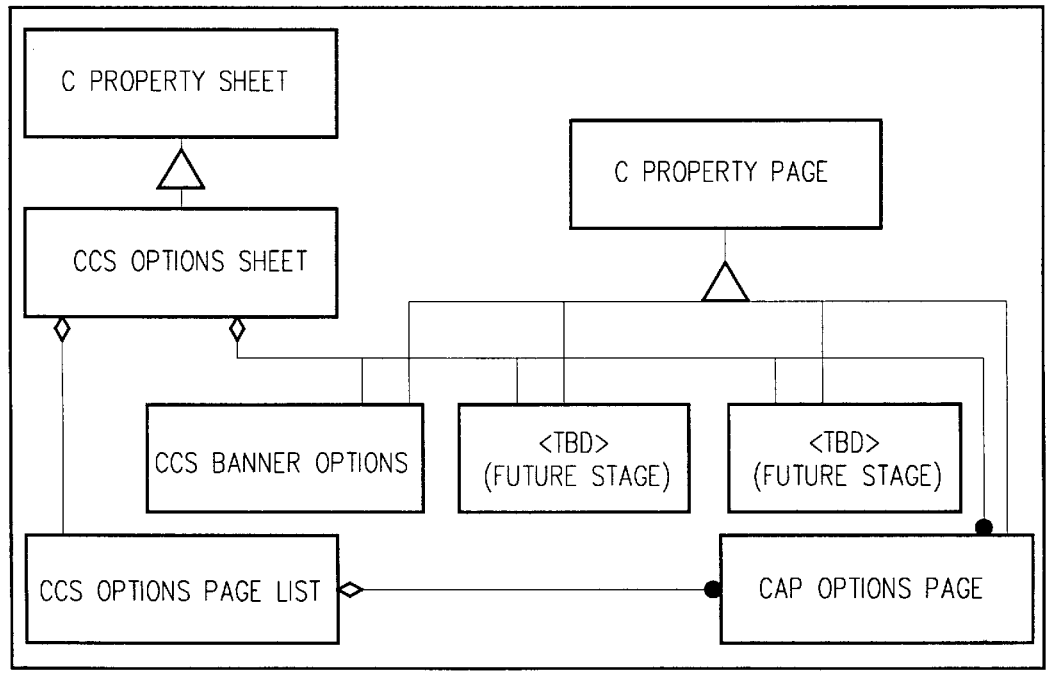
FIG. 80 is a diagrammatic view of the Workstation Client Shell "Options" dialog class of the present invention.
Figure 81:
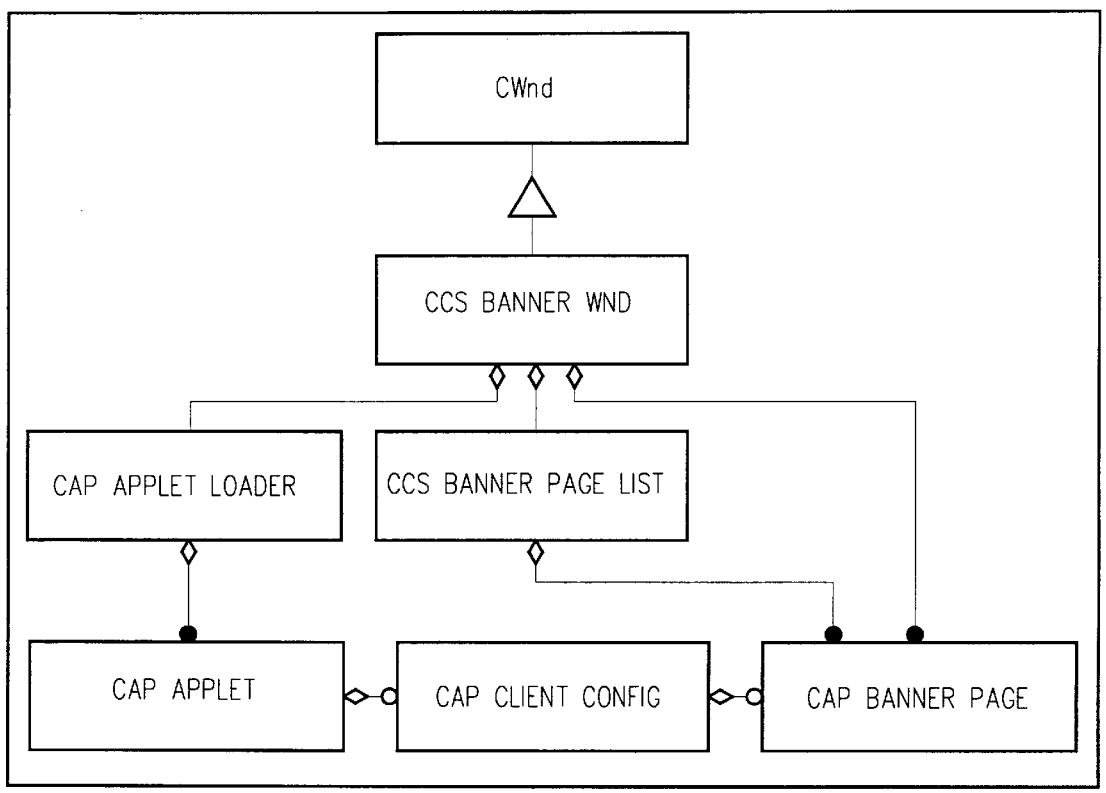
FIG. 81 is a diagrammatic view of the Workstation Client Shell "Banner" window class of the present invention.
Figure 82:
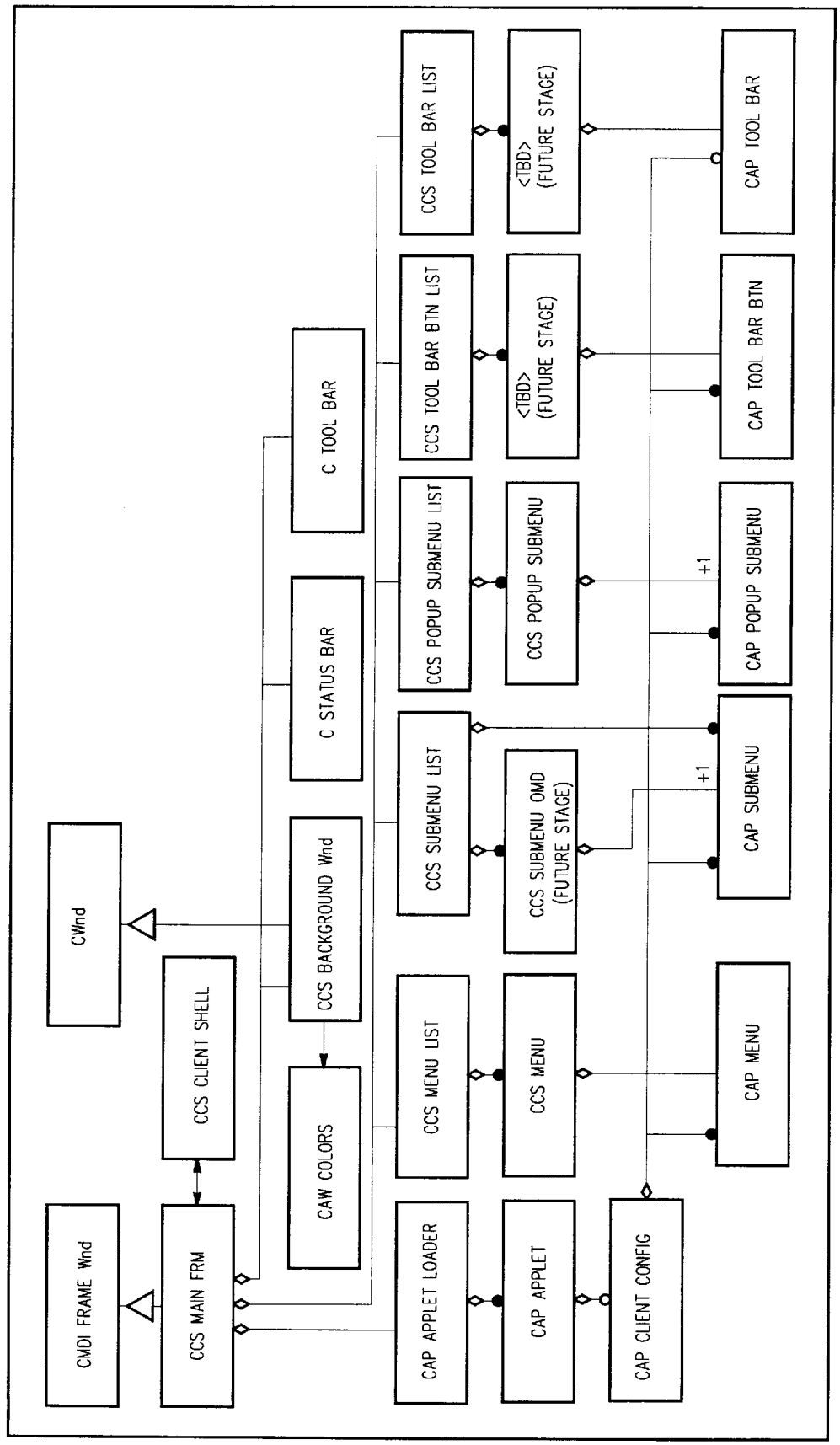
FIG. 82 is a diagrammatic view of the Workstation Client Shell main frame window class of the present invention.

The CcsAboutPg provides access to the CcsFileVersionInfoDlg. If requested, CcsAboutPg will construct a CcsFileVersionInfoDlg object displaying file version information from the Workstation Client Shell executable and all workstation products DLLs. The class CcsFileVersionInfo provides the actual retrieval of file version information from executable and DLL files. The file version information dialog created by CcsFileVersionInfoDlg is intended to assist field support of the product. The classes that preferably make up the "Options" dialog are shown in FIG. 80. As shown, the "Options" dialog is preferably a tabbed dialog consisting of a property sheet and multiple property pages. The classes that make up the "Banner" window are shown in FIG. 81. Initially, the "Banner" window will be a simple, fixed banner built into the Workstation Client Shell. Additionally, the "Banner" window may also be modified to contain an area in which it will display additional sub-banners optionally supplied by Client Applet DLLS. The flavor of this multiple banner display will be slightly like the banner displayed by Microsoft Developer Studio, which modifies itself during display to show which of four possible "products" are installed. The Workstation Client Shell banner will be much more generalized, providing support for any number of product-specific sub-banners. The classes that make up the main MDI frame window are shown in FIG. 82.

The class CcsClientShell from the Workstation Client Shell module preferably provides the main application interface between MFC and the Workstation Client Shell. The class CcsClietShell preferably includes various public methods such as "CcsClietShell," "~CcsClientShell," "InitInstance," "ExitInstance," "IsProcessNamed," "GetProcessName," "OnIdle" and "PreTranslateMessage". Additionally, this class also preferably includes various protected methods such as "OnUpdateAppExit," "OnAppExit," "OnAppAbout" and "OnAppOptions."

The class CcsCommandLineInfo from the Workstation Client Shell module preferably provides command line parsing at application startup. This class subclasses and modifies the behavior of the MFC class CCommandLineInfo. This class also preferably includes various public methods such as "CcsCommandLineInfo," "~CcsCommandLineInfo" and "ParseParam."

The class CcsBannerWnd is from the Workstation Client Shell module and preferably provides an initial product banner display which is also known as a splash screen. The class CcsBannerWnd preferably includes various public methods such as "~CcsBannerWnd," "EnableBannerWnd," "ShowBannerWnd," "PreTranslateAppMessage," "Create" and "HideBannerWnd." This class also preferably includes protected methods such as "PostNcDestroy," "PreCreateWindow," "OnCreate," "OnPaint" and "OnTimer."

The class CcsBannerPageList is from the Workstation Client Shell and preferably provides a container holding the Applet defined banner pages (CapBannerPage objects) to be displayed within the default banner window. This class preferably includes public methods such as "CcsBannerPageList" and "~CcsBannerPageList."

The class CcsMainFrm is from the Workstation Client Shell module and preferably provides the main MDI frame window for the Workstation Client Shell application. This class preferably includes a variety of public methods such as "CcsMainFrm," "~CcsainFrm," "Initialize," "SendToChildren," PreCerateWindow and "OnCmdMsg." This class also preferably includes protected methods such as "OnCommand," "OnCreateClient," "OnCreate," "OnUpdateFileNew," "OnFileNew," "OnUpdateWindowCloseAll" and "OnWindowCloseAll."

The class CcsBackgroundWnd is from the Workstation Client Shell module and preferably displays a background bitmap within the mainframe window. This background bitmap may be made invisible or may be made to appear as a watermark, depending on the current color settings of class CawColors. This class preferably includes a variety of public methods such as "CcsBackgroundWnd" and "~CcsBackgroundWnd." Additionally, this class includes various protected methods such as "OnEraseBkgnd," "OnPaint" and "OnWindowPosChanging."

The class CcsMenuList is from the Workstation Client Shell module and preferably provides a container used by class CcsMainFrm to hold CcsMenu objects, each of which is directly associated with a unique CapMenu object defined within an Applet. These CapMenu objects specify additional menu names to be added to the CcsMainFrm menus. The CcsMenu objects are ordered by the location of the new menu names, returned by CapMenu :: GetMenuLoc. The class CcsMenuList preferably includes various public methods such as "CcsMenuList," "~CcsMenuList," "GetMenuCount," "AddMenuList," "AddMenu" and "operator []."

The class CcsMenu is from the Workstation Client Shell module and preferably provides new menu items added to the CcsMainFrm. Each ccsMenu object is directly associated with a CapMenu object defined in an Applet. The class CcsMenu preferably includes various public methods such as "CcsMenu," "~CcsMenu," "operator==," operator!=," "operator CapMenu&" and "operator CapMenu*."

The class CcsSubmenuList is from the Workstation Client Shell module and preferably provides a container used by class CcsMainFrm to hold CapSubmenu objects defined within Applets. These CapSubmenu objects specify additional submenu names to be added to CcsMainFrm menus. The CapSubmenu objects are ordered by the location of the menu on which they are to appear (CapSubmenu :: GetMenuLoc), and within menu location, by the inverse (descending) submenu location within the menu (CapSubMenu :: GetSubmenuLoc). The class CcsSubmenuList also contains a CcsSubmenuCmd object for each unique Command ID specified by CapSubmenu objects (CapSubmenu :: GetCommandID). This unordered containment is mapped by Command ID. Each CcsSubmenuCmd object contains a list of one or more CapSubmenu objects for the specific Command ID represented by the CcsSubmenuCmd object. This containment is also unordered. The CcsSubmenuList class preferably includes a variety of public methods such as "CcsSubmenuList," "~CcsSubmenuList," "AddSubmenuList," "AddSubmenu" and "operator []."

The class CcsSubmenuCmd is from the Workstation Client Shell and preferably is a container holding all CapSubmenu objects which use a given Command ID value. This class includes a variety of public methods including "CcsSubmenuCmd," "~CcsSubmenuCmd," "GetCommandId," "GetSubmenuCount," "AddSubmenu," "OnUpdateSubmenu," "OnSubmenu," "operator==," "operator!=" and "operator[]."

The class CcsPopupSubmenuList is from the Workstation Client Shell module and preferably provides a container used by class CcsMainFrm to hold CcsPopupSubmenu objects which contain CapPopupSubmenu objects defined within Applets. This class preferably includes various public methods such as "CcsPopupSubmenuList" and "~CcsPopupSubmenuList."

The class CcsPopupSubmenu is from the Workstation Client Shell module and preferably provides a container used by class CcsPopupSubmenu to hold CapPopupSubmenu objects defined within Applets. This class preferably includes various public methods such as "CcsPopupSubmenu" and "~CcsPopupSubmenu."

The class CcsToolBarBtnList is from the Workstation Client Shell module and preferably provides a container which is used by class CcsMainFrm to hold, directly or indirectly, CapToolBarBtn objects defined within Applets. This class preferably includes various public methods such as "CcsToolBarBtnList" and "~CcsToolBarBtnList."

The class CcsToolBarList is from the Workstation Client Shell module and preferably provides a container used by class CcsMainFrm to hold, directly or indirectly, CapToolBar objects defined within Applets. This class preferably includes various public methods such as "CcsToolBarList" and "~CcsToolBarList."

Figure 83:
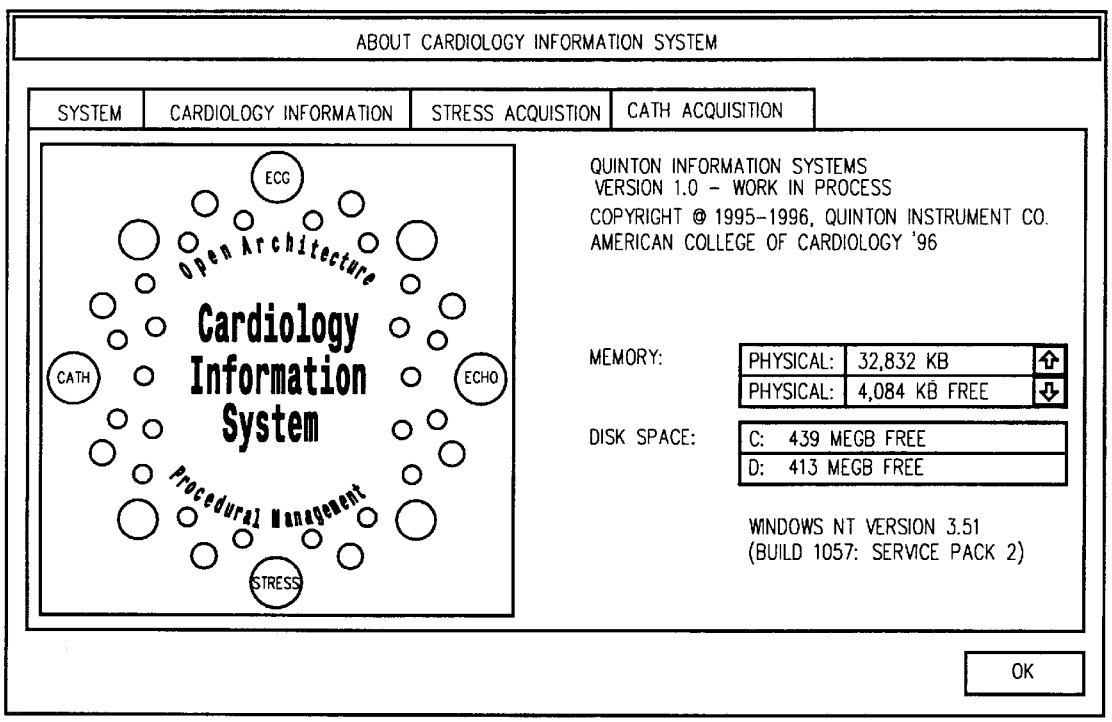
FIG. 83 is a diagrammatic view of the CcsAboutSheet dialog from the Workstation Client Shell of the present invention.

The class CcsAboutSheet is from the Workstation Client Shell and preferably provides a "Help About" dialog containing dialog pages defined by other classes. The first page is provided by class CcsAboutPg. The remaining pages, if any, are defined by objects of class CapAboutPage. The CcsAboutsheet dialog preferably appears similar to the example shown in FIG. 83, which includes three objects of class CapAboutPage. This class preferably includes various public methods such as "CcsAboutSheet," "~CcsAboutSheet" and "OnInitDialog."

Figure 84:
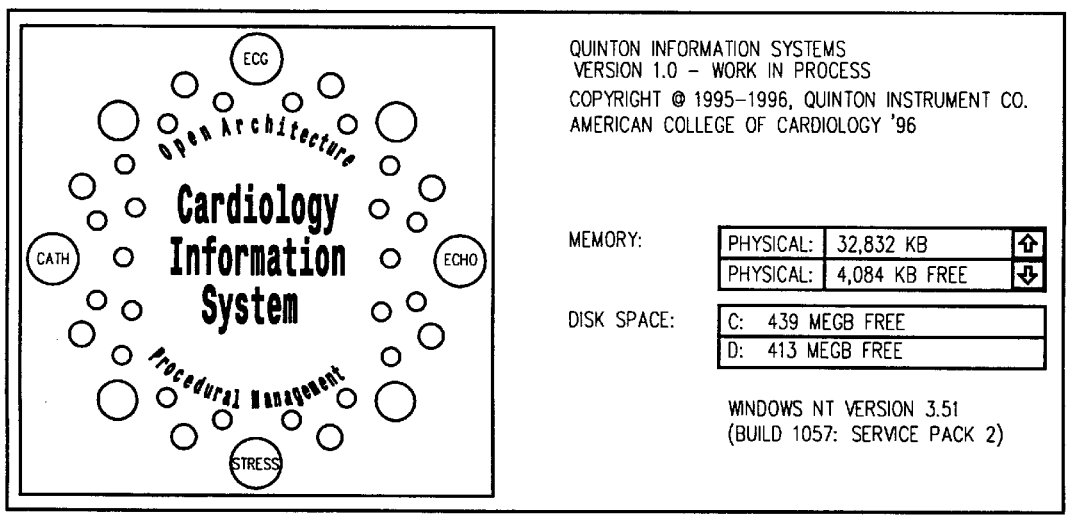
FIG. 84 is a diagrammatic view of the CcsAboutPg dialog from the Workstation Client Shell of the present invention.

The class CcsAboutPg is from the Workstation Client Shell and preferably provides the primary "Help About" dialog page contained within the CcsAboutSheet "Help About" dialog. This dialog page displays workstation framework version and copyright information, an animated workstation framework logo and list boxes containing current WINDOWS NT memory usage statistics and the amount of free space available on local hard drives. The CcsAboutPg class provides a hot key, Alt-F, that will activate the CcsFileVersionInfoDlg. This hot key is defined on a hidden control within the CcsAboutPg dialog. An example of the CcsAboutPg is shown in FIG. 84. This class preferably includes various public methods such as "CcsAboutPg," "~CcsAboutPg" and "DestroyWindow." Additionally, this class preferably includes protected methods such as "DoDataExchange," "OnInitDialog," "OnShowFiles" and "OnTimer."

The class CcsAboutPageList is from the Workstation Client Shell and preferably provides a container used to hold CapAboutPage objects defined within Applets. This class preferably includes various public methods such as "CcsAboutPageList" and "~CcsAboutPageList." The class CcsFileVersionInfoDlg is from the Workstation Client Shell module and preferably provides a dialog containing a list of all currently loaded program files located in the same directory as the Workstation Client Shell executable. Summary version information is provided for all program files. Detailed version information is provided for a single selected program file. This dialog is intended to assist with the field support of this product. This class includes various public methods including "CcsFileVersionInfoDlg" and "~CcsFileVersionInfoDlg." This class also includes various protected methods such as "DoDataExchange," "DoInitDialog" and "OnItemChangedFileversionInfo."

The class CcsFileVersionInfo is from the Workstation Client Shell module and preferably provides, for a specified file, read-only access to the WINDOWS NT directory information and, if available, the file version resource, VERSIONINFO, contained within many executable files, including DLLs. All data is made available as formatted strings. Date and time values are optionally returned as CTime objects. Selected fields may optionally be retrieved as boolean values. This class includes various public methods including "CcsFileVersionInfo," "~CcsFileVersionInfo," "GetFilePathName," "GetFileCreationTime," "GetFileLastAccessTime," "GetFileLastWriteTime," "GetFileSize," "GetFileName," "GetAlternateFileName," "GetInfoFileVersion," "GetInfoProductVersion," "GetInfoFileFlags," "GetInfoFileDebug," "IsInfoFilePreRelease," "IsInfoFilePatched," "IsInfoFilePrivateBuild," "IsInfoFileInfoInferred," "IsInfoFileSpecialBuild," "GetInfoFileO," "GetInfoFileType,"

"GetInfoFileTypeAbbrev," "IsFileTypeApp," "IsFileTypeDLL," "IsFileTypeDrv," "IsFileTypeFont," "IsFileTypeVxD," "IsFileTypeLib," "IsFileTypeunknown," "GetInfoFileTime," "GetCompanyName," "GetFileDescription," "GetFileVersion," "GetInternalName," "GetLegalCopyright," "GetOriginalFileName," "GetProductName," "GetProductVersion," GetWin32FindData" and "GetFixedFileInfo."

The class CcsOptionsSheet is from the Workstation Client Shell module and preferably provides a "Tools Option" dialog containing pages defined by other classes. The first page is provided by class CcsBannerOptions. The remaining pages, if any, are defined by objects of class CapOptionsPage. This class preferably includes various public methods such as "CcsOptionsSheet" and "~CcsOptionsSheet."

The class CcsBannerOptions is from the Workstation Client Shell module and preferably provides the primary "Tools" "Options" dialog page contained within the CcsOptionsSheet dialog. This class preferably includes various public methods such as "CcsBannerOptions" and "~CcsBannerOptions."

The class CcsOptionsPageList is from the Workstation Client Shell module and preferably provides a container used to hold CapOptionsPage objects defined within Applets. This class preferably includes various public methods such as "CcsOptionsPageList" and "~CcsOptionsPageList."

Figure 85:
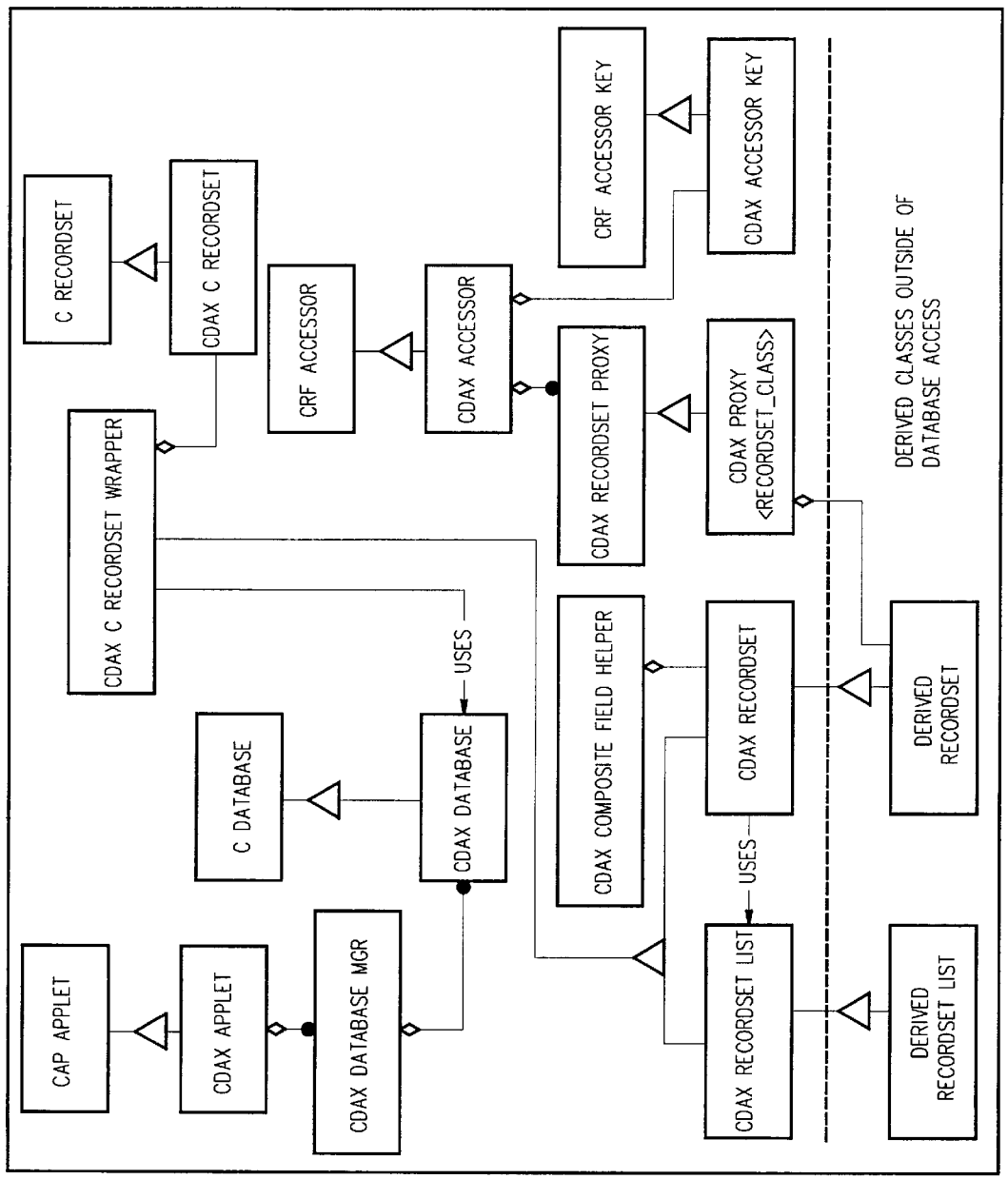
FIG. 85 is a diagrammatic view of an overview of the Database Access classes of the present invention.

FIG. 85 illustrates an overview of the relationships between the classes defined in the Database Access module and the relationships between classes within the Database Access module and classes within other workstation framework modules. Those classes whose inheritance is not explicitly shown are derived from CObject. The Database Access module provides an implementation of database recordsets which does not throw exceptions, but instead returns error codes to the caller. The class CdaxCRecordsetWrapper provides the functionality of the MFC class CRecordset, but catches all of the exceptions thrown by the CRecordset class and "translates" the exceptions to error codes. The class CdaxCRecordsetWrapper is implemented by containment of a CRecordset-derived class. The subset of the CRecordset-like methods which are provided by the Wrapper class simply call the corresponding CRecordset methods, with a "try/catch" wrapper around those methods which throw exceptions. It may seem natural to simply derive CdaxCRecordsetWrapper from CRecordset, but it does not work because CRecordset catches many of its own exceptions; and in some cases it throws a new exception, and in other cases it does not. If a derived class caught exceptions for some of the methods before CRecordset had a chance to catch them, then the behavior of CRecordset may be changed. By containing a CRecordset class, the exceptions are caught only at the outer layer. Additionally, changing the interface from that of exceptions to errors suggests changes to the public interface of the class. For example, CRecordset's Edit method is a void function which may throw exceptions. The CdaxCRecordsetWrapper changes this method to return BOOL, indicating success or failure; if the method fails, the user may query the class to see the nature of the error, which is translated from the exception thrown by the contained CRecordset. The inheritance is only advisable if the derived class maintains the interface of the base class. As shown, the Class CdaxCRecordsetWrapper does not actually contain a CRecordset class, but rather a class derived from CRecordset and CdaxCRecordset. This is preferred because CRecordset defines some pure virtual methods. The class CdaxCRecordset provides an implementation for the pure virtual methods of CRecordset. These CdaxCRecordset methods invoke the corresponding CdaxCRecordsetWrapper methods via a pointer to the CdaxCRecordsetWrapper object. The class CdaxRecordset derives from CdaxCRecordsetWrapper and adds the ability to store data to/from CffField objects. The CdaxRecordset is an abstract class, and it is intended as the base class for the concrete recordset classes used by framework-based applications. These derived concrete classes may be generated by the MFC Class Wizard.

Figure 86:
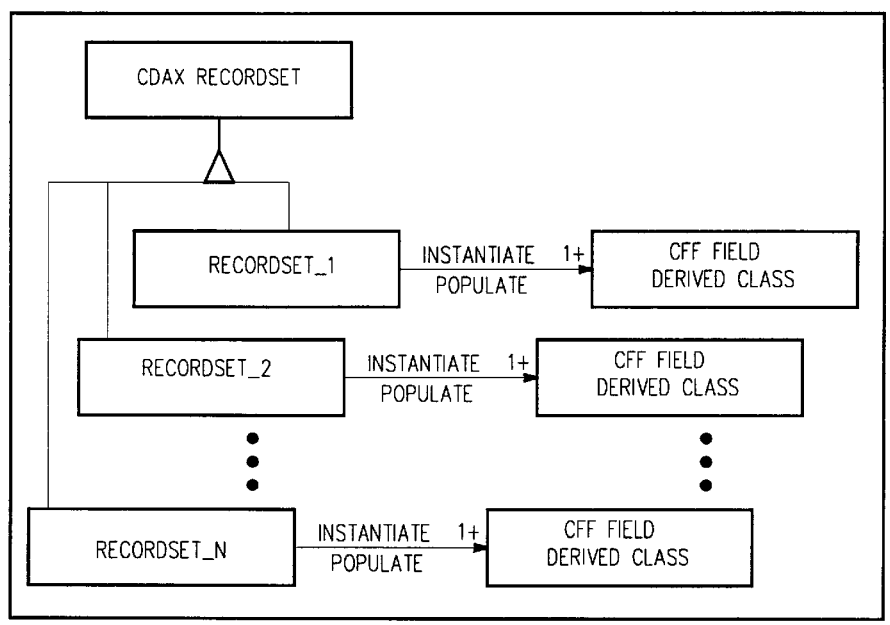
FIG. 86 is a diagrammatic view of the Database Access interactions with the Field Framework of the present invention.

As used herein, the term Recordset is used to refer to a CdaxRecordset-derived class or object, and the term Field is used to refer to a CffField-derived class or object. As shown in FIG. 86, each derived CdaxRecordset class provides the ability to instantiate and manipulate one or more CffField objects. Each of these Recordset classes provides an array of the Field IDs which it can support and provides methods for transferring data between the Field objects represented by the Field IDs and the recordset column(s).

Each derived Recordset class provides "Field Handler" methods as shown in FIG. 86. In the preferred embodiment, there is one Field Handler method for each CffField type which is provided by the Recordset. These Field Handler methods provide a mechanism for associating a CffField object with one or more attributes of the Recordset. "Wrapping" the attributes of the Recordset (which correspond to columns of the recordset) within a Field Handler method has the benefit that these methods may be identified in a static list to allow a way to "target" recordset columns in a static array which maps Field ID with the Field Handler method to populate the Field, and it provides a scheme for populating Composite and Array Fields. A Field Handler method may be used to populate a complex Field type with multiple recordset columns and/or multiple recordset rows. There is also a helper class, CdaxCompositeFieldHelper, which is preferably used to support the transfer of data between member data of a Recordset and a composite Field.

Figure 87:
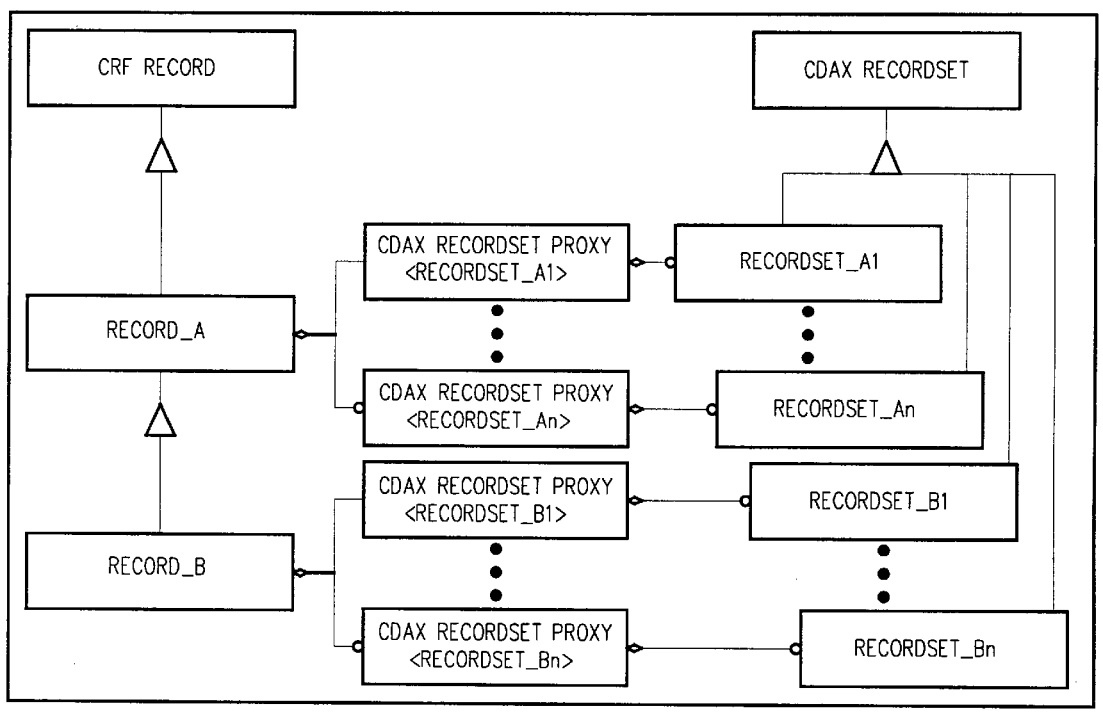
FIG. 87 is a diagrammatic view of the Database Access interactions with the Record Framework of the present invention.

As shown in FIG. 87, a CrfRecord object is a collection of one or more objects derived from the CdaxRecordset class, and interfaced through a CdaxRecordsetProxy template class. Each Recordset class is associated with a CrfRecord-derived class through a CdaxRecordsetProxy object. The Recordset class has static methods which allow a Record object to determine if a Recordset provides a particular Field object even if the Recordset object is not instantiated. The Proxy is a template class which provides an interface between the Record and the Recordset. The primary purpose of the Proxy is to defer instantiation of the Recordset object until it is necessary to do so; then the instantiation is transparent to the Record object. This "lazy construction" mechanism (not constructing an object until necessary) is intended to reduce the size of Record objects on the Client and to reduce network traffic in those instances when a record is opened and the user of the record needs only a subset of the data within the record.

The following discussions contain interface descriptions for the classes defined in the Database Access module. The Database Access module provides abstractions for getting information to and from a relational database via an ODBC driver. It incorporates and expands upon the features of the MFC classes CDatabase and CRecordset. The classes CdaxDatabase and CdaxCRecordsetWrapper catch exceptions thrown by MFC classes CDatabase and CRecordset. These exceptions are converted to error codes. These classes include the global definition "daxErrorCode" which is a global enumeration which defines the error codes that can be generated by methods within the Database Access module.

The class CdaxApplet is from the Database Access module and preferably provides the Applet interface for the Database Access module. On Applet initialization, the database connection for the "default" database is established. The default database is the database to which new records or records received via Data Transfer are stored. This Applet provides an interface for other Applets to request information about the available databases. The class CdaxAccessorKey is declared a friend to this class; the CdaxAccesssorKey class is used to get a connection to one of the available databases. The class CdaxApplet includes various public methods such as "CdaxApplet," "~CdaxApplet," "InitApplet", "ExitApplet," "GetAppletName," "GetApplettitle," "GetNumDatabases," "GetDatabaseTitle," "GetDatabase" and "releaseDatabase."

The class CdaxDatabaseMgr is from the Database Access module and preferably manages multiple connections to a single database source; each thread which needs access to a particular data source gets its own connection to the data source. This class is defined locally within CdaxApplet and is only usable by CdaxApplet. The CdaxApplet class creates one of these objects for each of its data sources. The class CdaxDatabaseMgr includes various public methods such as "CdaxDatabaseMgr," "~CdaxDatabaseMgr," "GetDatabase" and "ReleaseDatabase."

The class CdaxDatabase is from the Database Access module and preferably provides database connection support. This class is derived from the MFC class, CDatabase, to which it additionally catches exceptions which can be thrown by CDatabase's "open" method, by overriding the "open" method and wrapping a call to the base class method with try/catch. This class also performs direct ODBC calls during initialization to allow cursor preservation during transaction processing and sets up the base class, CDatabase, to allow transaction processing and which overcomes a shortcoming in the CDatabase/ODBC interface. This class also adds "time of connection" functionality and adds a "use count" attribute which monitors how many CdaxAccessorKey objects are connected to a CdaxDatabase object. When the user count goes to zero, the object may be destroyed. Additionally, this class supports a unique connection for each thread which requires database access. Creation of objects of this class is intended to be done only by the Database Access Applet. The class CdaxDatabase includes various public methods such as "CdaxDatabase," "~CdaxDatabase," "SetThreadID," "Open," "IncrementUseCount," "DecrementUseCount," "GetLastError," "GetLastException" and "GetConnectionTime."

The class CdaxAccessor is from the Database Access module and preferably is the implementation of the CrfAccessor base class which interfaces via the Database Access module to the ODBCSQL database. The class CdaxAccessor preferably includes various public methods such as "CdaxAccessor," "~CdaxAccessor," "GetField," "RefreshField," "StoreField," "IsReadOnly," "Lock," "Unlock," "QueryLock" and "Save."

The class CdaxAccessorKey is from the Database Access module and preferably is derived from the CrfAccessorKey. It defines a database connection through the Database Access (DAX) layer and the primary key which identifies a particular record on that database. This class preferably includes various public methods such as "CdaxAccessorKey," "~CdaxAccessorKey," "SetThread," "operator=," "operator==," "operator!=," "GetKeyString," "GetDatabase," "IsPrimaryKeyValid," "GetPrimaryKey," "SetPrimaryKey" and "InvalidatePrimaryKey."

The class CdaxRecordsetKey is from the Database Access module, and this class preferably provides a means of identifying the particular row(s) of a database which correspond to a particular record. This class specifies the database key for the Recordset. This class preferably includes various public methods such as "CdaxRecordsetKey," "~CdaxRecordsetKey," "operator==," "operator!=," "IDBKeyValid," "GetDBKey," "SetDBKey" and "InvalidateDBKey."

The class CdaxCRecordset is from the Database Access module and preferably serves as an intermediary between classes CdaxCRecordsetWrapper and CRecordset. This class provides a concrete CRecordset-derived class which may be contained by class CdaxCRecordsetWrapper. It modifies the CRecordset by requiring a valid pointer to a CDatabase object to be provided for class instantiation. The CRecordset constructor provides a default NULL value for CDatabase pointer; this class provides no default and does not allow a Null value. The CRecordset is also modified to require that a pointer to a CdaxCRecordsetWrapper object be provided for class instantiation. This is necessary so that the CdaxCRecordset class can invoke methods of its creating class. The CRecordset class is also modified to provide an implementation of the pure virtual methods of CRecordset class, GetDefaultSQL() and DoFieldExchanger(). This creates a concrete class which can provide the CRecordset functionality. These implementations call corresponding methods of CdaxCRecordsetWrapper class. The CdaxCRecordset class also preferably includes various public methods such as "CdaxCRecordset," "~CdaxCRecordset," "SetOwner," "GetDefaultSQL," "DoItFieldExchange," "SetNumFields," "SetNumParameters," "SetFilterString," "SetSortString" and "SetDefaultType."

The class CdaxCRecordsetWrapper is from the Database Access module and preferably provides a CRecordset-like interface and functionality, but catches all of the exceptions thrown by CRecordset and converts them into error codes. It also exposes a subset of the CRecordset interface. The CdaxCRecordsetWrapper class also preferably includes various public methods such as "CdaxCRecordsetWrapper," "~CdaxCRecordsetWrapper," "GetLastError," "GetLastException," "GetDefaultSQL," "DoFieldExchange," "CRecordset methods," "CRecordset methods with error status," "CRecordset methods with return status" and "CRecordset methods with return status added." The CdaxCRecordset class also preferably includes various protected methods such as "SetNumFields," "SetNumParams," "SetFilterString," "SetSortString" and "SetDefaultType."

The class CdaxRecordset is from the Database Access module and preferably provides mechanisms and support for transferring recordset data to or from CffField objects. It is an abstract class from which all the concrete workstation recordset classes are derived. Each derived class provides to this base class an array of the Field IDs which are represented in the derived recordset and a handler for each of the Fields; the handler is used to transfer data between the derived recordset and a Field object. The CdaxRecordset class preferably includes various public definitions such as "enum RECORDSET_TYPE" and "FIELD_NOT_FOUND." The CdaxRecordset class also preferably includes various protected definitions such as "enum DATA_DIRECTION" and "struct FIELD_HANDLER." The CdaxRecordset class also preferably includes various public methods such as "~CdaxRecordset," "GetField," "RefreshField" and "StoreField." The CdaxRecordset class also further preferably includes various protected methods such as "CdaxRecordset," "BuildFilterString," "BuildSortString," "FindField" and "AtomicFieldHandler."

The class CdaxRecordsetProxy is from the Database Access module and is preferably an abstract base class which defines the interface for the CdaxProxy template classes. The CdaxRecordsetProxy class preferably includes various public methods such as "CdaxRecordsetProxy," "~CdaxRecordsetProxy," "IsRecordsetAvailable," "HasField," "GetField," "RefreshField," "StoreFiled" and "Save."

The class CdaxProxy is from the Database Access module and is preferably a template class which serves as a "smart" interface to a CdaxRecordset-derived object. It takes, as a template parameter, a class derived from CdaxRecordset; operations which can be performed on a CdaxRecordset object are passed through the Proxy object, but the Proxy first checks that the Recordset object is instantiated and instantiates it if necessary. Thus, the owner of the Proxy object can deal with the Recordset as if the recordset were always available, and the Proxy makes up the difference. The CdaxProxy class preferably includes various public methods such as "CdaxProxy," "~CdaxProxy," "IsRecordsetAvailable," "HasField," "GetField," "RefreshField," "StoreFiled," "Save," "operator->" and "GetRecordset."

The class CdaxCompositeFieldHelper is from the Database Access module and preferably is a class which supports the transferring of data between a Recordset and a composite Field object. This class provides an overloaded "SetSubField" method for each of the atomic data types. The CdaxCompositeFieldHelper class preferably includes various public methods such as "CdaxCompositeFieldHelper," "~CdaxCompositeFieldHelper," "GetSubField" and "SetSubField."

The class CdaxRecordsetList is from the Database Access module and preferably provides support for "secondary" database tables which are referenced in other tables. For example, a CdaxRecordsetList-derived class might encapsulate the PERSONNEL table of the database. This derived class would then provide a static method for obtaining the personnel data given a PersonnelKey. These RecrodsetList classes may be available as "Fully cached" where the encapsulated table is read from the database at system initialization and cached; "As used," where as elements are requested from the encapsulated table, they are cached; "MRU cache," where elements are cached in a "Most-Recently-Used" fashion; or "Uncached," where each element is retrieved from the encapsulated table upon request.

The derived CdaxRecordset classes are from the Database Access module, and the class CdaxRecordset is preferably an abstract class from which all concrete recordset classes are derived. This section outlines the members of a hypothetical class derived from CdaxRecordset and CmyRecordset. This class preferably includes various public methods such as "CmyRecordset," "~CdaxRecordset" and "HasField."

Figure 88:
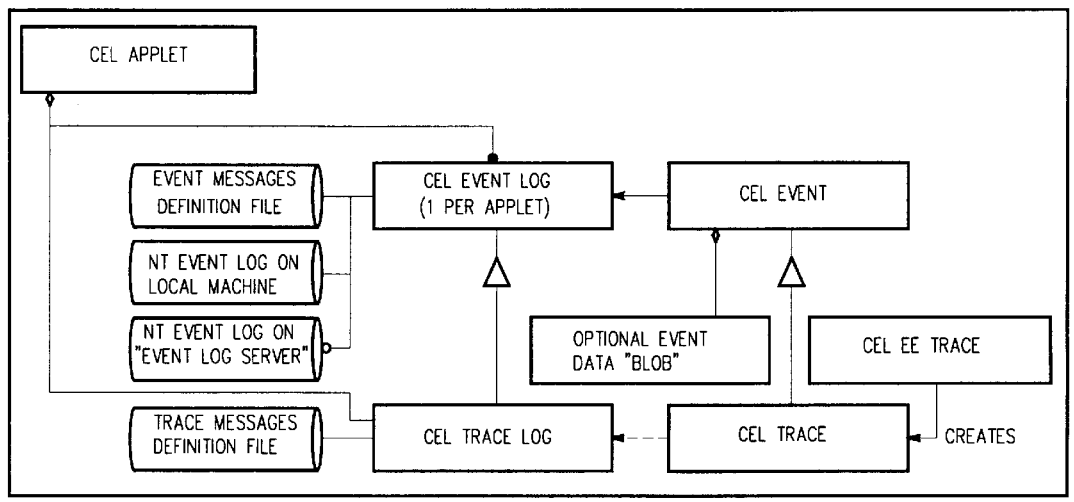
FIG. 88 is a diagrammatic view illustrating an overview of the Event Logger classes of the present invention.

The Event Logger is an Applet DLL that may be used either in a Workstation Client environment or in a Workstation Server environment. The Event Logger is preferably the first Applet initialized and the last one terminated. This is preferred to make event logging available to other Applets. A key to the Event Logger is the concept of an "Event Log Server," a designated computer in the preferred NT network on which all logging is to be performed. The Event Logger logs events to the NT event log on the "Event Log Server" machine, when available. The Event Logger logs events to the NT event log on the local machine only when the NT event log on the "Event Log Server" machine is unavailable. No independent event log is kept. The Event Logger manager, CelApplet, provides mechanisms for keeping track of the CelEventLogs that are instantiated by the Applets. In addition, the manager provides a mechanism for identifying the Event Log Server. FIG. 88 shows an overview of the Event Logger classes.

The multiple CelEventLog objects shown in FIG. 88 preferably do not imply multiple independent event logs. Each CelEventLog object specifies an Event Messages Definition File on disk containing message definitions needed by the NT Event Log mechanisms and additional information needed by the Event Logger to properly interface with the NT Event Log mechanism. All events logged by the Event Logger are written to the NT Event Logger, as they occur, regardless of which CelEventLog object is referenced by the individual CelEvent objects. The NT event log mechanism records in the NT event log the CelEvent object data plus NT registry information from the associated CelEventLog object. Time stamping of events is performed automatically by the NT event log mechanism and is not under application control. The CelEETrace class shown in FIG. 88 is intended for tracing the exit and entry of any method and to generate CelTrace objects to do the actual tracing.

Figure 89:
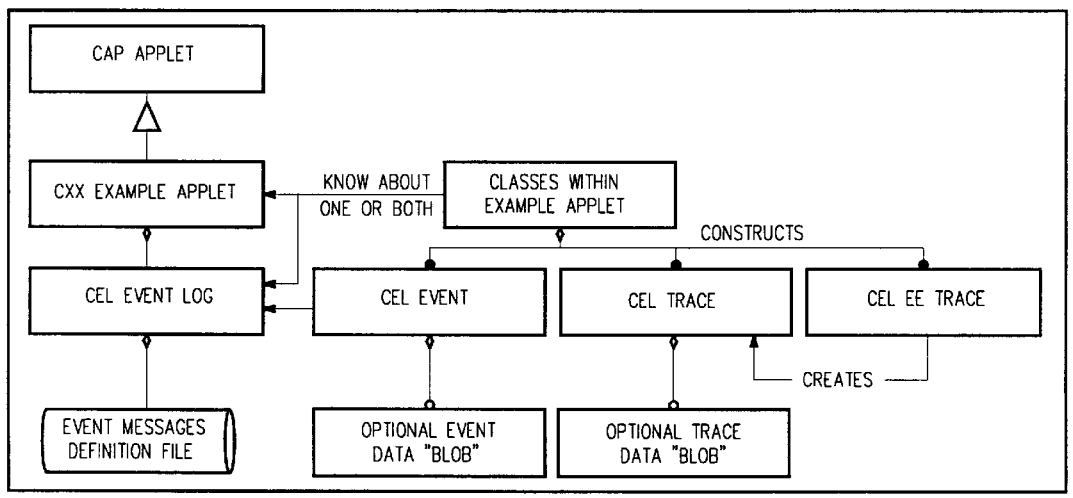
FIG. 89 is a diagrammatic view illustrating the Event Logger interactions with a typical Client or Server Applet DLL of the present invention.

Each Workstation Applet that requires event logging services preferably constructs a single CelEventLog object. Due to the overhead of creating this object, each CelEventLog object is typically constructed within InitApplet and deleted within ExitApplet. An event record is created by creating a CelEvent object and allowing it to be written to the event log controlled by the CelEventLog object. The CelEvent objects are intended for "application" events. Additional "software trace" events may also be created. To facilitate "software trace" events, the Event Logger constructs and maintains a CelTraceLog object which will automatically be used by CelTrace objects. An application creating a "software trace" event need only construct a CelTrace object and allow it to be written to the event log controlled by the CelTraceLog object. FIG. 89 shows the typical Applet use of the Event Logger.

Figure 90:
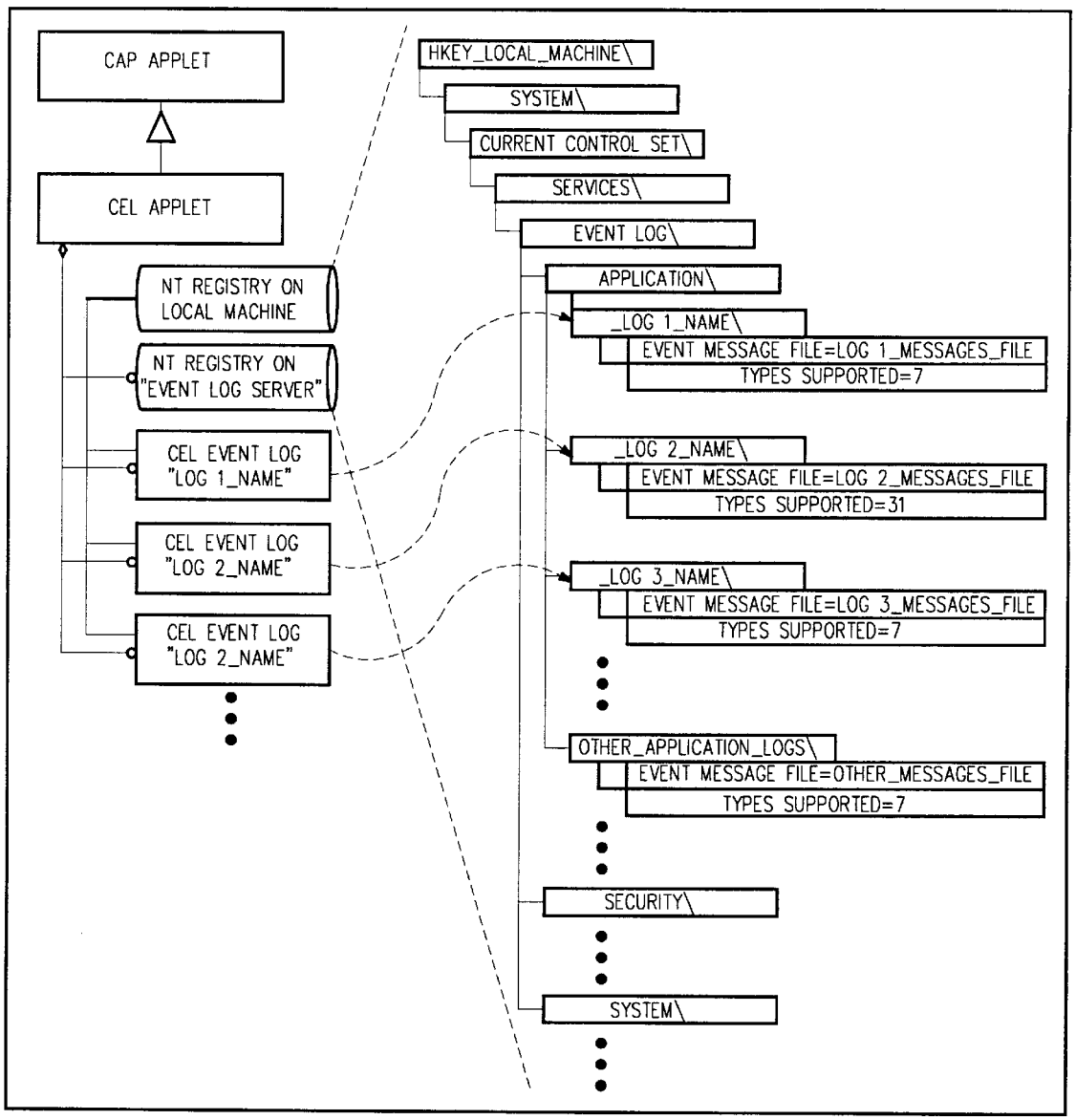
FIG. 90 is a diagrammatic view illustrating the Event Logger interactions with the NT Registry of the present invention.

When an Applet creates a CelEventLog object, the Event Logger checks to see if the registry entries required by the NT event logger are present in the registries of both the local machine and the Event Log Server machine. Missing registry entries, if any, are created by the Event Logger during the initialization of each CelEventLog object. The Event Logger registry entries are shown in FIG. 90. The Event Logger registry entries are the same on both the Local Machine and on the Event Log Server with the single exception that the path name included in the Logx__Messages__File file names may be different. As shown in FIG. 90, each CelEventLog object may be uniquely named and corresponds directly to a uniquely named registry key. With each CelEventLog object's registry key are the registry values shown, specifying the CelEventLog object's Event Messages Definition File (pszMessagesFileName value) and the types of NT event log records supported by the CelEventLog object (nTypesSupported value).

Figure 91A:
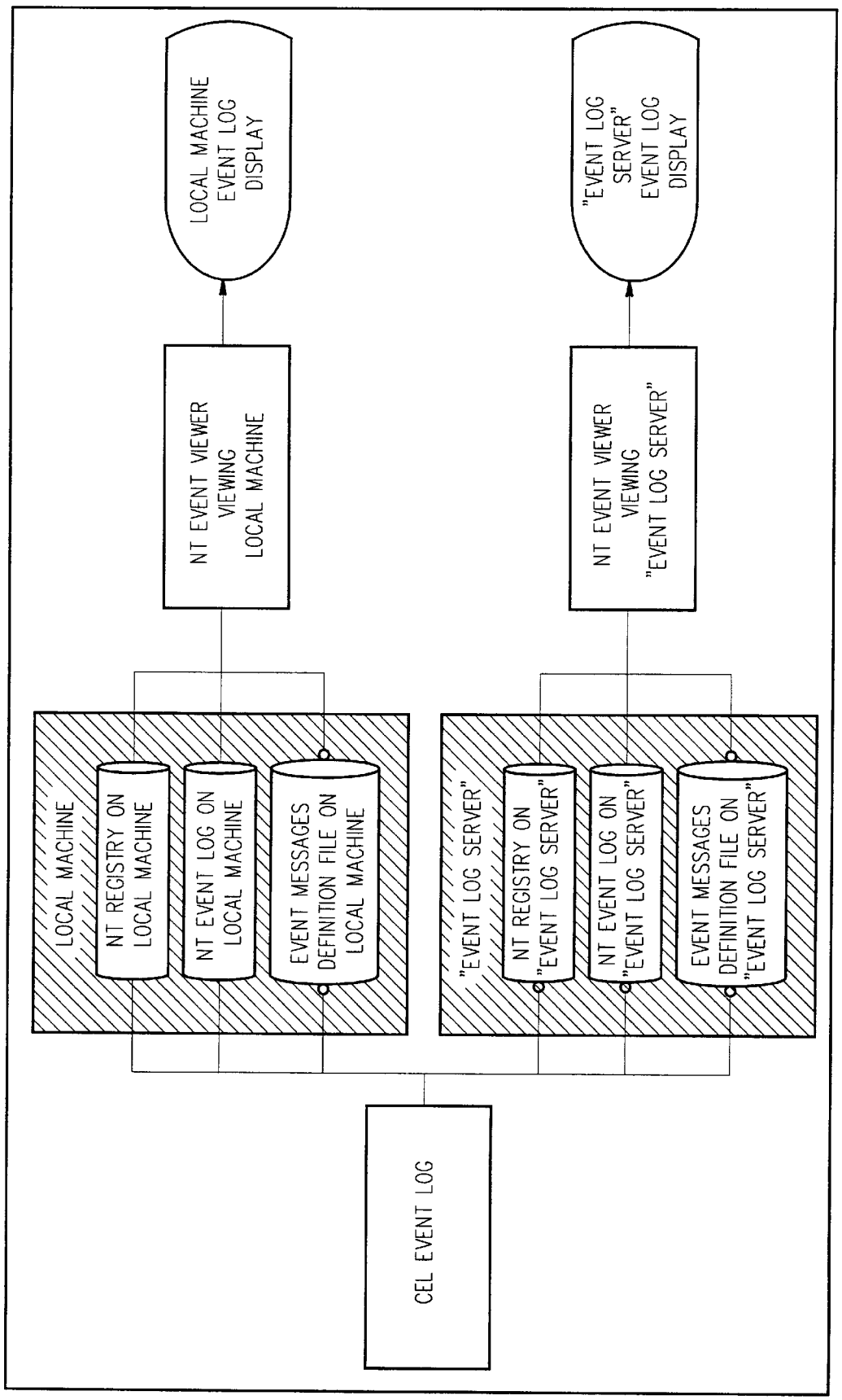
FIG. 91A is a diagrammatic view illustrating the Event Logger interactions with the Event Log Viewer of the present invention.

The Event Logger does not contain any facilities for viewing the event log. Since the Event Logger preferably uses the normal NT event log, the NT Event Viewer application may be used to view all or selected events logged with the Event Logger. The workstation framework may also provide a separate Event Log Viewer. Since a workstation framework Event Log Viewer may interface more tightly with the Event Logger module, the interactions are somewhat different than if the NT Event Viewer is used. Both these options are set forth in FIGS. 91A and 91B. Because there are no direct interactions between the Event Logger and the NT Event Viewer, the NT Event Viewer may look at an event log located on any single machine. By default, this is the local machine event log, but may also be the "Event Log Server" machine event log, or the event log on any other NT workstation or server PC. Regardless of the NT event log being viewed, the NT Event Viewer also looks in the registry of the machine containing the event log to find "Event Messages Definition" files. The NT Event Viewer displays the events on the NT event log using the message texts and field substitution definitions found in these "Event Messages Definition" files.

Like the NT Event Viewer, the workstation framework Event Log Viewer preferably does not have any direct interactions with the Event Logger. Unlike the NT Event Viewer, the workstation framework Event Log Viewer will either directly ask the Event Logger for the name of the "Event Log Server" or determine this name from a registry entry maintained by the Event Logger. This allows the workstation framework Event Log Viewer to automatically, and by default, display the NT event log located on the "Event Log Server" machine.

Figure 91B:
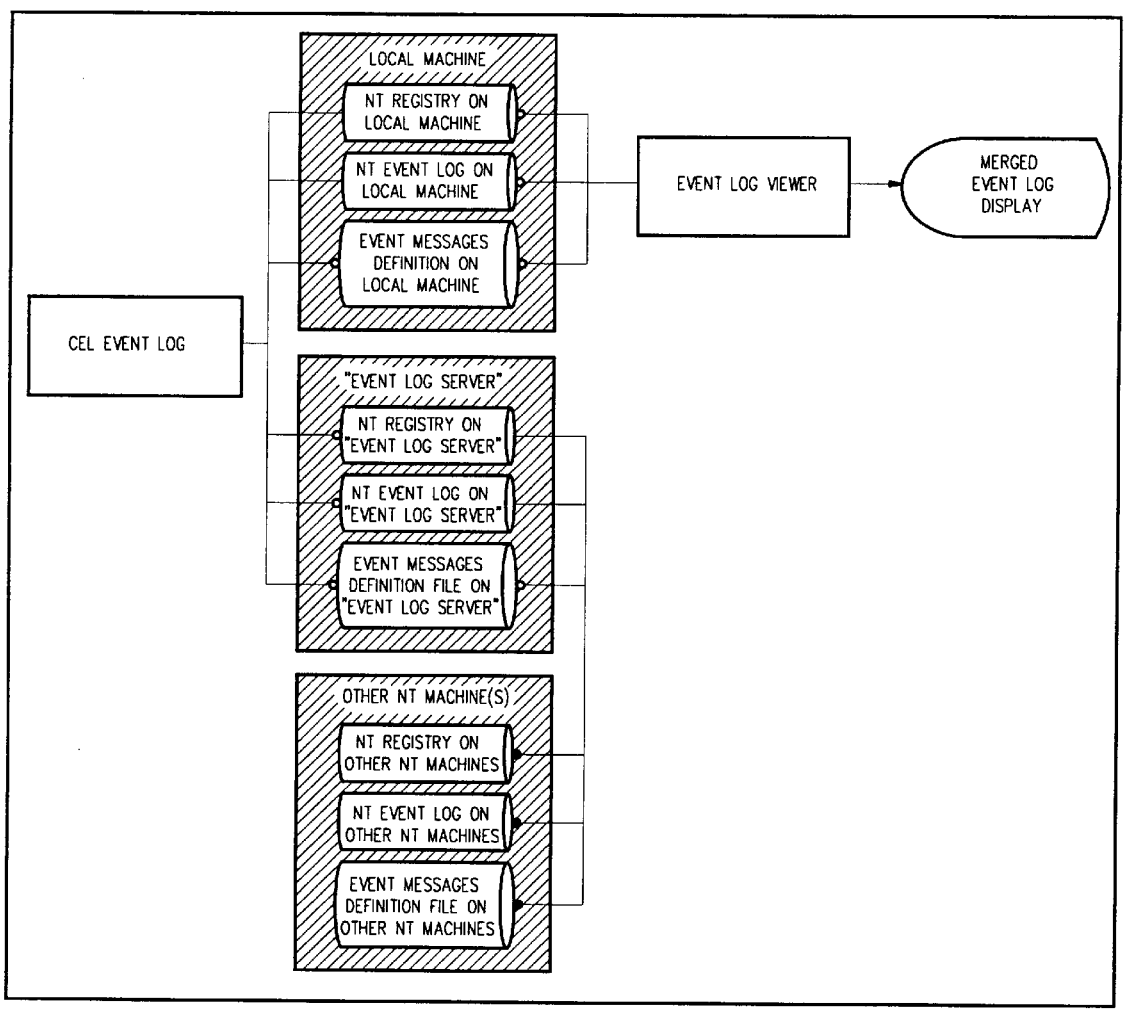
FIG. 91B is a diagrammatic view illustrating the Event Logger with the NT Event Viewer of the present invention.

The workstation framework Event Log Viewer preferably includes the capability to simultaneously display the NT event logs from multiple machines, merging the various event records into a consolidated display based on event time stamps. Filtering of displayed events is also more flexible than provided by the NT Event Viewer. Normally, only workstation framework event records will be displayed. By default, all Software Trace events are preferably omitted from this display. These relationships are shown in FIG. 91B.

The class CelApplet is from the Event Logger module and preferably provides management of the various CelEventLog objects and of the single CelTraceLog object. It also provides a mechanism for identifying the Event Log Server. The class CelApplet preferably includes various public methods such as "CelApplet," "~CelApplet," "GetAppletName," "GetAppletTitle," "AddEventLog," "RemoveEventLog," "SetServerLog" and "GetTraceLog." Additionally, the class CelApplet preferably includes protected methods such as "InitApplet" and "ExitApplet."

The class CelEventLog is from the Event Logger module and preferably defines the properties of a specific, named portion of the Event Log. All logging is preferably done through a CelEvent object. This class preferably includes various public methods such as "CelEventLog," "~CelEventLog," "InitializeEventLog," "GetServerLogHandle," "GetLocalLogHandle" and "IsEventLoggable."

The class CelEvent is from the Event Logger module and preferably provides for the creation of application messages which are written to the event log. This class preferably includes a public definition such as "EventType" and public methods such as "CelEvent," "~CelEvent," "AddData," "operator<<" and "LogEvent."

The class CelTraceLog is from the Event Logger module and preferably defines the properties of a specific, named portion of the Event Log used for application program trace messages. A single object of this class is provided by the Event Logger and is shared by all Applets. The class CelTraceLog preferably includes public methods such as "CelTraceLog," "~CelTraceLog," "GetEventID," "SetTraceMask," "GetTraceMask," "DisableAppletTracing," and "EnableAppletTracing," "IsAppletTracingEnabled," "IsEventLoggable," "DisableEventLogging," "EnableEventLogging".

The class CelTrace is from the Event Logger module and preferably provides tracing of application diagnostic messages which are written to the CelTraceLog object by the Event Logger. The globally defined macros are intended to provide public access to this class. The CelTrace class preferably includes various global definitions such as "elTraceType," "elTrace, elTracen" and "elTraceItem". The public methods for this class include various methods such as "CelTrace," "~CelTrace," "RaiseNestLevel," "LowerNestLevel," "NestLevelIndent," "DumpTraceType" and "LogEvent."

The class CelEETrace is from the Event Logger module and preferably traces the entry and exit of any method. This class also generates CelTrace objects to do the actual tracing. Exit tracing is done automatically when the class object goes out of scope and is destroyed. To use class CelEETrace, place an automatic CelEETrace variable, or either an macro or an elEETraceRC macro, at the start of the method. The resulting CelEETrace constructor will generate a TT_ENTRY trace record. When the program code exits this method C++ will automatically destroy the CelEETrace object, causing the destructor to create a TT_EXIT trace record. The elEETracen and elEETraceRCn macros can include any parameters passed to the method being traced in the TT_ENTRY trace. The CelEETrace class and the lEE-TraceRCn macro can include a single return value in the TT_EXIT trace. The class CelEETrace preferably includes public definitions such as "elEETraceParm" and "elEETrace, elEETracen, elEEraceRC, elEEraceRCn" as well as public methods such as "CelEETrace" and "~CelEE-trace."

The Event Logger module also preferably includes various Foundation Extensions which define macros and functions which output debug information indented at the current indention defined in CelTrace. These extensions include global macros such as "BEGIN_DUMP," "END_DUMP," "DumpLbItem," "DumpLbItem" and "DumpArray" and also global functions such as "DumpObject" and "Do_DumpArray."

Figure 92:
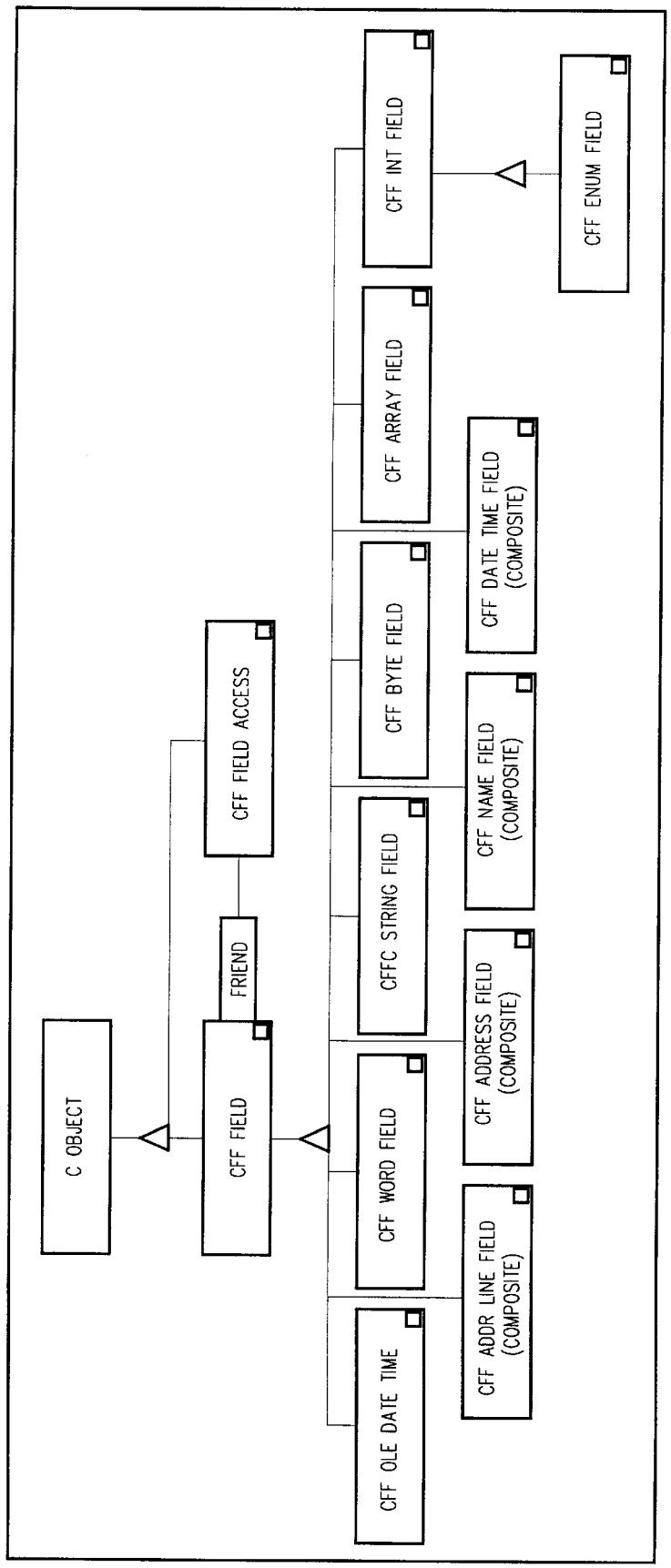
FIG. 92 is a diagrammatic view illustrating an overview of the Field Framework classes of the present invention.

The field framework module of the workstation client software portion of the workstation products framework product is described in further detail below. This section also describes the CffField hierarchy defined in the field framework module as well as the relationships between classes within the field framework module and classes within other workstation framework modules. The Field Framework is preferably an Applet DLL which encapsulates data-specific knowledge and serves as the data formatter. Each data element on the database can be represented as a field object with that object knowing how to format and manipulate the data element contained within it. As shown in FIG. 92, the CffField provides the primary interface between Field Framework and the other modules of the workstation products framework. The CffField derived classes are used to encapsulate the specific data representation with the access to this information done through virtual CffField class methods. This allows users of fields to use them as if they were all of the same class instead of multiple derived classes.

Figure 93:
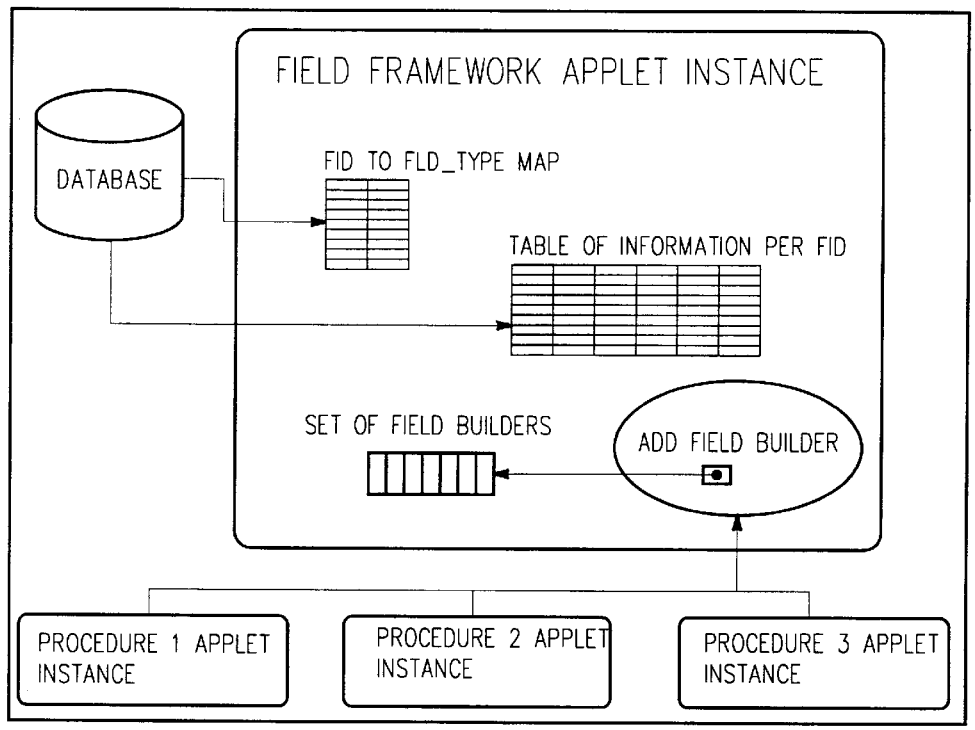
FIG. 93 is a diagrammatic view illustrating the initialization of the Field Framework of the present invention.

The field framework, and specifically each field object, is responsible for any data formatting that may be necessary in order to properly display, print or store the data contained within the field. The formatting information for each Field Id is maintained in tables. This information may be loaded from the database on initialization. The information for each Field ID includes the minimum allowable value for this field, the maximum allowable value for this field, the default value for this field, the Field Type and the list of acceptable values for Enum type fields. The specific information retrieved into these tables may vary by Field Type and may expand to include more than what is described herein. The desire to store this information on the database is driven by the desire not to duplicate the effort of maintaining and deriving this information. It is preferably designed once and then maintained on the database. Also, the loading of these items may be made to include all fields which are currently known to the database. Since other Applets may add fields (either derived classes or new Field IDs or both), there may be new fields in the future which the current field framework is unaware of. If the framework were responsible for maintaining the table information, the framework would need to change for every new field incorporated into the system. With the database storing this information, the field need only retrieve this information. Also, at initialization, the field framework Applet begins an array of function pointers to field builders which are to be added to by other Applets. The field builders are methods which construct specific fields based on a Field Id. Any Applet which wishes to define a new type of field, which will be derived from CffField, must also supply a method by which that field can be constructed. This removes the burden from the field framework for having to know about all types of fields. By allowing other Applets to define their own fields, the other Applets will be able to extend the field framework without directly affecting the basic structure of the field framework as shown in FIG. 93.

One goal for the field framework design is the encapsulation of the data representation. Data representation encapsulation is preferred so that changes to a data element's data representation do not ripple throughout the software code. The data representation for each field is influenced initially by the database with the understanding that the database representation may change in the future. Since a user of a field is responsible for initializing the internal data of the field, a method which sets the value in the field is necessary. This method preferably includes a typed parameter. Also the contents of the field are preferably retrievable thereby necessitating a method for getting a typed value from the field. If these methods are public, the main goal of encapsulation of the data representation has been compromised as any owner of fields may retrieve a typed copy of the data stored in the field. However, disallowing owners of fields to manipulate the value within the field is undesirable as well. Therefore, a compromise solution which can partially fulfill both needs must be achieved by the Field Framework design.

Figure 94A:
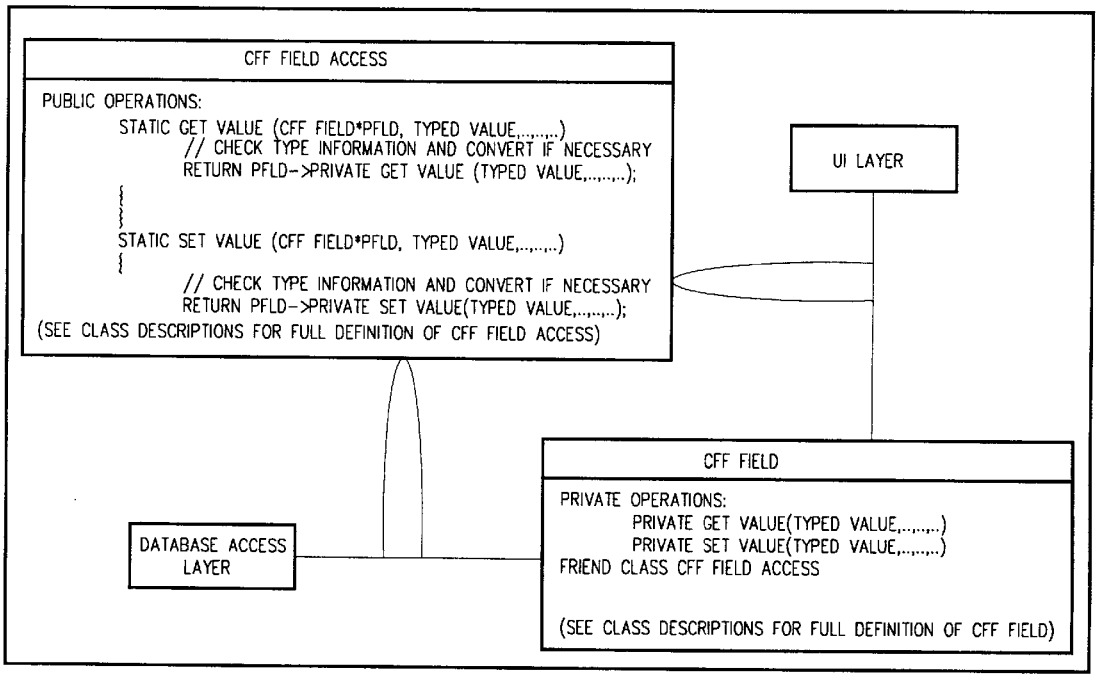
FIG. 94A is a diagrammatic view illustrating the atomic Data Access data type in the Field Framework of the present invention.

The first part of this solution is to make the get and set methods of the field framework classes protected. This disallows other classes from using these methods and promotes encapsulation. Then, an intermediate class, which lives in the field framework, is preferably designed to allow access to the get and set methods of the field hierarchy. This is accomplished by making the intermediate class a friend of the CffField class. Then the intermediate class defines public get and set methods for each atomic data type. The external world will then be able to use these methods to request that a field (passed as a parameter) be updated to a new value or that the data from the field be retrieved. These methods are flexible enough to perform needed conversions and, in general, form an isolation layer between the applications and the field framework. The addition of the intermediate class corrupts the encapsulation because an application may now be able to retrieve a typed value from the field. It does, however, preserve the field's data representation by providing conversions which both the application and the field are unaware of. These conversions preferably allow the data representation to be modified without causing many lines of code to be located and modified as well. FIG. 94A illustrates this concept.

Composite fields are groupings of other fields. They differ from atomic fields in that they contain other fields. Fields defined in the Field Framework are predominately atomic and map to the atomic data representations of the database. For example, on the database there is a signed 4-byte integer type so a CffIntField with a signed, 4-byte internal representation has been defined. However, future Applets may wish to define new field classes as composite. The field framework must be designed to allow this expansion without modifying the framework for each new occurrence of a composite type.

Figure 94B:
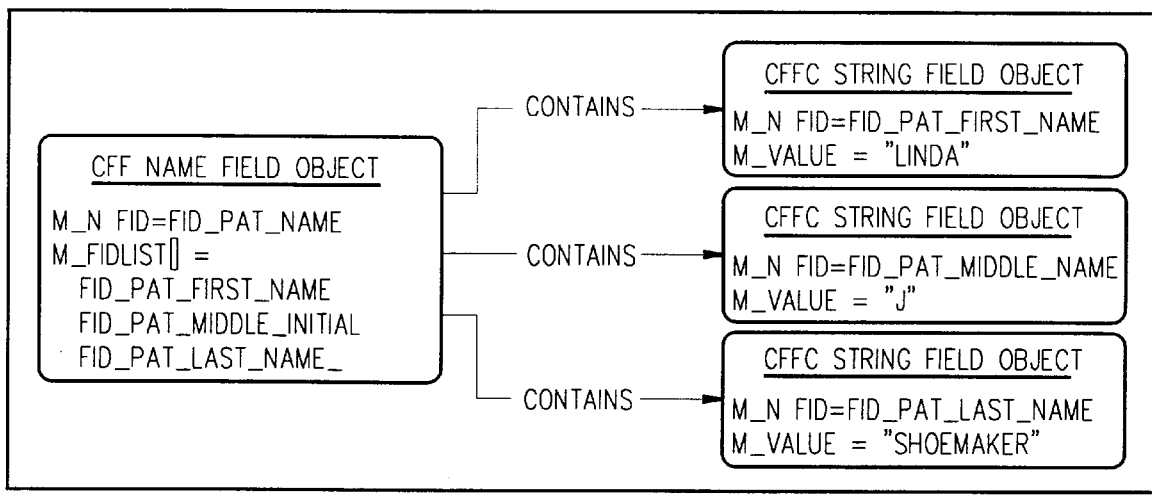
FIG. 94B is a diagrammatic view illustrating the Composite Fields data type in the Field Framework of the present invention.

As shown in FIG. 94B, an example of a composite field is patient name. Each element of the patient name may have its own minimum and maximum lengths or its own rules for handling abbreviations. However, the patient name can also be considered one element with a defined format. A field for patient name will be uniquely identified by a field ID such as FID_PATIENT_NAME. A CffNameField type, which is derived from CffField, can be defined such that it is a composite of the fields FID_PAT_FIRST_NAME, FID_PAT_MIDDLE_NAME, and FID_PAT_LAST_NAME each of which, for this example, will be of field type CffCStringField. The objects for a patient's name are shown in FIG. 94B.

Each of the name part fields can handle formatting and checking itself while the composite field is able to format the whole name. For example, using the values defined above, a call to the GetFormattedString method of the CffNameField Object would return "Linda J. Shoemaker" or "Shoemaker, Linda J." depending on the defined format. The defined format may be determined by a system API call or by a field from the database. A call to the GetFormattedString method of the CffCStringField Object for the FID_PAT_MIDDLE_NAME might return "J.". Although a rule about placing a period after a single letter middle name may be encapsulated within the field object since the field for the middle name in this example is a generic type of field, there is no place for the rule to be encapsulated. To encapsulate the rule, FID_PAT_MIDDLE_NAME would have to use a field class which is derived from CffCStringField and adds the desired behavior. This last call necessitates that the user of a CffNameField must be able to access the objects within it. Methods within CffField and overridden in derived classes allow the user to retrieve from a given field object a list of the ids for the fields which this object contains. This is shown as m_fidlist in FIG. 94B. The user will also be able to retrieve any sub-field object of a given field using the sub-field id. These two methods allow the user to traverse a composite field to any depth. In this name example, the owner of the CffNameField Object will be able to get the m_fidlist and then get each of the field objects using this list. Once the desired field is retrieved, the owner may invoke methods which manipulate the underlying data element.

Figure 94C:
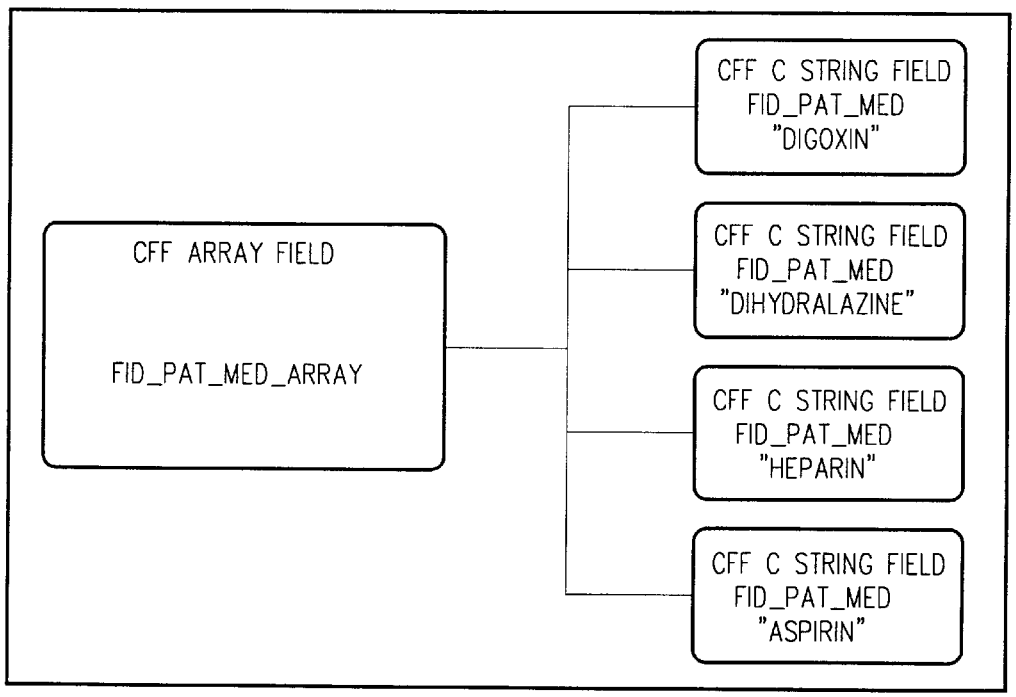
FIG. 94C is a diagrammatic view illustrating the Array Fields data type in the Field Framework of the present invention.

An array field is a field object which contains other field objects. The contained field objects, or elements, all have the same Field Id and the array field object has a different Field Id. As shown in FIG. 94C, an example of this type is an array of current patient medications. The array could be uniquely identified as FID_PAT_MED_ARRAY and could be an array of FID_PAT_MEDs where the number of FID_PAT_MEDs is variable from patient to patient. FIG. 58 illustrates an object description of a FID_PAT_MED_ARRAY field object.

The method to access individual sub-fields of FID_PAT_MED_ARRAY must be different from the patient name example above because all the sub-fields have the same id. When attempting to retrieve a particular sub-field from the FID_PAT_MED_ARRAY object, the owner must specify which FID_PAT_MED object is to be retrieved. To facilitate this, CffField provides support for determining which field objects are array fields and how many elements are contained within the array. Then the operator[] is overloaded by the CffField class and overridden by the CffArrayField class to retrieve a particular field object within the array field. If the field object is not an array field, the default behavior, as defined in CffField, for the operator[] is to return a NULL.

The successful use of array fields also involves being able to set the number of elements dynamically. So when the array object, an object of type CffArrayField, is created, it is initially empty. Elements have to be dynamically added to and deleted from the array object. When an element is added to an array field, the array field assumes ownership of that field object. The InsertField(), ReplaceField() and RemoveField() methods may be added to the CffField class and overridden in the CffArrayField class. These methods may also be useful to types of fields which are composite.

It is anticipated that the CffArrayField class will be suitable for all types of arrays and that it will not need to be subclassed. However, there is nothing in the design of the present embodiment to prevent a subclass of the CffArrayField class. There will be a member attribute which specifies the Field Id of the elements which can be added to the CffArrayField object. The Field Id of the elements is dependent on the Field Id of the CffArrayField object. So, for example, the FID_PAT_MED_ARRAY would be of type CffArrayField, and the only elements which could be added to the object would be FID_PAT_MEDS. All of this default information is stored on the database.

The need to protect the identity of the patient is paramount in medical and hospital information systems. In order to facilitate this, certain key demographic fields are altered to hide the true field value. Encryption has been chosen in the present invention so that the mechanism of altering the data is repeatable and each encrypted field is unique. For example, the medical record number (MRN) field will need to be encrypted, but the MRN is one of the distinguishing fields for a patient so it still needs to be unique from all other encrypted MRNs. Also, if the same patient has multiple procedures, every encrypted version of the MRN for that patient should be the same. The CffCStringField class will be responsible for providing an encryption of data when requested. Currently no other classes will provide the encryption. However, there is a new field flag, FLD_FLAG_ENCRYPT, which can be passed to any field. Therefore, other fields may be able to provide encryption as needed. Any field in which encryption is not supported will ignore the field flag for encryption if it is passed to the field's methods. The Patient Name (includes all name parts), Patient MRN, Patient SSN, Patient Address (includes all address parts), Patient Phone Number, and Patient Billing Number fields are the minimum set of data which is encrypted.

The field framework provides a number of enum definitions for use with fields. These enums exist on a global scale due to their wide use and the cumbersome task of always scoping them. The enums for Field ID (FID) are used to uniquely identify each element on the database. The FIDs are heavily used throughout the client software to refer to specific data elements. The enums for FLD_TYPE identify the base storage type which will be used for each defined FID. As the design of the preferred embodiment expands and grows to include further modules, it is anticipated that the number of FLD_TYPEs will grow. The enums for FLD_ERR identify the errors that may occur within the Field Framework. The enums for FLD_FLAG identify how the field should treat a particular situation or value.

The class CffApplet is from the Field Framework module and preferably provides the applet interface class for the field framework. The field framework applet object initializes the tables which are used by the CffField derived classes. The class CffApplet preferably includes various public methods such as "CffApplet," "~CffApplet," "InitApplet," "ExitApplet," "GetAppletName," "GetAppletTitle" and "GetEventLog."

Figure 95:
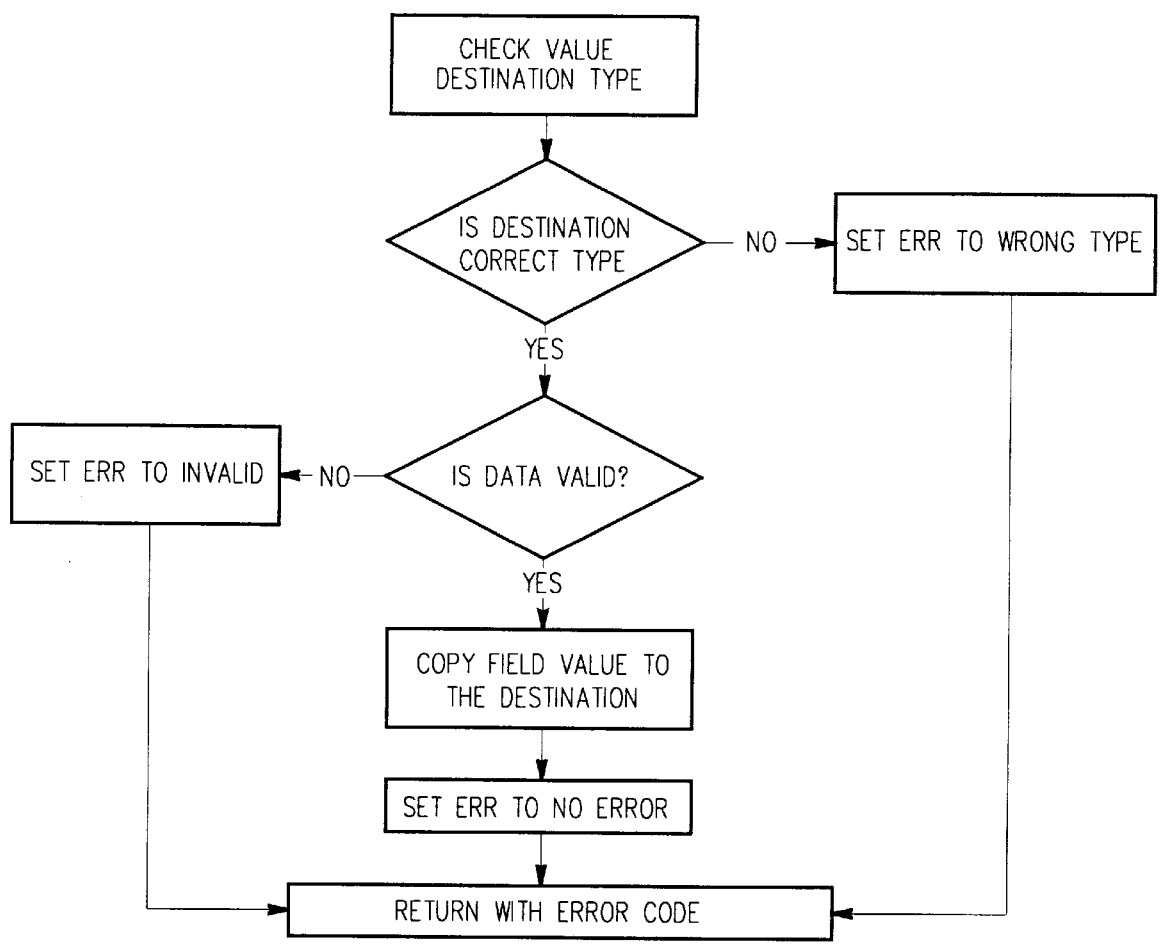
FIG. 95 is a flow diagram illustrating the operation of a portion of the class CffField from the Field Framework module of the present invention.

The class CffField is from the Field Framework module and preferably provides the applications with a cohesive and elementary way to interact with specific items of data within a record. An example of this approach is shown in FIG. 95. This class is an abstract base class and as such it cannot be instantiated as an object. The class CffField preferably includes global definitions such as "NOT_AN_ARRAY" and "LPFLDBLDR." This class also preferably includes public methods such as "CffField," "~CffField," "GetFormattedString," "AddFieldBuilder," "RemoveFieldBuilder," "AddTypeMap," "DeleteID2TypeMap," "GetSubField," "GetFIDList," "IsArray," "GetArrayCount," "InsertField," "RemoveField," "ReplaceFeld," "operator[]," "GetLine," "GetLabel," "CheckEntry," "GetFID," "IsDataValid," "SetDataValid," "GetFieldType," "GetLastError," "GetExtent" and "FieldFactory." This class further includes private methods such as "SetValue" and "GetValue."

The class CffFieldAccess is from the Field Framework module and preferably provides an isolation layer between the Get and Set value methods of the fields and the outside world. The class CffFieldAccess preferably includes public methods such as "SetValue" and "GetValue" and also private methods such as "CffFieldAccess" and "~CffFieldAccess."

The class CffNameField is from the Field Framework module and preferably is a composite field which groups the components of the any name. The formatting of the name is also handled with this field. The name of the patient and the name of the physician as well as the names of other entities are identical in the components and the formatting of those components. This field will support any of these by using the database to indicate which FIDs correspond to which collection. In other words, the database will maintain a list of the FIDs which go with FID_PAT_NAME and a list of the FIDs that go with FID_PHY_NAME. The FIDs for the components are different because they represent unique quantities on the database. However, for formatting purposes, those components can be treated identically. However, because the FIDs are actually different from one name to another, the order in which they appear in the list of FIDs (on the database and in the field object) is critical. If the order is wrong, the formatting will be wrong. The class CffNameField preferably includes various public methods such as "CffNameField," "~CffNameField," "GetFormattedString," "GetSubField" and "GetFIDList."

The class CffAddressField is from the Field Framework module and preferably is a composite field which maintains and formats the components of the patient address. This class preferably includes various public fields such as "CffAddressField," "~CffAddressField," "GetFormattedString," "GetSubField," "GetFIDList" and "GetLine."

The class CffArrayField is from the Field Framework module and preferably provides a field collection class in which each member of the collection has the same FID. This class preferably includes various public methods such as "CffArrayField," "~CffArrayField," "InsertField," "RemoveField," "ReplaceField," "IsArray," "GetArrayCount" and "GetFormattedString."

The CffAddrLineField is from the Field Framework module and preferably is a composite field used to describe the contents of a line of an address. The composition of an address line varies as the address format varies so the list of sub-fields included in this composite field is dynamic. This class preferably includes various public methods such as "CffAddrLineField," "~CffAddrLineField," "GetFormattedString," "InsertField," "RemoveField" and "ReplaceField."

The class CffDateTimeField is from the Field Framework module and preferably is a composite field which contains sub-fields for the numeric representation for a date and time value and the formats for the data and time. Many of the data elements which will be mapped to this field type will not contain both the date and time field type. The sub-fields will be managed with this consideration. The ENUM_FLD_DT_TYPE specifies which components of the date and time are valid. This in turn indicates which of the sub-fields are valid. The class CffDateTimeField preferably includes various public methods such as "CffDateTimeField," "~CffDateTimeField," "GetFormattedString" and "GetSubField."

The class CffOleDateTime is from the Field Framework module and is preferably used to encapsulate a COleDateTime object. The encapsulation is done to allow the COleDateTime class to fit into the Field Framework Paradigm. The CffOleDateTime class is used as a member of the composite class CffDateTimeField. The class CffOleDateTime preferably includes various public methods such as "CffOleDateTime," "~CffOleDateTime," "GetFormattedString," "SetFormat," "GetValue" and "SetValue."

The Atomic CffField-Derived class as well as the other derived classes all preferably have similar behavior. In order for a class to have common behavior, it must implement a Public operator=method, a private copy constructor and an overridden GetFormatted String method. In the present invention, there are a few things that are delegated to the derived class. One of the primary delegated functions is the generation and maintenance of the table which contains min, max, default and other field class specific information. The derived classes also provide protected methods to access this information. This information is referenced through various flags on the parameter list of several base class methods but only the derived class can get to the specific information. Also delegated to the derived classes is the implementation of the CheckEntry method. This is not a required method and each derived class can choose to implement or not. The base class returns TRUE for this method.

The CffByteField derived class contains a static attribute, gm_ByteFieldTable, which is a collection of the static information for each FID which is defined to be a FLD_TYPE_BYTE. The static information contains three items. The first item is that the Min represents the minimum value that the field object may have. The second item is that the Max represents the maximum value that the field object may have. The third item is that Default represents the default value for this field object. The pieces of information are grouped together by a structure definition with gm_ByteFieldTable being a collection of these structures. The methods used to retrieve this information are defined as protected so that classes derived from the CffByteField may override these methods if the default behavior is inadequate.

The CffStringField derived class contains a static attribute gm_CStringFieldTable, which is a collection of the static information for each FID which is defined to be a FLD_TYPE_CSTRING. The static information preferably contains three items. The first item is that Min represents the minimum number of characters that the field object may have and is therefore not a valid value for the field. The second item is that Max represents the maximum number of characters that the field object may have and is also not a valid value for the field. The third item is that Default represents the default value for this field object and represents a valid value for the field object. The methods used to retrieve the information from gm_CStringFieldTable are defined as protected so that classes derived from CffStringField may override these methods if the default behavior is inadequate.

The CffIntField derived class contains a static attribute, gm_IntFieldTable, which is a collection of the static information for each FID which is defined to be a FLD_TYPE_INT. The static information contains three items. The first item is that the Min represents the minimum value that the field object may have. The second item is that the Max represents the maximum value that the field object may have. The third item is that Default represents the default value for this field object. The pieces of information are grouped together by a structure definition with gm_IntFieldTable being a collection of these structures. The methods used to retrieve this information are defined as protected so that classes derived from the CffIntField may override these methods if the default behavior is inadequate.

The CffEnumField derived class contains a static attribute, gm_EnumFieldTable, which is a collection of the static information for each FID which is defined to be a FLD_TYPE_ENUM. The static information contains three items. The first item is that PossibleValues is a list of all the acceptable values for this FID and includes both the int value and the CString representation. The second item is that the Count is the number of entries in possiblevalues. The third item is that Default represents the default value for this field object. The pieces of information are grouped together by a structure definition with gm_EnumFieldTable being a collection of these structures. The methods used to retrieve this information are defined as protected so that classes derived from the CffEnumField may override these methods if the default behavior is inadequate.

The CffWordField derived class contains a static attribute gm_WordFieldTable, which is a collection of the static information for each FID which is defined to be a FLD_TYPE_WORD. The static information preferably contains three items. The first item is that Min represents the minimum value that the field object may have. The second item is that Max represents the maximum value that the field object may have. The third item is that Default represents the default value for this field object. The methods used to retrieve the information from gm_CffWordField are defined as protected so that classes derived from CffWordField may override these methods if the default behavior is inadequate.

As mentioned above, the workstation framework is built using macros, libraries, and classes which are preferably provided with the compiler, such as the Microsoft Visual C++ compiler. Collectively, these macros, libraries, and classes provide an application framework. The framework provided with the Microsoft Visual C++ compiler is often referred to as the Microsoft Foundation Class library or MFC. Technically this is inaccurate since MFC builds upon macros and libraries which are not part of MFC but rather are typically provided with any C/C++ compiler. The full compiler-provided framework includes all the compiler-provided library routines, all the compiler-provided macros, all the compiler-provided header files and MFC. This compiler-provided framework is referred to herein as the Foundation Framework. The Foundation Framework has been designed for extensibility. The two types of extensions which form part of the present invention are Foundation Framework extensions and Custom Application extensions. The Foundation Framework extensions are macros, functions and classes that properly belong within the Foundation Framework itself, as part of the standard tool-set provided by the Foundation Framework to all users of that framework. They represent natural extensions to the framework within the design intent of the framework. These extensions are completely general purpose in nature, suitable for and fully applicable to any application. The Custom Application extensions are classes and occasionally macros and functions which provide a more powerful application framework than the Foundation Framework, but a framework that is less general purpose in nature. The Custom Application extensions provide specialized facilities specific to a narrower class of applications than that served by the general purpose Foundation Framework. These Custom Application extensions often utilize variations of the Foundation Framework extensions. The Foundation Framework extensions, known as Foundation Extensions, are provided as part of the Workstation Products Framework. The rest of the Workstation Products Framework is a Custom Application extension to the compiler-defined framework provided with Visual C++, as extended by Foundation Extensions.

As mentioned above, the Foundations Extensions module of the present invention preferably includes various global definitions such as DEBUG and others. This module also includes the class CqDisableUpdates. This class disables screen changes to the CWnd object specified in the object constructor until the CqDisableUpdates is destroyed. When CqDisableUpdates is destroyed, the screen are specified on the CqDisableUpdates constructor is invalidated, forcing redrawing of the affected area, and the background is optionally erased. Typically a variable of class CqDisableUpdates is declared and automatically constructed at the beginning of a compound statement or method within which many screen updates area made. The CqDisableUpdates object declared is automatically destroyed when the compound statement or method is exited. The class CqDisableUpdates preferably includes public methods such as "CqDisableUpdates" and "~CqDisableUpdates."

Figure 96:
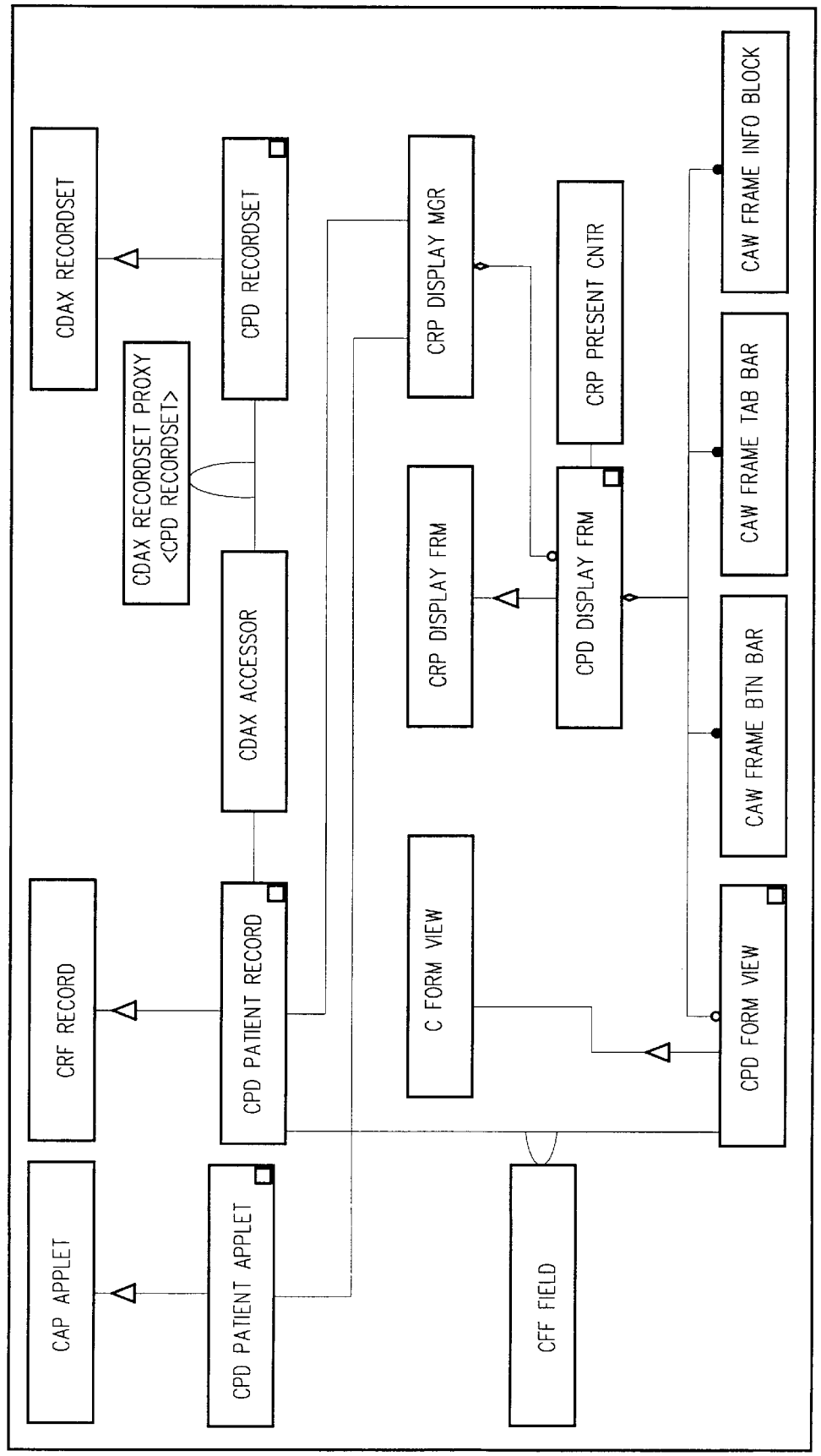
FIG. 96 is a diagrammatic view illustrating an overview of the Patient Demographics classes of the present invention.

FIG. 96 shows the relationships between the classes defined in the Patient Demographics module as well as the relationships between classes within the Patient Demographics module and classes within other workstation framework modules. The class CpdApplet provides the initialization necessary for the Patient Demographics Applet. On initialization of the Patient Demographics Applet, the record builder for the CpdPatientRecord will be added to the list of record builders maintained in the Record Framework as shown in FIG. 97.

The record builder provided with the Patient Demographics Applet preferably builds only one type of record, a CpdPatientRecord. The CrfRecordClass contains information on the specific class of record to be built and includes the unique applet ID and a sub-class attribute. As described above, each Applet determines how the sub-class attribute is to be used. The sub-class attribute is preferably ignored in Patient Demographics because there is only one defined CrfRecord-derived class supported in this Applet.

The process of creating a CpdPatientRecord requires several steps examples of which are illustrated in FIG. 98 and described below. The record framework will call the PatRecBuilder when the CrfRecordClass for the desired record contains the unique Applet ID for the Patient Demographics Applet. In the present embodiment, it is intended that the elements within the CrfRecordClass class will be stored on the persistent storage medium and accessible to the Record List Applet or whichever Applet or process is attempting to create the record object. The record builder will create the correct accessor class based on the AccessorKey passed to the record builder. In the preferred form of the present invention, a CdaxAccessor will preferably always be built. The PatRecBuilder constructs a Recordset Proxy and passes ownership of the AccessorKey and the Recordset Proxy to the Accessor object. Once the accessor object has been constructed, the PatRecBuilder will construct the CpdPatientRecord passing the newly created accessor object as well as other construction parameters. The PatRecBuilder then passes ownership of the RecClass object and the accessor object to the Record object. The PatRecBuilder returns a pointer to the newly created CpdPatientRecord and relinquishes ownership.

The class CpdApplet is from the Patient Demographics module and preferably provides the initialization necessary for the Patient Deographics Applet. This class includes various public methods such as "CpDApplet," "~CpdApplet," "InitApplet," "ExitApplet," "GetAppletName," "GetAppletTitle," "PatRecBuilder" and "GetDisplayMgr." This class also preferably includes private attributes such as "gm_pDisplaygr."

The class CpdPatientRecord is from the Patient Demographics module and preferably provides the specific information needed for a patient record. This class includes various public methods such as "CpdPatientRecord," "~CpdPatientRecord," "GetOpIDList" and "DoOperation."

The class CpdRecordset is from the Patient Demographics module and preferably provides the database interface necessary to retrieve and store patient records from and to the database. This class preferably includes public methods such as "CpdRecordset," "~CpdRecordset," "HasField," "GetDefaultSQL" and "DoFieldExchange."

The class CpdPatientFrmView is from the Patient Demographics database and preferably provides a view object in which to display fields within the Patient Demographics Record. It is anticipated that in other embodiments of the present invention, this class may be removed and replaced with elements from the Record Presentation Applet. The content of the CpdPatientFrmView class is governed by the UI. The CpdDisplayFrame class handles all of the messages so no message handlers are defined in this view. The class CpdPatientFrmView preferably includes various public methods such as "CpdPatientFrmView" and "~CpdPatientFrmView."

The class CpdDisplayFrm is from the Patient Demographics module and preferably provides the derived frame for the Patient Demographics module. This frame preferably handles all the commands coming from the CpdPatientFrmView and will ease the transition to further embodiments of record presentation. The CpdDisplayFrm preferably includes a variety of public methods such as "CpdDisplayFrm," "~CpdDisplayFrm" and "OnCommandHandler."

Figure 99:
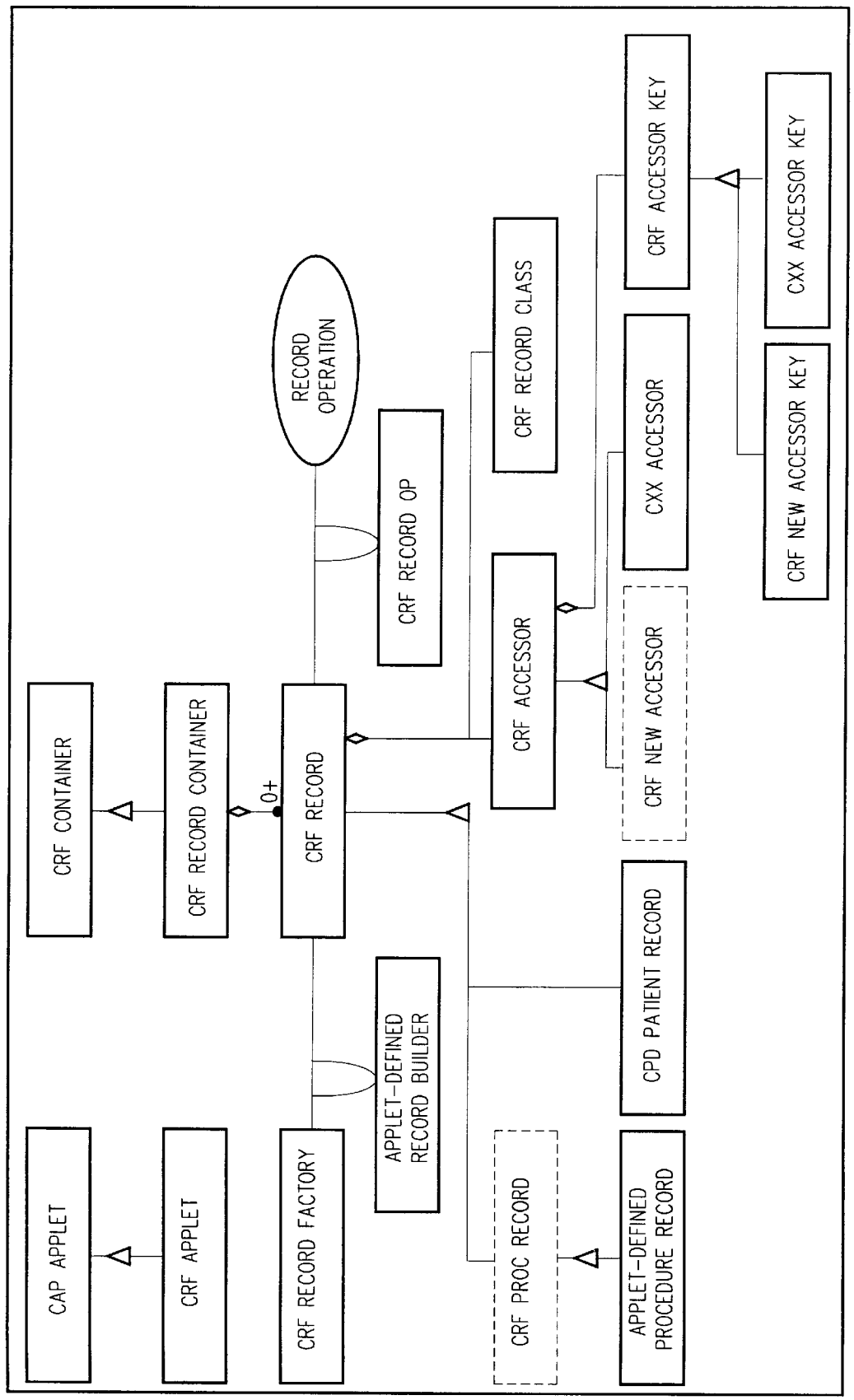
FIG. 99 is a diagrammatic view illustrating an overview of the classes of the Record Framework module of the present invention.

FIG. 99 shows the relationships among the classes defined in the Record Framework classes as well as the relationships between classes within the Record Framework module and classes within other workstation framework modules. Those Record Framework classes whose inheritance is not shown are preferably derived from CObject. The Record Framework Applet provides several classes from which other record-based Applets derive. As used herein, the classes which are defined by the Record Framework DLL include CrfApplet, which is a CapApplet-derived class that provides a minimal Applet interface. The CrfRecord is an abstract base class from which all record classes, Patient Demographics and Procedures, are derived, and it mandates an interface for Record Locking, Saving and other Operations. The Applet which defines a derived Record class must provide a RecordBuilder method for constructing objects of that Record class as described below with respect to CrfRecordFactory. The CrfProcRecord is an abstract base class derived from CrfRecord, and all Procedure record classes are derived from it. The Procedure record classes are defined by other Applets. The CrfRecordClass defines the attributes which are necessary to identify a particular CrfRecord-derived class and is used by the CrfRecordFactory methods to construct CrfRecord-derived objects. The CrfRecordOp class encapsulates the information needed to perform an operation on a record and contains an operation identifier (OpID) and parameters whose meaning is defined for each operation. The CrfAccessor is a base class which abstracts the means of transferring data between some persistent storage medium and a Client-based Record object. A subclass may be derived from this class for each supported persistent storage medium. The CrfAccessorKey is a base class which abstracts the information needed to identify a persistent storage medium and identify the data corresponding to a particular record. The CrfNewAccessor is an Accessor class which corresponds to no persistent storage medium, and the user of this Accessor directly updates the Fields of a Record. The CrfNewAccessorKey is an AccessorKey class which identifies a CrfNewAccessor class. The CrfRecordFactory is a class containing a handful of static methods to support the creation of CrfRecord-derived objects and has a method which other Applets use to register a RecordBuilder method. When creation of a CrfRecord-derived object is requested, the RecordFactory invokes the RecordBuilder method of the Applet, which defines the derived Record class to construct an object of the proper class. The CrfContainer is a template class which defines an interface for a collection of pointers to Record or Record-based objects. The CrfRecordContainer is a concrete class of CrfContainer in which the contained objects are pointers to CrfRecord-derived objects. CrfRecordContainer class adds a DoOperation method which invokes the requested operation on each of the contained Record objects.

Figure 100A:
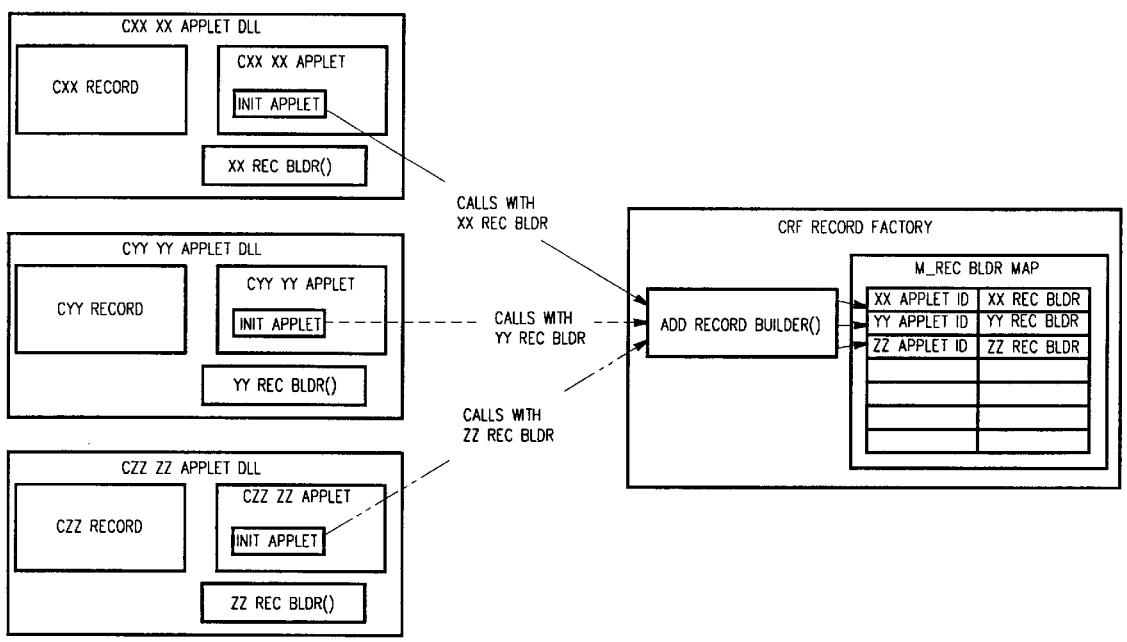
FIGS. 100A and 100B are diagrammatic views illustrating the Record Framework interactions with other Applets in the present invention.

Each Applet-based DLL which defines a CrfRecord-derived class must provide a record builder for the derived class. The record builder is preferably registered with the CrfRecordFactory class through the AddRecordBuilder method. This may be done during the InitApplet method of the derived CapApplet class as shown in FIG. 100A. Another required call is the call to RemoveRecordBuilder() to remove the record builder from the map maintained by the CrfRecordFactory when the Applet is terminated. As shown in FIG. 100A, three Applet-based DLLs each define at least one CrfRecord-derived class. The CxxXXApplet DLL defines the CxxRecord class; the CyyYYApplet DLL defines the CyyRecord class, and the CzzZZApplet DLL defines the CzzRecord class. Each of the DLLs also provides a record builder for its derived record class. The record builders are added to the CrfRecordFactory during each Applet's initialization (and should be removed when each Applet is terminated).

Figure 100B:
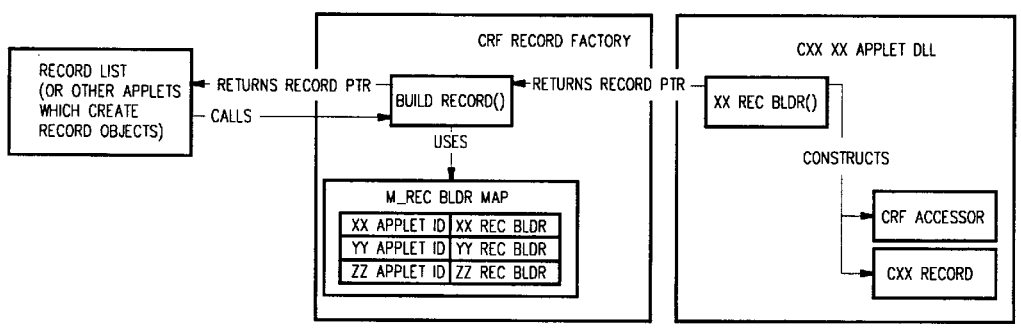

As shown in FIG. 100B, when a record object is desired by the RecordList Applet, a call to the BuildRecord method of the CrfRecordFactory is made, which in turn calls the appropriate record builder (if registered). Each registered record builder is only a pointer to a method within another Applet. That method is able to build both the CrfAccessor object or a derived type object and the CrfRecord-derived object and return a pointer to the Record object. In the preferred embodiment, the Accessor object is contained within the Record object. Once a record builder has returned with a valid record pointer, the BuildRecord method returns that pointer to the caller. The caller is then responsible for deleting the Record object.

Figure 101:
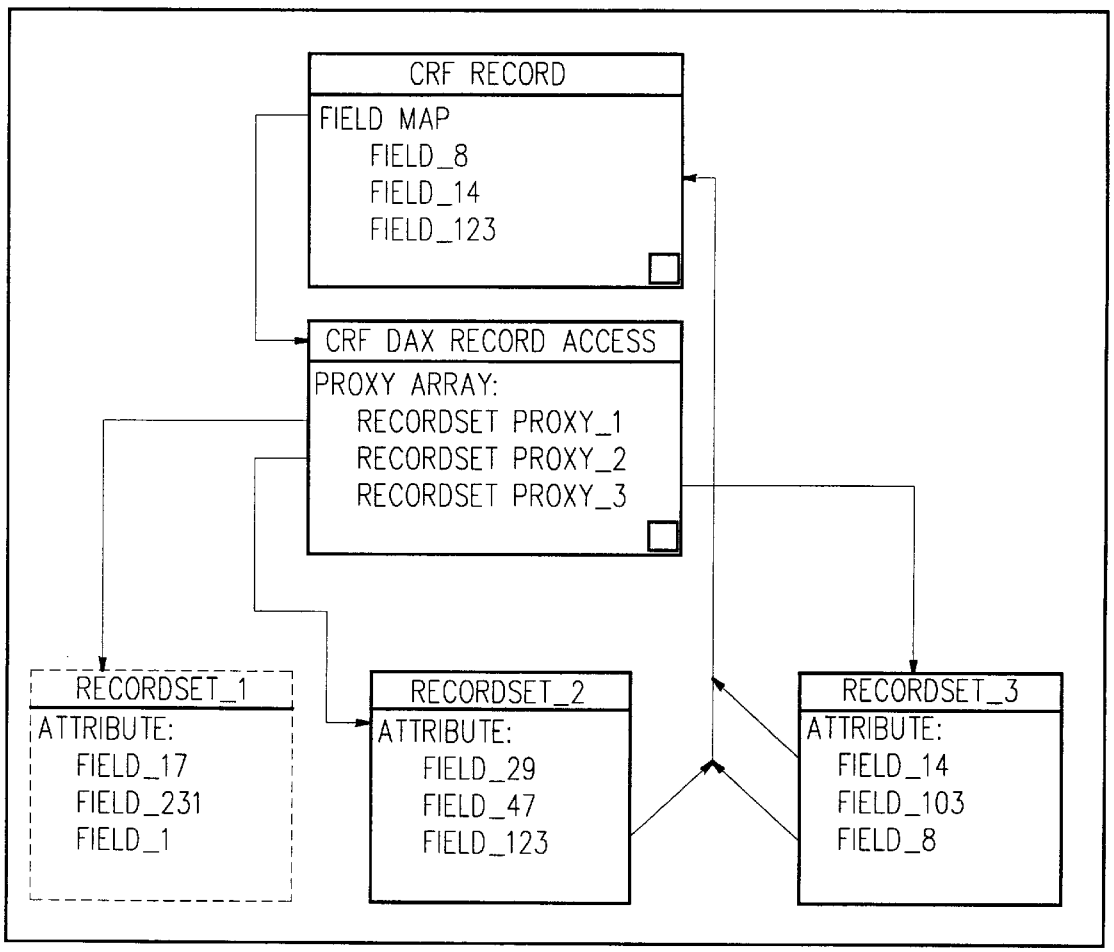
FIG. 101 is a diagrammatic view illustrating the Record Framework interactions with the Database in the present invention.

From the viewpoint of the DaxAccessor, the database access layer is a collection of Recordsets each of which contains Fields. When the owner of a Record (whose Accessor is Dax) requests a Field, the Record queries its associated DaxAccessor object, which in turn queries each of its Recordsets until one of those Recordsets responds with a valid Field object to satisfy the request. When the Accessor returns a Field object, the Record places that Field and the Field ID in a local map. This map is then used to access the Field on subsequent requests with the same Field ID. It is important to note that in the preferred embodiment of the present invention, the DaxAccessor object does not actually contain Recordsets, but rather it contains objects called RecordsetProxies. Each Proxy is a stand-in for the Recordset because the Recordset object itself is not instantiated, and the database query for that Recordset is not performed until one of the Fields from that Recordset is requested. This is the "lazy construction" mechanism referred to above that greatly reduces the number of database hits and the size of records on the client. In FIG. 101, it is presumed that Fields with identifiers 8, 14 and 123 have been requested of a Record whose Accessor is Dax. This has caused Recordsets 2 and 3 to be instantiated and populated from the database server to satisfy those requests. Pointers to the Field objects returned from the Recordsets have been placed in the Record's Field map. Since no Fields have been requested from recordset_1, it is not instantiated. To continue the example shown in FIG. 101, the following actions will occur in response to requests for different Fields:

| | |
|---|---|
| Field_8 | the Record will return a pointer to Field_8 from the Record's FieldMap. |
| Field_29 | the Record will request Field_29 from its Accessor. The DaxAccessor will query each RecordsetProxy until satisfied. This will occur when RecordsetProxy_2 is queried. Recordset_2 will create and populate Field_29 which will be returned to the Record and placed in the Record's FieldMap. |
| Field_17 | the Record will request Field_17 from its Accessor. The DaxAccessor will request Field_17 from RecordsetProxy_1. Because Recordset_1 provides a Field of this type, the Proxy will instantiate Recordset_1. An object for Field_17 will be created and populated with data from |

| | |
|---|---|
| | Recordset_1 and returned to the Record. The Record will place Field_17 in its FieldMap. |
| Field_999 | the Accessor will search through each of the Recordsets and the requested Field will not be created since this Field ID is not represented in any of the Recordsets. The Accessor will return a NULL pointer to the Record; the Record will not adjust its FieldMap. |

Figure 102:
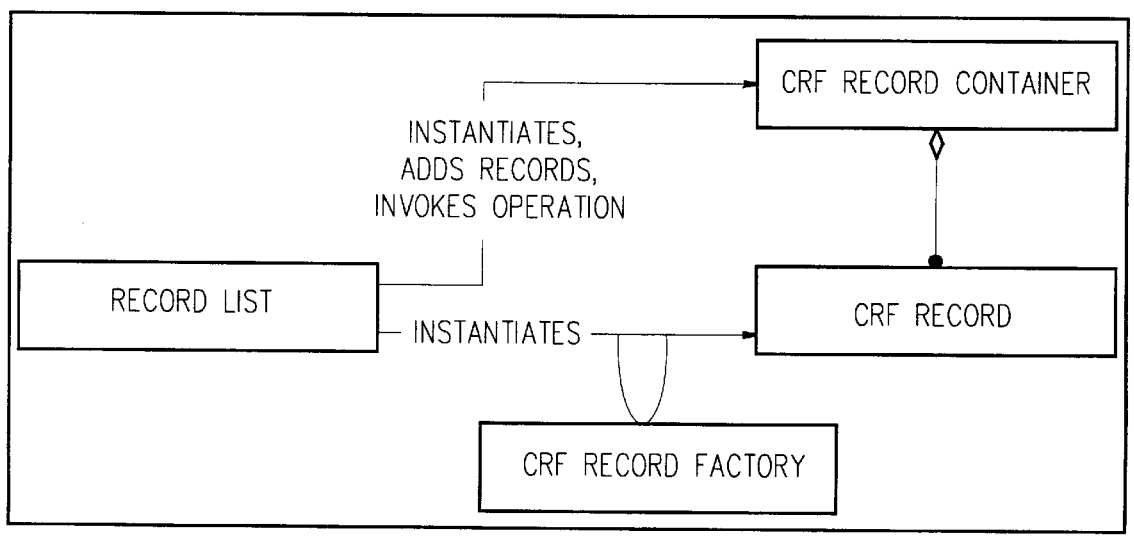
FIG. 102 is a diagrammatic view illustrating the Record Framework interactions with Record Lists in the present invention.

As shown in FIG. 102, the Record List Applet presents a list of records to the user, allowing the user to select one or more entries from the list and perform some operation(s) on them. While in the Record List, the entries are not CrfRecord objects; they simply reflect the result of a database query. To perform an operation, the selected Record List entries must be instantiated as CrfRecord objects; this is performed through the services of the RecordFactory. These objects are then placed in a CrfRecordContainer object, and the desired operation is performed on each of the record objects within the container by invoking the "DoOperation" method of the container.

Figure 103:
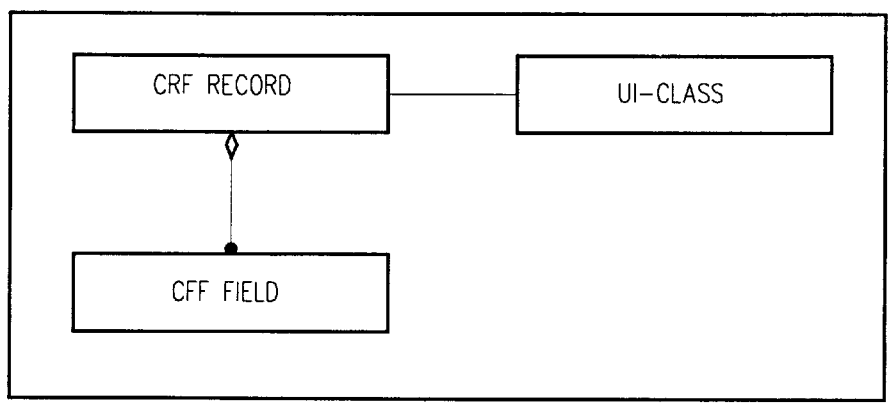
FIG. 103 is a diagrammatic view illustrating Record Framework interactions with User Interface elements in the present invention.

As shown in FIG. 103, for User Interface needs, the record appears as a collection of Field objects. When the need to print, edit or view a record arises, the owner of a record can obtain the data elements of that record as CffField objects for presentation.

The class CrfApplet is from the Record Framework module and preferably provides the Applet with the interface for the Record Framework module. This class preferably includes public methods such as "CrfApplet," "~CrfApplet," "ExitApplet," "GetAppletName" and "GetAppletTitle."

The class CrfRecordClass is from the Record Framework module and preferably provides a means of identification of a specific CrfRecord-derived class. This class identifies the Applet which defines a CrfRecord-derived class and a sub-specifier for use within that Applet. It is used by class CrfRecordFactory via an Applet-defined Record Builder method to create an object of the correct CrfRecord-derived class. It is preferred that these RecordClass attributes are stored as part of the persistent image of a record. When the persistent image is retrieved, the RecordClass data can be used to construct the correct Record object. The CrfRecordClass preferably includes various public methods such as "CrfRecordClass," "~CrfRecordClass," "operator==," "operator!=," "GetRecordAppletID" and "GetRecordSubID."

The class CrfRecord is from the Record Framework module and is preferably an abstract base class. This class captures the concept of a record as a collection of data elements which can be stored and retrieved, and upon which various operations such as edit, print, delete, etc. may be performed. The CrfRecord class preferably includes a global definition such as "enum rfRECORD STATE" and a public definition such as "Struct RecordLockStatus." This class also preferably includes various public methods such as "CrfRecord," "~CrfRecord," "GetRecordClass," "GetAccessor," "IsLocked," "Lock," "Unlock," "QueryLock," "GetPersistentKey," "GetField," "RefreshField," "Save," "GetOpIDList" and "DoOperation."

The class CrfRecordOp is from the Record Framework module and is preferably provides an encapsulation of the Record Operation parameters supplied on the CrfRecord's DoOperation method. This class preferably includes global definitions such as "enum OpId" and "enum OpStatus" as well as public methods such as "CrfRecordop," "~CrfRecordOp," "GetOpId," "GetwParam" and "GetlParam."

The class CrfAccessorKey is from the Record Framework module and preferably is the base class for the Record-Framework "AccessorKey" classes. An AccessorKey class identifies a persistent storage medium and a particular record on that medium. A derived class refines the concept for a particular storage device. The class CrfAccessorKey preferably includes public definitions such as "enum ACCESSOR_TYPE" and "enum RECORD_CATEGORY" as well as public methods such as "CrfAccessorKey," "~CrfAccessorKey," "GetAccessorType," "GetRecordCategory" and "GetKeyString."

The class CrfAccessor is from the Record Framework module and is preferably the base class for RecordFramework Accessor classes. An Accessor class makes transparent the implementation of the persistence for a CrfRecord-derived object. It is intended that this class be derived for different persistent storage types such as databases, files, SCP, etc.; and, if necessary, derived from there to support the derived Record objects. The CrfAccessor class preferably includes public methods such as "CrfAccessor," "~CrfAccessor," "GetAccessorKey," "GetField," "RefreshField," "StoreField," "IsReadOnly," "Lock," "Unlock," "QueryLock", "IsLocked," "PrepareToSave" and "Save."

The class CrfNewAccessorKey is from the Record Framework module and is preferably the implementation of CrfAccessorKey which does not correspond to any storage device. This class preferably includes public methods such as "CrfNewAccessorKey," "~CrfNewAccessorKey" and "GetStringKey."

The class CrfNewAccessor is from the Record Framework module and is preferably the implementation of Accessor which does not correspond to any storage device. It is preferably always "read only." A Record-based Applet may provide an array of Field IDs to this class; this array is used to qualify the Fields which the GetField method will create. If no array of Field IDs is given, the GetField method will attempt to create a Field for every request. The Fields returned from the GetField are unpopulated. This class preferably includes public definitions such as "CrfNewAccessor," "~CrfNewAccessor," "GetField," "RefreshField," "StoreField," "IsReadOnly," "Lock," "Unlock," "QueryLock," "IsLocked" and "Save."

The class CrfRecordFactory is from the Record Framework module and preferably provides the ability to instantiate a record object. Any Applet may provide one static "RecordBuilder" method which is able to create objects of CrfRecord-derived classes applicable to that Applet. The Applet registers its "RecordBuilder" method with this RecordFactory class. When a record object needs to be created, the Record Factory calls the appropriate RecordBuilder to create an object of the correct CrfRecord-derived class. The class CrfRecordFactory preferably includes a public definition such as "LPRECBLDR" and public methods such as "IsEmpty," "AddRecordBuilder," "RemoveRecordBuilder" and "BuildRecord."

The class CrfContainer is from the Record Framework module and is preferably a template class with methods to store and manipulate a collection of pointers to objects of a templatized class. The class CrfContainer preferably includes public methods such as "CrfContainer," "~CrfContainer," "GetCount," "IsEmpty," "Add," "InsertAt," "GetAt," "Remove," "DeleteAll" and "operator []."

The class CrfRecordContainer is from the Record Framework module and preferably provides a place to store a collection of pointers to CrfRecord objects and perform operations on each of the CrfRecord objects within the container. The class CrfRecordContainer preferably includes public methods such as "CrfRecordContainer," "~CrfRecordContainer" and "DoOperation".

The class CrfAssocProc is from the Record Framework module and is preferably a helper class used as an aid in creating a CrfRecordContainer which is populated with Procedure Records which are related to some other record (such as Patient or Procedure). All of the Assoc records selected by this class belong to the same patient. The class constructors essentially set up database queries with which to populate a container. The records are stored within the container with the oldest record first and the most recent record last; this order allows the "Next" and "Prev" methods to have the correct temporal meaning. This class preferably includes public definitions such as "ALL_RECORDS," "THIS_PROC_TYPE" and "ALL_PROC_TYPES" as well as public methods such as "CrfAssocProc," "~CrfAssocProc" and "GetRecordContainer." This class also preferably includes private methods such as "CrfAssocProc" and "operator=."

The class CrfProcRecord is from the Record Framework module and preferably provides the basic functionality for procedure records. This is an abstract base class to be derived for actual procedures. It is derived from the CrfRecord class and adds two recordsets. One of the recordsets is used for basic patient information, and the other recordset is used for basic procedure information. This class preferably includes public methods such as "DoPublish," "DoPreSubscribe" and "DoPostSubscribe."

This section discusses the relationships between the classes defined in the Record List module as well as the relationships between classes within the Record List module and classes within other Cardiology Information System modules. The crux of what Record Lists do is provide the user with a list of records from which to choose according to a selected hierarchy. The information contained in the list should be enough for the user to uniquely identify the record and should be ordered (sorted) in such a way so as to make the list usable. These two items, information and information order, make up what is referred to herein as a filter.

Figure 104A:
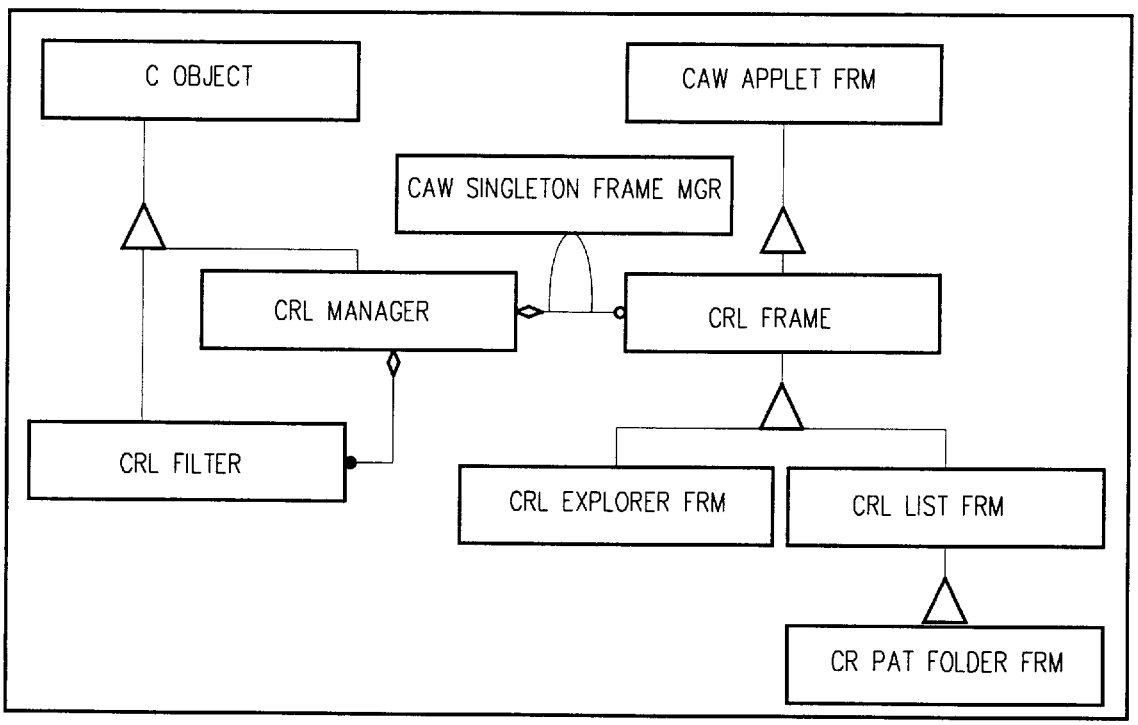
FIGS. 104A–E are diagrammatic views of the hierarchy of the Record List classes illustrating the Frame, View, Common Control, Populator and Recordset hierarchy of the present invention.

The user may select explorer activation from a Shell button or Shell menu item, a specific filter from a Shell menu item, or a patient from a list of patients. Each of these actions will cause the CrlManager to activate a frame through the CawSingletonFrameMgr. If a frame for the selection already exists, that frame will be activated. Otherwise, a new frame will be created. The type of frame created, CrlExplorerFrm, CrlListFrm or CrlPatListFrm, depends on the user selection. FIG. 104A illustrates the Frame Hierarchy referred to herein. The CrlManager maintains a list of CrlFilter objects which are used by the frames to determine what to present to the user. Only one copy of each CrlFilter object exists so that column order or row order changes to a specific filter which will be reflected in all subsequent frames that use that filter.

Figure 104B:
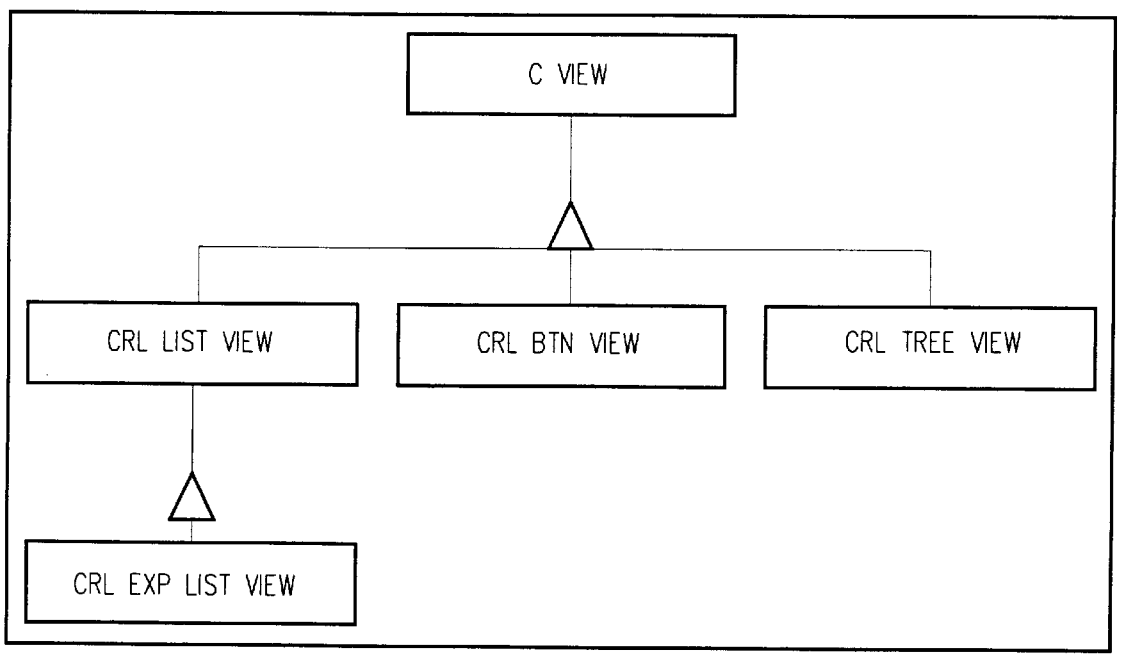

FIG. 104B shows the relationships between the various view classes for the record list module. All views are derived from the MFC class CView. The CrlListView presently contains a CrlListCtrl which manages the listing of all the records returned from the database but also may include other data sources as desired. The CrlExpListView, which is derived from CrlListView, has an additional control, a CEdit Control. The CrlBtnView contains a CawBtnBar which manages the buttons for user selection. The specific buttons displayed depend on the current set of records in the CrlListCtrl. The CrlTreeView contains a CTreeCtrl. The specific views instantiated are determined by the frame.

Figure 104C:
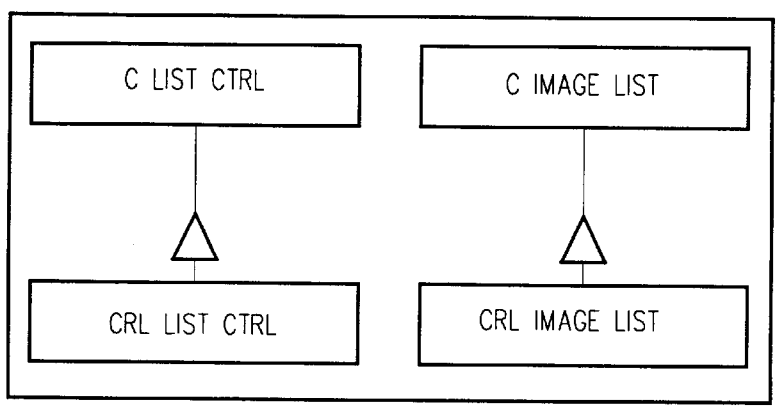

FIG. 104C shows a simple inheritance hierarchy for the classes listed based on common control of the classes. Most of the base class behavior is used with changes mainly to the selection process and the message handling aspects of these classes.

Figure 104D:
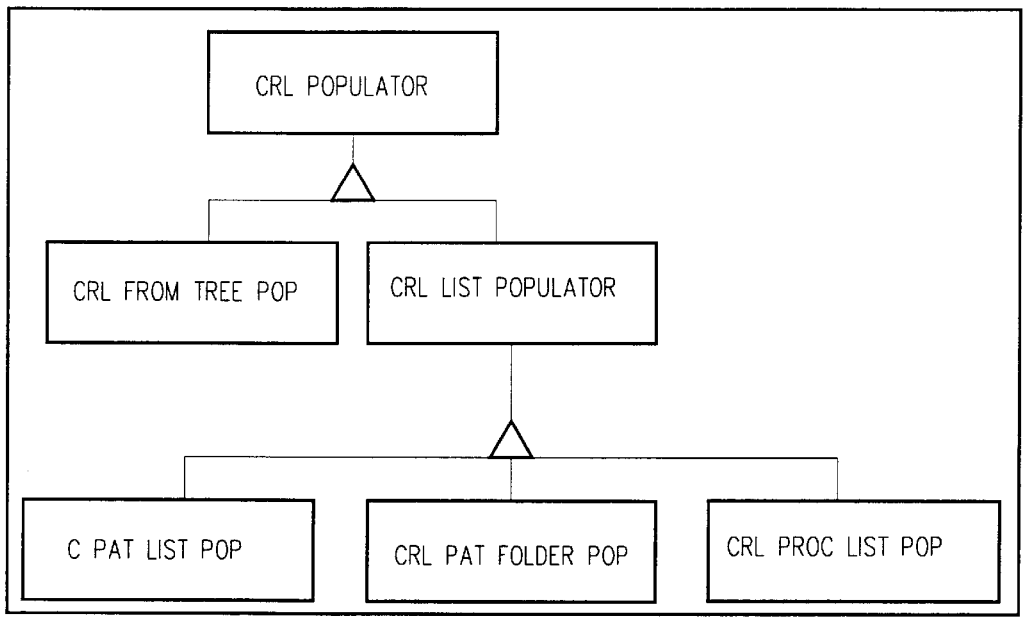

As shown in FIG. 104D, Populators may be used to fill the CrlListCtrl object in a CrlListView or a CrlExpListView. A populator is used to hide the source of the list items. The list may be filled from the tree control or from a recordset or other data sources as may be desired. The populator is preferably contained within the CrlListCtrl and may be swapped out for another populator when the user actions suggest a different data source. The CrlFromTreePop class is able to provide the needed list items from the CTreeCtrl class within the CrlTreeView class. This is preferably only used in the Explorer context. The CrlPatListPop class provides the CdaxRecordset derived classes necessary to get the needed information from the database for a list of patients. The CrlPatFolderPop class provides the CdaxRecordset derived classes necessary to get the needed information from the database for a list of all procedure records and the patient demographics record for a given patient which may be selected from a list of patients. The CrlProcListPop class provides the CdaxRecordset derived classes necessary to get the needed information from the database for a list of procedure records. The populators provide the header information, if any is needed, for the CrlListCtrl class and provide the CrlListCtrl class with formatted strings to use in populating the control. In opening the recordsets, the populators use information from a filter object to determine the sort criteria for the recordset.

Figure 104E:
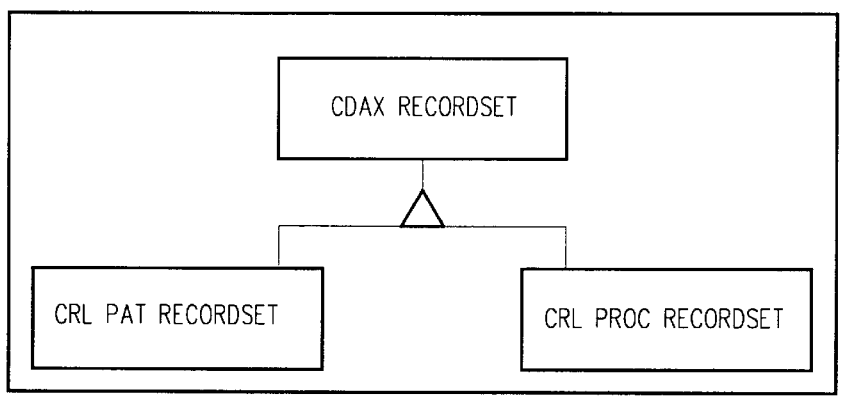

As shown in FIG. 104E, the recordsets used in record lists are derived from the CdaxRecordset class. They provide all the fields which will be available for display in the list control.

Figure 105:
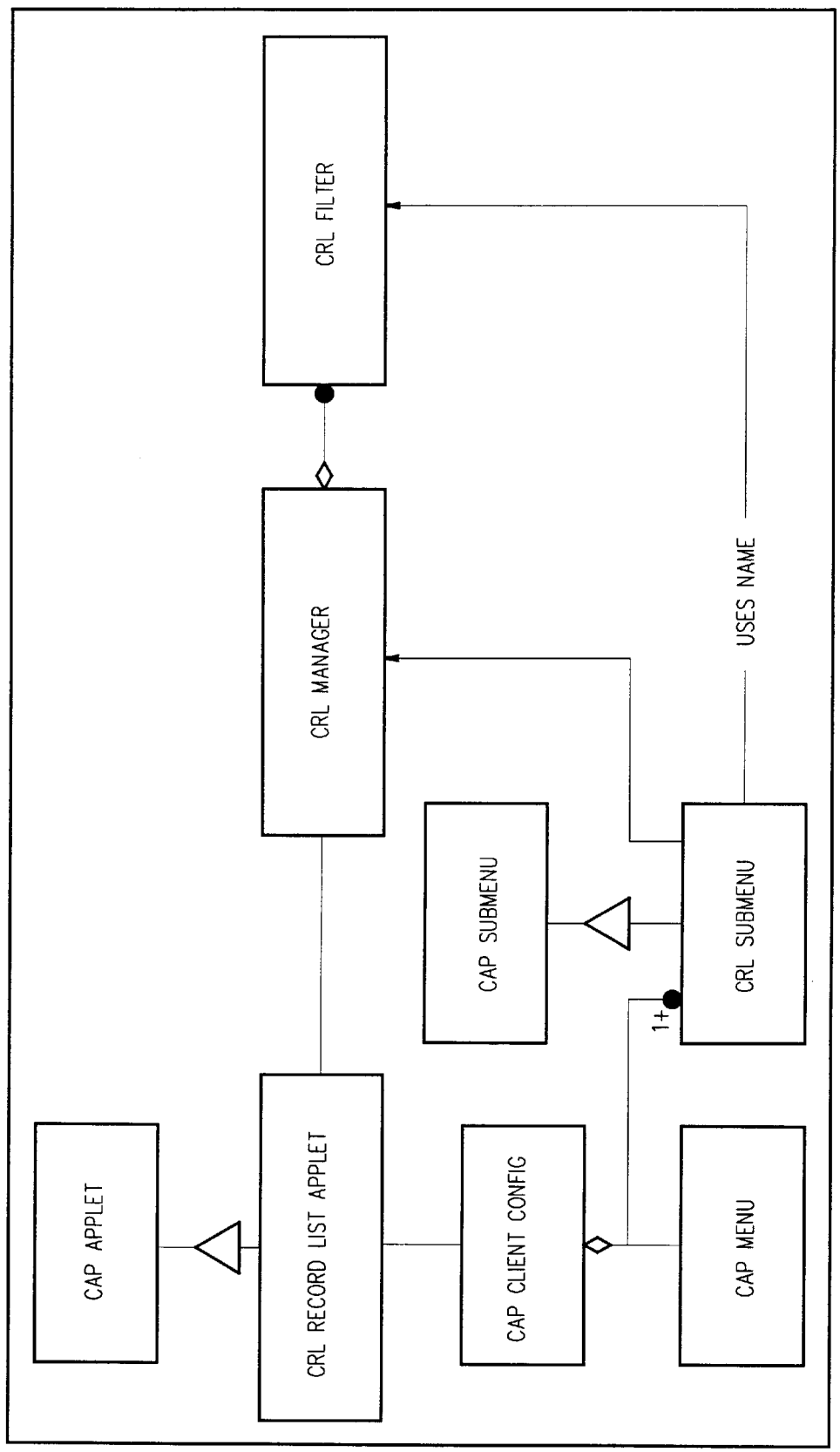
FIG. 105 is a diagrammatic view illustrating the initialization of the Record List of the present invention.

During Record List Applet initialization, several tasks must be accomplished. First, a CrlManager object must be instantiated. Then all the CrlFilter objects must be created and initialized from values which will preferably be on the database, although they may also be hard-coded. Once the filter objects are created, the menu and submenu items can be created. There is only one menu item, and the name for that menu item will be a string resource for "Lists." The submenus will be objects of a CapSubmenu derived class. The derivation from CapSubmenu is preferably necessary to add the command handler routine. The derived class, CrlSubmenu, will also contain a CrlManager pointer because all commands will be passed to the CrlManager object for further handling. FIG. 105 illustrates the classes which participate in the initialization process.

Figure 106A:
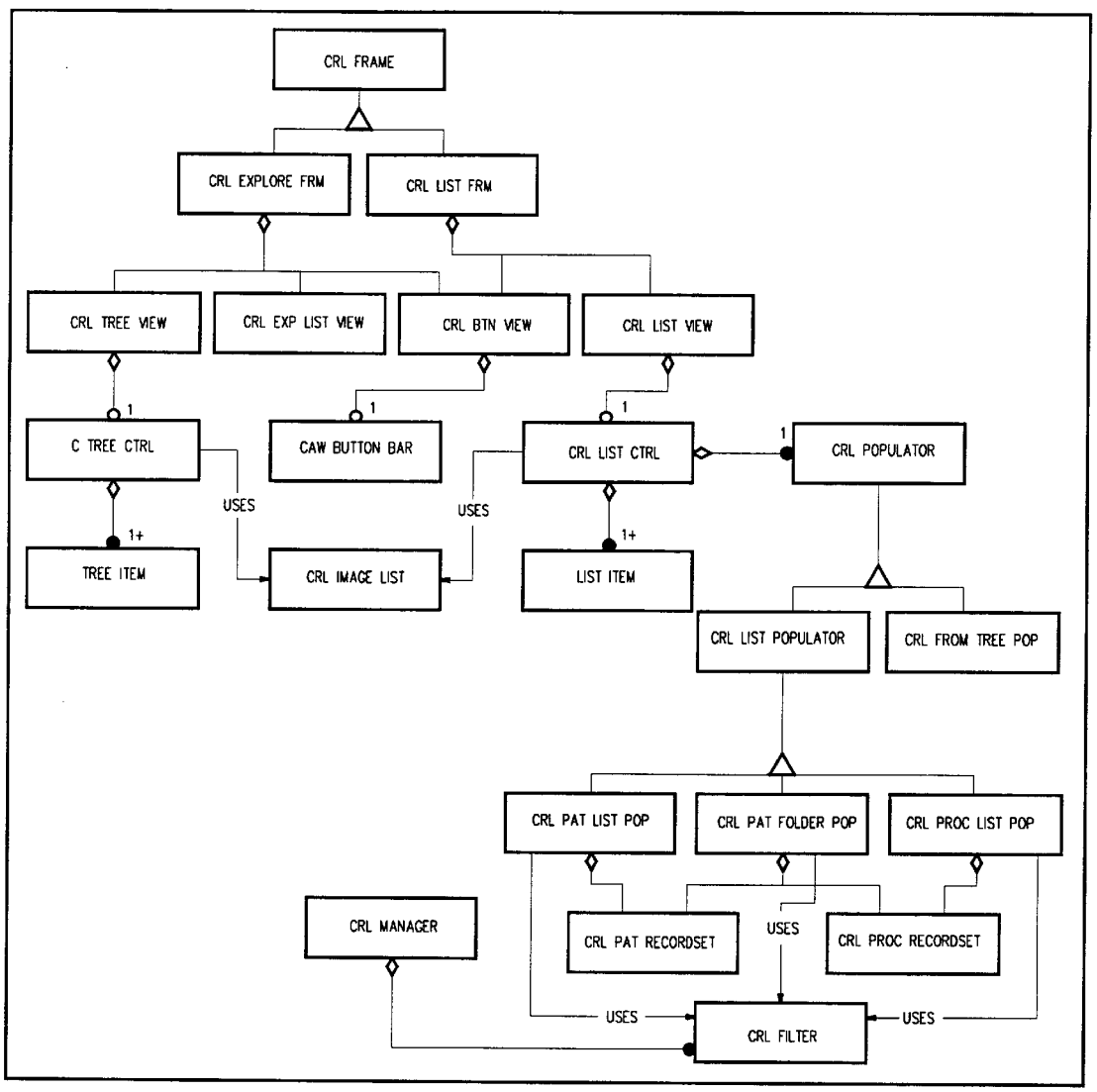
FIGS. 106A–E are diagrammatic views illustrating the associations, interactions and manipulation of the Record List of the present invention.

The following paragraphs summarize how the various classes within the Record List Applet interact with each other and with other Applet's classes. FIG. 106A shows how the classes defined in the previous sections are interconnected. Not all of the frame classes are shown in this figure, but the interactions are depicted in earlier sections along with the hierarchies. The details of the relationships shown in FIG. 106A are illustrated in further detail in FIGS. 106B–D.

Figure 106B:
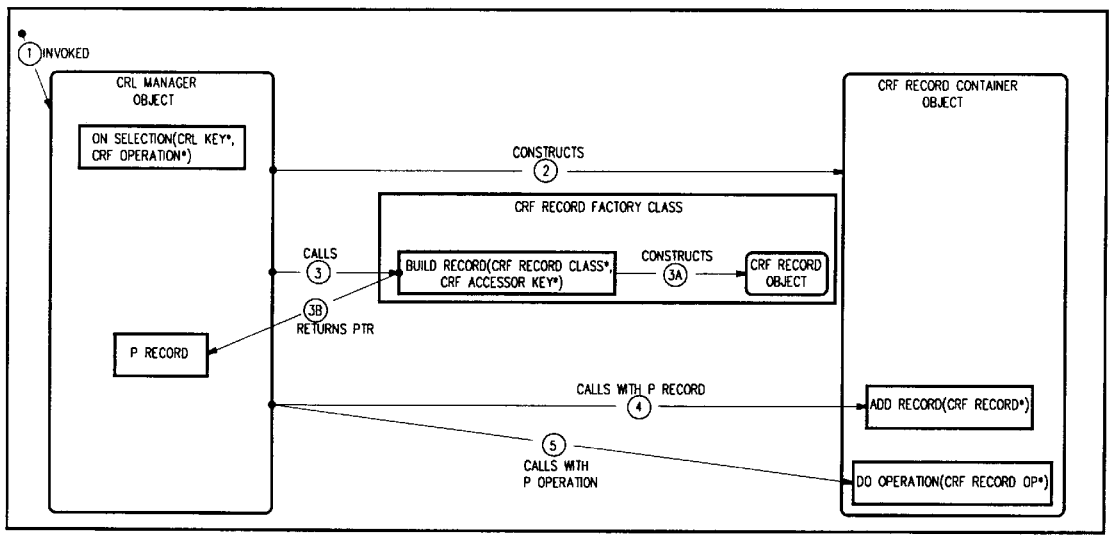

FIG. 106B shows the steps taken by record list to create records and pass them off for processing. Step 1 is indicating that one or more records must be selected and an action requested on those records. Step 2 shows the CrlManager object constructing a container which will hold the records which will be constructed. Step 3 is the construction of the record. Step 3a shows the record being constructed by a record builder, and step 3b is the return of the pointer to the constructed object. Step 4 shows the CrlManager adding the newly created record object to the container object. Step 5 shows the CrlManager passing the requested operation to the container which will pass the operation to each of the contained records. If, in step 1, there were multiple records selected, steps 3 & 4 will be repeated for each record, prior to performing step 5.

Figure 106C:
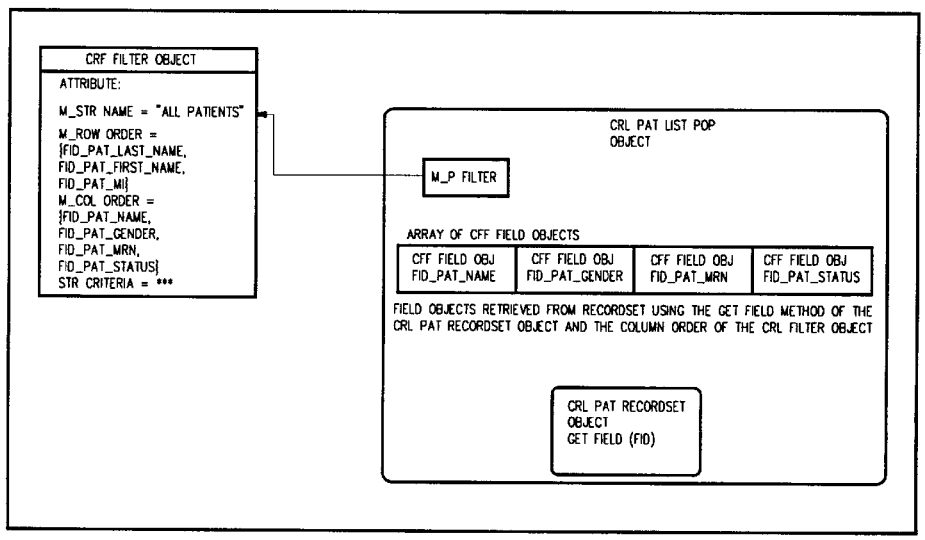
Figure 106D:
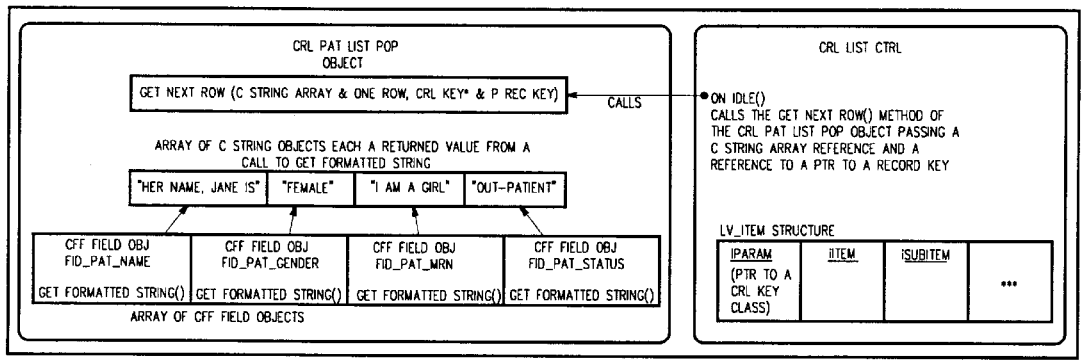

The Record List Applet uses field objects as tools to accomplish the conversion of a data element from the data representation on the database to the CString object needed to build the list. FIG. 106C shows some of the internal implementation of the populator classes. In this figure, a filter object is pointed to by the m_pFilter attribute of the populator. The CffField objects within an array in populator are in the order specified by the column order of the filter object. The field objects are created and populated through the contained CrlPatRecordset class.

When the list control is filling its list using the CapApplet idle-time processing interface, it requests a row of information at a time. This row is supplied by the populator to the list control in a CStringArray which is passed by reference. Also, with each row, a key element is stored. This is kept for later use for interaction with the record framework. In the example shown in FIG. 106D, the OnIdle method calls the GetNextRow method of the populator passing it a CStringArray reference (OneRow) and a reference to a key pointer (pRecKey). The populator fills the CStringArray by calling the GetFormattedString method of each CffField object within its array. The RecKey is filled directly from the contained Recordset object. Once returned, the RecKey value is stored within the row structure as the LPARAM. The CStrings are displayed in the list control.

Figure 106E:
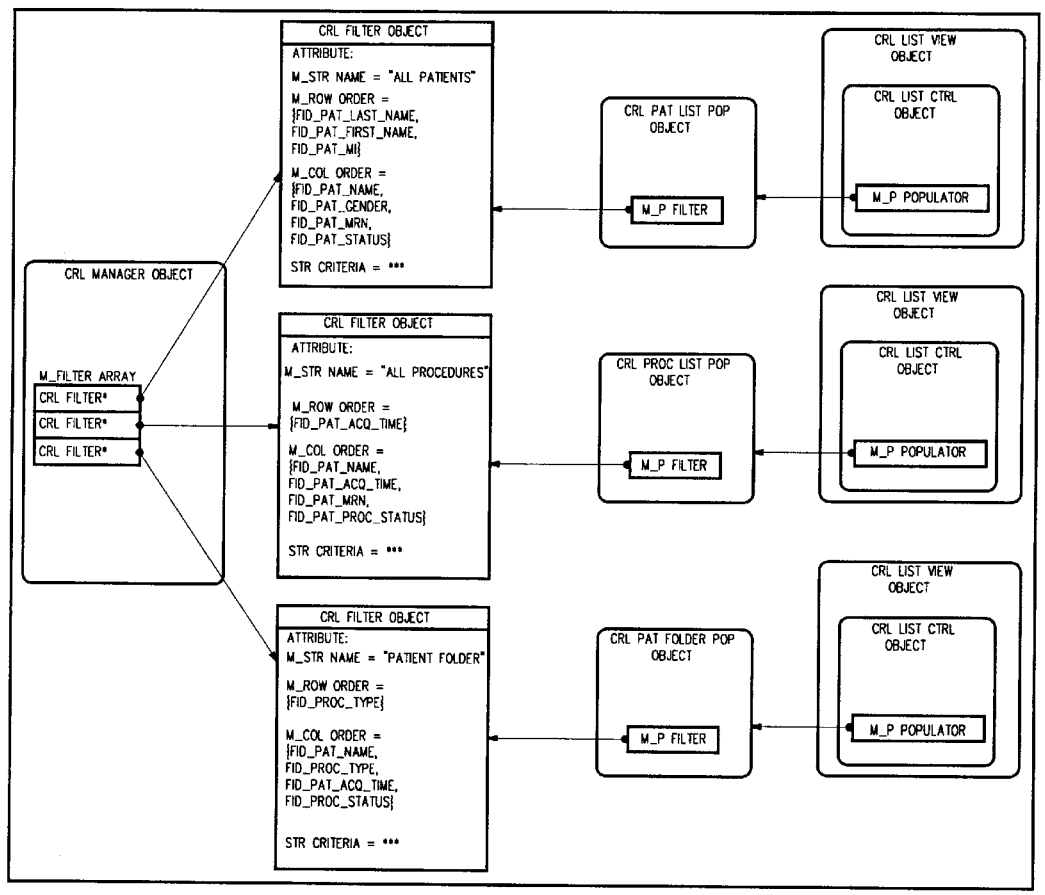

The pseudo-object diagram of FIG. 106E shows how filter objects are shared between the CrlManager object and the populators. When the CrlListView object is deleted, the CrlListCtrl object will be deleted and will also delete the CrlPopulator object pointed to by the m_ppopulator attribute of the CrlListCtrl. The object pointed to by the m_pFilter attribute of the various populator classes will not be deleted by the populator. The filter objects are owned by the CrlManager object. The one exception is for the CrlPatFolderPop. This populator contains two filters. One filter contains the criteria, which will be specific to a patient, and the other filter contains the row and column orders, which will be the same for all patients. The filter object containing the specific patient criteria is owned by the populator and will be deleted when the populator is deleted.

The class CrlApplet is from the Record List module and preferably initialization of items from the database and initialization of new menus and submenus needed for this Applet. The class CrlApplet preferably includes public methods such as "CrlApplet," "~CrlApplet," "InitApplet," "ExitApplet," "GetAppletName," "GetAppletTitle" and "GetClientConfig."

The class CrlSubmenu is from the Record List module and preferably provides command handlers and submenu items for each of the CrlFilter objects which require then. This class preferably includes pubic methods such as "CrlSubmenu," "~CrlSubmenu," "OnSubmenu" and "SetManagerPtr."

The class CrlManager is from the Record List module and preferably includes the public definition "enum rlOpID" which is a list that enumerates all of the valid operations that are handled by the OnSelection method. This class also preferably includes public methods such as "CrlManager," "~CrManager," "OnFilterSelect," "OnSelection," "GetCurrentDatabase," "GetFilter," "GetFirstFilter," "GeNexFilter" and "m_nCurrentFilterIndex."

The class CrlFilter is from the Record List module and preferably provides encapsulation of the information stored on the database (referred to as a filter) about what information is to be retrieved from the database and in what order it is to be displayed (both row and column). A CrlFilter object is only used in certain types of populators where the sort order or subset of items may be defined by the end user. The class CrlFilter preferably includes public definitions such as "enum rlFilterType" and "enum rlFrameType". This class also preferably includes public methods such as "CrlFilter," "~CrlFilter," "CreatePopulator," "GetName," "GetFilterType," "GetFrameTyp," "GetRoworder," "GetColumnOrder," "GetColumnName," "GetColumnWidth," "GetCriteria," "SetName," "SetFilterType," "SetFrameType," "SetRoworder," "SetColumnOrder" and "SetCriteria."

The class CrlFrame is from the Record List module and preferably maintains an interface to the CrlManager who controls the CrlFilter objects. The CrlFrame class preferably includes a public definition such as "enum rlinit" as well as public methods such as "CrlFrame," "~CrlFrame" and "InitBase."

The class CrlListFrm is from the Record List module and preferably is a frame which is invoked through the CawSingletonFrameMgr, when the end user selects a filter type from the available menu list of filters. This frame will preferably have singleton behavior based on a CrlFilter object. This frame preferably contains a static (non-adjustable), horizontal, 2-pane splitter window. The top pane contains a CrlListView, and the bottom pane contains a CrlBtlView. This frame handles messages from both the CrlListView and the CrlBtnView regarding the selection of an item from the list or the button bar. The action taken depends on the type of item and action selected. This class preferably includes a variety of public methods such as "CrlListFrm," "~CrlListFrm," "OnCreateClinet," "Initialize," "GetListView" and "GetBtnView."

The class CrlPatFolderFrm is from the Record List module and preferably provides a frame for a specific patient folder which lists the patient demographics record and all procedure records for a specific patient. This frame is invoked, through the CawSingletonFrameMgr, when a patient folder is selected from a list of patients. This frame will have singleton behavior based on the selected patient. This class preferably includes a variety of public methods such as "CrlPatFolderFrm," "~CrlPatFolderFrm" and "Initialize."

The class CrlExplorerFrm is from the Record List module and preferably is invoked as a frame through a CawSingletonFrameMgr when the end user selects an Explorer command. This frame will have singleton behavior so that there will only be one explorer frame. This frame preferably contains two splitter windows. The first is a vertical, 2-pane, adjustable splitter. The second, which is contained within the right pane of the first splitter window, is a static (non-adjustable), horizontal, 2-pane splitter window. The left pane contains a CrTreeView. The top pane on the right-hand side contains a CrlExpListView, and the bottom pane on the right-hand side contains a CrlBtnView. This frame preferably handles messages from all of the views indicating user actions. This allows the frame to synchronize changes in the CrlTreeView with changes in the CrlExpListView and vice versa. Any actions requiring the creation of new frames or the instantiation of records will be passed to CrlManager for processing. The class CrlExplorerFrm preferably includes public methods such as "CrlExplorerFrm," "~CrlexplorerFrm," "OnCreateClient," "Initialize," "OnTreeItemSelected," "GetListView," "GetBtnView" and "GetTreeView."

The class CrlSplitterWnd is from the Record List module and preferably prevents static splitter bars from tracking. This is used by CrlListFrm, CrlPatFolderFrm and CrlExplorerFrm to keep the pane that contains the CrlBtnView from being re-sized by the user. This class preferably includes public methods such as "CrlSplitterWnd" and "~CrlSplitterWnd" as well as protected methods such as "OnLButtonDown," "OnLButtonUp," "OnLButtonDblClK" and "OnMouseMove."

The class CrlBtnView is from the Record List module and preferably provides a window which may contain a CawFrameBtnBar class which will be utilized by both the CrlExplorerFrm and the CrlListFrm. The CrlListFrm may use the default CawFrameBtnBar behavior of being attached directly to a frame and not contained within a window, but then the CrlListFrm and the CrlExplorerFrm would each have their own mechanism for doing the exact same thing. In the interest of consistency, the CrlListFrm will have the CrlBtnView just as the CrlExplorerFrm does. This class preferably includes various public methods such as "CrlBtnView," "~CrlBtnView," "SetButtonBar" and "GetButtonBar."

The class CrlListView is from the Record List module and is preferably a CView derived class which contains a CrlListCtrl and methods for interacting with it. This class preferably includes various public methods such as "CrlListView," "~CrlListView," "GetListCtrl" and "InitList."

The class CrlExpListView is from the Record List module and is preferably a CFormView derived class which contains a CrlListCtrl and a CStatic control used to display the title of the list. The CrlExpListView class preferably includes various public methods such as "CrlExpListView," "~CrlExpListView," "InitList," "GetListCtrl" and "SetStaticCtrl".

The class CrlTreeView is from the Record List module and is preferably a CFormView derived class which contains a CTreeCtrl and the methods to interact with it. The class CrlTreeView preferably includes various public methods such as "CrlTreeView," "~CtrlTreeView," "initTree" and "GetTreeCtrl."

The class CrlListCtrl is from the Record List module and is preferably derived from ClistCtrl. CListCtrl provides basic behavior for displaying lists of information in a defined format. The report view format has a column header which contains titles for each of the columns. The header items can be selected using the mouse. The selection behavior, however, is not supplied and must be added in a derived class. The CrlListCtrl contains a CrlPopulator attribute which is then used to populate the rows of the control. The CrlPopulator is also used to determine the column header titles and order. The CrlListCtrl will allow for modifying the sort order of the items in the list by the selection of a header item. For example, if the rows are currently sorted by Last Name and the end user selects the MRN header, the rows will be resorted by the MRN. The column order will not be affected. Within the CListCtrl class, each row contains an LPARAM which is available for use and will be used to indicate how to handle the row if selected. The class CrlListCtrl preferably includes various public methods such as "CrlListCtrl," "~CrlListCtrl" and "SetPopulator."

The class CrlKey is from the Record List module and preferably provides an encapsulation of the information needed to build a record. With each row which is retrieved from the database, the necessary information to completely build the record represented by that row is collected in this class. This class then maintains the two classes required by the record builders, CdaxAccessorKey and CrfRecordClass. The information stored in this class is also used by the populators to correctly build the recordsets with the correct database and database key. This class preferably includes public methods such as "CrlKey," "~CrlKey," "GetAccessorKey" and "GetRecordClass."

The class CrlPopulator is from the Record List module and preferably provides a CrlListCtrl with a constant mechanism for populating its rows without having to know where the data is from. The CrlPopulator hides the location of the data from the CrlListCtrl and just provides it with an array of CStrings for each row. This allows the CrlListCtrl to concentrate on what it does best, which is to display the list of items. The class CrlPopulator preferably includes various public methods such as "CrlPopulator," "~CrlPopulator," "CreateButtonBar, to "GetFirstRow," "GetNextRow" and "GetTitleString."

The class CrlFromTreePop is from the Record List module and preferably provides a CrlListCtrl object with the row information which is reflected from the CTreeCtrl object. This populator uses the CTreeCtrl object to retrieve the needed information. This class preferably includes various public methods such as "CrlFromTreePop," "~CrlFromTreePop," "CreateButtonBar," "GetFirstRow," "GetNextRow" and "GetColumnHeader."

The class CrlProcListPop is from the Record List module and preferably contains a derived CdaxRecordset and a CrlFilter. This class provides data elements to the CrlListCtrl by using the CdaxRecordset as specified by the CrlFilter to populate field objects which then return CString formats for all the values which the CrlListCtrl draws on the screen. This class preferably includes various public methods such as "CrlProcListPop," "~CrlProcListPop," "CreateButtonBar," "GetFirstRow," "GetNextRow" and "GetColumnHeader."

The class CrlPatListPop is from the Record List module and preferably contains a CdaxRecordset derived class and a CrlFilter class. The CrlFilter class specifies how to use the CdaxRecordset in order to return the correct data items in the correct order. This class can provide a list of CStrings for the CrlListCtrl to use. This class preferably includes various public methods such as "CrlPatListPop," "~CrlPatListPop," "CreateButtonBar," "GetFirstRow," "GetNextRow" and "GetColumnHeader."

The class CrlPatFolderPop is from the Record List module and preferably provides a cross between a PatList and a ProcList in that a Patient Demographics Record is displayed along with any procedure records which the system is aware of for the patient. This class preferably includes various public methods such as "CrlPatFolderPop," "~CrlPatFolderPop," "CreateButtonBar," "GetTitleString," "GetFirstRow" and "GetNextRow."

The class CrlPatRecordset is from the Record List module and preferably provides the list control with all the data that will be available to put in the list for each patient. This class preferably includes various public methods such as "CrlPatRecordset," "~CrlPatRecordset," "HasField", "SetSortOrder," "GetKey," "SetKey," "BuildFilterString" and "BuildSortString."

The class CrlProcRecordset is from the Record List module and preferably provides the list control with all the data that will be available to put in the list for each patient. The class CrlProcRecordset preferably includes various public methods such as "CrlProcRecordset," "~CrlProcRecordset," "HasField", "SetSortOrder," "GetKey," "SetKey," "BuildFilterString" and "BuildSortString."

The following discusses the relationships between all classes defined in the Record Presentation module as well as the relationships between classes within the Record Presentation module and classes within other workstation framework modules. The Record Presentation module provides either a "display context" for the foreground processing of records, typically used for actions such as editing or viewing of records or a "background context" for the hidden, background processing of records, typically used for actions such as printing or archiving of records. These two different processing contexts are separately discussed in the following paragraphs.

Figure 107:
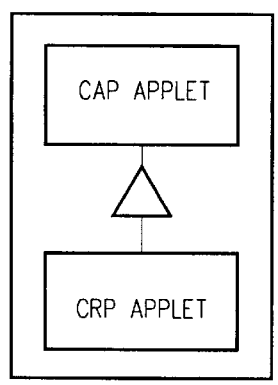
FIG. 107 is a diagrammatic view illustrating the Record interactions with an Applet Interface of the present invention.

The Record Presentation module is an Applet DLL, so it includes a class, CrpApplet, which inherits from CapApplet. In the presently preferred embodiment, class CrpApplet does nothing beyond providing the minimal functionality required by CapApplet. These relationships are shown in FIG. 107. An object of class CrpDisplayMgr is defined for each unique "display context," consisting of a unique, singleton CrpDisplayFrm object representing a frame window on the display and a list of records being processed within that frame window. The list of records is a CrpPresentCntrEx object contained within the CrpDisplayFrm object. The CrpPresentCntrEx object holds CrpPresentItem objects which represent and contain the records being processed within the frame. For each record added to the CrpPresentCntrEx object, a CrpPresentItem object is constructed to hold both the record and a CrfRecordop object representing the operation that was requested on that record. The CrpDisplayFrm object can scroll between the various records contained within the CrpPresentCntrEx object.

The CrpDisplayFrm object also contains a CrpDisplayVw object on which a portion of the contents of a record can be displayed. The CrpDisplayVw object uses a CrpDisplayFmt object to determine the specific record fields (CffField objects) to be displayed and the location of each field within the view. The CrpDisplayFmt object to be used for displaying a particular record (CrfRecord object) is determined by the record itself.

If the display of an associated record is requested, a CrfAssocProc object is preferably used to build a CrfRecordContainer object containing the associated record objects (class CrfRecord) and attached to the CrpPresentItem object. This construction of a CrfRecordContainer is not done if one is already contained within the appropriate CrpPresentItem object. The CrpDisplayFrm then creates a singleton CrpAssocDisplayFrm object if none currently exists. The current record's CrfRecordContainer object (containing associated records) is then attached to the CrpAssocDisplayFrm object. The CrpAssocDisplayFrm object can scroll between the various records contained within the CrfRecordContainer object which contains associated records.

Figure 108:
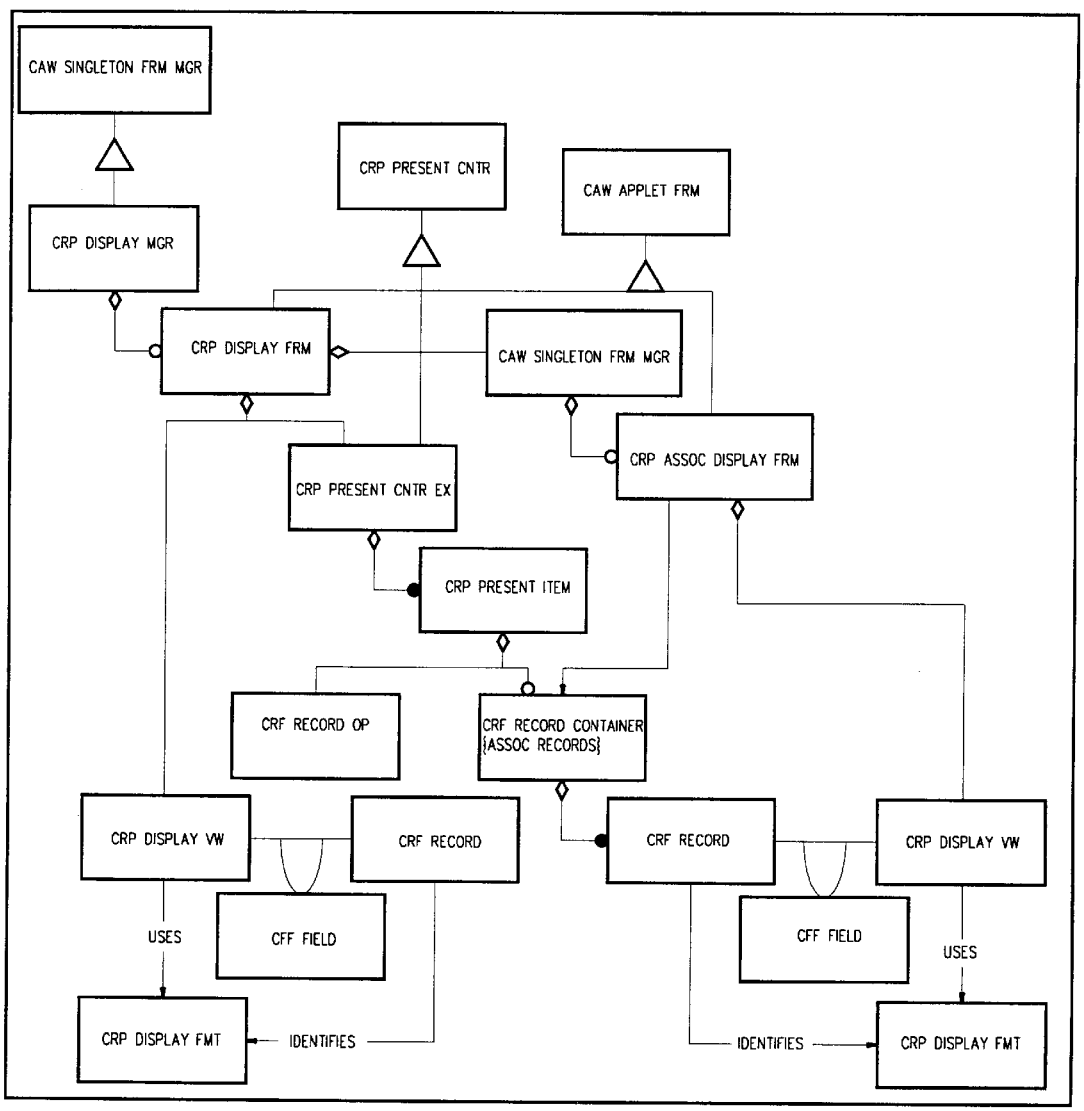
FIG. 108 is a diagrammatic view illustrating an overview of the Display Record Presentation classes of the present invention.

Just like the CrpDisplayFrm object, the CrpAssocDisplayFrm object also contains a CrpDisplayVw object on which a portion of the contents of a record, in this case an associated record, can be displayed. The CrpDisplayVw object uses a CrpDisplayFmt object to determine the specific or associated record fields, CffField objects, to be displayed and the location of each field within the view. The CrpDisplayFmt object to be used for displaying a particular record, CrfRecord object, is determined by the record itself, which in this case is an associated record. The CrpDisplayFrm and CrpAssocDisplayFrm objects intercommunicate to handle commands that need processing within both frames. Selecting a new record to be displayed within the CrpDisplayFrm window causes selection and, if needed, construction of the CrfRecordContainer object which contains associated records corresponding to the record being displayed. CrpDisplayFrm tells CrpAssocDisplayFrm when to switch to a different CrfRecordContainer object, which contains associated records. Closing the CrpDisplayFrm window will cause the CrpAssocDisplayFrm window, if it currently exists, to also be closed. Closing a CrpAssocDisplayFrm window that is tiled on the screen with its associated CrpDisplayFrm window causes the CrpDisplayFrm window to become maximized. These relationships are shown in FIG. 108.

Figure 109A:
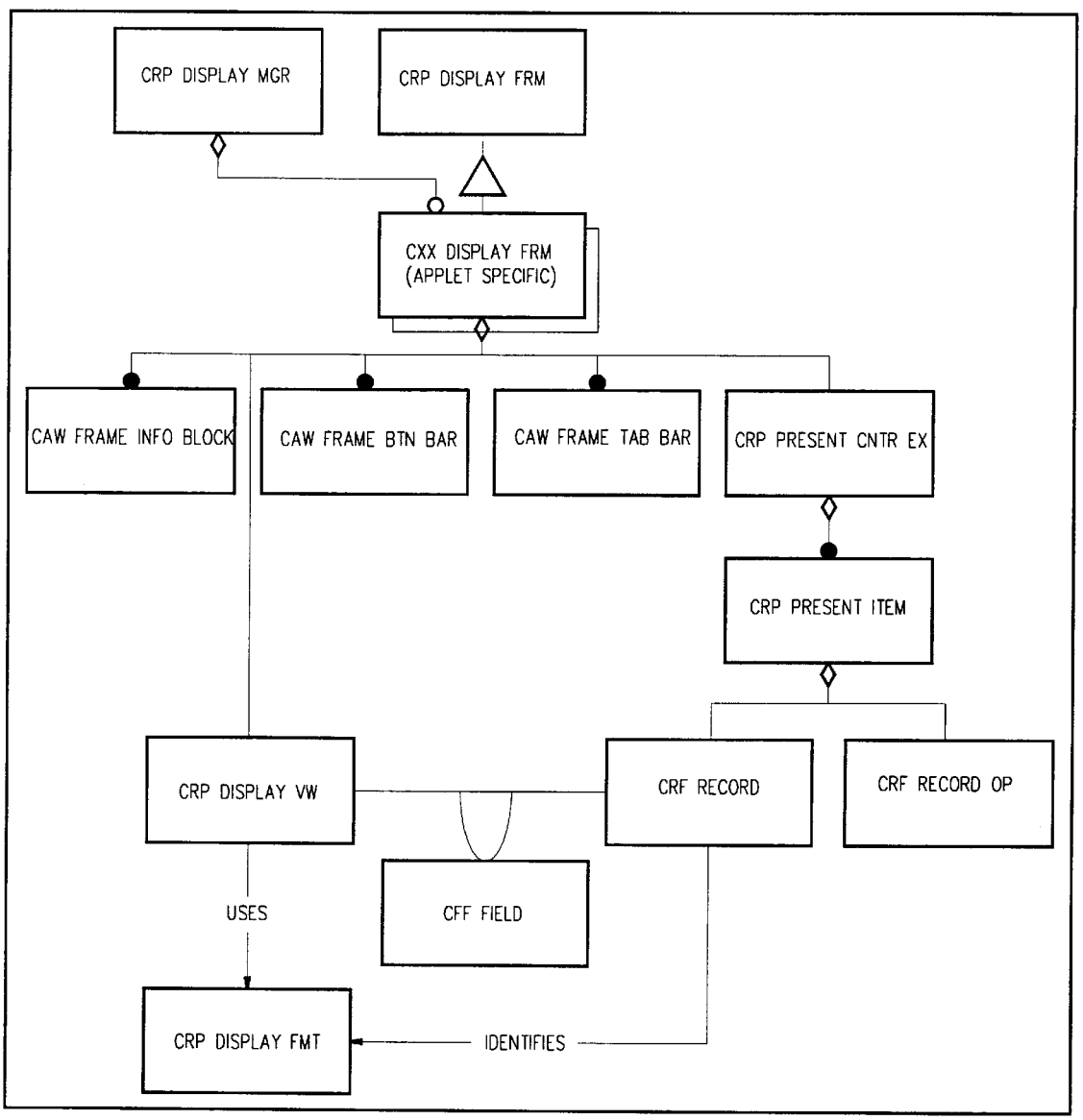
FIGS. 109A–E are diagrammatic views illustrating the Display Record interactions with typical Record Processing Applets of the present invention.
Figure 109B:
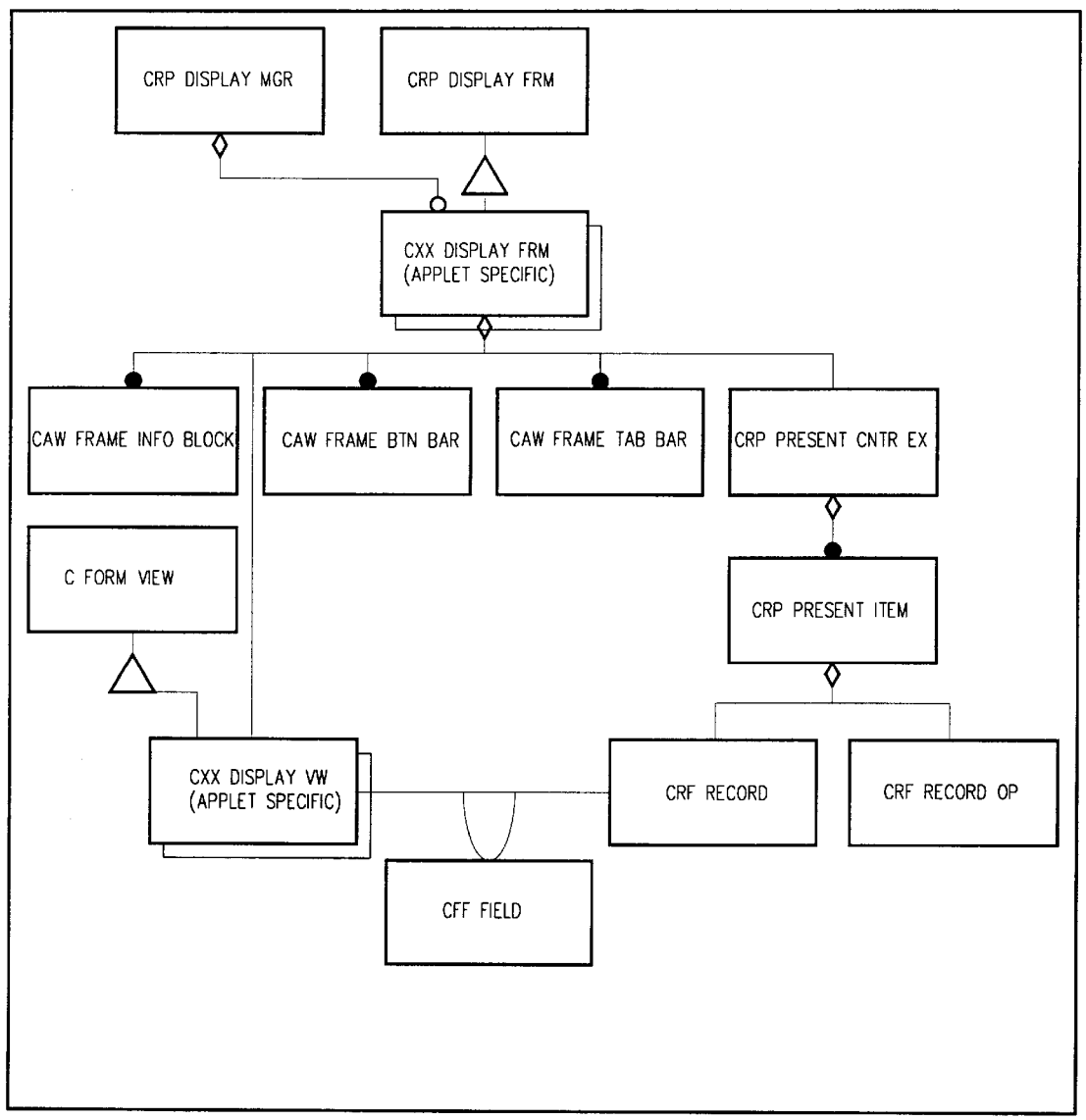

The paragraph discusses the interactions between Record Presentation and a typical record processing Applet which provides editing and/or viewing of a simple list of records and does not associate additional records with the primary records in this list. This is typical of the Patient Demographics Applet. In one form of the present invention, it is anticipated that an Applet will provide a child class of CrpDisplayFrm, shown in FIG. 109A as class CxxDisplayFrm. This class will preferably provide command handlers needed for processing specific to an Applet. In a preferred form of the present invention, an Applet will provide its own view class, derived from CView. For simplicity, it is anticipated that this class may be derived from CFormView. This Applet supplied view class is shown as CxxDisplayvw in FIG. 109B.

Figure 109C:
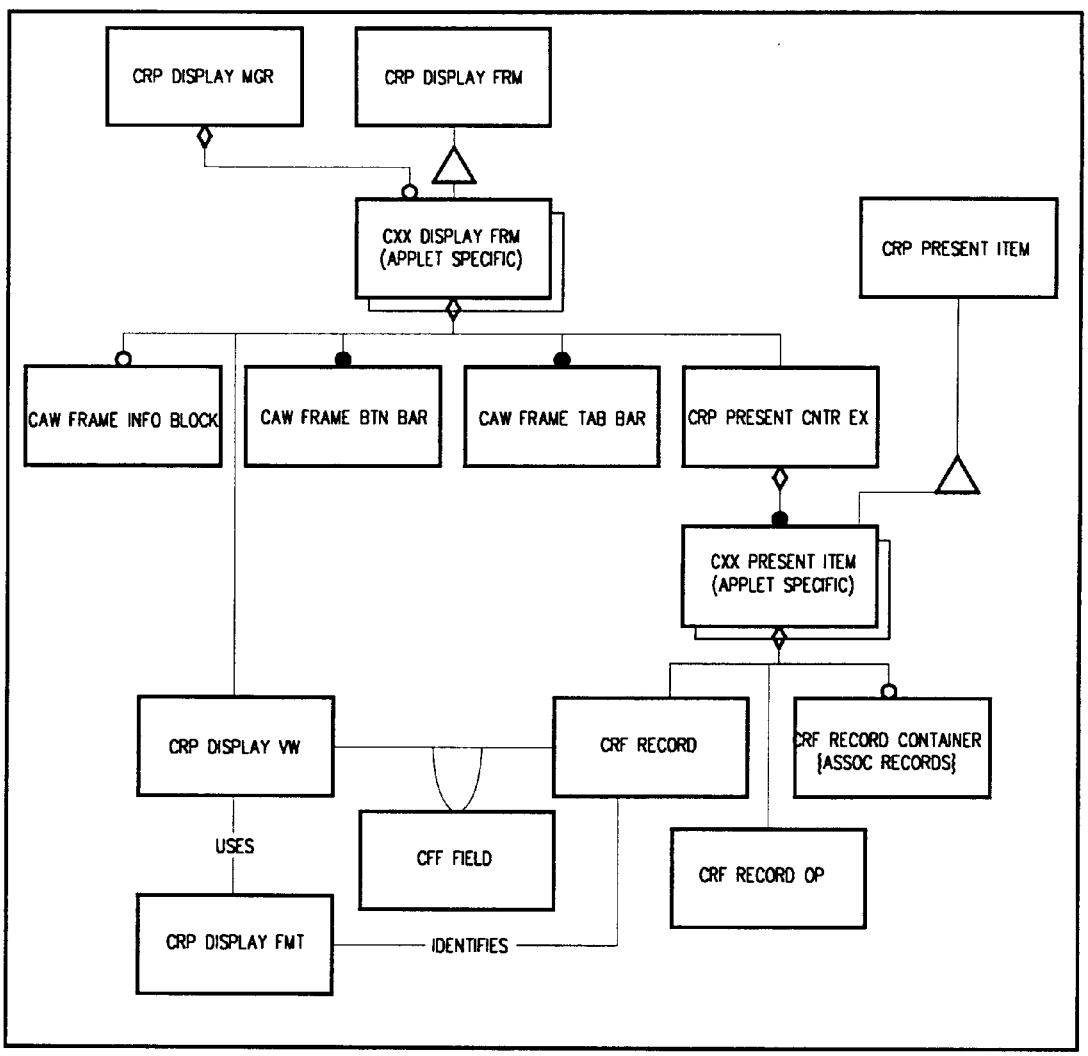

This paragraph discusses the interactions between Record Presentation and a typical record processing Applet which provides editing and/or viewing of a list of records and optionally associates additional records with one or more of the primary records in this list. This is typical of the editing or viewing of procedure records. Because of the complexity, the interaction between display Record Presentation and a typical associated records Applet is shown in two figures and followed by a consolidated drawing giving the complete overview. FIG. 109C focuses on the primary record relationships while FIG. 109D focuses on the associated record relationships. It is anticipated that an Applet will provide a child class of CrpDisplayFrm, shown in FIG. 109C as class CxxDisplayFrm. This class would provide command handlers needed for processing specific to an Applet. If an Applet needs to control how associated records are selected for a given primary record, it may choose to provide its own child class of CrpPresentItem, shown in FIG. 109C as class CxxPresentItem. It is anticipated that this will be unnecessary for most Applets since the default record association logic built into CrpPresentCntrEx is expected to be adequate for the current implementation of the present invention.

Figure 109D:
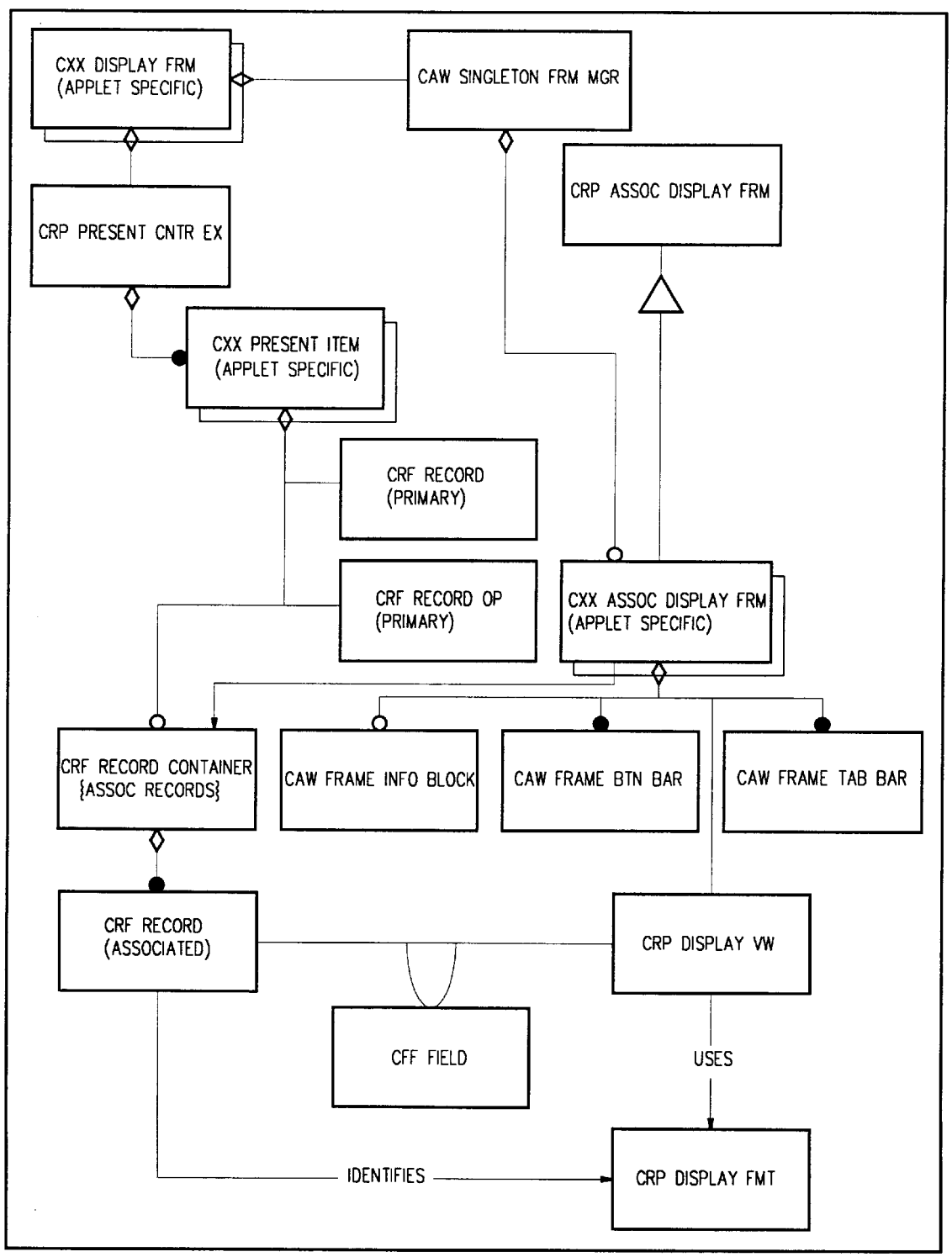

It is further anticipated that an Applet will provide a child class of CrpAssocDisplayFrm, shown in FIG. 109D as class CxxAssocDisplayFrm. This class provides command handlers needed for processing specific to an Applet. Additionally, an Applet may provide its own child class of CrpPresentItem, shown in FIG. 109D as class CxxPresentItem.

Figure 109E:
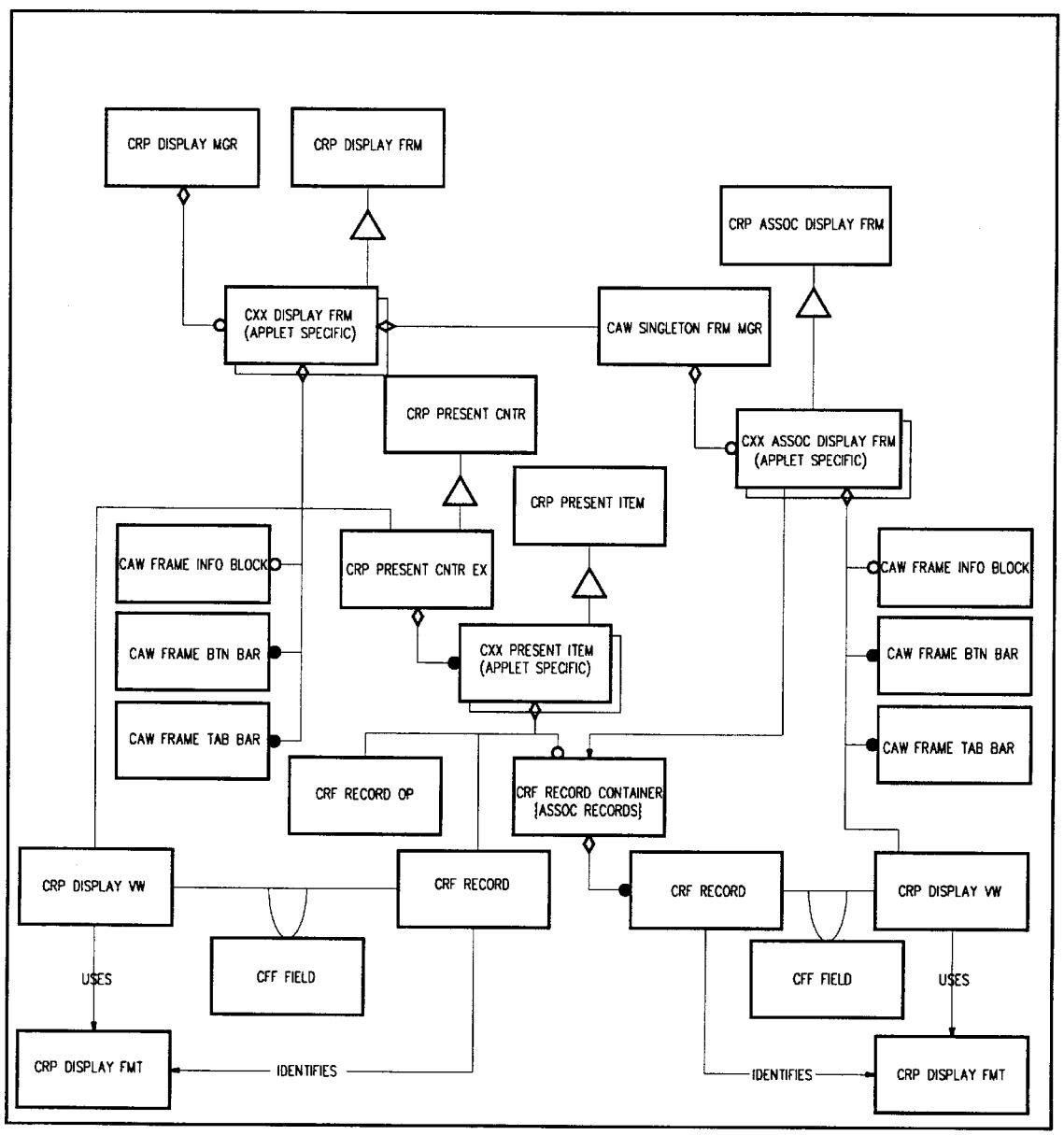

An Applet may also provide a child class of CrpDisplayFrm and a child class of CrpAssocDisplayFrm, shown in FIG. 109E as class CxxDisplayFrm and class CxxAssocDisplayFrm, respectively. An Applet of the present invention may also provide its own child class of CrpPresentItem, shown in FIG. 109E as class CxxPresentItem.

Figure 110:
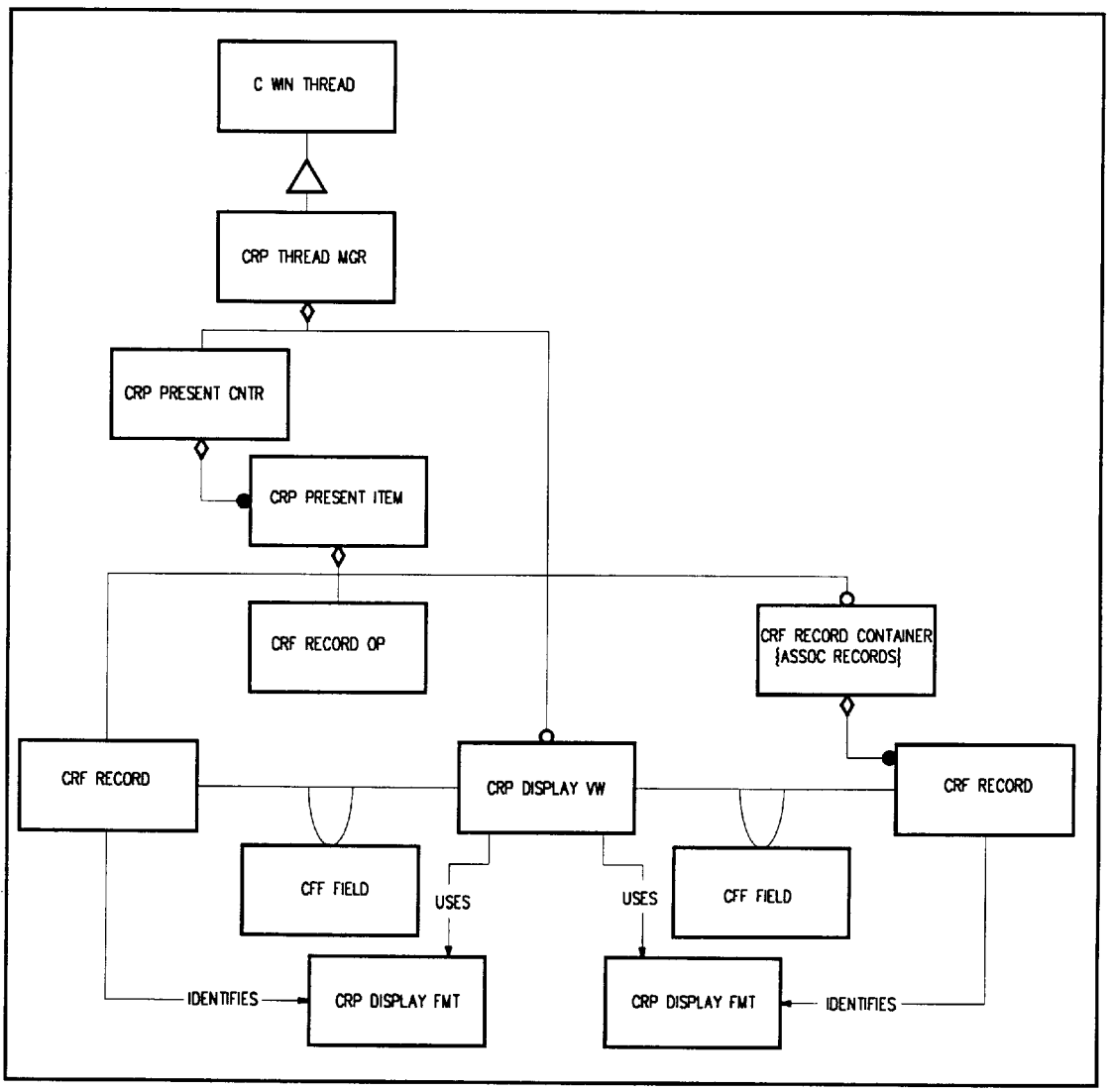
FIG. 110 is a diagrammatic view illustrating an overview of the Background Record Presentation classes of the present invention.

As shown in FIG. 110, an object of class CrpThreadMgr is defined for each unique "background context," containing a list of records being processed within that context. The list of records is a CrpPresentCntr object contained within the CrpThreadMgr object. The CrpPresentCntr object holds CrpPresentItem objects representing the records being processed. For each record added to the CrpPresentCntr object, a CrpPresentItem object is constructed to hold both the record and a CrfRecordOp object representing the operation that was requested on that record. The CrpThreadMgr object also contains a CrpDisplayVw object on which a portion of the contents of a record can be rendered. The CrpDisplayVw object uses a CrpDisplayFmt object to determine the specific record fields (CffField objects) to be rendered and the location of each field within the view. The CrpDisplayFmt object to be used for rendering a particular record (CrfRecord object) is determined by the record itself. If a list of associated records for a primary record is needed, a CrfAssocProc object is used to build a CrfRecordContainer object containing the associated record objects (class CrfRecord) and attached to the CrpPresentItem object. This construction of a CrfRecordContainer is not performed if one is already contained within the appropriate CrpPresentItem object. The CrpDisplayVw object uses a possibly different CrpDisplayFmt object to determine the specific record fields (CffField objects) to be displayed from an associated record and the location of each field within the view. The CrpDisplayFmt object to be used for displaying a particular associated record (CrfRecord object) is determined by the associated record itself.

Figure 111A:
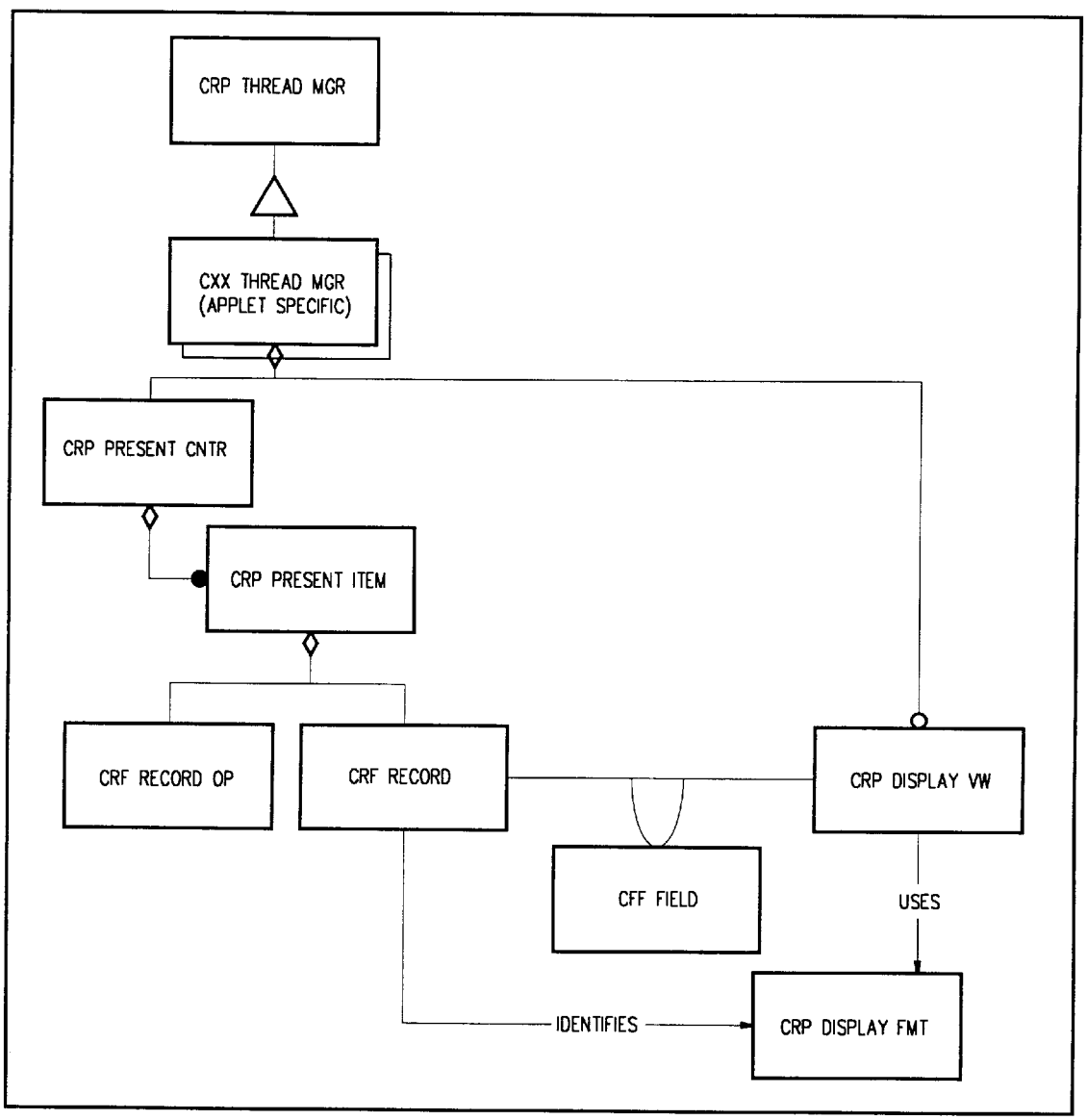
FIGS. 111A and 111B are diagrammatic views illustrating the Background Record Presentation interactions with typical Record Processing Applets of the present invention.

This paragraph discusses the interactions between Record Presentation and a typical record processing Applet which provides background processing (such as printing) of a simple list of records and does not associate additional records with the primary records in this list. It is anticipated that an Applet may provide a child class of CrpThreadMgr, shown in FIG. 111A as class CxxThreadMgr. This class may also provide command handlers needed for processing specific to an Applet.

Figure 111B:
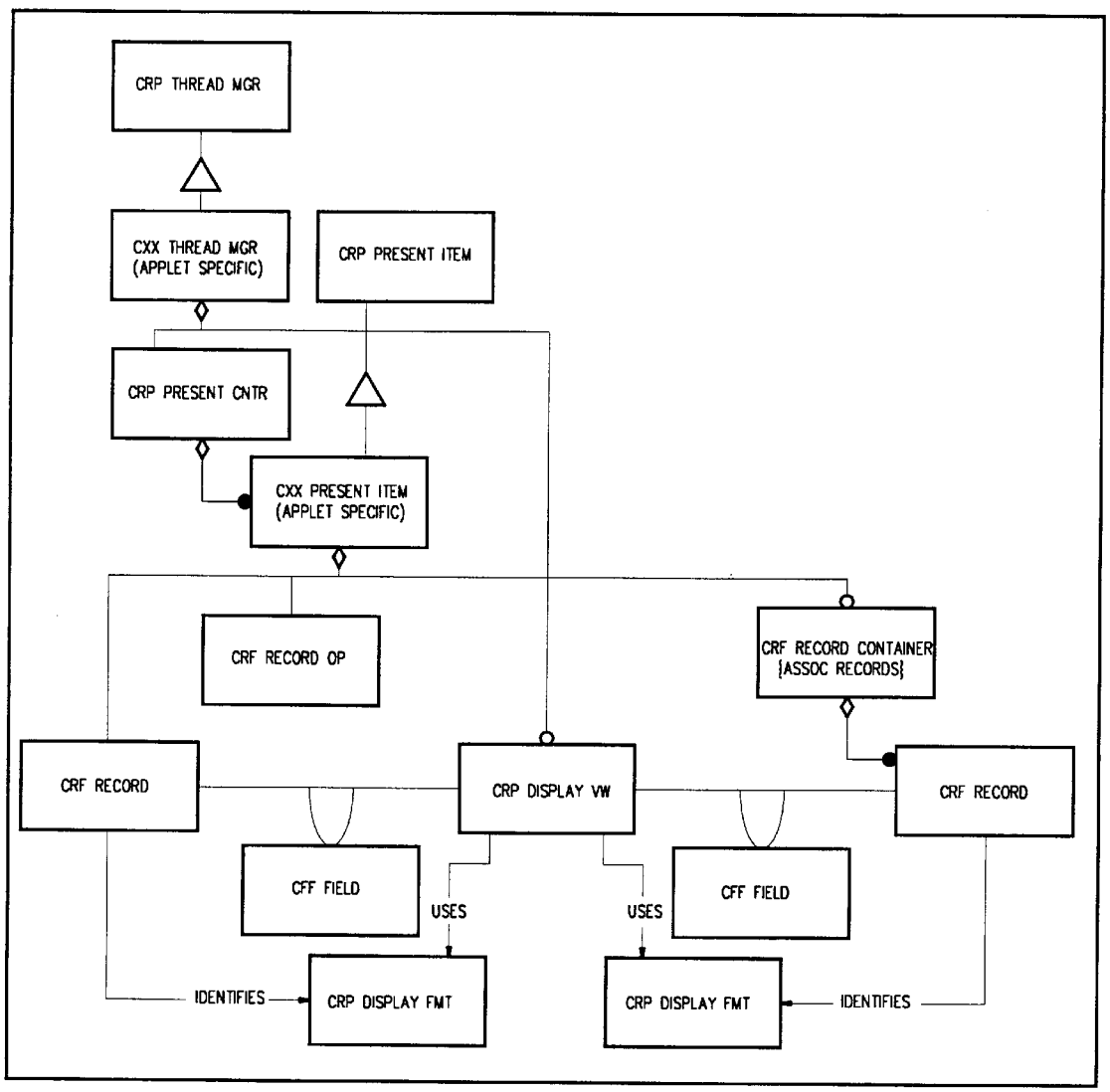

This paragraph discusses the interactions between Record Presentation and a typical record processing Applet which provides background processing (such as printing) of a list of records and optionally associates additional records with one or more of the primary records in this list. It is anticipated that an Applet may provide a child class of CrpThreadMgr, shown in FIG. 111B as class CxxThreadMgr. This class may also provide command handlers needed for processing specific to an Applet. If an Applet needs to control how associated records are selected for a given primary record, it may choose to provide its own child class of CrpPresentItem, shown in FIG. 111B as class CxxPresentItem. It is anticipated that this may be unnecessary for most Applets since the default record association logic built into CrpPresentCntr is expected to be adequate for most implementations of the present invention.

Figure 112:
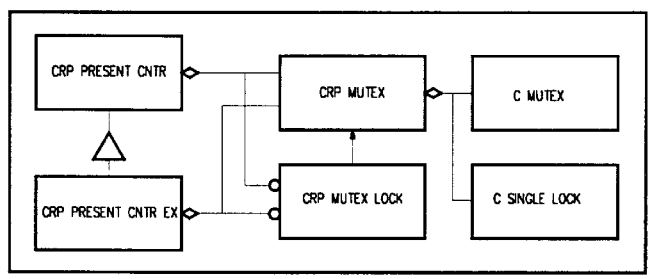
FIG. 112 is a diagrammatic view illustrating the Record Presentation Container Access Control of the present invention.

Record Presentation is designed for use by multiple threads within a single Win32 process. It allows simultaneous access to objects from multiple concurrent threads. Such simultaneous access may potentially cause different concurrent threads to adversely impact each other. To prevent this, the CrpPresentCntr and CrpPresentCntrEx classes preferably utilize a locking mechanism, temporarily delaying access from other threads during critical container manipulations. This access locking mechanism is provided by various classes such as CrpMutex and CrpMutexLock. The CrpPresentCntr and CrpPresentCntrEx classes preferably each contain a single object of class CrpMutex. The CrpMutex class contains a single object of MFC class CMutex, providing a Win32 Mutex lock, and a single object of MFC class CSingleLock to provide a mechanism for acquiring, releasing and testing the current state of the lock provided by the CMutex object. The CrpMutexLock class provides a mechanism that acquires the CrpMutex lock when a CrpMutexLock object is constructed and automatically releases this lock when the CrpMutexLock object is deleted. This provides an automatic mechanism for releasing a lock when leaving a block of code that acquires the lock by declaring an automatic variable of class CrpMutexLock. The CrpPresentCntr and CrpPresentCntrEx classes create and delete automatic CrpMutexLock objects as needed. These relationships are shown in FIG. 112.

One of the key design approaches used in Record Framework is that all operations upon records appear to be performed by the records themselves, rather than being performed upon records by some external controller object. An operation can also be performed upon a list of records contained within a CrfRecordContainer by simply performing the desired operation upon the CrfRecordContainer object. Record Presentation is instrumental in making this work. When a CrfRecord object is told to perform an operation such as by a call to CrfRecord :: DoOperation, it must first determine the processing context for that operation. If the processing context is a display context, the CrfRecord object selects the appropriate crpDisplayMgr object which manages the selected display context, constructs a CrfRecordOp object defining the requested operation, and calls CrpDisplayMgr :: AddRecord. The CrpDisplayMgr object creates its CrpDisplayFrm object, if it does not exist, and calls CrpDisplayFrm :: AddRecord to process the record. The CrpDisplayFrm object constructs a CrpPresentItem object containing both the CrfRecord object and the CrfRecordOp object and then calls CrpPresentCntrEx :: AddItem to process the CrpPresentItem object. If the CrfRecord object is contained within a CrfRecordContainer object, CrpPresentCntrEx will remove the CrfRecord object from the CrfRecordContainer object.

Figure 113A:
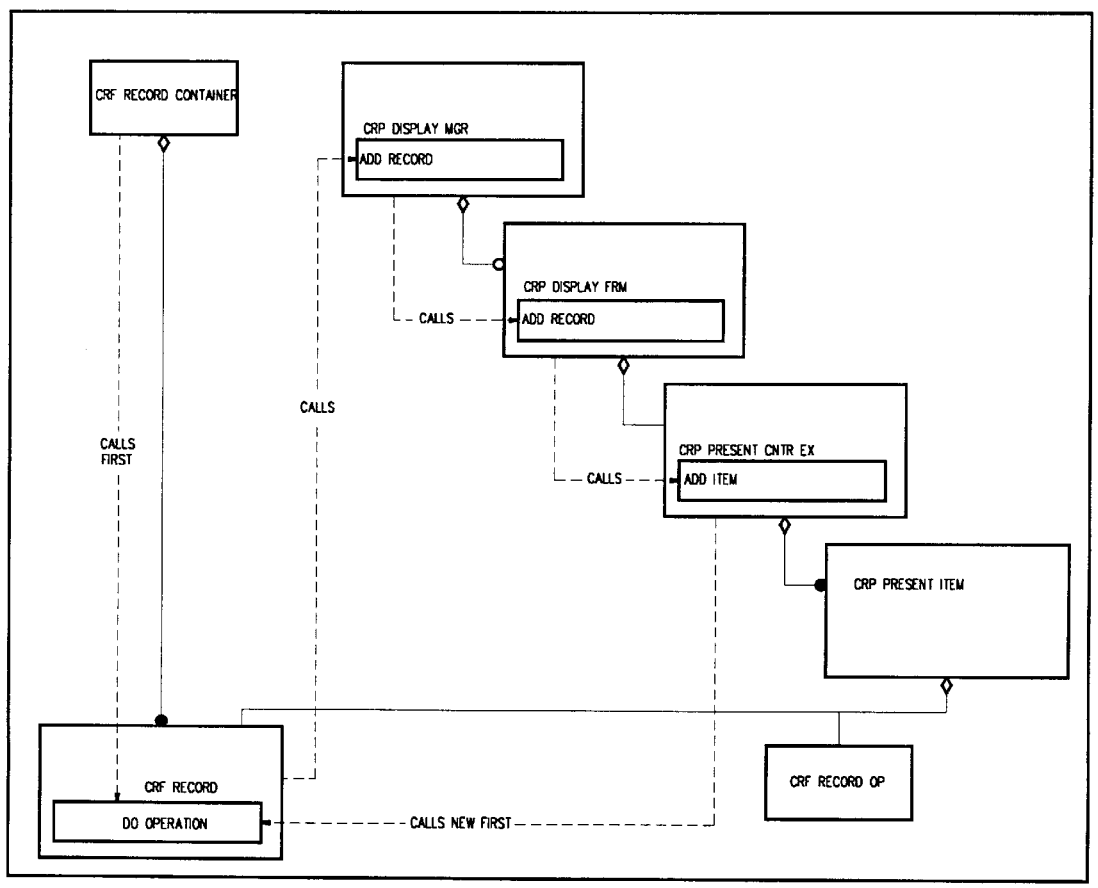
FIGS. 113A and 113B are diagrammatic views illustrating the Display Record Presentation interactions with the Record Framework of the present invention.

The first time CrpPresentCntrEx :: AddItem is called to process a CrfRecord object within a specific CrfRecordContainer object, CrpPresentCntrEx will repeatedly call CrfRecord :: DoOperation on the first record within the same CrfRecordContainer object. CrpPresentCntrEx will continue calling DoOperation on the first CrfRecord object within the CrfRecordContainer object until the CrfRecordContainer object is empty. As each CrfRecord object's DoOperation method is called, each CrfRecord object will request that it be processed by the appropriate processing context. The CrpDisplayMgr object performs the processing for display contexts. The processing context will place the CrfRecord object in the appropriate CrpPresentCntrEx and remove the CrfRecord object from the CrfRecordContainer object. In the present example, CrpDisplayMgr will place the CrfRecord object in the CrpPresentItemObject. Since each CrpPresentCntrEx object calls other records' Dooperation only when processing the first record within a CrfRecordContainer object, the maximum level of recursion of CrpPresentCntrEx :: AddItem is two. This processing is shown in FIG. 113A.

The various CrfRecord objects contained within a single CrfRecordContainer object may all select the same processing context such as CrpDisplayMgr object for display contexts or may select multiple processing contexts. For example, rest procedure records may be processed within a different display context than stress procedure records. Thus, each time CrfRecord :: Dooperation is called within CrpPresentCntrEx :: AddItem, a different display context could possibly be selected. The first time a second display context is chosen, the CrpPresentCntrEx :: AddItem for that display context will recognize itself as the first call within that processing context to process a CrfRecord object contained in a specific CrfRecordContainer object. Therefore, CrpPresentCntrEx will repeatedly call CrfRecord :: DoOperation on the first record within the same CrfRecordContainer object, even though this is already being done by a different CrpPresentCntrEx within a different processing context. There is no harm in this occurring. The maximum level of recursion within any one processing context's CrpPresentCntrEx :: AddItem remains at two. This looping through CrfRecord :: DoOperation by multiple processing contexts will simultaneously end for all processing contexts as the returns unwind through the nested calls. The preferable maximum level of recursion becomes two times the number of processing contexts actually used.

Figure 113B:
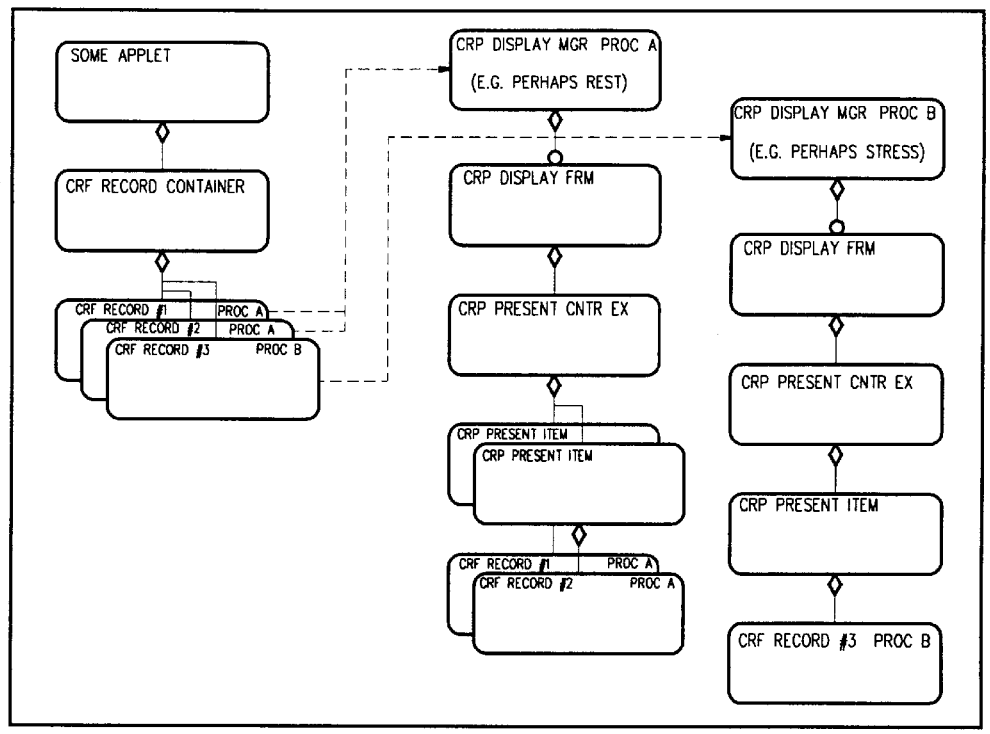

The example shown in FIG. 113B is illustrative of a CrfRecordContainer object containing three CrfRecord objects: two for procedure type A (e.g., Resting ECG Procedures) and one for procedure type B (e.g., Exercise Stress Test Procedures). When CrfRecordContainer :: DoOperation is called, CrfRecord objects one and two (both procedure type A) request the CrpDisplayMgr object for procedure type A to process them, and CrfRecord object three (procedure type B) requests CrpDisplayMgr object for procedure type B to process it. As a result, the CrpDisplayFrm objects are created, if they don't exist, and the CrfRecord objects are moved to their destination CrpPresentCntrEx objects and removed from the CrfRecordContainer object.

Figure 114A:
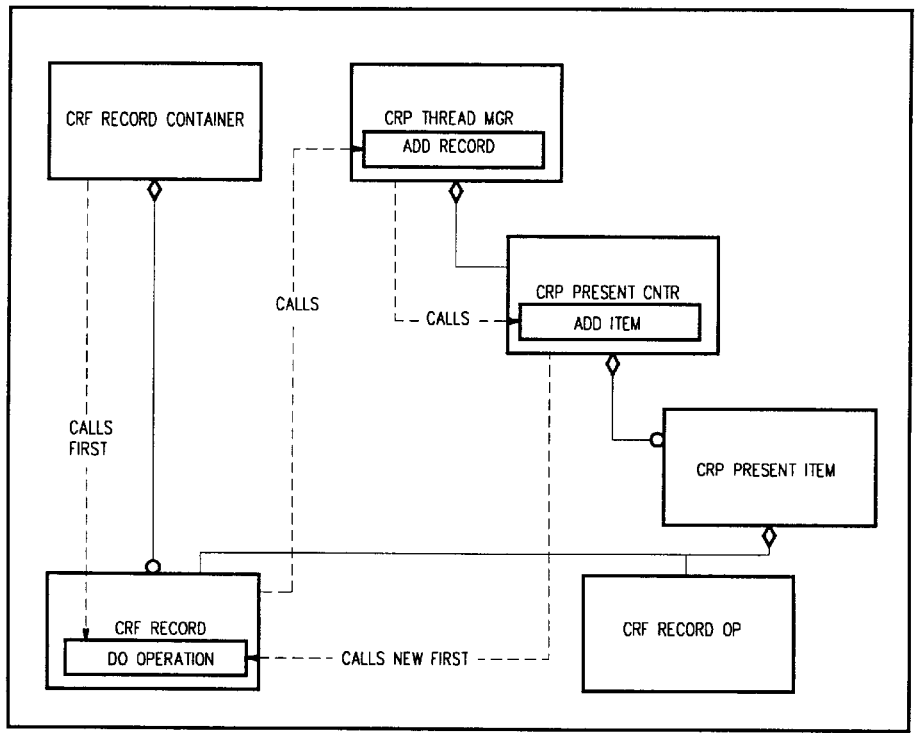
FIGS. 114A and 114B are diagrammatic views illustrating the Background Record Presentation interactions with the Record Framework of the present invention.

If a CrfRecord object is told to perform an operation (by a call to CrfRecord :: DoOperation) and choose a background processing context, the CrfRecord object selects the appropriate CrpThreadMgr object which manages the elected background context, constructs a CrfRecordOp object defining the requested operation and calls CrpThreadMgr :: AddRecord. The CrpThreadMgr object constructs a CrpPresentItem object containing both the CrfRecord object and the CrfRecordop object and then calls CrpPresentCntr :: AddItem to process the CrpPresentItem object. If the CrfRecord object is contained within a CrfRecordContainer object, CrpPresentCntr will remove the CrfRecord object from the CrfRecordContainer object. The first time CrpPresentCntr :: AddItem is called to process a CrfRecord object within a specific CrfRecordContainer object, CrpPresentCntr will repeatedly call CrfRecord :: DoOperation on the first record within the same CrfRecordContainer object. CrpPresentCntr will continue calling DoOperation on the first CrfRecord object within the CrfRecordContainer object until the CrfRecordContainer object is empty. As each CrfRecord object's DoOperation method is called, each CrfRecord object will request that it be processed by the appropriate processing context. The CrpThreadMgr object is used for processing background contexts. The appropriate processing context (CrpThreadMgr) will place the CrfRecord object in the appropriate CrpPresentCntr, i.e., CrpPresentItem object, and remove the CrfRecord object from the CrfRecordContainer object. Since each CrpPresentCntr object calls other records' DoOperation only when processing the first record within a CrfRecordContainer object, the maximum level of recursion of CrpPresentCntr :: AddItem is two. This processing is shown in FIG. 114A.

The various CrfRecord objects contained within a single CrfRecordContainer object may all select the same processing context or may select multiple processing contexts. In this example, the CrpThreadMgr object may be used for all background contexts. In the present embodiment, rest procedure records may be processed within a different processing context than stress procedure records. Thus, each time CrfRecord :: DoOperation is called within CrpPresentCntr :: AddItem, a different processing context could possibly be selected. The first time a second processing context is chosen, the CrpPresentCntr :: AddItem for that processing context will recognize itself as the first call within that processing context to process a CrfRecord object contained in a specific CrfRecordContainer object. Therefore, CrpPresentCntr will repeatedly call CrfRecord :: DoOperation on the first record within the same CrfRecordContainer object, even though this is already being done by a different CrpPresentCntr within a different processing context. There is no harm in this occurring. The maximum level of recursion within any one processing context's CrpPresentCntr :: AddItem remains at two. This looping through CrfRecord Dooperation by multiple processing contexts will simultaneously end for all processing contexts as the returns unwind through the nested calls. The maximum level of recursion becomes two times the number of processing contexts actually used.

Figure 114B:
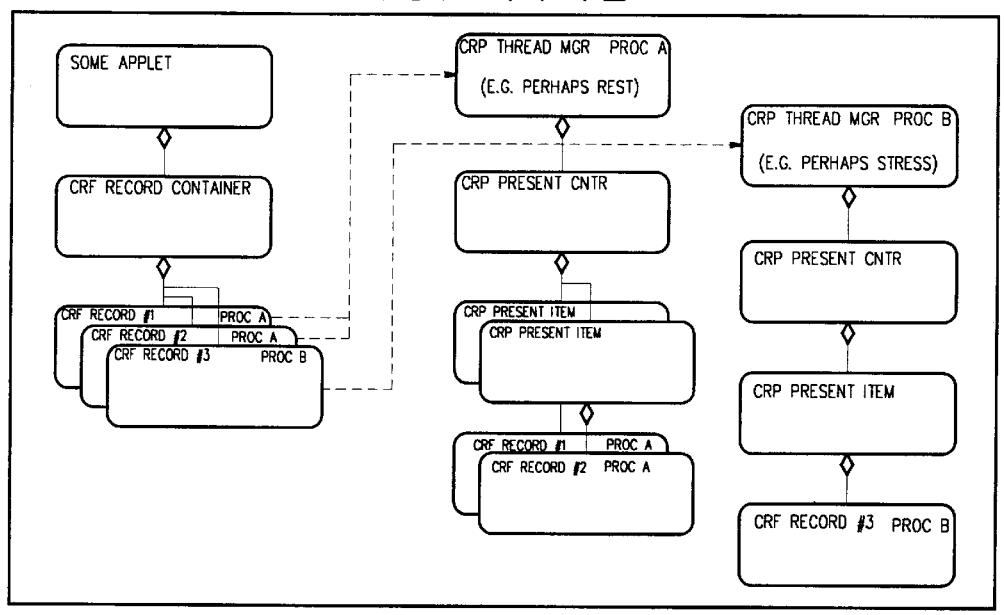

The example shown in FIG. 114B includes a CrfRecordContainer object containing three CrfRecord objects, two for procedure type A (e.g., perhaps Resting ECG Procedures) and one for procedure type B (e.g., perhaps Exercise Stress Test Procedures). When CrfRecordContainer :: Dooperation is called, CrfRecord objects one and two (both procedure type A) request the CrpThreadMgr object for procedure type A to process them, and CrfRecord object three (procedure type B) requests the CrpThreadMgr object for procedure type B to process it. As a result, the CrfRecord objects are moved to their destination CrpPresentCntr objects and removed from the CrfRecordContainer object.

Figure 115A:
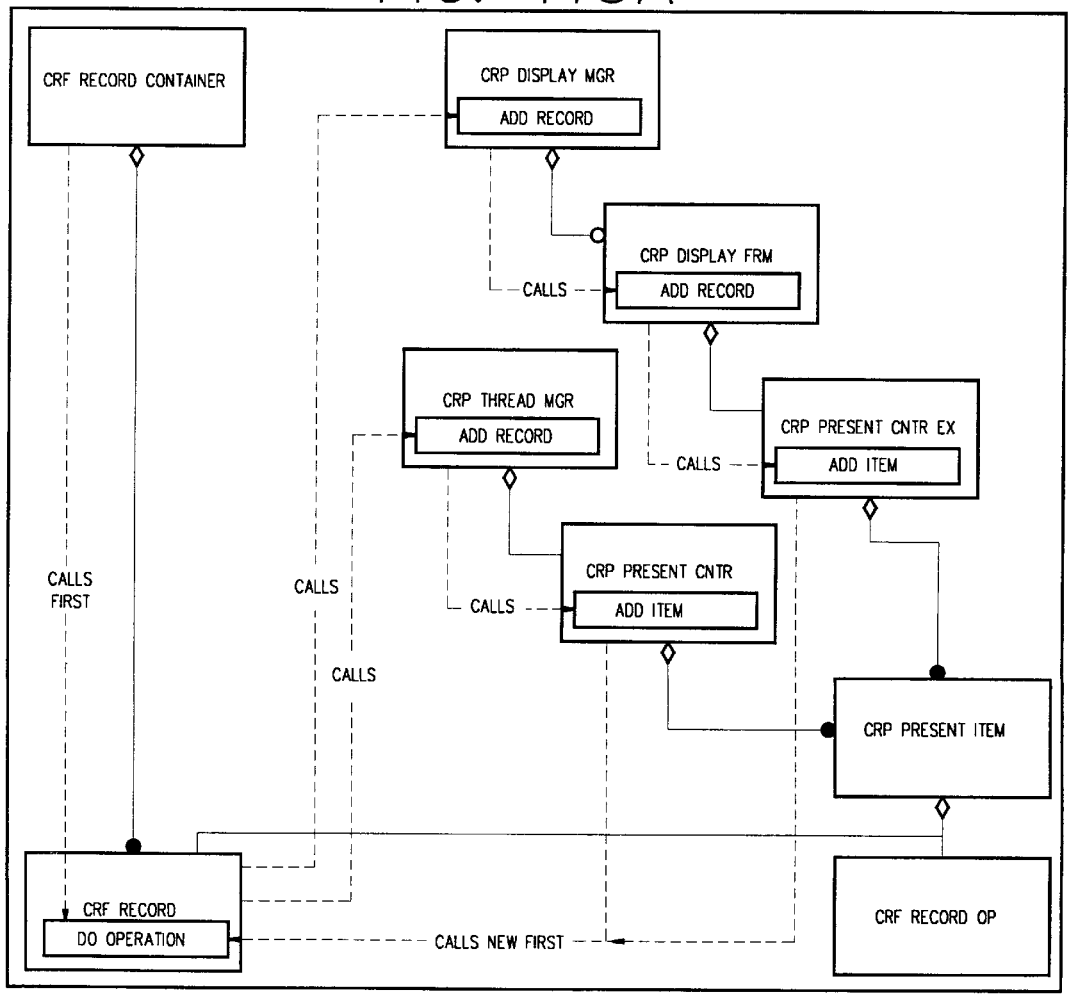
FIGS. 115A and 115B are diagrammatic views illustrating the mixed Record Presentation interactions with the Record Framework of the present invention.

In the preferred embodiment of the present invention, it is entirely possible that some CrfRecord objects within a given CrfRecordContainer object may select a display processing context while other CrfRecord objects within that same CrfRecordContainer object select a background processing context for the same DoOperation command. This is shown in FIG. 115A. The preferred maximum level of recursion within any one processing context's CrpPresentCntr(Ex) AddItem remains at two. The looping through CrfRecord :: DoOperation by multiple processing contexts results in a maximum level of recursion of two times the number of processing contexts actually used.

Figure 115B:
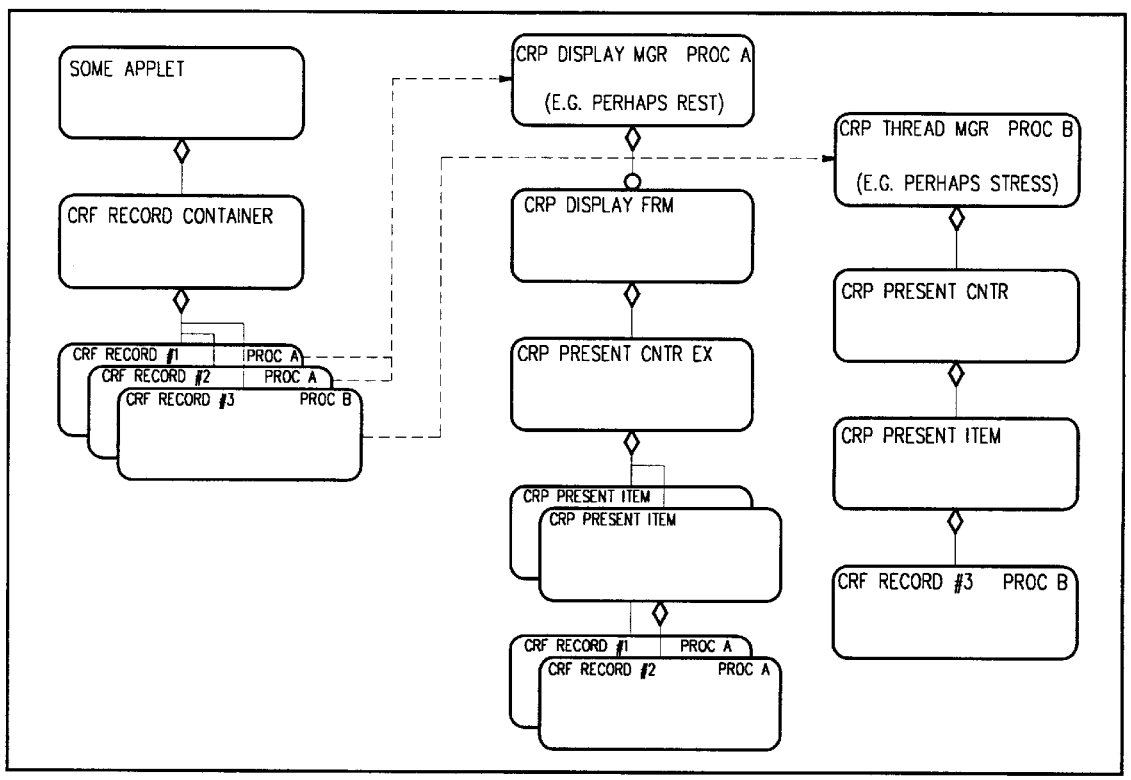

The example illustrated in FIG. 115B, shows a CrfRecordContainer object containing three CrfRecord objects, two for procedure type A (e.g., perhaps Resting ECG Procedures) and one for procedure type B (e.g., perhaps Exercise Stress Test Procedures). When CrfRecordContainer :: DoOperation is called, CrfRecord objects one and two (both procedure type A) request the display context provided by the CrpDisplayMgr object for procedure type A to process them, and CrfRecord object three (procedure type B) requests the background context provided by the CrpThreadMgr object for procedure type B to process it. As a result, the CrpDisplayFrm object for procedure type A is created, if it does not exist, and the CrfRecord objects are moved to their destination CrpPresentCntr(Ex) objects and removed from the CrfRecordContainer object.

The class CrpApplet is from the Record Presentation module. The Record Presentation is an Applet DLL, so it includes a class, CrpApplet, which inherits from CapApplet. This class preferably includes various public methods such as "CrpApplet," "~CrpApplet," "GetClientConfig," "GetServerConfig," "GetAppletName" and "GetAppletTitle."

This class also preferably includes protected methods such as "InitApplet" and "ExitApplet." The class CrpDisplayMgr is from the Record Presentation module and preferably provides the orchestration of the activities required to implement the displaying of records. Each CrpDisplayMgr object manages a unique, singleton CrpDisplayFrm object containing a list of records (CrfRecord objects) being processed, or about to be processed, by that unique CrpDisplayFrm object. CrpDisplayMgr inherits from and utilizes CawSingletonFrameMgr to create this singleton CrpDisplayFrm object as needed. When records (CrfRecord objects) are directed to process a particular record operation (by calling CrfRecord :: DoOperation), the record object determines the processing context of that command. If this processing context requires record display, the record selects the appropriate CrpDisplayMgr object (i.e., the CrpDisplayMgr object that knows how to process this record), and requests the CrpDisplayMgr to process the record (by calling CrpDisplayMgr :: AddRecord). This causes the CrpDisplayMgr to create its singleton CrpDisplayFrm object, if not currently in existence, and request the CrpDisplayFrm to process the record (by calling CrpDisplayFrm :: AddRecord). This class preferably includes various public methods such as "CrpDisplayMgr," "~CrpDisplayMgr" and "AddRecord."

The class CrpDisplayFrm is from the Record Presentation module and preferably provides a window containing a list of records (CrfRecord objects) being processed, or about to be processed. Each CrpDisplayFrmm object is created, managed and owned by a unique CrpDisplayMgr object. For each record received by a CrpDisplayFrm object (by calls to AddRecord), a Presentation Item (CrpPresentItem object) is constructed containing the record. This Presentation Item is then passed to the CrpPresentCntrEx object contained within each CrpDisplayFrm Object (by calling CrpPresentCntrEx :: AddItem) for processing. In addition to the above, a further preferred embodiment communication may be further increased and/or enabled between each CrpDisplayFrm object and any associated CrpAssocDisplayFrm object. The CrpDisplayFrm class preferably includes a private definition such as "EditToggle" as well as public methods such as "CrpDisplayFrm, " "~CrpDisplayFrm," "AddRecord," "LoadFrame" and "OnRefresh." Additionally, the class may also include various protected methods such as "GetPresentCntr," "FirstRecord," "NextRecord," "PrevRecord," "LastRecord," "SelectRecord," "ActivateAssocFrame," "IsAssocFrameOpen," "CloseAssocFrame," "BuildPresentItem" and "GetPresentItemClass."

The class CrpAssocDisplayFrm is from the Record Presentation module and preferably provides a window containing a list of records (CrfRecord objects) associated with the currently displayed record within a CrpDisplayFrm object which owns this CrpAssocDisplayFrm object. This class preferably includes various public methods such as "CrpAssocDisplayFrm" and "~CrpAssocDisplayFrm."

The class CrpThreadMgr is from the Record Presentation module and preferably provides the orchestration of the activities required to implement the background processing of records. Each CrpThreadMgr object is a unique, singleton thread containing a list of records (CrfRecord objects) being processed, or about to be processed. CrpThreadMgr inherits from and utilizes CWndThread. When records (CrfRecord objects) are directed to process a particular record operation (by calling CrFRecord :: Dooperation), the record object determines the processing context of that command. If this processing context requires background processing, the record selects the appropriate CrpThreadMgr object (i.e., the CrpthreadMgr object that knows how to process this record), and requests the CrpThreadMgr to process the record (by calling CrpThreadMgr :: AddRecord). For each record received by CrpThreadMgr :: AddRecord, a Presentation Item (CrpPresentItem object) is constructed containing the record. This Presentation Item is then passed to the CrpPresentCntr object contained within each CrpThreadMgr object (by calling CrpPresentCntr AddItem) for processing. This class preferably includes various public methods such as "CrpThreadMgr," "~CrpthreadMgr," "AddRecord," "BuildPresentItem" and "GetPresentItemClass."

The class CrpPresentCntr is from the Record Presentation module and preferably, in combination with sub-class CrpPresentCntrEx, provides the guts of the orchestration of the activities required to implement processing of records, either the display of records or the background processing of records. Each CrpPresentCntr object contains a list of records (CrfRecord objects) being processed, or about to be processed. Each record received by a CrpPresentCntr object (by calls to AddItem) is in the form of a Presentation Item (CrpPresentItem object) containing the record to be added to the CrpPresentCntr object. If a record being added is contained within a CrfRecordContainer object, it is deleted from that container. If a record being added is contained within a CrfRecordContainer object, and if this CrpPresentCntr object is not currently in the midst of adding a previous record from the same CrfRecordContainer object (that is, if this CrpPresentCntr object's AddItem method has not been called recursively for the same CrfRecordContainer object), then AddItem loops calling the DoOperation method of the first record within the CrfRecordContainer object until the CrfRecordContainer object is empty. Since some or all of these records within the CrfRecordContainer object will find their way to this CrpPresentCntr object, the CrpPresentCntr :: AddItem method can end up being called recursively, but only to a preferred maximum recursion depth of two. Since CrpPresentCntr methods can be called from any thread, all non-const public methods use a CrpMutex synchronization object to prevent simultaneous use by multiple threads. The CrpPresentCntr class preferably includes various public methods such as "CrpPresentCntr," "~CrpPresentCntr," "AddItem," "RemoveCurrent," "DeleteCurrent," "GetCount," "Isempty," "HasNext," "HasPrev," "GetFirst," "GetNext," "GetPrev," "GetLast," "GetCurrent," Select" and "GetItemNames." This class also preferably includes a protected method such as "Remove."

The class CrpPresentCntrEx is from the Record Presentation module and preferably builds upon class CrpPresentCntr to implement display processing of records. Each record received by a CrpPresentCntrEx object (by calls to AddItem) is in the form of a Presentation Item (CprPresentItem object) containing the record to be added to the CrpPresentCntrEx object. Each record received by a CrpPresentCntrEx object (by calls to AddItem) are processed by the base class CrpPresentCntr :: AddItem, providing default CrpPresentCntr behavior. If a record being added is already contained within this CrpPresentCntrEx object, the new Presentation Item object being added is deleted, the existing Presentation Item object is removed from the list, and the existing Presentation Item object is added in place of the new Presentation Item object. In other words, the existing record is moved to the end of the list. Since CrpPresentCntrEx methods can be called from any thread, all non-const public methods use a synchronization object to prevent simultaneous use by multiple threads. The class CrpPresentCntrEx preferably includes various public methods such as "CrpPresentCntrEx," "~CrpPresentCntrEx," "AddItem" and "RemoveCurrent" as well as a protected method such as "Remove."

The class CrpPresentItem is from the Record Presentation module and preferably is an object which associates with a primary CrfRecord object; an optional CrfRecordContainer object containing CrfRecord objects associated with the primary CrfRecord object; a CrfRecordop object specifying the operation on the primary CrfRecord object; some state flags concerning the current state of the primary CrfRecord object and optional additional data associated with the primary CrfRecord object, specified in a subclass of CrpPresentItem. The class CrpPresentItem preferably includes various public methods such as "CrpPresentItem," "~CrpPresentItem," "Initialize," "SetRecordop," "GetRecord," "GetRecordPOKey," "GetRecordOperation," "HaveAssocContainer," "CanModifyRecord," "SetCanModifyRecord," "IsRecordDirty," "SetRecordDirty" and "IsModifyRecordAllowed."

The class CrpMutex is from the Record Presentation module and preferably provides and exclusive lock mechanism. Class CrpMutex contains a single object of MFC class CMutex, providing a Win32 Mutex lock, and a single object of MFC class CSingleLock, providing a mechanism for acquiring, releasing and testing the current state of the lock provided by the CMutex object. The class CrpMutex preferably includes various public methods such as "CrpMutex," "~CrpMutex," "Lock," "Unlock" and "IsLocked."

The class CrpMutexLock is from the Record Presentation module and preferably provides a mechanism that acquires the CrpMutex lock when a CrpMutexLock object is constructed and automatically releases this lock when the CrpMutexLock object is deleted. This provides an automatic mechanism for releasing a lock when leaving a block of code that acquires the lock by declaring an automatic variable of class CrpMutexLock. Classes CrpPresentCntr and CrpPresentCntrEx create and delete automatic CrpMutexLock objects as needed. This class preferably includes various public methods such as "CrpMutexLock," "~CrpMutexLock," "Lock," "Unlock" and "IsLocked."

The class CrpDisplayVw is from the Record Presentation module and preferably provides a scrollable view of the selected segment of the current display format (object of class CrpDisplayFmt). This class preferably includes various public methods such as "CrpDisplayVw" and "~CrpDisplayVw."

The class CrpDisplayFmt is from the Record Presentation module and preferably provides a collection of segment layouts, each offering different representations of a record. Each segment layout contains a list of Field IDs and a position on the page or screen for each Field. The class CrpDisplayFmt preferably includes various public methods such as "CrpDisplayFmt," "~CrpDisplayFmt" and "operator=."

The foregoing extensively describes the preferred functionality and implementation of the present invention. The implementation of the present invention is further illustrated by the software code which is attached hereto as a microfiche appendix and is incorporated herein as if fully set forth below. It is anticipated that various modifications may be made to the present invention without departing from the true scope and breadth of the present invention which is defined by the following claims.

What is claimed is:

1. A clinical information reporting system for use in coordinating cardiology related patient information, said system including a platform hardware component and an application software component and said system further comprising:

A data input means for the receipt of physiological signals acquired from a patient;

a patient demographic information input means for the receipt of the demographic information of a patient;

said application software component of said system including object oriented software modules having a plurality of tiers including a top tier, a second tier and a third tier with at least one interface for communication between said top tier and said second tier and at least one further interface for communication between said second tier and said third tier;

a database for the receipt of said physiological signals received from said data input means and said demographic information from said demographic information input means in said third tier;

means for arranging said information and said signals in said database to correspond to records containing the said demographic information of the patient for which said physiological signals were acquired in said second tier; and report generating means for the generation of reports relating to said physiological signals and said demographic information of the patient in said top tier.

2. The system of claim 1 wherein said system includes a workstation means having said platform hardware component and said application software component therein and said application software component includes at least one framework shell module.

3. The clinical information reporting system of claim 2 wherein said application software component includes a dynamically loadable cardiology information system applet for resting ECG interpretation therein.

4. The clinical information reporting system of claim 3 wherein said cardiology information system applet includes analysis software to evaluate said physiological signals generated from a resting ECG report module for a patient to assist the user with the diagnosis of a patient.

5. The clinical information reporting system of claim 2 wherein said application software component includes a dynamically loadable cardiology information system applet for stress testing ECG interpretation therein.

6. The clinical information reporting system of claim 5 wherein said cardiology information system applet includes analysis software to evaluate said physiological signals generated from a stress ECG report module for a patient to assist the user with the diagnosis of a patient.

7. The clinical information reporting system of claim 2 wherein said said at least one framework shell module includes a client shell module and an applet interface therein to provide the basic functionality of said workstation means.

8. The clinical information reporting system of claim 7 wherein said client shell module of said application software component is the sole executable module of said application software component.

9. The clinical information reporting system of claim 2 wherein said application software component includes an administrative reports module therein and said administrative reports module is a dynamically loadable applet which performs the administrative reporting functions of said application software component to enable the user of said system to create an administrative report containing said physiological signals and said demographic information therein.

10. The clinical information reporting system of claim 2 wherein said application software component includes a patient demographics module therein and said patient demographics module is a dynamically loadable applet which performs the patient demographics related functions of said application software component to enable the user of said system to create a demographic report containing said demographic information of the patients in said database.

11. The clinical information reporting system of claim 2 wherein said application software component includes a print/fax/preview module therein and said print/fax/preview module is a dynamically loadable applet which performs the record receipt, transmission and viewing functions of said application software component to enable the user of said system to print and fax said physiological signals and said demographic information from said database.

12. The clinical information reporting system of claim 2 wherein said application software component includes a record workflow module therein and said record workflow module is a dynamically loadable applet to perform the data flow and data processing functions of said application software component.

13. A clinical information reporting system for use in coordinating cardiology related patient information, said system including a platform hardware component and an application software component and said system further comprising:

A data input means for the receipt of physiological signals acquired from a patient;

a patient demographic information input means for the receipt of demographic information of a patient;

said application software component of said system including object oriented software modules having a plurality of tiers including a top tier a second tier and a third tier with at least one interface for communication between said top tier and said second tier and at least one further interface for communication between said second tier and said third tier;

said application software component further including an object oriented database for the receipt of said physiological signals from said data input means and said patient demographic information from said patient demographic information input means means for arranging said database to correlate said patient demographic information and said physiological signals of the patient for which physiological signals were acquired;

a framework shell module having an applet interface therein for communication between said top tier and said second tier; and a dynamically loadable cardiology information system applet in one of said tiers and having further modules therein to perform resting ECG analysis and stress testing ECG analysis on said physiological signals.

14. A method of processing cardiology related information for use in a clinical information reporting system the method including the steps of;

providing an application software component including object oriented software modules having a plurality of tiers including a top tier, a second tier and a third tier with at least one interface for communication between said top tier and said second tier and at least one further interface for communication between said second tier and said third tier; acquiring as input, physiological signals from a patient;

storing the physiological signals from a patient in a database having demographic information for the patient wherein the database is located in the third tier of the application software component;

storing procedural information for medical procedures in the third tier of the application software component;

storing administrative information for a health care facility in the third tier of the application software component;

storing record workflow requirements for processing reports generated by the system in the top tier of the application software component; and generating reports for viewing, editing and/or printing based on the combined data related to the physiological signals of the patient, procedural information and administrative information in accordance with the record workflow requirements of the system in the second tier of the application software component.

* * * * *